US007869957B2

(12) United States Patent
Palsson et al.

(10) Patent No.: US 7,869,957 B2
(45) Date of Patent: Jan. 11, 2011

(54) METHODS AND SYSTEMS TO IDENTIFY OPERATIONAL REACTION PATHWAYS

(75) Inventors: Bernhard O. Palsson, La Jolla, CA (US); Markus W. Covert, South Pasadena, CA (US); Markus Herrgard, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 223 days.

(21) Appl. No.: 10/833,584

(22) Filed: Apr. 27, 2004

(65) Prior Publication Data

US 2004/0210398 A1    Oct. 21, 2004

Related U.S. Application Data

(63) Continuation-in-part of application No. 10/367,248, filed on Feb. 14, 2003, now Pat. No. 7,734,420.

(60) Provisional application No. 60/419,023, filed on Oct. 15, 2002, now abandoned, provisional application No. 60/562,055, filed on Apr. 13, 2004.

(51) Int. Cl.
G06F 19/00    (2006.01)
(52) U.S. Cl. ............................................... 702/19
(58) Field of Classification Search .................. None
See application file for complete search history.

(56) References Cited

U.S. PATENT DOCUMENTS

| 5,273,038 | A | 12/1993 | Beavin et al. | |
|---|---|---|---|---|
| 5,556,762 | A | 9/1996 | Pinilla et al. | |
| 5,639,949 | A | 6/1997 | Ligon et al. | |
| 5,689,633 | A | 11/1997 | Cotner et al. | |
| 5,914,891 | A | 6/1999 | Arkin et al. | |
| 5,930,154 | A | 7/1999 | Thalhammer-Reyero | |
| 5,947,899 | A | 9/1999 | Scollan et al. | |
| 6,132,969 | A | 10/2000 | Stoughton et al. | |
| 6,165,709 | A | 12/2000 | Friend et al. | |
| 6,200,803 | B1 | 3/2001 | Roberts | |
| 6,221,597 | B1 | 4/2001 | Roberts | |
| 6,302,302 | B1 | 10/2001 | Albisetti | |
| 6,326,140 | B1 | 12/2001 | Rine et al. | |
| 6,329,139 | B1 | 12/2001 | Nova et al. | |
| 6,351,712 | B1 | 2/2002 | Stoughton et al. | |
| 6,370,478 | B1 | 4/2002 | Stoughton et al. | |
| 6,379,964 | B1 | 4/2002 | Del Cardayre | |
| 6,500,710 | B2 | 12/2002 | Nakagawa | |
| 6,983,227 | B1 | 1/2006 | Thalhammer-Reyero | |
| 7,127,379 | B2 * | 10/2006 | Palsson et al. .................. | 703/2 |
| 2002/0012939 | A1 | 1/2002 | Palsson et al. | |
| 2002/0051998 | A1 | 5/2002 | Schmidt et al. | |
| 2002/0168654 | A1 | 11/2002 | Maranas et al. | |
| 2003/0059792 | A1 | 3/2003 | Palsson et al. | |
| 2003/0113761 | A1 * | 6/2003 | Tan et al. ....................... | 435/6 |
| 2003/0224363 | A1 | 12/2003 | Park et al. | |
| 2003/0233218 | A1 | 12/2003 | Schilling | |
| 2004/0009466 | A1 | 1/2004 | Maranas et al. | |
| 2004/0029149 | A1 | 2/2004 | Palsson et al. | |
| 2004/0072723 | A1 | 4/2004 | Palsson et al. | |
| 2006/0147899 | A1 | 7/2006 | Famili et al. | |
| 2007/0111294 | A1 | 5/2007 | Burgard et al. | |
| 2008/0176327 | A1 | 7/2008 | Palsson et al. | |

FOREIGN PATENT DOCUMENTS

| WO | WO 92/09300 | 6/1992 |
|---|---|---|
| WO | WO 00/46405 | 8/2000 |
| WO | WO 01/36658 A | 5/2001 |
| WO | WO 01/57775 | 8/2001 |
| WO | WO 02/055995 | 7/2002 |
| WO | WO 02/061115 | 8/2002 |
| WO | WO 03/106998 | 12/2003 |

OTHER PUBLICATIONS

Edwards et al. Biotech. Prog. (2000) vol. 16, pp. 927-939.*
Stephanopoulos. Current Opinion in Biotechnology (1994) vol. 5, pp. 196-200.*
Covert et al., Metabolic Modeling of Microbial Strains in silico, *TIBS*, Mar. 2001. vol. 26, No. 3, pp. 179-186.
Schilling et al., Assessment of the Metabolic Capabilities of *Heamophilis influenza* Rd through a Genome-scale Pathway Analysis, *J. Theoretical Biology*, 2000, vol. 203, pp. 249-273.
Schilling et al., The underlying pathway structure of biochemical reaction networks, *PNAS*, Apr. 1998, vol. 95, pp. 4193-4198.
Mendes et al., Non-linear optimization of biochemical pathways: Applications to metabolic engineering and parameter estimation, *Bioinformatics*, 1998, vol. 14, No. 10, pp. 869-883.
Edwards et al., In silico predictions of *Escherichia coli* metabolic capabilities are consistent with experimental data., *Nature Biotechnology*, Feb. 2001, vol. 19, pp. 125-130.
Bialy, H., Living on the Edges, *Nature Biotechnology*, Feb. 2001, vol. 19, pp. 111-112.
Varner et al., Mathematical models of metabolic pathways, *Current Opinion in Biotechnology*, 1999, vol. 10, pp. 146-150.

(Continued)

*Primary Examiner*—Lori A Clow
(74) *Attorney, Agent, or Firm*—DLA Piper LLP (US)

(57) ABSTRACT

The present invention provides a method of refining a biosystem reaction network. The method consists of: (a) providing a mathematical representation of a biosystem; (b) reconciling said mathematical representation of said biosystem; (c) determining differences between observed behavior of a biosystem and in silico behavior of said mathematical representation of said biosystem under similar conditions; (d) modifying a structure of said mathematical representation of said biosystem, and (e) determining differences between said observed behavior of said biosystem and in silico behavior of said modified mathematical representation of said biosystem under similar conditions.

18 Claims, 29 Drawing Sheets

OTHER PUBLICATIONS

Jamshidi et al., In silico model-driven assessment of the effects of single nucleotide polymorphisms (SMPs) on human red blood cell-metabolism, *Genome Research*, Nov. 2002, vol. 12, No. 11, pp. 1687-1692.

Edwards et al., The *Escherichia coli* MG1655 in silico metabolic genotype: Its definition, characteristics, and capabilities. *PNAS*, May 2000, vol. 97, No. 10, pp. 5528-5533.

Beard et al., "Energy Balance for Analysis of Complex Metabolic Networks", *Biophysical Journal*, 83(1):79-86 (2002).

Covert et al., "Regulation of Gene Expression in Flux Balance Models of Metabolism", *Journal of Theoretical Biology*, 213(1):73-88 (2001).

Delgado & Liao, "Identifying Rate-Controlling Enzymes in Metabolic Pathways without Kinetic Parameters", *Biotechnology Progress*, 7(1):15-20 (1991).

Forst, C.V., "Network genomics—A novel approach for the analysis of biological systems in the post-gnomic era", *Molecular Biology Reports*, 29(3):265-280 (2002).

Price et al., "Network-based analysis of metabolic regulation in the human red blood cell", *Journal of Theoretical Biology*, 225(2):185-194 (2003).

Akutsu, "Genetic Network Interference Algorithm," Mathematical Science (Sur-Kagaku) *Science* 37(6):40-46 (1999).

Aristidou and Penttila, "Metabolic engineering applications to renewable resource utilization," *Curr. Opin. Biotechnol.* 11(2):187-198 (2000).

Callis, "Regulation of Protein Degradation," *Plant Cell* 7:845-857 (1995).

Carrier and Keasling, "Investigating Autocatalytic Gene Expression Systems through Mechanistic Modeling," *J. Theor. Biol.* 201(1):25-36 (1999).

Chartrain, et al., "Metabolic engineering and directed evotion for the production of pharmaceuticals," *Curr. Opin. Biotechnol.* 11(2):209-214 (2000).

Dafoe, et al., "In Silico Knowledge Discovery Biomedical databases," *Proceedings of the SPIE Fifth Workshop on Neural Networks*, San Francisco, Nov. 7-10, 1993.

DeRisi, et al., "Use of cDNA microarray to analyse gene expression patters in human cancer," *Nat. Gene.* 14:457-460 (1996).

Duarte, et al., "Reconstruction and validation of *Saccharomyces cerevisiae* iND750, a fully compartmentalized genome-scale metabolic model," *Genome Res.* 14(7):1298-1309 (2004).

Feist and Palsson, "The growing scope of applications of genome-scale metabolic reconstructions using *Escherichia coli*," *Nat. Biotechnol.* 26(6):659-667 (2008).

Fotheringham, "Engineering biosynthetic pathways: new routes to chiral amino acids," *Curr. Opin. Chem. Biol.* 4(1):120-124 (2000).

Gombert and Nielsen, "Mathematical modeling of metabolism," *Curr. Opin. Biotechnol.* 11(2):180-186 (2000).

Guardia, et al., "Cybernetic modeling and regulation of metabolic pathways in multiple steady states of hybridoma cells," *Biotechnol. Prog.* 16(5):847-853 (2000).

Kaufman, et al., "Towards a logical analysis of the immune response," *J. Theor. Biol.* 114(4):527-561 (1985).

Lee, et al., "Incorporating qualitative knowledge in enzyme kinetic models using fuzzy logic," *Biotechnol. Bioeng.* 62(6):722-729 (1999).

Lynd, et al., "Biocommodity Engineering," *Biotechnol. Prog.* 15:777-793 (1999).

McAdams and Shapiro, "Circuit simulation of genetic networks," *Science* 269:650-656 (1995).

McAdams and Arkin, "Stochastic mechanisms in gene expression," *Proc. Natl. Acad. Sci. USA* 94(3):814-819 (1997).

McAdams and Arkin, "It's a noisy business! Genetic regulation at the nanomolar scale," *Trends Genet.* 15(2):65-69 (1999).

Mendz, et al., "Glucose utilization and lactate production by *Helicobacter pylori*," *J. Gen. Microbiol.* 139(12):3023-3028 (1993).

Ostergaard, et al., "Increasing galactose consumption by *Saccharomyces cerevisiae* through metabolic engineering of the GAL gene regulatory network," *Nat. Biotechnol.* 18:1283-1286 (2000).

Ozcan, et al., "Glucose uptake and catabolite repression in dominant HTR1 mutants of *Saccharomyces cerevisiae.*," *J. Bacteriol.* 175(17):5520-5528 (1993).

Pieper and Reineke, "Engineering bacteria for bioremediation," *Curr. Opin Biotechnol.* 11(3):262-270 (2000).

Raclot et al., "Selective release of human adipocyte fatty acids according to molecular structure," *Biochem. J.* 324 (Pt3):911-915 (1997).

Rao and Arkin "Control motifs for intracellular regulatory networks," *Annu. Rev. Biomed. Eng.* 3:391-419 (2001).

Savageau, "Development of fractal kinetic theory for enzyme-catalysed reactions and implications for the design of biochemical pathways," *Biosystems* 47(1-2):9-36 (1998).

Savinell and Palsson, "Network Analysis of Intermediary Metabolism using Linear Optimization. II. Interpretation of Hybridoma Cell Metabolism," *J. Theor. Biol.* 154:455-473 (1992).

Savinell and Palsson, "Network Analysis of Intermediary Metabolism using Linear Optimization. I. Development of Mathematical Formalism," *J. Theor. Biol.* 154:421-454 (1992).

Somogyi and Sniegoski, C "Modeling the complexity of genetic networks: understanding the multigenic and pleitropic regulation," *Complexity* 1(6):45-63 (1996).

Tandeitnik, et al., "Modeling of biological neurons by artificial neural networks," *Nineteenth Convention of Electrical and Electronics Engineers in* Israel, Jerusalem, Israel, New York, NY USA, pp. 239-242 (1996).

Thieffry and Thomas, "Dynamical behavior of biological regulatory networks II. Immunity control in bacteriophage lambda," *Bull. Math. Biol.* 57(2):277-297 (1995).

Varner, "Large-scale prediction of phenotype: concept," *Biotech. Bioeng.* 69(6):664-678 (2000).

Vaseghi, et al., "In vivo Dynamics of the pentose phosphate pathway in *Saccharomyces cerevisiae*," *Metab. Eng.* 1:128-140 (1999).

Vo, et al., "Reconstruction and functional characterization of the human mitochondrial metabolic network abased on proteomic and biochemical dataz," *J. Biol. Chem.* 279(38):39532-39540 (2004).

Xie and Wang, "Material Balance Studies on Animal Cell Metabolism Using a Stoichiometrically Based Reaction Network," *Biotech. Bioeng.* 52:579-590 (1996).

Xie and Wang, "Energy metabolism and ATP Balance in Animal Cell Cultivation Using a Stoichiometrically Based Reaction Network," *Biotech. Bioeng.* 52:591-601 (1996).

Adamowicz et al., "Nutritional complementation of oxidative glucose metabolism in *Escherichia coli* via pyrroloquinoline quinone-dependent glucose dehydrogenase and the Entner-Doudoroff pathway," *Appl Environ Microbiol*, 57(7):2012-2015 (1991).

Alberty, "Calculation of Biochemical Net Reactions and Pathways by Using Matrix Operations," *Biophys J*, 71(1):507-515 (1996).

Alm "Genomic-sequence comparison of two unrelated isolates of the human gastric pathogen *Helicobacter pylori*," *Nature*, 397(6715):176-80 (1999).

Alon et al., "Broad patterns of gene expression revealed by clustering analysis of tumor and normal colon tissues probed by oligonucleotide arrays," *Proc Natl Acad Sci U.S.A.*, 96(12):6745-6750 (1999).

Alter et al., "Singular value decomposition for genome-wide expression data processing and modeling," *Proc Natl Acad Sci U.S.A.*, 97(18):10101-10106 (2000).

Altschul et al., "Gapped BLAST and PSI-BLAST: A New Generation of Protein Database Search Programs," *Nucl Acids Res*, 25(17):3389-3402 (1997).

Alves et al., "Systemic properties of ensembles of metabolic networks: application of graphical and statistical methods to simple unbranched pathways," *Bioinformatics*, 16(6):534-547 (2000).

Andre, "An overview of membrane transport proteins in *Saccharomyces cerevisiae*," *Yeast*, 11(16):1575-1611 (1995).

Anonymous, "The yeast genome directory" *Nature*, 387(6632 Suppl):5 (1997).

Appel et al., "A new generation of information retrieval tools for biologists: the example of the ExPASy WWW server," *Trends Biochem Sci*, 19(6):258-260 (1994).

Arigoni et al., "A Genome-Based Approach for the Identification of Essential Bacterial Genes," *Nature Biotechnology*, 16(9):851-856 (1998).

Attanoos et al., "Ileostomy polyps, adenomas, and adenocarcinomas," *Gut*, 37(6):840-844 (1995).
Baba et al., "Construction of *Escherichia coli* K-12 in-frame, single-gene knockout mutants: the Keio collection," *Mol Syst Biol*, 2:2006-2008 (2006).
Bailey, "Complex Biology With No Parameters," *Nat Biotechnol*, 19(6):503-504 (2001).
Bailey, TL and Elkan, C, "Fitting a mixture model by expectation maximization to discover motifs in biopolymers," *Proc Int Conf Intell Syst Mol Biol*, 2:28-36 (1994).
Bailey, TL and Gribskov, M, "Combining evidence using p-values: application to sequence homology searches," *Bioinformatics*, 14(1):48-54 (1998).
Bairoch, A, and Apweiler, R, "The SWISS-PROT Protein Sequence database and its supplement TrEMBL in 2000," *Nucleic Acids Res*, 28(1):45-48 (2000).
Ball et al., "Integrating functional genomic information into the Saccharomyces genome database," *Nucleic Acids Res*, 28(1):77-80 (2000).
Baltz et al., "DNA Sequence Sampling of the Streptococcus Pneumonia Genome to Identify Novel Targets for Antibiotic Development," *Microbial Drug Resistance*, 4(1):1-9 (1998).
Ban et al., "Thymine and uracil catabolism in *Escherichia coli*," *J Gen Microbiol*, 73(2):267-272 (1972).
Bansal, "Integrating co-regulated gene-groups and pair-wise genome comparisons to automate reconstruction of microbial pathways," *Bioinformatics and Bioengineering Conference*, 209-216 (2001).
Bard et al., "Sterol mutants of *Saccharomyces cerevisiae*: chromatographic analyses," *Lipids*, 12(8):645-654 (1977).
Baxevanis, "The Molecular Biology Database Collection: 2002 update," *Nucleic Acids Res*, 30:1-12 (2002).
Beckers et al., "Large-Scale Mutational Analysis for the Annotation of the Mouse Genome," *Curr Opin Chem Biol*, 6(1)17-23 (2002).
Bell et al., "Composition and functional analysis of the *Saccharomyces cerevisiae* trehalose synthase complex," *J Biol Chem.*, 273(50):33311-33319 (1998).
Benjamini and Hochberg, "Controlling the false discovery rate: a practical and powerful approach to multiple testing," *J Roy Stat Soc Ser B (Methodological)*, 57:289-300 (1995).
Benson et al., "GenBank," *Nucleic Acids Res*, 28(1):15-18 (2000).
Berry, "Improving production of aromatic compounds in *Escherichia coli* by metabolic engineering," *Trends Biotechnol*, 14(7):250-256 (1996).
Bianchi, P, and Zanella, A, *Blood Cells, Molecules, and Diseases*, 15:47-53 (2000).
Biaudet et al., "Micado—a network-oriented database for microbial genomes," *Comput Appl Biosci*, 13(4):431-438 (1997).
Birkholz, "Fumarate reductase of *Helicobacter pylori*—an immunogenic protein," *J Med Microbiol*, 41(1):56-62 (1994).
Birner et al., "Roles of phosphatidylethanolamine and of its several biosynthetic pathways in *Saccharomyces cerevisiae*," *Mol Biol Cell*, 12(4):997-1007 (2001).
Blackstock, WP and Weir, MP, "Proteomics: quantitative and physical mapping of cellular proteins," *Trends Biotechnol*, 17(3):121-127 (1999).
Blattner et al., "The Complete Genome Sequence of *Escherichia coli* K-12," *Science*, 277(5331):1453-1474 (1997).
BMES/EMBS Conference, Proceedings of the First Joint, vol. 2, p. 1217 (1999).
Bochner, "New technologies to assess genotype-phenotype relationships," *Nat Rev Genet*, 4(4):309-314 (2003).
Boles, E et al., "Identification and characterization of MAE 1, the *Saccharomyces cerevisiae* structural gene encoding mitochondrial malic enzyme," *J Bacteriol.*, 180(11):2875-2882 (1998).
Boles et al., "A family of hexosephosphate mutases in *Saccharomyces cerevisia*," *Eur J Biochem*, 220(1):83-96 (1994).
Boles et al., "Characterization of a glucose-repressed pyruvate kinase (Pyk2p) in *Saccharomyces cerevisiae* that is catalytically insensitive to fructose-1,6-bisphosphate," *J Bacteriol*, 179(9):2987-2993 (1997).
Bonarius et al., "Flux Analysis of Underdetermined Metabolic Networks: The Quest for the Missing Constraints," *Trends Biotechnol*, 15(8):308-314 (1997).
Bonarius et al., "Metabolic flux analysis of hybridoma cells in different culture media using mass balances," *Biotechnol Bioeng*, 50(3):299-318 (1996).
Bono et al., "Reconstruction of amino acid biosynthesis pathways from the complete genome sequence," *Genome Research*, 8(3):203-210 (1998).
Bottomley et al., "Cloning, sequencing, expression, purification and preliminary characterization of a type II dehydroquinase from *Helicobacter pylori*," *Biochem. J*, 319(Pt 2):559-565 (1996).
Bourot, S and Karst, F, "Isolation and characterization of the *Saccharomyces cerevisiae* SUT1 gene involved in sterol uptake," *Gene*, 165(1):97-102 (1995).
Burgard, AP and Maranas, CD, "Probing the Performance Limits of the *Escherichia coli* Metabolic Network Subject to Gene Additions or Deletions," *Biotechnol Bioeng*, 74(5):364-375 (2001).
Burgard, AP and Maranas, CD, "Review of the Enzymes and Metabolic Pathways (EMP) Database," *Metab Eng*, 3(3):193-194(2) (2001).
Burgard et al., "Minimal reaction sets for *Escherichia coli* metabolism under different growth requirements and uptake environments," *Biotechnol Prog*, 17(5):791-797 (2001).
Burgard et al., "Optknock: a bilevel programming framework for identifying gene knockout strategies for microbial strain optimization," *Biotechnol Bioeng*, 84(6):647-657 (2003).
Burns, "Acetyl-CoA carboxylase activity in *Helicobacter pylori* and the requirement of increased $CO_2$ for growth," *Microbiology*, 141(Pt 12):3113-3118 (1995).
Chadha et al., "Hybrid process for ethanol production from rice straw," *Acta Microbiol Immunol Hung*, 42(1):53-59 (1995).
Chadha et al., "Simultaneous saccharification and fermentation of rice straw into ethanol," *Acta Microbiol Immunol Hung.*, 42(1):71-75 (1995).
Chalker et al., "Systematic identification of selective essential genes in Helicobacter pylori by genome prioritization and allelic replacement mutagenesis," *J Bacteriol*, 183(4):1259-1268 (2001).
Chen et al., "Characterization of the respiratory chain of Helicobacter pylori," *FEMS Immunol Med Microbiol*, 24(2):169-174 (1999).
Cherry et al., "SGD: Saccharomyces Genome Database," *Nucleic Acids Res*, 26(1):73-79 (1998).
Christensen, B and Nielsen, J, "Metabolic network analysis. A powerful tool in metabolic engineering," *Advances in Biochemical Engineering/Biotechnology*, 66:209-231 (2000).
Ciriacy, M and Breitenbach, I, "Physiological effects of seven different blocks in glycolysis in *Saccharomyces cerevisiae*," *J Bacteriol*, 139(1):152-160 (1979).
Clarke, "Complete set of steady states for the general stoichiometric dynamical system," *J Chem Phys*, 75(10):4970-4979 (1981).
Clarke, "Stoichiometric network analysis," *Cell Biophys*, 12:237-253 (1988).
Clarke, *Stability of Complex Reaction Networks. Advances in Chemical Physics*, 43:1-125 (1980).
Clifton, D and Fraenkel, DG, "Mutant studies of yeast phosphofructokinase," *Biochemistry*, 21(8):1935-1942 (1982).
Clifton et al., "Glycolysis mutants in *Saccharomyces cerevisiae*," *Genetics*, 88(1):1-11 (1978).
Compan, I and Touati, D et al., "Anaerobic activation of arcA transcription in *Escherichia coli*: roles of Fnr and ArcA," *Mol Microbial*, 11(5):955-964 (1994).
Costanzo et al., "YPD, PornbePD and WormPD: model organism volulmes of the BioKnowledge library, an integrated resource for protein information," *Nucleic Acids Res*, 29(1):75-9 (2001).
Cotter et al., "Aerobic regulation of cytochrome d oxidase (cydAB) operon expression in *Escherichia coli*: roles of Fnr and ArcA in repression and activation," *Mol Microbiol*, 25(3):605-615 (1997).
Cover, TL and Blaser, MJ, "Helicobacter pylori infection, a paradigm for chronic mucosal inflammation: pathogenesis and implications for eradication and prevention," *Adv Intern Med*, 41:85-117 (1996).
Covert and Palsson, "Constraints-based models: regulation of gene expression reduces the steady-state solution space" *J Theor Biol*, 216 (2003).
Covert and Palsson, "Transcriptional regulation in constraints-based metabolic models of *Escherichia coli*," *J Biol Chem*, 277(31):28058-28064 (2002).

Cupp, JR and McAlister-Henn, L, "Cloning and Characterization of the gene encoding the IDH1 subunit of NAD(+)-dependent isocitrate dehydrogenase from *Saccharomyces cerevisiae*," *J Biol Chem*, 267(23):16417-16423 (1992).

D'Haeseleer et al., "Genetic network inference: from co-expression clustering to reverse engineering," *Bioinformatics*, 16(8):707-726 (2000).

Danchin, "Comparison Between the *Escherichia coli* and *Bacillus subtilis* Genomes Suggests That a Major Function of Polynucleotide Phosphorylase is to Synthesize CDP," *DNA Research*, 4(1):9-18 (1997).

Dandekar et al., "Pathway Alignment: Application to the Comparative Analysis of Glycolytic Enzymes," *Biochem J*, 343(Pt 1):115-124 (1999).

Dantigny et al., "Transition rate kinetics from ethanol oxidation to glucose utilisation within a structured model of baker's yeast," *Appl Microbiol Biotechnol*, 36:352-357 (1991).

Datsenko, KA and Wanner, BL, "One-step inactivation of chromosomal genes in *Escherichia coli* K-12 using PCR products," *Proc Natl Acad Sci U.S.A.*, 97(12):6640-6645 (2000).

Daum et al., "Biochemistry, cell biology and molecular biology of lipids of *Saccharomyces cerevisiae*," *Yeast*, 14(16):1471-1510 (1998).

Daum et al., "Systematic analysis of yeast strains with possible defects in lipid metabolism," *Yeast*, 15(7):601-614 (1999).

Dauner et al., "*Bacillus subtilis* Metabolism and Energetics in Carbon-Limited and Excess-Carbon Chemostat Culture," *J Bacteriol*, 183(24):7308-7317 (2001).

Dauner et al., "Metabolic Flux Analysis with a Comprehensive Isotopomer Model in *Bacillus subtilis*," *Biotechnol Bioeng*, 76(2):144-156 (2001).

Dauner, M and Sauer, U, "Stoichiometric Growth Model for Riboflavin-Producing *Bacillus subtilis*," *Biotechnol Bioeng*, 76(1):132-143 (2001).

de Jong, H., "Modeling and simulation of genetic regulatory systems: a literature review," *J Comput Biol*, 9(1):67-103 (2002).

De Reuse et al., "The Helicobacter pylori ureC gene codes for a phosphoglucosamine mutase," *J Bacteriol*, 179(11):3488-3493 (1997).

Demain et al., "Cellulase, clostridia, and ethanol," *Microbiol Mol Biol Rev*, 69(1):124-154 (2005).

Department of Energy, *Breaking the Biological Barriers to Cellulosic Ethanol* (2006).

DeRisi et al, "Exploring the Metabolic and Genetic Control of Gene Expression on a Genomic Scale," *Science*, 278(5338):680-686 (1997).

Devine, KM, "The *Bacillus subtilis* Genome Project: Aims and Progress," *Trends Biotechnol*, 13(6):210-216 (1995).

Dickson, "Sphingolipid functions in *Saccharomyces cerevisiae*: comparison to mammals," *Annu Rev Biochem*, 67:27-48 (1998).

Dickson et al., "Serine palmitoyltransferase," *Methods Enzymol*, 311:3-9 (2000).

DiRusso, CC and Black, PN, "Long-chain fatty acid transport in bacteria and yeast. Paradigms for defining the mechanism underlying this protein-mediated process," *Mol.Cell Biochem*, 192(1-2):41-52 (1999).

Dooley et al., "An all D-amino acid opiod peptide with central analgesic activity from a combinatorial library," *Science*, 266(5193):2019-2022 (1994).

Edwards et al., "Characterizing the Metabolic Phenotype: A Phenotype Phase Plane Analysis," *Biotech Bioeng*, 77(1):27-36 (2002).

Edwards, JS and Palsson, BO, "How Will Bioinformatics Influence Metabolic Engineering," *Biotechnol Bioeng*, 58(2-3):162-169 (1998).

Edwards, JS and Palsson, BO, "Systems properties of the *Haemophilus influenzae* Rd metabolic genotype," *J Biol Chem*, 274(25):17410-17416 (1999).

Edwards, JS, and Palsson, BO, "Metabolic flux balance analysis and the in silico analysis of *Escherichia coli a* K-12 gene deletions," *BMC Bioinformatics*, 1:1-10(2000).

Edwards et al., "Genomically Based Comparative Flux Balance Analysis of *Escherichia coli* and Haemophilus Influenza," Abstract of Papers, *American Chemical Society*, 213(1-3):BIOT 50. San Francisco (13-17, 1997).

Eisen et al., "Cluster analysis and display of genome-wide expression patterns," *Proc Natl Acad Sci U.S.A.*, 95:14863-14868 (1998).

Eisenberg et al., "Protein Function in the Post-Genomic Era," *Nature*, 405(6788):823-826 (2000).

Ermolaeva et al., "Prediction of Operons in Microbial Genomes," *Nucl Acids Research*, 29(5):1216-1221 (2001).

Everett et al., "Pendred Syndrome is Caused by Mutations in a Putative Sulphate Transporter Gene (PDS)," *Nat Genet*, 17:411-422 (1997).

Fell, DA and Small, JR, "Fat Synthesis in Adipose Tissue. An Examination of Stoichiometric Constraints," *Biochem J*, 238(3):781-786 (1986).

Fiehn, "Metabolomics—the link between genotypes and phenotypes," *Plant Mol Biol*, 48(1-2):155-171 (2002).

Finel, "Does NADH play a central role in energy metabolism in Helicobacter pylori?," *Trends Biochem Sci*, 23(11):412-413 (1998).

Fiorelli et al., "Chronic non-spherocytic haemolytic disorders associated with glucose-6-phosphate dehydrogenase variants," *Bailliere's Clinical Haematology*, 13:39-55(2000).

Fleischmann, "Whole-genome random sequencing and assembly of *Haemophilus influenzae* Rd," *Science*, 269(5223):496-512 (1995).

Flikweert et al., "Pyruvate decarboxylase: an indispensable enzyme for growth of *Saccharomyces cerevisiae* on glucose," *Yeast*, 12(3):247-257 (1996).

Forster et al., "Large-scale evaluation of in silico gene deletions in *Saccharomyces cerevisiae*," *Omics*, 7(2)193-202 (2003).

Fraenkel, "The accumulation of glucose 6-phosphate from glucose and its effect in an *Escherichia coli* mutant lacking phosphoglucose isomerase and glucose 6-phosphate dehydrogenase," *J Biol Chem*, 243(24):6451-6457 (1968).

Fraser et al., "Microbial genome sequencing," *Nature*, 406:799-803 (2000).

Fromont-Racine et al., "Toward a functional analysis of the yeast genome through exhaustive two-hybrid screens," *Nat Genet*, 16(3):277-282 (1997).

Fukuchi et al., "Isolation, overexpression and disruption of a *Saccharomyces cerevisiae* YNK gene encoding nucleoside diphosphate kinase," *Genes*, 129(1):141-146 (1993).

Gaasterland, T. and Selkov, E., "Reconstruction of Metabolic Networks Using Incomplete Information," *Proc Int Conf Intell Syst Mol Biol*, 3:127-135 (1995).

Galperin, MY and Brenner, SE, "Using Metabolic Pathway Databases for Functional Annotation," *Trends Genet*, 14(8):332-333 (1998).

Gancedo, C and Delgado, MA, "Isolation and characterization of a mutant from *Saccharomyces cerevisiae* lacking fructose 1,6-bisphosphatase," *Eur J Biochem*,139:651-655 (1984).

Gangloff et al., "Molecular cloning of the yeast mitochondrial aconitase gene (ACO1) and evidence of a synergistic regulation of expression by glucose plus glutamate," *Mol Cell Biol*, 10(7):3551-3561 (1990).

Ge et al., "Cloning and functional characterization of Helicobacter pylori fumarate reductase operon comprising three structural genes coding for subunits C, A and B," *Gene*, 204(1-2):227-234 (1997).

Glasner et al., "ASAP, a systematic annotation package for community analysis of genomes," *Nucleic Acids Res*, 31(1):147-151 (2003).

Goffeau, A, "Four years of post-genomic life with 6000 yeast genes," *Febs Lett*, 480(1):37-41 (2000).

Goryanin et al., "Mathematical simulation and analysis of cellular metabolism and regulation," *Bioinformatics*, 15(9):749-758 (1999).

Goto et al., "LIGAND database for enzymes, compounds and reactions," *Nucleic Acids Res*, 27(1):377-379 (1999).

Goto et al., "LIGAND: chemical database for enzyme reactions," *Bioinformatics*, 14(7):591-599 (1998).

Grewal et al., "Computer Modelling of the Interaction Between Human Choriogonadotropin and Its Receptor," *Protein Engineering*, 7(2):205-211 (1994).

Griffin et al., "Complementary profiling of gene expression at the transcriptome and proteome levels in *Saccharomyces cerevisiae*," *Mol Cell Proteomics*, 1:323-333 (2002).
Grundy et al., "Regulation of the *Bacillus subtilis* acetate kinase gene by CcpA." *J Bacteriol*, 175(22):7348-7355 (1993).
Guelzim et al., "Topological and causal structure of the yeast transcriptional regulatory network," *Nat Genet*, 31(1):60-63 (2002).
Guetsova et al., "The isolation and characterization of *Saccharomyces cerevisiae* mutants that constitutively express purine biosynthetic genes," *Genetics*, 147(2):383-397 (1997).
Halvorson et al., *American Society for Microbiology*, Washington, D.C., pp. 212-224 (1972).
Hardison et al., "Globin Gene Server: A Prototype E-Mail Database Server Featuring Extensive Multiple Alignments and Data Compilation for Electronic Genetic Analysis," *Genomics*, 21(2):344-353 (1994).
Hartig et al., "Differentially regulated malate synthase genes participate in carbon and nitrogen metabolism of *S. cerevisiae*," *Nucleic Acids Res*, 20(21):5677-5686 (1992).
Hasty et al., "Computational Studies of Gene Regulatory Networks: In Numero Molecular Biology," *Nat Rev Genet*, 2(4):268-279 (2001).
Hata et al., "Characterization of a *Saccharomyces cerevisiae* mutant, N22, defective in ergosterol synthesis and preparation of [28-14C]ergosta-5,7-dien-3 beta-ol with the mutant," *J Biochem*, 94(2):501-510 (1983).
Hatzimanikatis et al., "Analysis and Design of Metabolic Reaction Networks Via Mixed-Interger linear Optimization," *AIChE Journal*, 42(5):1277-1292 (1996).
Hazell et al., "How Helicobacter pylori works: an overview of the metabolism of Helicobacter pylori," *Helicobacter*, 2(1):1-12 (1997).
Heijnen et al., "Application of balancing methods in modeling the penicillin fermentation," *Microbiol Biochem*, 21:1-48 (1979).
Heinisch et al., "Investigation of two yeast genes encoding putative isoenzymes of phosphoglycerate mutase," *Yeast*, 14(3):203-213 (1998).
Heinrich et al., "Metabolic regulation and mathematical models," *Prog Biophys Mol Biol*, 32(1):1-82 (1977).
Henriksen et al., "Growth energetics and metabolism fluxes in continuous cultures of *Penicillium chrysogenum*," *J of Biotechnol*, 45(2):149-164 (1996).
Heyer et al., "Exploring expression data: identification and analysis of coexpressed genes," *Genome Res*, 9(11):1106-1115 (1999).
Holter et al., "Dynamic modeling of gene expression data," *Proc Natl Acad Sci U.S.A.*, 98(4):1693-1698 (2001).
Holter et al., "Fundamental patterns underlying gene expression profiles: simplicity from complexity," *Proc Natl Acad Sci U.S.A.*, 97:8409-9414 (2000).
Houghten, "Generation and use of synthetic peptide combinatorial libraries for basic research and drug discovery," *Nature*, 354(6348):84-86 (1991).
Hughes et al., "Functional discovery via a compendium of expression profiles," *Cell*, 102(1):109-126 (2000).
Hughes et al., "Helicobacter pylori porCDAB and oorDABC genes encode distinct pyruvate: flavodoxin and 2-oxoglutarate:acceptor oxidoreductases which mediate electron transport to NADP," *J Bacteriol*, 180(5):1119-1128 (1998).
Ideker et al., "Integrated Genomic and Proteomic Analyses of a Systematically Perturbed Metabolic Network," *Science*, 292(5518):929-934 (2001).
Ince, JE and Knowles, CJ, "Ethylene formation by cell-free extracts of *Escherichia coli*," *Arch Microbiol*, 146(2):151-158 (1986).
Ishii et al., "DBTBS: a database of *Bacillus subtilis* promoters and transcription factors," *Nucleic Acids Res*, 29(1):278-280 (2001).
Iyer et al., "Genomic binding sites of the yeast cell-cycle transcription factors SBF and MBF," *Nature*, 409(6819):533-538 (2001).
Jamshidi et al., "Dynamic simulation of the human red blood cell metabolic network," *Bioinformatics*, 17(3):286-287 (2001).
Jenkins, LS and Nunn, WD, "Genetic and molecular characterization of the genes involved in short-chain fatty acid degradation in *Escherichia coli*: the ato system," *J Bacteriol*, 169(1):42-52 (1987).
Jenssen et al., "A Literature Network of Human Genes for High-Throughput Analysis of Gene Expression," *Nat Genet*, 28(1):21-28 (2001).

Jorgensen et al., "Metabolic flux distributions in *Penicillium chrysogenum* during fed-batch cultivations." *Biotechnol Bioeng*, 46(2):117-131 (1995).
Joshi, A and Palsson, BO, "Metabolic dynamics in the human red cell. Part I—A comprehensive kinetic model," *J Theor Biol*, 141(4):515-528 (1989).
Juty et al., "Simultaneous Modeling of Metabolic, Genetic, and Product-Interaction Networks," *Briefings in Bioinformatics*, 2(3):223-232 (2001).
Kanehisa, M and Goto, S, "Kyoto Encyclopedia of Genes and Genomes database (KEGG)," *Nucleic Acids Res*, 28(1):27-30 (2000).
Karp, "An ontology for biological function based on molecular interactions," *Bioinformatics*, 16(3):269-285 (2000).
Karp, "Metabolic Databases," *Trends Biochem Sci*, Elsevier Publication, Cambridge, 23(3):114-116 (1998).
Karp et al., "Eco Cyc: encyclopedia of *Escherichia coli* genes and metabolism," *Nucleic Acids Res*, 27(1):55-58 (1999).
Karp et al., "EcoCyc: Encyclopedia of *Escherichia coli* Genes and Metabolism," *Nucleic Acids Research*, 25(1):43-50 (1997).
Karp et al., "HinCyc: A knowledge base of the complete genome and metabolic pathways of *H. influenzae*," *Proc Int Conf Intell Syst Mol Biol*, 4:116-124 (1996).
Karp et al., "Integrated pathway-genome databases and their role in drug discovery," *Trends Biotechnol*, 17(7):275-281 (1999).
Karp et al., "The EcoCyc and MetaCyc (2000). databases," *Nucleic Acids Resarch*, 28(1):56-59 (2000).
Kather et al., "Another unusual type of citric acid cycle enzyme in Helicobacter pylori: the malate:quinone oxidoreductase," *J Bacteriol*, 182(11):3204-3209 (2000).
Keating et al., "An ethanologenic yeast exhibiting unusual metabolism in the fermentation of lignocellulosic hexose sugars," *J Ind Microbiol Biotechnol*, 31(5):235-244 (2004).
Kelly, "The physiology and metabolism of the human gastric pathogen Helicobacter pylori," *Adv Microb Physiol*, 40:137-189 (1998).
Kim et al., "*Saccharomyces cerevisiae* contains two functional citrate synthase genes," *Mol Cell Biol*, 6(6):1936-1942 (1986).
Kirkman et al., "Red cell NADP+ and NADPH in glucose-6-phosphate dehydrogenase deficiency," *Journal of Clinical Investigation*, 55(4):875-878 (1975).
Kremling et al., "The organization of metabolic reaction networks. III. Application for diauxic growth on glucose and lactose," *Metab Eng*, 3(4):362-379 (2001).
Kunst et al., "The Complete Genome Sequence of the Gram-positive Bacterium *Bacillus subtilus*," *Nature*, 390(6557):249-256 (1997).
Lacroute, "Regulation of pyrimidine biosynthesis in *Saccharomyces cerevisiae*" *J Bacteriol*, 95(3):824-832 (1968).
Latif, F and Rajoka, MI, "Production of ethanol and xylitol from corn cobs by yeasts," *Bioresour Technol*, 77(1):57-63 (2001).
Lendenmann, U and Egli, T, "Is *Escherichia coli* growing in glucose-limited chemostat culture able to utilize other sugars without lag?," *Microbiology*, 141(Pt 1):71-78 (1995).
Leyva-Vasquez, MA and Setlow, P, "Cloning and nucleotide sequences of the genes encoding triose phosphate isomerase, phosphoglycerate mutase, and enolase from *Bacillus subtilis*," *J Bacteriol*, 176(13):3903-3910 (1994).
Li, C and Wong, WH, "Model-based analysis of oligonucleotide arrays: expression index computation and outlier detection," *Proc Natl Acad Sci U.S.A.*, 98(1):31-36 (2001).
Liao et al., "Pathway Analysis, Engineering, and Physiological Considerations for Redirecting Central Metabolism," *Biotechnol Bioeng*, 52(1):129-140 (1996).
Liao, JC and Oh, MK, "Toward predicting metabolic fluxes in metabolically engineered strains," *Metab Eng*,1(3):214-223 (1999).
Link et al., "Methods for generating precise deletions and insertions in the genome of wild-type *Escherichia coli*: Application to open reading frame characterization," *J Bacteriol*, 179(20):6228-6237 (1997).
Loftus et al., "Isolation, characterization, and disruption of the yeast gene encoding cytosolic NADP-specific isocitrate dehydrogenase," *Biochemistry*, 33(32):9661-9667 (1994).
Lopez et al., "The yeast inositol monophosphatase is a lithium- and sodium-sensitive enzyme encoded by a non-essential gene pair," *Mol Microbiol*, 31(4):1255-1264 (1999).

Mahadevan, R and Schilling, CH, "The effects of alternate optimal solutions in constraint-based genome-scale metabolic models," *Metab Eng*, 5(4):264-276 (2003).

Maier et al., "Hydrogen uptake hydrogenase in Helicobacter pylori," *FEMS Microbiol Lett*, 141(1):71-76 (1996).

Majewski, RA and Domach, MM, "Simple Constrained-Optimization View of Acete Overflow in *E. coli*," *Biotechnol Bioeng*, 35(7):732-738 (1990).

Marcelli et al., "The respiratory chain of Helicobacter pylori: identification of cytochromes and the effects of oxygen on cytochrome and menaquinone levels," *FEMS Microbiol Lett*, 138(1):59-64 (1996).

Marshall, B.J and Warren, J.R., "Unidentified curved bacilli in the stomach of patients with gastritis and peptic ulceration," *Lancet*, 1(8390):1311-1315 (1984).

McAdams, HH and Arkin, A, "Simulation of Prokaryotic Genetic Circuits," *Annual Review of Biophysics and Biomolecular Structure*, 27:199-224 (1998).

McAdams, HH and Shapiro, L, "Circuit simulation of genetic networks." *Science*, 269(5224):650-656 (1995).

McAlister-Henn, L and Thompson, LM, "Isolation and expression of the gene encoding yeast mitochondrial malate dehydrogenase," *J Bacteriol*, 169(11):5157-5166 (1987).

McGee, D.J., "Helicobacter pylori rocF is required for arginase activity and acid protection in vitro but is not essential for colonization of mice or for urease activity," *J Bacteriol*, 165(1):65-76 (1998).

Meldrum, "Automation for genomics, part one: preparation for sequencing," *Genome Res*, 10(8):1081-1092 (2000).

Mendz et al., "Characterisation of glucose transport in Helicobacter pylori," *Biochim Biophys Acta*, 1244(2-3):269-276 (1995).

Mendz et al., "Characterization of fumarate transport in Helicobacter pylori," *J Membr Biol*, 165(1):65-76 (1998).

Mendz et al., "De novo synthesis of pyrimidine nucleotides by Helicobacter pylori," *J Appl Bacteriol*, 77(1):1-8 (1994).

Mendz et al., "Fumarate reductase: a target for therapeutic intervention against Helicobacter pylori," *Arch Biochem Biophys*, 321(1):153-159 (1995).

Mendz et al., "Glucose utilization and lactate production by Helicobacter pylori," *J Gen Microbiol*, 139(12):3023-3028 (1993).

Mendz et al., "In situ characterization of Helicobacter pylori arginase," *Biochim Biophys Acta*, 1388(2):465-477 (1998).

Mendz et al., "Purine metabolism and the microaerophily of Helicobacter pylori," *Arch Microbiol*, 168(6):448-456 (1997).

Mendz et al., "The Entner-Doudoroff pathway in Helicobacter pylori," *Arch Biochem Biophys*, 312(2):349-356 (1994).

Mendz, GL and Hazell SL, "Aminoacid utilization by Helicobacter pylori," *Int J Biochem Cell Biol*, 27(10):1085-1093 (1995).

Mendz, GL and Hazell, SL, "Fumarate catabolism in Helicobacter pylori," *Biochem Mol Biol Int*, 31(2):325-332 (1993).

Mendz, GL and Hazell, SL, "Glucose phosphorylation in Helicobacter pylori," *Arch Biochem Biophys*, 300(1):522-525 (1993).

Mendz, GL et al., "Pyruvate metabolism in Helicobacter pylori," *Arch Microbiol*, 162(3):187-192 (1994).

Mendz, GL et al., "Salvage synthesis of purine nucleotides by Helicobacter pylori," *J Appl Bacteriol*, 77(6):674-681 (1994).

Mewes et al., "MIPS: A database for genomes and protein sequences," *Nucleic Acids Research*, 30(1):31-34 (2002).

Mitchell, "The GLN1 locus of *Saccharomyces cerevisiae* encodes glutamine synthetase," *Genetics*, 111(2):243-258 (1985).

Moszer, "The Complete Genome of *Bacillus subtilis*: From Sequence Annotation to Data Management and Analysis," *FEBS Lett*, 430(1-2):28-36 (1998).

Moszer et al., "SubtiList: the reference database for the *Bacillus subtilis* genome," *Nucleic Acids Res*, 30(1):62-65 (2002).

Mulquiney, PJ and Kuchel, PW, "Model of 2,3-bisphosphoglycerate metabolism in the human erythrocyte based on detailed enzyme kinetic equations: computer simulation and metabolic control analysis," *Biochem J*, 342(Pt 3):597-604 (1999).

Murray, M and Greenberg, ML, "Expression of yeast INM1 encoding inositol monophosphatase is regulated by inositol, carbon source and growth stage and is decreased by lithium and valproate," *Mol Microbiol*, 36(3):651-661 (2000).

Nedenskov, "Nutritional requirements for growth of Helicobacter pylori," *Appl Environ Microbiol*, 60(9):3450-3453 (1994).

Nissen et al., "Expression of a cytoplasmic transhydrogenase in *Saccharomyces cerevisiae* results in formation of 2-oxoglutarate due to depletion of the NADPH pool," *Yeast*, 18(1):19-32 (2001).

Nissen et al., "Flux distributions in anaerobic, glucose-limited continuous cultures of *Saccharomyces cerevisiae*," *Microbiology*, 143(Pt 1):203-218 (1997).

Ogasawara, "Systematic function analysis of *Bacillus subtilis* genes," *Res Microbiol*, 151(2):129-134 (2000).

Ogata et al., "KEGG: Kyoto Encyclopedia of Genes and Genomes," *Nucleic Acids Res* 27(1):29-34 (1999).

Oh, MK and Liao, JC, "Gene expression profiling by DNA microarrays and metabolic fluxes in *Escherichia coli*," *Biotech Prog*, 16:278-286 (2000).

Olsson et al., "Separate and simultaneous enzymatic hydrolysis and fermentation of wheat hemicellulose with recombinant xylose utilizing *Saccharomyces cerevisiae*," *Appl Biochem Biotechnol*, 129-132:117-129 (2006).

Otto et al., "A mathematical model for the influence of fructose 6-phosphate, ATP, potassium, ammonium and magnesium on the phosphofructokinase from rat erythrocytes," *Eur J Biochem*, 49(1):169-178 (1974).

Ouzounis, CA and Karp, PD, "Global Properties of the Metabolic Map of *Escherichia coli*," *Genome Res*, 10(4):568-576 (2000).

Overbeek et al., "WIT: Integrated System for High-Throughput Genome Sequence Analysis and Metabolic Reconstruction" *Nucleic Acids Res*, 28(1):123-125 (2000).

Overkamp et al., "In vivo analysis of the mechanisms for oxidation of cytosolic NADH by *Saccharomyces cerevisiae* mitochondria," *J Bacteriol*, 182(10):2823-2830 (2000).

Ozcan, S., Freidel, K., Leuker, A. & Ciriacy, M., "Glucose uptake and catabolite repression in dominant HTR1 mutants of *Saccharomyces cerevisiae*," *J Bacteriol*, 175(17):5520-5528 (1993).

Pallotta et al., "*Saccharomyces cerevisiae* mitochondria can synthesise FMN and FAD from externally added riboflavin and export them to the extramitochondrial phase," *FEBS Lett*, 428(3):245-249 (1998).

Palmieri et al., "Identification and functions of new transporters in yeast mitochondria," *Biochim Biophys Acta*, 1459(2-3):363-369 (2000).

Palmieri et al., "Identification of the yeast ACR1 gene product as a succinate-fumarate transporter essential for growth on ethanol or acetate," *FEBS Lett*, 417(1):114-118 (1997).

Palmieri et al., "Identification of the yeast mitochondrial transporter for oxaloacetate and sulfate," *J Biol Chem*, 274(32):22184-22190 (1999).

Palmieri et al., "Yeast mitochondrial carriers: bacterial expression, biochemical identification and metabolic significance," *J Bioenerg Biomembr*, 32(1):67-77 (2000).

Palsson, "The Challenges of in Silico Biology," *Nat Biotechnol*, 18(11):1147-1150 (2000).

Palsson, "What Lies Beyond Bioinformatics," *Nat Biotechnol*, 15:3-4 (1997).

Papin et al., "The genome-scale metabolic extreme pathway structure in *Haemophilus influenzae* shows significant network redundancy," *J Theor Biol*, 215(1):67-82 (2002).

Parks, "Metabolism of sterols in yeast," *CRC Crit Rev Microbiol*, 6(4):301-341 (1978).

Parks et al., "Use of sterol mutants as probes for sterol functions in the yeast, *Saccharomyces cerevisiae*," *Crit Rev Biochem Mol Biol*, 34(6):399-404 (1999).

Patel, BN and West, TP, ",Degradation of the pyrimidine bases uracil and thymine by *Escherichia coli* B" *Microbios*, 49(199):107-113 (1987).

Paulsen et al., "Unified inventory of established and putative transporters encoded within the complete genome of *Saccharomyces cerevisiae*," *FEBS Lett*, 430(1-2):116-125 (1998).

Pearson et al., "Comparison of DNA Sequences With Protein Sequences," *Genomics*, 46(1):24-36 (1997).

Pennisi, "Laboratory Workhouse Decoded," *Science*, 277(5331):1432-1434 (1997).

Persson et al., "Phosphate permeases of *Saccharomyces cerevisiae*: structure, function and regulation," *Biochim Biophys Acta*, 1422(3):255-272 (1999).

Peterson et al., "The Comprehensive Microbial Resource," *Nucleic Acids Res*, 29(1):123-125 (2001).

Pharkya et al., "Exploring the overproduction of amino acids using the bilevel optimization framework OptKnock," *Biotechnol Bioeng*, 84(7):887-899 (2003).

Phelps et al., "Metabolomics and microarrays for improved understanding of phenotypic characteristics controlled by both genomics and environmental constraints," *Curr Opin Biotechnol*, 13(1):20-24 (2002).

Pitson et al., "The tricarboxylic acid cycle of *Helicobacter pylori*," *Eur J Biochem*, 260(1):258-267 (1999).

Pramanik, J and Keasling, J, "Stoichiometric Model of *Escherichia coli* Metabolism: Incorporation of Growth-Rate Dependent Biomass Composition and Mechanistic Energy Requirements," *Biotechnol Bioeng*, 56(4):398-421 (1997).

Price et al., "Determination of redundancy and systems properties of the metabolic network of *Helicobacter pylori* using genome-scale extreme pathway analysis," *Genome Res*, 12(5):760-769 (2002).

Price et al., "Genome-scale models of microbial cells: evaluating the consequences of constraints," *Nat Rev Microbiol*, 2(11):886-897 (2004).

Przybyla-Zawislak et al., "Genes of succinyl-CoA ligase from *Saccharomyces cerevisiae*," *Eur J Biochem*, 258(2):736-743 (1998).

Qian et al., "Ethanol production from dilute-Acid softwood hydrolysate by co-culture," *Appl Biochem Biotechnol*, 134(3):273-284 (2006).

Reed et al., "An expanded genome-scale model of *Escherichia coli* K-12 (iJR904 GSM/GPR)," *Genome Biol*, 4(9):R54 (2003).

Reed, JL and Palsson, BO, "Thirteen years of building constraint-based in silico models of *Escherichia coli*" *J Bacteriol*, 185(9):2692-2699 (2003).

Regenberg et al., "Substrate specificity and gene expression of the amino-acid permeases in *Saccharomyces cerevisiae*," *Curr Genet*, 36(6):317-328 (1999).

Remize et al., "Engineering of the pyruvate dehydrogenase bypass in *Saccharomyces cerevisiae*: role of the cytosolic Mg(2+) and mitochondrial K(+) acetaldehyde dehydrogenases Ald6p and Ald4p in acetate formation during alcoholic fermentation," *Appl Environ Microbiol*, 66(8):3151-3159 (2000).

Ren et al., "Genome-wide location and function of DNA binding proteins," *Science*, 290(5500):2306-2309 (2000).

Repetto, B and Tzagoloff, A, "In vivo assembly of yeast mitochondrial alpha-ketoglutarate dehydrogenase complex," *Mol Cell Biol*, 11(8):3931-3939 (1991).

Reynolds, DJ and Penn, CW, "Characteristics of *Helicobacter pylori* growth in a defined medium and determination of its amino acid requirements," *Microbiology*, 140(Pt 10):2649-2656 (1994).

Rhee et al., "Activation of gene expression by a ligand-induced conformational change of a protein-DNA complex," *J Biol Chem*, 273(18):11257-11266 (1998).

Romero, PR and Karp, P, "Nutrient-Related Analysis of Pathway/Genome Databases," *Pac Symp Biocomput*, 471-482 (2001).

Saier, MH, "Genome sequencing and informatics: new tools for biochemical discoveries," *Plant Physiol*, 117(4):1129-1133 (1998).

Salgado et al., "RegulonDB (version 3.2): transcriptional regulation and operon organization in *Escherichia coli* K-12," *Nucleic Acids Res*, 29(1):72-74 (2001).

Salmon et al., "Global gene expression profiling in *Escherichia coli* K12. The effects of oxygen availability and FNR," *J Biol Chem*, 278(32):29837-29855 (2003).

Sauer et al., "Metabolic Capacity of *Bacillus subtilis* for the Production of Purine Nucleosides, Riboflavin, and Folic Acid," *Biotechnol Bioeng*, 59(2):227-238 (1998).

Sauer et al., "Metabolic flux ratio analysis of genetic and environmental modulations of *Escherichia coli* central carbon metabolism," *J Bacteriol*, 181(21):6679-6688 (1999).

Sauer, U and Bailey, JE, "Estimation of P-to-O Ratio in *Bacillus subtilis* and Its Influence on Maximum Riboflavin Yield," *Biotechnol Bioeng*, 64(6):750-754 (1999).

Sauer, Uwe, "Evolutionary Engineering of Industrially Important Microbial Phenotypes," *Adv in Biochem Eng Biotechnol*, 73:129-169 (2001).

Savageau, "Biochemical systems analysis. I. Some mathematical properties of the rate law for the component enzymatic reactions," *J Theor Biol*, 25(3):365-369 (1969).

Schaaff-Gerstenschlager, I and Zimmermann, FK, "Pentose-phosphate pathway in *Saccharomyces cerevisiae*: analysis of deletion mutants for transketolase, transaldolase, and glucose 6-phosphate dehydrogenase," *Curr Genet*, 24(5):373-376 (1993).

Schaff et al., "the Virtual cell" *Proceedings of the Pacific Symposium on Biocomputing*, 228-239 (1999).

Schena et al., "Quantitative monitoring of gene expression patterns with a complementary DNA microarray," *Science*, 270(5235):467-470 (1995).

Schilling et al., "Combining Pathway Analysis with Flux Balance Analysis for the Comprehensive Study of Metabolic Systems," *Biotechnol Bioeng*, 71(4):286-306 (2000-2001).

Schilling et al., "Genome-scale metabolic model of *Helicobacter pylori* 26695," *J Bacteriol*, 184(16):4582-4593 (2002).

Schilling et al., "Metabolic Pathway Analysis: Basic Concepts and Scientific Applications in the Post-genomic Era," *Biotechol Prog*, 15(3):296-303 (1999).

Schilling et al., "Theory for the Systematic Definition of Metabolic Pathways and Their Use in Interpreting Metabolic Function from a Pathway-Oriented Perspective," *J Theor. Biol*, 203(3):229-248 (2000).

Schilling et al., "Toward Metabolic Phenomics: Analysis of Genomic Data Using Flux Balances," *Biotechnol Prog*, 15(3):288-295 (1999).

Schneider et al., "The *Escherichia coli* gabDTPC operon: specific gamma-aminobutyrate catabolism and nonspecific induction," *J Bacteriol*, 184(24):6976-6986 (2002).

Schuster et al., "A general definition of metabolic pathways useful for systematic organization and analysis of complex metabolic networks," *Nature Biotechnol*, 18(3):326-332 (2000).

Schuster et al., "Detection of elementary flux modes in biochemical networks: a promising tool for pathway analysis and metabolic engineering," *Trends Biotechnol*, 17(2):53-60 (1999).

Schuster et al., "Exploring the pathway structure of metabolism: decomposition into subnetworks and application to *Mycoplasma pneumoniae*," *Bioinformatics*, 18(2):351-361 (2002).

Schuster, S and Hilgetag, C, "On elementary flux modes in biochemical reaction systems at steady state," *J Biol Syst*, 2(2):165-182 (1994).

Schwikowski et al., "A network of protein-protein interactions in yeast," *Nature Biotechnol*, 18(12):1257-1261 (2000).

Scott et al., "The Pendred Syndrome Gene Encodes a Chloride-Iodide Transport Protein," *Nat Genet*, 21(4):440-443 (1999).

Sedivy, JM and Fraenkel, DG, "Fructose bisphosphatase of *Saccharomyces cerevisiae*. Cloning, disruption and regulation of the FBP1 structural gene," *J Mol Biol*, 186(2):307-319 (1985).

Selkov et al., "A reconstruction of the metabolism of *Methanococcus jannaschii* from sequence data," *Gene*, 197(1-2):GC11-26 (1997).

Selkov et al., "Functional Analysis of Gapped Microbial Genomes: Amino Acid Metabolism of Thiobacillus Ferroxidans," *Proc Natl Acad Sci U.S.A.*, 97(7):3509-3514 (2000).

Selkov et al., "MPW: the metabolic pathways database," *Nucleic Acids Res*, 26(1):43-45 (1998).

Selkov et al., "The metabolic pathway collection from EMP: the enzymes and metabolic pathways database," *Nucleic Acids Res*, 24(1):26-28 (1996).

Shen-Orr et al., "Network motifs in the transcriptional regulation network of *Escherichia coli*," *Nat Genet*, 31(1):64-68 (2002).

Sherlock et al., "The physiology of L-methionine catabolism to the secondary metabolite ethylene by *Escherichia coli*," *Curr Opin Immunol*, 12:201-205 (2000).

Shipston, N. and Bunch, AW, "The physiology of L-methionine catabolism to the secondary metabolite ethylene by *Escherichia coli*," *J Gen Microbiol*, 135(6), 1489-by 1497 (1989).

Silve et al., The immunosuppressant SR 31747 blocks cell proliferation by inhibiting a steroid isomerase in *Saccharomyces cerevisiae*,' *Mol Cell Biol*, 16(6):2719-2727 (1996).

Skouloubris et al., "The *Helicobacter pylori* UreI protein is not involved in urease activity but is essential for bacterial survival in vivo," *Infect Immun*, 66(9):4517-4521 (1998).

Smith et al., "Functional analysis of the genes of yeast chromosome V by genetic footprinting," *Science*, 274(5295):2069-2074 (1996).

Sorlie et al., "Gene expression patterns of breast carcinomas distinguish tumor subclasses with clinical implications," *Proc Natl Acad Sci U.S.A.*, 98(19):10869-10874 (2001).

Stark et al., "Amino acid utilisation and deamination of glutamine and asparagine by *Helicobacter pylori*," *J Med Microbiol*, 46(9):793-800 (1997).

Stephanopoulos, "Metabolic Engineering," *Biotechnol Bioeng*, 58(2-3):119-120 (1998).

Summers et al., "*Saccharomyces cerevisiae* cho2 mutants are deficient in phospholipid methylation and cross-pathway regulation of inositol synthesis" *Genetics*, 120(4):909-922 (1988).

Swartz, "A PURE approach to constructive biology," *Nat Biotechnol*, 19(8):732-733 (2001).

Syvanen, "Accessing genetic variation: Genotyping single nucleotide polymorphisms," *Nat Rev Genet*, 2(12):930-942 (2001).

Szambelan et al., "Use of *Zymomonas mobilis* and *Saccharomyces cerevisiae* mixed with *Kluyveromyces fragilis* for improved ethanol production from Jerusalem artichoke tubers,"*Biotechnol Lett*, 26(10):845-848 (2004).

Tamayo et al., "Interpreting patterns of gene expression with self-organizing maps: methods and application to hematopoietic differentiation," *Proc Natl Acad Sci U.S.A.*, 96(6):2907-2912 (1999).

Tanaka, KR, and Zerez, CR, "Red cell enzymopathies of the glycolytic pathway," *Semin Hematol*, 27(2):165-185 (1990).

Taniguchi, M and Tanaka, T, "Clarification of interactions among microorganisms and development of co-culture system for production of useful substances," *Adv Biochem Eng Biotechnol*, 90:35-62 (2004).

Tao et al., "Engineering a homo-ethanol pathway in *Escherichia coli*: increased glycolytic flux and levels of expression of glycolytic genes during xylose fermentation," *J Bacteriol*, 183(10):2979-2988 (2001).

Ter Linde et al., "Genome-wide transcriptional analysis of aerobic and anaerobic chemostat cultures of *Saccharomyces cerevisiae*," *J Bacteriol*, 181(24):7409-7413 (1999).

Thomas, "Boolean Formalization of Genetic Control Circuits," *J Theor Biol*, 42(3):563-585 (1973).

Thomas, "Logical Analyses of Systems Comprising Feedback Loops," *J Theor Biol*, 73(4):631-656 (1978).

Thomas, D and Surdin-Kerjan, Y, "Metabolism of sulfur amino acids in *Saccharomyces cerevisiae*," *Microbiol Mol Biol Rev*, 61(4):503-532 (1997).

Tomb et al., "The complete genome sequence of the gastric pathogen *Helicobacter pylori*," *Nature*, 388(6642):539-547 (1997).

Tomita et al., "E-Cell: Software Environment for Whole-Cell Simulation," *Bioinformatics*, 15(1):72-84 (1999).

Trotter et al., "A genetic screen for aminophospholipid transport mutants identifies the phosphatidylinositol 4-kinase, STT4p, as an essential component in phosphatidylserine metabolism," *J Biol Chem*, 273(21):13189-13196 (1998).

Uetz et al., "A comprehensive analysis of protein-protein interactions in *Saccharomyces cerevisiae*," *Nature*, 403(6770):623-627 (2000).

Van den Berg, MA and Steensma, HY, "ACS2, a *Saccharomyces cerevisiae* gene encoding acetyl-coenzyme A synthetase, essential for growth on glucose," *Eur J Biochem*, 231(3):704-713 (1995).

Van Dijken et al., "Alcoholic fermentation by 'non-fermentative' yeasts," *Yeast*, 2(2):123-127 (1986).

Van Dijken et al., "Kinetics of growth and sugar consumption in yeasts," *Antonie Van Leeuwenhoek*, 63(3-4):343-352 (1993).

Vanrolleghem et al., "Validation of a Metabolic Network for *Saccharomyces cerevisiae* Using Mixed Substrate Studies," *Biotechnol Prog*, 12(4):434-448 (1996).

Varma, A and Palsson, BO, "Metabolic capabilities of *Escherichia coli*. II: Optimal Growth Patterns," *J Theor Biol*, 165:503-522 (1993).

Varma, A and Palsson, BO, "Metabolic capabilities of *Escherichia coli*: I. Synthesis of Biosynthetic Precursors and Cofactors," *J Theor Biol*, 165:477-502 (1993).

Varma, A and Palsson, BO, "Parametric sensitivity of stoichiometric flux balance models applied to wild-type *Escherichia coli* metabolism," *Biotechnol Bioeng*, 45(1):69-79 (1995).

Varma, A and Palsson, BO, "Predictions for Oxygen Supply Control to Enhance Population Stability of Engineered Production Strains," *Biotechnol Bioeng*, 43(4):275-285 (1994).

Varma, A and Palsson, BO, "Stoichiometric flux balance models quantitatively predict growth and metabolic by-product secretion in wild-type *Escherichia coli* W3110," *Appl. Environ Microbiol*, 60(10):3724-3731 (1994).

Varma, A. et al., "Metabolic Flux Balancing: Basic Concepts, Scientific and Practical Use," *Biotechnology*, 12:994-998 (1994).

Varma et al., "Biochemical Production Capabilities of *Escherichia coli*," *Biotechnol Bioeng*, 42(1):59-73 (1993).

Varma et al., "Stoichiometric Interpretation of *Escherichia coli* Glucose Catabolism Under Various Oxygenation Rates," *Appl Environ Microbiol*, 59(8):2465-2473 (1993).

Velculescu et al., "Analysing uncharted transcriptomes with SAGE," *Trends Genet*,16(10):423-425 (2000).

Venter et al., "Shotgun sequencing of the human genome," *Science*, 280(5369):1540-1542 (1998).

Verduyn, "Physiology of yeasts in relation to biomass yields," *Antonie Van Leeuwenhoek*, 60(3-4):325-353 (1991).

Verduyn et al., "A theoretical evaluation of growth yields of yeasts," *Antonie Van Leeuwenhoek*, 59(1):49-63 (1991).

Verduyn et al., "Energetics of *Saccharomyces cerevisiae* in anaerobic glucose-limited chemostat cultures," *J Gen Microbiol*, 136:405-412 (1990).

Vissing et al., "Paradoxically Enhanced Glucose Production During Exercise in Humans with Blocked Glycolysis Caused by Muscle Phosphofructokinase Deficiency," *Neurology*, 47(3):766-771 (1996).

Wang et al., "Computer-aided baker's yeast fermentations," *Biotechnol and Bioeng*, 19(1):69-86 (1977).

Wang et al., "Computer control of bakers' yeast production," *Biotechnol and Bioeng*, 21:975-995 (1979).

Waterston, R and Sulston, JE, "The Human Genome Project: reaching the finish line," *Science*, 282(5386):53-54 (1998).

Wen et al., "Large-scale temporal gene expression mapping of central nervous system development," *Proc Natl Acad Sci U.S.A.*, 95(1):334-339 (1998).

Wiback, SJ and Palsson, BO, "Extreme pathway analysis of human red blood cell metabolism," *Biophys J*, 83:808-818 (2002).

Wieczorke et al., "Concurrent knock-out of at least 20 transporter genes is required to block uptake of hexoses in *Saccharomyces cerevisiae*," *FEBS Lett*, 464(3):123-128 (1999).

Wills, C and Melham, T, "Pyruvate carboxylase deficiency in yeast: a mutant affecting the interaction between the glyoxylate and Krebs cycles," *Arch Biochem Biophys*, 236(2):782-791 (1985).

Wingender et al., "The TRANSFAC system on gene expression regulation," *Nucleic Acids Res*, 29(1):281-283 (2001).

Winzeler et al., "Functional characterization of the *S. cerevisiae* genome by gene deletion and parallel analysis," *Science*, 285(5429):901-906 (1999).

Wong, P. et al., "Mathematical Model of the Lac Operon: Inducer Exclusion, Catabolite Repression, and Diauxic Growth on Glucose and Lactose," *Biotechnol Prog*, 13(2):132-143 (1997).

Xie, L and Wang, D, "Integrated Approaches to the Design of Media and Feeding Strategies for Fed-Batch Cultures of Animal Cells," *Trends Biotechnol*, 15(3):109-113 (1997).

Yamada et al., "Effects of common polymorphisms on the properties of recombinant human methylenetetrahydrofolate reductase," *Proc Natl Acad Sci U.S.A.*, 98(26):14853-14858 (2001).

Yeung et al., "Reverse engineering gene networks using singular value decomposition and robust regression," *Proc Natl Acad Sci U.S.A.*, 99(9):6163-6168 (2002).

Yeung et al., *Bioinformatics*, "Model-based clustering and data transformations for gene expression data," 17(10):977-87 (2001).

Yoshida et al., "Combined transcriptome and proteome analysis as a powerful approach to study genes under glucose repression in *Bacillus subtilis*," *Nucleic Acids Res*, 29(3):683-692 (2001).

Zanella, A and Bianchi, P, "Red cell pyruvate kinase deficiency: from genetics to clinical manifestations," *Bailliere's Best Pract Res Clin Haematol* 13(1):57-81 (2000).

Zeng et al., "Use of respiratory quotient as a control parameter for optimum oxygen supply and scale-up of 2,3-butanediol production under microaerobic conditions," *Biotechnol Bioeng*, 44(9):1107-1114 (1994).

Zhu, J and Zhang, MO, "SCPD: a promoter database of the yeast *Saccharomyces cerevisiae*," *Bioinformatics*, 15(7-8):607-611 (1999).

Zigova, "Effect of RQ and pre-seed conditions on biomass and galactosyl transferase production during fed-batch culture of *S. cerevisiae* BT150," *J Biotechnol*, 80(1):55-62 (2000).

Zweytick et al., "Biochemical characterization and subcellular localization of the sterol C-24(28) reductase, erg4p, from the yeast *Saccharomyces cerevisiae*," *FEBS Lett*, 470(1):83-87 (2000).

URL Dictionary.com pp. 1-2 (2004), Matrix.

URL Genome.jp Website, KEGG *Bacillus subtillis*, 1-7 (2005).

URL mips.gsf.de/proj/yeast/pathways/ on Jun. 6, 2008, MIPS, website: Comprehensive Yeast Genome Database—Pathways (1998).

\* cited by examiner

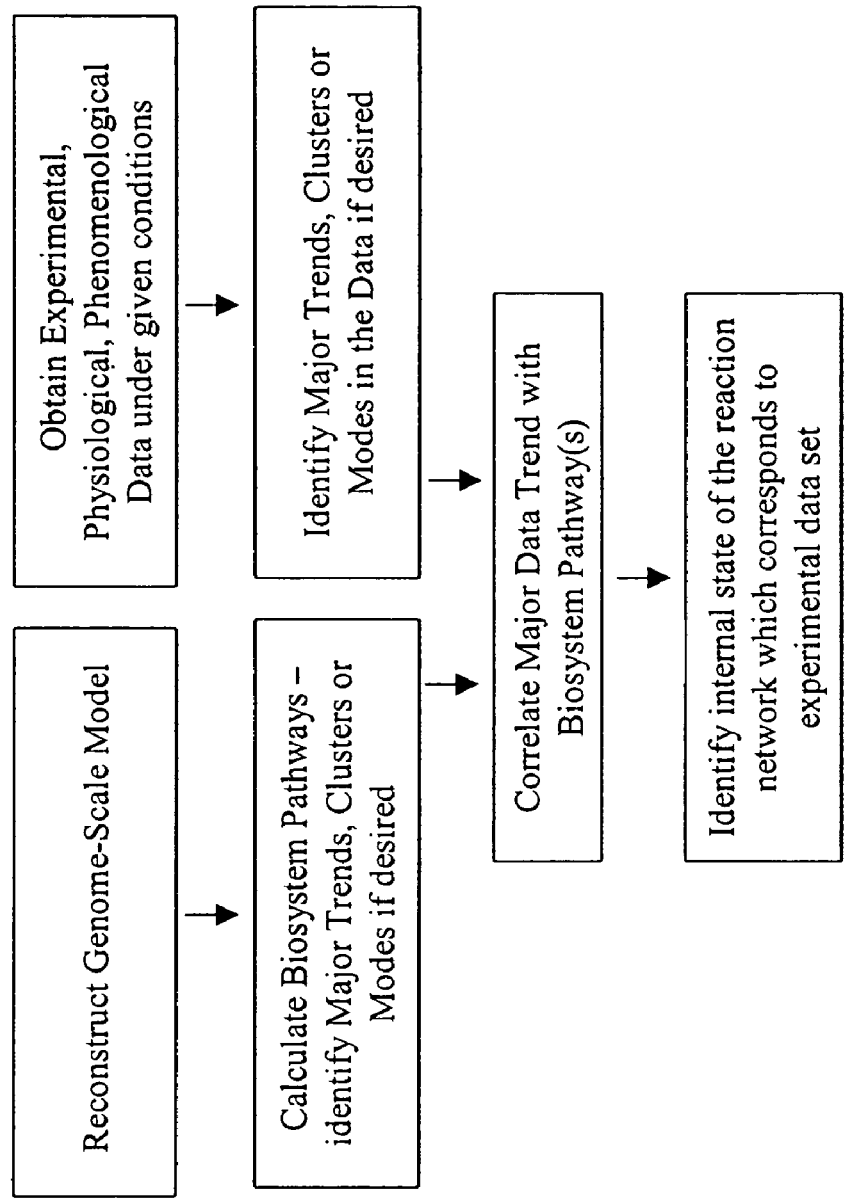

— Removed shading

| Exp in model | y1 | y2 |
|---|---|---|
| Pred total | 75 | 128 |
| Exp total | 457 | 457 |
| ▲ ▽ or ▼ | 161 | 161 |
| ■ | 23 | 100 |
| ▲ ▼ or ▼ | 608 | 628 |
| ▲ ◁ | 1 | 2 |
| ▲ □ or ▼ | 23 | 0 |
| ■ ▷ or ■ | 127 | 49 |

No comparison possible

| | y1 | y2 |
|---|---|---|
| ▲ ? or ▼ | 28 | 28 |
| ■ ? | 197 | 198 |
| ? ▷ or ? ◁ | 268 | 268 |
| ? □ | 2,067 | 2,067 |
| ? ? | 889 | 889 |

METHODS AND SYSTEMS TO IDENTIFY OPERATIONAL REACTION PATHWAYS

CROSS REFERENCE TO RELATED APPLICATIONS

This application is a continuation-in-part of U.S. Ser. No. 10/367,248, filed Feb. 14, 2003, now U.S. Pat. No. 7,734,420, which under 35 U.S.C. §119(e) claims benefit of 60/419,023 filed Oct. 15, 2002; and Application Ser. No. 60/562,055, filed Apr. 13, 2004, the contents of which are herein incorporated by reference in their entirety.

BACKGROUND OF THE INVENTION

This invention relates generally to the construction of in silico model organisms and, more specifically, methods and systems specifying operational reaction pathways and for the generation of optimal in silico models of actual organisms.

Therapeutic agents, including drugs and gene-based agents, are being rapidly developed by the pharmaceutical industry with the goal of preventing or treating human disease. Dietary supplements, including herbal products, vitamins and amino acids, are also being developed and marketed by the nutraceutical industry. Additionally, efforts for faster and more effective methods for biological fermentation and other bioprocessing of food stuffs and industrial compounds has been under development. Faster and more efficient production of crops and other agricultural products is also yet another area of intense development in the food industry.

Because of the complexity of biochemical reaction networks in and between cells of an organism, even relatively minor perturbations caused by a therapeutic agent, change in a dietary component or environmental or growth conditions, can affect hundreds of biochemical reactions. Such changes or perturbations can lead to both desirable and undesirable effects in any therapeutic, industrial or agricultural process involving living cells. It would therefore be beneficial if a particular process could predict the effects on a living system such as a cell or organism of such perturbations.

However, current approaches to therapeutic, industrial and agricultural development for compounds and processes used therein do not take into account the effect of perturbations on cellular behavior at the level of accuracy needed for efficient and economical production of products. In order to design effective methods of manipulating cellular activities for the optimization of such processes or to achieve the optimal intended effect of an applied a compound, it would be helpful to understand cellular behavior from an integrated perspective.

However, cellular behaviors involve the simultaneous function and integration of many interrelated genes, gene products and chemical reactions. Because of this interconnectivity, it is difficult to predict a priori the effect of a change in a single gene or gene product, or the effect of a drug or an environmental factor, on cellular behavior. The ability to accurately predict cellular behavior under different conditions would be extremely valuable in many areas of medicine and industry. For example, if it were possible to predict which gene products are suitable drug targets, it would considerably shorten the time it takes to develop an effective antibiotic or anti-tumor agent. Likewise, if it were possible to predict the optimal fermentation conditions and genetic make-up of a microorganism for production of a particular industrially important product, it would allow for rapid and cost-effective improvements in the performance of these microorganisms.

Thus, there exists a need for models and modeling methods that can be used to accurately simulate and effectively analyze the behavior of cells and organisms under a variety of conditions. The present invention satisfies this need and provides related advantages as well.

SUMMARY OF THE INVENTION

The present invention provides a method of refining a biosystem reaction network. The method consists of: (a) providing a mathematical representation of a biosystem; (b) reconciling said mathematical representation of said biosystem; (c) determining differences between observed behavior of a biosystem and in silico behavior of said mathematical representation of said biosystem under similar conditions; (d) modifying a structure of said mathematical representation of said biosystem, and (e) determining differences between said observed behavior of said biosystem and in silico behavior of said modified mathematical representation of said biosystem under similar conditions.

BRIEF DESCRIPTION OF THE DRAWINGS

FIG. 1 shows a schematic diagram for steps involved in determining operational pathways of a biochemical reaction network.

FIG. 19 shows calculation of the expression of regulated genes in an actual organism and model system resulting from phase I of an iterative process of the invention.

DETAILED DESCRIPTION OF THE INVENTION

Figure 2A:
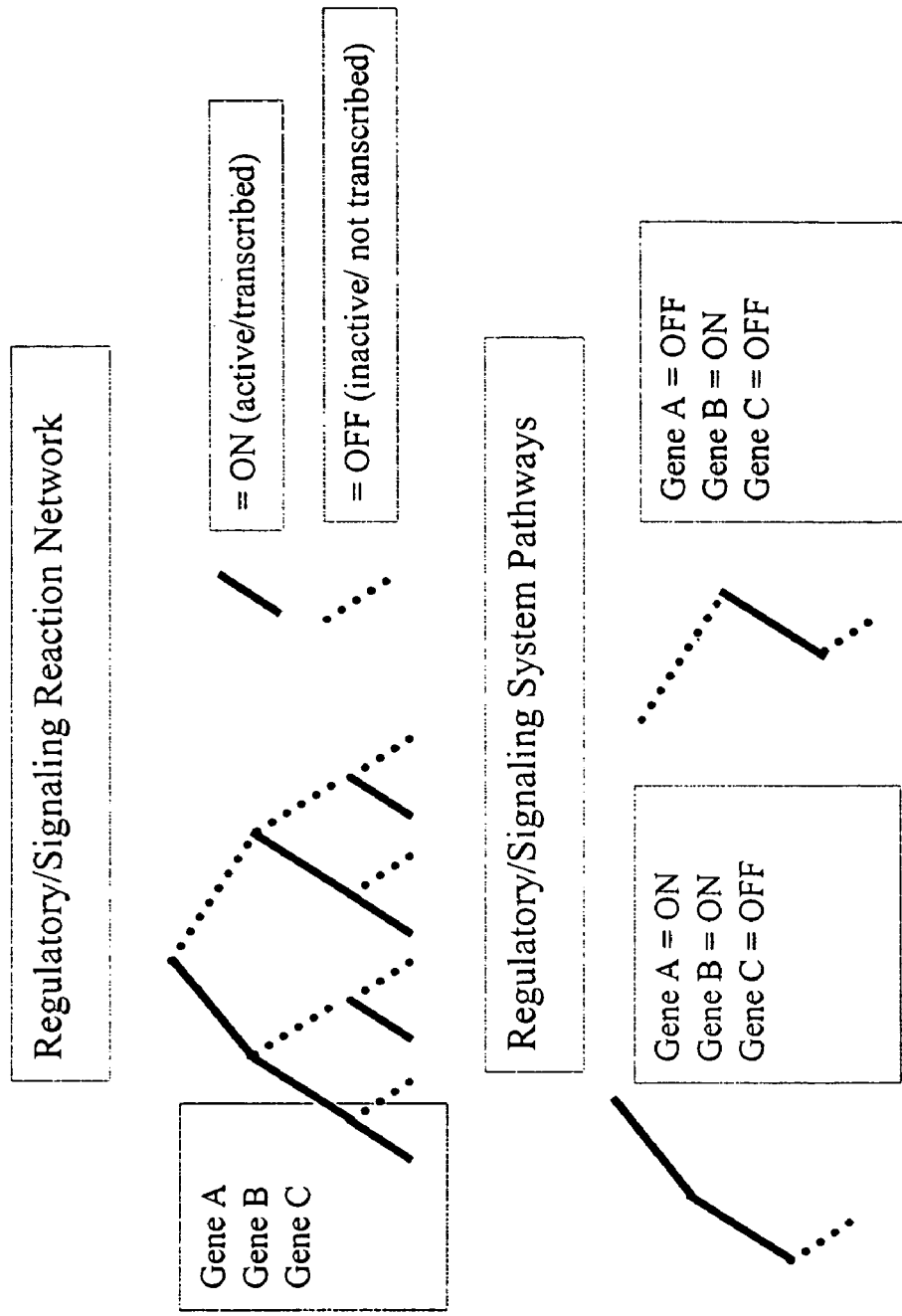
FIG. 2A shows a schematic representation of systemic reaction pathways as one branch of a regulatory tree with the regulated genes shown on the horizontal axis.

The invention provides methods and systems for determining the interaction, integration and coordination of a set of components of a biosystem. The invention can thus be used to rapidly and systematically specify a reconstructed biochemical reaction network at the genome-scale and to relate the activity of the components and their interaction to a specific phenotype or physiological state. Understanding which components are operational under particular conditions allows for improved methods of engineering desirable functions into living cells, fixing malfunctioning circuits, and controlling endogenous circuits by the proper manipulation of the cells' environment. Furthermore, a rapid method for characterizing a biochemical network allows for the characterization of a virtually uncharacterized biosystem with a minimum of experimental effort.

The invention provides a method for determining the operational pathways of a biochemical reaction network. The invention method is practiced by (a) providing a biochemical reaction network, comprised of reactions which can be regulated; (b) providing a set of experimental data which represent various physiological or pathological states of the biosystem under given conditions; (c) determining a set of systemic pathways which define the biosystem in whole or in part; (d) determining a set of phenomenological reaction pathways which describe the experimental states of the biosystem; and (e) determining the operational pathways common to both the systemic and phenomenological pathways sets both at whole-genome and biosystem subcomponent scale (FIG. 1).

As used herein, the term "reaction" is intended to mean a chemical conversion that consumes a substrate or forms a product. A conversion included in the term can occur due to the activity of one or more enzymes that are genetically encoded by an organism, or can occur spontaneously in a cell or organism. A conversion included in the term can be, for example, a conversion of a substrate to a product, such as one due to nucleophilic or electrophilic addition, nucleophilic or electrophilic substitution, elimination, reduction or oxidation. A conversion included in the term can also be a change in location, such as a change that occurs when a reactant is transported across a membrane or from one compartment to another. The substrate and product of a reaction can be differentiated according to location in a particular compartment, even though they are chemically the same. Thus, a reaction that transports a chemically unchanged reactant from a first compartment to a second compartment has as its substrate the reactant in the first compartment and as its product the reactant in the second compartment. The term "reaction" also includes a conversion that changes a macromolecule from a first conformation, or substrate conformation, to a second conformation, or product conformation. Such conformational changes can be due, for example, to transduction of energy due to binding a ligand such as a hormone or receptor, or from a physical stimulus such as absorption of light. It will be understood that when used in reference to an in silico biochemical reaction network, a "reaction" is intended to be a representation of a conversion as described above.

As used herein, the term "reactant" is intended to mean a chemical that is a substrate or a product of a reaction. The term can include substrates or products of reactions catalyzed by one or more enzymes encoded by an organism's genome, reactions occurring in an organism that are catalyzed by one or more non-genetically encoded catalysts, or reactions that occur spontaneously in a cell or organism. Metabolites are understood to be reactants within the meaning of the term. It will be understood that when used in the context of an in silico model or data structure, a reactant is understood to be a representation of chemical that is a substrate or product of a reaction.

As used herein the term "substrate" is intended to mean a reactant that can be converted to one or more products by a reaction. The term can include, for example, a reactant that is to be chemically changed due to nucleophilic or electrophilic addition, nucleophilic or electrophilic substitution, elimination, reduction or oxidation or that is to change location such as by being transported across a membrane or to a different compartment. The term can include a macromolecule that changes conformation due to transduction of energy.

As used herein, the term "product" is intended to mean a reactant that results from a reaction with one or more substrates. The term can include, for example, a reactant that has been chemically changed due to nucleophilic or electrophilic addition, nucleophilic or electrophilic substitution, elimination, reduction or oxidation or that has changed location such as by being transported across a membrane or to a different compartment. The term can include a macromolecule that changes conformation due to transduction of energy.

As used herein, the term "regulatory reaction" is intended to mean a chemical conversion or interaction that alters the activity of a catalyst. A chemical conversion or interaction can directly alter the activity of a catalyst such as occurs when a catalyst is post-translationally modified or can indirectly alter the activity of a catalyst such as occurs when a chemical conversion or binding event leads to altered expression of the catalyst. Thus, transcriptional or translational regulatory pathways can indirectly alter a catalyst or an associated reaction. Similarly, indirect regulatory reactions can include reactions that occur due to downstream components or participants in a regulatory reaction network. When used in reference to a data structure or in silico model, the term is intended to mean a first reaction that is related to a second reaction by a function that alters the flux through the second reaction by changing the value of a constraint on the second reaction.

A regulatory reaction can further include information about inhibitory or inducing effects of an active or inactive regulator on transcription of a gene. For example, a regulatory reaction may have one or more regulators associated with it which effect transcription of a gene.

A regulatory reaction can further include information about the interaction of regulators which influence gene expression. For example a regulatory reaction may have a combination of two or more regulators associated with it which are dependent upon each other to effect transcription of a gene.

A regulatory reaction can further include information in the form of Boolean logic statements which indicates the interaction and dependency of regulators for transcription of a particular gene. For example, a particular gene may have a Boolean logic assigned to it which describes the necessary regulators and regulatory interactions required for expression of that gene.

As used herein, the term "regulator" refers to a substance which regulates transcription, post-transcriptional modification or activity of one or more genes, proteins, mRNA transcripts. Such a regulator may be a regulatory protein, small molecule and the like.

As used herein, the term "regulatory event" is intended to mean a modifier of the flux through a reaction that is independent of the amount of reactants available to the reaction. A modification included in the meaning of the term can be a change in the presence, absence, or amount of an enzyme that catalyzes a reaction. A modifier included in the term can be a regulatory reaction such as a signal transduction reaction or an environmental condition such as a change in pH, temperature, redox potential or time. It will be understood that when used in reference to an in silico model or data structure a regulatory event is intended to be a representation of a modifier of the flux through a reaction that is independent of the amount of reactants available to the reaction.

As used herein, the term "reaction network" refers to a representation of the functional interrelationships between a collection of reactions and reaction components. Reaction components included in a reaction network can be any component involved in a reaction, such as a substrate, product, enzyme, cofactor, activator, inhibitor, transporter, and the like. Functional interrelationships include, for example, those between a substrate and its product; those between a substrate or product and the enzyme that catalyzes the conversion from substrate to product; those between an enzyme and its cofactor, activator or inhibitor; those between a receptor and a ligand or other pairs of macromolecules that physically interact; those between a macromolecule and its transporter; those between proteins involved in transcriptional regulation and their DNA-binding sites in regulatory regions regulating specific target genes; and the like.

A reaction network can further include information regarding the stoichiometry of reactions within the network. For example, a reaction component can have a stoichiometric coefficient assigned to it that reflects the quantitative relationship between that component and other components involved in the reaction.

A reaction network can further include information regarding the reversibility of reactions within the network. A reaction can be described as occurring in either a reversible or irreversible direction. Reversible reactions can either be represented as one reaction that operates in both the forward and reverse direction or be decomposed into two irreversible reactions, one corresponding to the forward reaction and the other corresponding to the backward reaction.

A reaction network can include both intra-system reactions and exchange reactions. Intra-system reactions are the chemically and electrically balanced interconversions of chemical species and transport processes, which serve to replenish or drain the relative amounts of certain reactants. Exchange reactions are those which constitute sources and sinks, allowing the passage of reactants into and out of a compartment or across a hypothetical system boundary. These reactions represent the demands placed on the biological system. As a matter of convention the exchange reactions are further classified into demand exchange and input/output exchange reactions. Input/output exchange reactions are used to allow components to enter or exit the system. A demand exchange reaction is used to represent components that are required to be produced by the cell for the purposes of creating a new cell, such as amino acids, nucleotides, phospholipids, and other biomass constituents, or metabolites that are to be produced for alternative purposes.

A reaction network can further include both metabolic and regulatory reactions. Metabolic reactions can be represented by stoichiometry and reversibility while regulatory reactions can be represented by Boolean logic statements which both depend on and effect the presence or absence, activity or inactivity of metabolic or regulatory proteins.

A reaction network can be represented in any convenient manner. For example, a reaction network can be represented as a reaction map with interrelationships between reactants indicated by arrows. For mathematical manipulation according to the methods of the invention, a reaction network can conveniently be represented as a set of linear algebraic equations or presented as a stoichiometric matrix. A stoichiometric matrix, S, can be provided, which is an m×n matrix where m corresponds to the number of reactants and n corresponds to the number of reactions in the network. Stoichiometric matrices and methods for their preparation and use are described, for example, in Schilling et al., *Proc. Natl. Acad. Sci. USA* 95:4193-4198 (1998). As a further example, a reaction network can conveniently be represented as a set of linear algebraic equations and Boolean logic equations. The Boolean logic equations may be evaluated and lead to the removal or addition of certain reactions from the stoichiometric matrix, due to the inhibitory or inducing effect of regulatory events. Such a representation is described, for example, in Covert M W, Schilling C H, Palsson B. *J. Theor Biol.* 213: 73-88 (2001).

The invention methods can be practiced with reaction networks of either low or high complexity, such as networks that include substantially all of the reactions that naturally occur for a particular biosystem. Thus, a reaction network can include, for example, at least about 10, 50, 100, 150, 250, 400, 500, 750, 1000, 2500, 5000 or more reactions, which can represent, for example, at least about 5%, 10%, 20%, 30%, 50%, 60%, 75%, 90%, 95% or 98% of the total number of naturally occurring reactions for a particular biosystem.

A reaction network represents reactions that participate in one or more biosystems. As used herein, the term "biosystem" refers to an entire organism or cell therefrom, or to a "biological process" that occurs in, to or by the organism or cell. Thus, a reaction network can represent reactions that occur at the whole organismal, whole cell or subcellular level. Additionally, the reaction network may represent interactions between different organisms or cells.

The term "organism" refers both to naturally occurring organisms and to non-naturally occurring organisms, such as genetically modified organisms. An organism can be a virus, a unicellular organism, or a multicellular organism, and can be either a eukaryote or a prokaryote. Further, an organism can be an animal, plant, protist, fungus or bacteria. Exemplary organisms include pathogens, and organisms that produce or can be made to produce commercially important products, such as therapeutics, enzymes, nutraceuticals and other macromolecules. Examples of organisms include *Arabidopsis thaliana, Bacillus subtilis, Bos taurus, Caenorhabditis elegans, Chlamydomonas reihardtii, Danio rerio, Dictyostelium discoideum, Drosophila melanogaster, Escherichia coli,* hepatitis C virus, *Haemophilus influenzae,* Helicobacter pylori, *Homo sapiens, Mus musculus, Mycoplasma pneumoniae, Oryza sativa, Plasmodium falciparum,* Pnemocystis carinii, *Rattus norvegicus, Saccharomyces cerevisiae, Schizosaccharomyces pombe,* Takifugu rubripes, *Xenopus laevis, Zea mays,* and the like.

A "biological process" of an organism or cell refers to a physiological function that requires a series of integrated reactions. A biological process can be, for example, cellular metabolism; cell motility; signal transduction (including transduction of signals initiated by hormones, growth factors, hypoxia, cell-substrate interactions and cell-cell interactions); cell cycle control; transcription; translation; degradation; sorting; repair; differentiation; development; apoptosis; and the like. Biological process are described, for example, in Stryer, L., Biochemistry, W.H. Freeman and Company, New York, 4th Edition (1995); Alberts et al., Molecular Biology of The Cell, Garland Publishing, Inc., New York, 2nd Edition (1989); Kuby, Immunology, 3rd Edition, W.H. Freeman & Co., New York (1997); and Kornberg and Baker, DNA Replication, W.H. Freeman and Company, New York, 2nd Edition (1992).

In one embodiment, the biosystem includes the biological process of cellular metabolism, and the reaction network representing the biosystem, referred to as a "metabolic reaction network," includes cellular metabolic reactions. A basic review of cellular metabolism can be found, for example, in Stryer, L., Biochemistry, W.H. Freeman and Company, New York, 4th Edition (1995). Cellular metabolism can be usefully divided into central and peripheral metabolic reactions. Central metabolism includes reactions that belong to glycolysis, pentose phosphate pathway (PPP), tricarboxylic acid (TCA) cycle and respiration. Peripheral metabolism, which includes all metabolic reactions that are not part of central metabolism, includes reactions involved in the biosynthesis of an amino acid, degradation of an amino acid, biosynthesis of a purine, biosynthesis of a pyrimidine, biosynthesis of a lipid, metabolism of a fatty acid, biosynthesis of a cofactor, metabolism of a cell wall component, transport of a metabolite or metabolism of a carbon source, nitrogen source, phosphate source, oxygen source, sulfur source, hydrogen source or the like.

In another embodiment, the biosystem includes the biological process of transcriptional regulation, and the reaction network representing the biosystem, referred to as a "transcriptional regulatory reaction network," includes cellular transcriptional regulatory reactions. A basic review of cellular transcriptional regulation can be found, for example, in Alberts et al., Molecular Biology of The Cell, Garland Publishing, Inc., New York, 2nd Edition (1989). Transcriptional regulatory events may be grouped by the types of genes regulated, for example those genes associated with metabolism, cell cycle, flagellar biosynthesis and the like.

In another embodiment, the biosystem includes the biological processes of cellular metabolism and transcriptional regulation and the reaction network representing the biosystem includes both metabolic and transcriptional regulatory reactions.

A reaction network that includes substantially all of the reactions of a whole organism or cell, or substantially all of the reactions of a particular biological process of an organism or cell, is referred to as a "genome-scale" reaction network. Genome-scale reaction networks representing the metabolism of various organisms have been described, including *E. coli* (PCT publication WO 00/46405); *H. pylori* (Schilling et al., *J. Bacteriol.* 184:4582-4593 (2002)); and *H. influenzae* Edwards J. S. and Palsson B. O. *J. Biol. Chem.* 274:17410-6 (2001)).

For other biosystems, genome-scale reaction networks can be prepared by methods known in the art. Generally, these methods involve first generating a comprehensive list of reactions that are capable of occurring in the organism, cell or biosystem, and determining their interconnectivity. The list can include reactions determined from an analysis of the annotated genome of the organism, supplemented as required from scientific literature and from experimental data. Also included can be transport reactions, biomass composition demands, growth associated energy requirements, and the like.

The genome sequences of a large number of animals, plants, protists, fungi, bacteria and viruses have been completed or are in progress (see, for example, genome entries in The Institute for Genome Research (TIGR) database (www.tigr.org/tdb/) and in the NCBI Entrez Genome database (www.ncbi.nlm.nih.gov/entrez/query.fcgi?db=Genome)). Other World Wide Web-based sources of annotated genome sequence information and reconstructed network information include EcoCyc, Metabolic pathways database (MPW), Kyoto Encyclopedia of Genes and Genomes (KEGG), What is There (WIT) and Biology Workbench.

For organisms whose genomes have not yet been sequenced, a variety of methods for obtaining the genomic sequence are known in the art. In most large-scale genome sequencing methods, every step from isolating DNA, cloning or amplifying DNA, preparing sequencing reactions, and separating and detecting labeled fragments to obtain sequence, is automated (Meldrum, Genome Res. 10: 1081-1092 (2000)). Most methods use a combination of sequencing methods, such as a combination of random shotgun sequencing with a directed finishing phase. Other methods use a whole-genome shotgun approach, in which random fragments of total genomic DNA are subcloned directly, and high-throughput sequencing is used to provide redundant coverage of the genome. Another approach is to sequence each end of every BAC in a genome library, and match a finished sequence to a BAC end sequence to select the next clone (Venter et al., *Science* 280:1540-1542 (1998); Waterston et al, *Science* 282:53-54 (1998)).

For a newly sequenced genome, the open reading frames (ORFs) or coding regions may be distinguished from the rest of the DNA sequence by variety of methods. Determining the location of an ORF in a DNA sequence, its strand, and nucleotide composition may be conducted by searching for gene signals (e.g., promoters, binding sites, start and stop codon, etc.) or by analzying gene content (e.g., codon preference, positional base frequency, etc.), or a combination of both methods. Algorithms and computational tools are available to determine the ORFs of an entire DNA sequence using these methods available through institutes such as the University of Wisconsin Genetics Computer Group and National Center for Biotechnology Information. Furthermore, other computational algorithms have been developed by which bacterial or eukaryotic genes may be identified by algorithmic methods such as hidden Markov models, which routinely find more than 99% of protein-coding regions and RNA genes (Pevzner, "Computational molecular biology: an algorithmic approach," in *Computational Molecular Biology*. Cambridge, Mass.:MIT Press, xviii, p. 314 (2000); Baldi et al., "Bioinformatics: the machine learning approach," in *Adaptive Computation and Machine Learning*. Cambridge, Mass.: MIT Press xviii, p. 351 (1998); Fraser et al., Nature 406:799-803 (2000)).

In order to assign function to the coding regions, newly identified ORFs are searched against databases containing genes and protein sequences of known function for sequence similarity. Several algorithms such as the BLAST and FASTA family of programs have been developed and are available publically by which the similarity of a functionally unknown ORF may be determined against functionally annotated genes. A major portion of unidentified genes in a newly sequence organism can be assigned functionally with this procedure.

If the putative function of a gene is not established by gene or protein sequence similarity, other techniques such as gene clustering by function or location may be used to assess the role of a gene in the network. Gene products that participate in the same overall function can constitute a pathway in the cell. "Missing links" in a pathway constructed from an initial sequence annotation suggests the existence of genes that have not yet been identified. Searching the sequence against other organisms provides clues about the possible nucleotide sequence of the missing genes, which in turn facilitates targeting functionality of the unassigned coding regions. Algorithms have been developed that perform this procedure in various genome databases such as KEGG and WIT. In addition, genes of the neighboring location may be clustered into operons that are regulated and function in a coordinated fashion when the DNA sequence is compared to that of other organisms. From the annotated genetic information, together with biochemical and physiological information, the interrelatedness of reactions and reaction components is determined and the reaction network is completed.

In addition to defining the ORFs or coding regions of the genome, regulatory regions can be defined by variety of methods. Regulatory regions contain binding sites for transcriptional regulators and components of the transcriptional machinery. These sites determine the specificity of transcriptional regulation as the ability of transcriptional regulators to regulate the gene controlled by the regulatory region. The methods to identify regulatory regions and sites include comparing non-coding regions of closely related genomes to identify highly conserved segments of the genome that may correspond to regulatory regions. Groups of non-coding regions of a genome can also be searched for commonly occurring sequence fragments to identify specific binding site patterns in the genome. These groups can be defined for example by similarity in biological function of the genes controlled by the regulatory regions. In addition existing definitions of binding site patterns for specific transcriptional regulators stored in specific databases such as Saccharomyces Promoter Database (Zhu and Zhang, *Bioinformatics* 15:607-611 (1999)) or TRANSFAC (Wingender et al., *Nucl. Acids Res.* 29:281-283 (2001)) can be used to search the genome for new binding sites for a regulator. Identifying regulatory sites for specific transcription regulators allows establishing potential target genes regulated by these regulators and thus suggesting new regulatory reactions to be added to the regulatory network.

As used herein, the term "reaction pathway" refers to a route through a reaction network through which reaction components, regulatory information or signaling molecules can potentially flow. It will be appreciated that the actual amount and/or rate of substrate to product conversion through a reaction pathway (also known as "flux") is a function of the physiological state of the biosystem under consideration, and that reaction pathways (including operational, extreme and phenomenological reaction pathways as described below) are generally specified in connection with the physiological state of the biosystem. The term "physiological state" is intended to refer to any specified internal and external parameters that affect, or are likely to affect, flux through a biosystem. Parameters that can affect flux include, for example, the actual or intended inputs to the biosystem (such as the carbon, nitrogen, phosphorus, sulfur or hydrogen source; the presence or amount of oxygen, nutrients, hormones, growth factors, inhibitors and the like); the actual or intended outputs of the biological system (such as biomass components, secreted products and the like) and environmental variables (such as temperature, pH and the like). Other parameters that can affect flux include, for example, the state of differentiation or transformation of the cell; cell age; its contact with a substrate or with neighboring cells; the addition or deletion of expressed genes; and the like.

As used herein, term "systemic reaction pathway" refers to a reaction pathway identified by an automated method applied to a suitable representation of a reaction network. The method may involve mathematical or algorithmic operations to identify the reaction pathways, and it may include user definable parameters that influence the identification of reaction pathways. The systemic reaction pathways need not to be unique and they may only apply to a subset of the reaction network.

Methods of identifying systemic reaction pathways using convex analysis have been described in the art. Such methods include, for example, stoichiometric network analysis (SNA) (Clarke, *Cell Biophys*. 12:237-253 (1988); elementary mode analysis (Schuster et al., *Trends Biotech*. 17:53-60 (1999); and extreme pathway analysis (Schilling et al., *J. Theor. Biol*. 203:229-248 (2000); Schilling et al., *Biotechnol. Bioeng*. 71:286-306 (2001)). The distinctions between these types of analysis are described in Schilling et al. supra (2000).

In one embodiment, the systemic reaction pathway is an extreme pathway. The term "extreme pathway" refers to a systemically independent pathway that spans a convex, high-dimensional space that circumscribes all potential steady state flux distributions achievable by a defined reaction network.

It will be understood that the steps needed to "provide" a set of systemic reaction pathways for use in the invention methods will depend on the amount and type of information already available regarding the biosystem and reaction network. For certain biosystems and physiological states, sets of extreme reaction pathways have been described in the art. For example, extreme pathways for a human red blood cell metabolic network are described in Wiback et al., *Biophys. J*. 83:808-818 (2002). Extreme pathways for a *H. influenzae* metabolic network are described in Schilling et al., *J. Theor. Biol*. 203:249-283 (2000) and Papin et al., *J. Theor. Biol*.

215:67-82 (2002). Extreme pathways for a *H. pylori* metabolic network are described in Price et al., *Genome Res.* 12:760-769 (2002).

Extreme reaction pathways can also be determined de novo, using methods known the art (Schilling et al. supra (2000); Schilling et al. supra (2001)). Appropriate stoichiometric and thermodynamic constraints can be imposed on the intrasystem and exchange reactions in the reaction network under steady-state conditions. Constraints can also be imposed on the input and output of reactants to and from the biosystem. Optionally, regulatory constraints can also be imposed (Covert et al., *J. Theor. Biol.* 213:73-88 (2001); Covert and Palsson, *J. Biol. Chem.* 277:28058-28064 (2002)). This results in a system of linear equalities and inequalities that can be solved using convex analysis. The solution space corresponds geometrically to a convex polyhedral cone in high-dimensional space emanating from the origin, which is referred to as the steady state "flux cone." Within this flux cone lie all of the possible steady-state solutions, and hence all the allowable flux distributions of the biosystem. The extreme pathways correspond to vectors that define the edges of the flux cone.

In another embodiment, the systemic reaction pathway is one branch of a regulatory tree. The regulated genes of a biosystem may be depicted as shown in FIG. 2A with the regulated genes shown on the horizontal axis. In a Boolean representation, each protein and each gene may be considered "on" or "off" (active or inactive, respectively). The combination of the activity state of all genes and proteins in a biosystem may be considered a "systemic regulatory pathway" or a "systemic signaling pathway".

In another embodiment, the systemic reaction pathway is a set of regulators and regulatory reactions influencing the activity of a regulated gene or the set of genes regulated by a regulator or a group of regulators. These sets may be identified by analyzing the connectivity of a regulatory network represented as a graph and identifying nodes in the network connected to a particular node (regulator or regulated gene). The smallest possible set of such kind is one involving one regulatory reaction between a regulator and a target gene.

As used herein, the term "phenomenological reaction pathway" refers to a reaction pathway defined through analyzing experimental data to describe the state of the biosystem in whole or part. The data types that can be used to define phenomenological reaction pathways include but are not limited to transcriptomic, proteomic, metabolomic, fluxomic, protein-protein interaction, and DNA-binding site occupancy data. The data analysis methods used to define the phenomenological pathways from the experimental data include but are not limited to systems identification, statistical, algorithmic, or signal processing techniques.

Phenomenological information about the reactions and reactants of a biosystem can be determined by methods known in the art, and can be either qualitative or quantitative. For example, phenomenological information can be obtained by determining transcription of genes, expression or interactions of proteins, production of metabolites or other reactants, or use of reactions in the biosystem. By analogy to the term "genome," such information, when obtained at the scale of substantially the whole organism or cell, is called, respectively, the "transcriptome," "proteome," "metabolome" and "fluxome."

Methods of determining gene expression at the transcriptome scale (also known as "transcriptomics") are known in the art and include, for example, DNA microarray methods, which allow the simultaneous analysis of all transcripts simultaneously (Shena et al., *Science* 270:467-470 (1995); DeRisi et al., *Science* 278:680-686 (1997)) and serial analysis of gene expression (SAGE) methods (Velculescu et al., *Trends Genet.* 16:423-425 (2000)); Methods of determining protein expression (also known as "proteomics") are also known in the art. Expression proteomic methods generally involve separation of proteins, such as by two-dimensional gel electrophoresis, followed by protein imaging using radiolabels, dyes or stains. Separated proteins are then identified using methods such as peptide mass fingerprinting by mass spectrometry and peptide-sequence tag analysis by nanoelectrospray (Blackstock et al., *Trends Biotechnol.* 17:121-127 (1999)).

Method for determining interactions between biological molecules in the cell at a large scale are also known in the art. Protein-protein interaction information, which allows inferences as to a protein's function, can be obtained, for example, using large-scale two-hybrid analysis to identify pairwise protein interactions (Fromont-Racine et al., *Nat. Genet.* 16:277-282 (1997). Indirect protein-DNA interaction information can be obtained using chromatin immunoprecipitation chip (ChIP-ChIP) methods, which allows the genome-scale identification of genomic binding sites of DNA-binding proteins and genomic targets of transcription factors (Iyer et al., *Nature* 409:533-538 (2001)).

Methods of determining the complement of metabolites in a cell (also known as "metabolomics") are also known in the art and include, for example, nuclear magnetic resonance (NMR) spectroscopy such as 13C-NMR; mass spectroscopy such as gas chromatography/time-of-flight mass spectroscopy (GC/TOFMS); and liquid chromatography (Fiehn, *Plant Mol. Biol.* 48:155-171 (2002); Phelps et al., *Curr. Opin. Biotech.* 13:20-24 (2002)).

Likewise, methods of measuring the fluxes through reaction pathways (also known as "fluxomics") are known in the art, such as metabolic flux ratio analysis (METAFoR) (Sauer et al., *J. Bacteriol.* 181:6679-6688 (1999)). METAFoR quantifies the relative abundance of intact carbon bonds in biomass constituents that originate from uniformly isotopically labeled precursor molecules, which reflects the metabolic pathways used.

By repeatedly varying the physiological state of the biosystem, either experimentally or in silico, a series of phenomenological measurements at different states can be obtained or predicted. These data can be organized in vectorial form and represented in matrix or tabular formats. For example, a set of gene array expression data can be organized as a matrix where each row is a gene, each column is an experiment, and each value is an expression level or ratio. As another example, a set of fluxome data can be organized as a matrix where each row is a reaction, each column is an experiment and each value is a flux level or ratio. As a further example, a set of phenotypic data can be organized as a matrix where each row is an experiment, each column is an environmental component (such as nutrients, waste products, or biomass) and each value is a rate of uptake, secretion, or growth.

The phenomenological information can be analyzed by various methods known in the art, such as methods of system identification, statistical data analysis, combinatorial algorithms, or signal processing to determine a set of phenomenological reaction pathways.

Methods of system identification are known in the art and include, for example, various types of clustering analysis methods (reviewed in Sherlock et al., *Curr. Opin. Immunol.* 12:201-205 (2000)). Clustering methods can be applied to experimental data in matrix or tabular formats to extract groups of genes that are co-expressed. These groups that can either be disjoint or overlapping can be used as definitions of phenomenological pathways. Alternatively, a data vector within each cluster can be chosen to be a representative phenomenological pathway for that cluster—this vector could for example be the mean value of the data points within the cluster also known as the centroid of the cluster.

Clustering analysis methods include, for example, hierarchical clustering analysis (Eisen et al., *Proc. Natl. Acad. Sci. USA* 95:14863-14868 (1998); Wen et al., *Proc. Natl. Acad. Sci. USA* 95:334-339 (1998)), whereby single reactant profiles are successively joined to form nodes, which are then joined further. The process continues until all individual profiles and nodes have been joined to form a single hierarchical tree. Clustering analysis methods also include divisive clustering analysis (Alon et al., *Proc. Natl. Acad. Sci. USA* 96:6745-6750 (1999)), in which two vectors are initialized randomly, and each reactant is assigned to one of the two vectors using a probability function. The vectors are iteratively recalculated to form the centroids of the two clusters, and each cluster is successively split in the same manner until each cluster consists of a single profile. Clustering analysis methods also include methods in which the data is partitioned into reasonably homogeneous groups. Clustering methods that incorporate partitioning include, for example, self-organizing maps (Kohenen, "Self Organizing Maps," Berlin: Springer (1995); Tamayo et al., *Proc. Natl. Acad. Sci. USA* 96:2907-2912 (1999)) and k-means clustering (Everitt, "Cluster Analysis 122," London: Heinemann (1974)).

Another method of system identification is principal component analysis of the data, which is closely related to the singular value decomposition (SVD) of the data matrix (Holter et al., *Proc. Natl. Acad. Sci. USA* 97:8409-9414 (2000); Alter et al., *Proc. Natl. Acad. Sci. USA* 97:10101-10106 (2000); Holter et al., *Proc. Natl. Acad. Sci. USA* 98:1693-1698 (2001)). Principal component analysis is a statistical technique for determining the key variables in a multidimensional data set that explain the differences in the observations, and can be used to simplify the analysis and visualization of multidimensional data sets. SVD is a linear transformation of data, such as gene expression data, from genes x arrays space to reduced diagonalized "eigengenes" x "eigenarrays" space, where the eigengenes (or eigenarrays) are unique orthonormal superpositions of the genes (or arrays). After normalization and sorting of the data, the individual genes and arrays become grouped according to similar regulation and function, or similar physiological state, respectively. Principal component and SVD analysis output a set of vectors in the data space (e.g. n dimensional where n is the number of genes) ordered by how much of the variability in the data each vector each principal component or mode captures. These vectors can each be interpreted as phenomenological pathways describing the major modes of usage of the gene/protein complement of the organism under specific conditions that the experiments analyzed represent.

Software for various types of large-scale data analysis, including hierarchical clustering, self-organizing maps, K-means clustering and principal component analysis, is known in the art or can be developed for a particular application. Exemplary analysis software includes "XCluster" (see genome-www.stanford.edu/~sherlock/cluster.html on the World Wide Web), "Cluster" software (see rana.lbl.gov/EisenSoftware.htm on the World Wide Web) and "Genesis" software (see genome.tugraz.at/Software/Genesis/Description.html on the World Wide Web).

The skilled person can determine which method, or which combination of methods, is suitable to analyze phenomenological information to determine a set of phenomenological reaction pathways.

As used herein, the term "operational reaction pathway" refers to a systemic reaction pathway of a biosystem that is feasible taking into account the reactants present in, or fluxes through, the biosystem. Operational reaction pathways thus constitute a subset of systemic reaction pathways that are likely to actually exhibit flux in the biosystem. The subset of systemic pathways that are consistent with phenomenological information about the biosystem are determined to identify operational reaction pathways consistent with the reactants present or reaction fluxes through the biosystem.

Once a set of systemic reaction pathways and a set of phenomenological reaction pathways have been provided, the two sets are compared, and common pathways identified. As described above, the two sets of pathways can be represented in vectorial form, or in the form of groups of genes participating in the pathways, or in other convenient ways. There are a number of mathematical methods known in the art by which two vectors or two groupings can be compared.

For example, the two sets of vectors can be compared using a number of measures for pairwise similarity between vectors including: (1) Euclidean distance, which corresponds to the squared distance between two points in space, or in this case tow vectors, taking into account both the direction and the magnitude of the vectors (Hubbard J. H. and Hubbard B. B. *Vector Calculus, Linear Algebra, and Differential Forms*, Prentice-Hall (1999)); (2) Pearson correlation coefficient, which measures the angle between two vectors whose length is normalized to one, and is thus independent of the length of the vectors (Larsen R. J. and Marx M. L. *An Introduction to Mathematical Statistics and Applications*, Prentice Hall, New Jersey (1986)); or (3) Jackknife correlation coefficient, which is similar to Pearson correlation coefficient, but is corrected for the effect of single outliers components of the vectors to provide a more robust measure (Heyer et al., *Genome Res.* 9:1106-1115 (1999)). Other methods for comparing vectors are known in the art.

Similarly, methods for comparing groupings of genes based on systemic and phenomenological definitions include: (1) the Rand index, which measures the overlap between two different groupings of the same set of genes (Yeung K. Y et al. *Bioinformatics* 17:177 (2001)); and (2) correspondence analysis, which provides a two-dimensional graphical representation of the agreement between two groupings such that the systemic and phenomenological pathways that are most similar to each other are shown to be located closest to each other (Johnson R. A. and Wichern D. W., *Applied Multivariate Statistical Analysis*, 5th Ed., Prentice Hall, New Jersey (2002)).

The skilled person can determine which method, or which combination of methods, is suitable for comparing systemic reaction pathways and phenomenological reaction pathways to identify operational reaction pathways.

The invention also provides a method determining the effect of a genetic polymorphism on whole cell function. The method consists of: (a) generating a reaction network representing a biosystem with a genetic polymorphism-mediated pathology; (b) applying a biochemical or physiological condition stressing a physiological state of the reaction network, and (c) determining a sensitivity to the applied biochemical or physiological condition in the stressed physiological state compared to a reaction network representing a normal biosystem, wherein the sensitivity is indicative of a phenotypic consequence of the genetic polymorphism-mediated pathology. The biochemical or physiological condition can be, for example, a change in flux load, pH, reactants, or products as well as system or subsystem changes such as those in oxidative or energy load.

Briefly, the above methods for analyzing physiological states of a biosystem, comparing them to systemic reaction pathways and determining one or more operational reaction pathways can similarly be employed to determine the effect of genetic polymorphisms on a biosystem or subcomponent thereof. For example, phenomenological information used for comparison with systemic reactions can be obtained from either actual or simulated genetic mutations of enzymes or other polypeptides. Changes in activity of the enzyme or polypeptide due to the mutation can be obtained from sources describing the defect or estimated based on available information or predictive computations using a variety of methods well known in the art. The activities that can be assessed include, for example, catalytic function of an enzyme or binding activity of a polypeptide such as a transcription regulator.

In silico models constituting a reaction network of a genetic polymorphism can be constructed as described previously and the effect of the polymorphism can be assessed in context of the biosystem as a whole. Conditions that the reaction network are subjected to can be varied and the effect of single or multiple, combined polymorphisms can be determined on whole biosystem function or as the polymorphism relates to subsystems thereof. For example, systemic pathways or operational pathways can be calculated in the presence or absence of the genetic polymorphism. Comparison of systemic pathways, operational pathways or a phenotypic manifestation between the two reaction networks can be performed to determine the differences, if any, between the native reaction network and the polymorphic counterpart. Such differences can include, for example, creation of a new systemic or operational pathway, omission of such a pathway and changes in the rate or magnitude of such a pathway. The result of such changes between the normal and polymorphic states also will reveal the consequential impact on biochemical or physiological function or on phenotypic expression of the genetic polymorphism.

Conditions that can be varied include, for example, any biochemical or physiological component of the system. Such conditions can be either external to the biosystem including, for example, external environmental growth conditions such as temperature, pH, carbon source and other input/output reactions which allow components to enter or exit the biosystem. Alternatively, such biochemical or physiological conditions can be internal to the biosystem. Specific examples of internal conditions include, for example, exchange reactions indicative of sources and sinks allowing passage of reactants across a system or subsystem boundary, intra-system reactions that replenish or drain reactants, and demand reactions which represent categories of components produced by the cell. Biochemical or physiological conditions internal to the biosystem also can include changes in pH, utilization of carbon sources, availability of metabolites, cofactors, substrates and products. Other changed internal conditions can include, for example, alterations in system loads such as oxidative or energy load on its corresponding subsystem. Various other biochemical or physiological conditions well known to those skilled in the art can similarly be varied in the methods of the invention to obtain comparative reaction network simulations for determining the effect of a genetic polymorphism on biosystem function.

Altering or changing a condition for each biosystem will generally be sufficient for a comparison between a native and a counterpart polymorhic biosystem. However, the effect can be enhanced when the biochemical or physiological condition is applied to the native and polymorphic biosystem at a magnitude sufficient to stress the biosystem or a correlative subsystem thereof. For example, where the activity of a polymorphic enzyme is altered only slightly compared to its native counterpart, the difference in activity may not substantially affect cellular function within an activity range tested. In part, an insignificant impact on cellular function can be due to the production of sufficient product to perform normal cellular activity regardless of an activity deficiency. However, where the activity of the polymorphic enzyme is tested under stressed conditions, it can be unable to fulfill the added cellular demand due to the additional work required of the system. Accordingly, under stressed conditions, a comparison of the native reaction network functioning and that of the polymorphic reaction network will more readily reveal those activity effects of the polymorphic enzyme due to failure of product production under excess requirements.

The term "stress" or "stressing" as used in reference to applying a biochemical or physiological condition is intended to mean placing a biosystem, reaction network or subsystem thereof under a state of strain or influence of extra effort. The stress can be mild or intense so long as it applies demands, loads or effort on the components extra to that under the normal or nominal state of the biosystem, reaction network or subsystem thereof. Therefore, stressing a system state is intended to include imposing a condition that causes the system to exert additional effort toward achieving a goal. Specific examples of applying a biochemical or physiological condition to a biosystem that stresses a physiological state is described further below in Example III.

Genetic polymorphisms can constitute, for example, single nucleotide polymorphisms (SNPs) and well as multiple changes within a encoding gene resulting in a polymorphic region within the gene or its polypeptide coding region. Polymorphisms in gene or coding region structure can alter the expression levels of the harboring nucleic acid, activity of the encoded polypeptide or both. Polymorphisms well known to those skilled in the art of genetics and genomics include, for example, allelic variants of genes, SNPs and polymorphic regions of a referenced nucleic acid. Specific examples, of genetic polymorphisms include those variations in coding sequence described in Example III for glucose-6-phosphate dehydrogenase (G6PD) and pyruvate kinase (PK). Numerous other genetic polymorphisms and their associated diseases are similarly well known to those skilled in the art.

Given the teachings and guidance provided herein, the methods of the invention for determining the effect of a genetic polymorphism on cellular function can be used with any known or subsequently determined genetic polymorphism. Similarly, the linkage between the genetic defect and the pathology mediated also can be previously known or subsequently determined. Moreover, and as described further below, it can be used to diagnose previously undetermined genetic polymorphisms that alter an activity of an enzyme or polypeptide. However, by determining the effect of the defect in the context of a whole biosystem, a more accurate phenotype and assessment of the functional abilities of the biosystem can be obtained. Accurate determination of phenotypic and functional attributes of such complicated systems can be advantageously applied for a more meaningful treatment of the genetic polymorphism-mediated disease.

Sensitivities of the polymorphic enzyme to the stressed condition can be more or less pronounced depending on which polymorphisim is incorporated into the reaction system, the degree of polypeptide activity change due to the polymorphism and the level of stress that is exerted on the system. Those skilled in the art will know or can determine, given the teachings and guidance provided herein, what sensitivities are indicative of a particular polymorphic enzyme or other polypeptide. For example, glucose-6-phosphate dehydrogenase (G6PD) functions in the oxidative branch of the pentose pathway and is sensitive to changes in maximum velocity ($V_{max}$) and cofactor binding affinity ($K_{i\text{-}NADPH}$). Enzymes with alterations in these activities result in changed in oxidative requirements which can be used as indicators of the metabolic state for G6PD's having altered activity. For example, one sensitive indicator of the metabolic state of the biosystem is the NADPH/NADP ratio. This ratio can be measured under stressed conditions and compared between the polymorphic reaction network with that of the normal network to determine the phenotypic and functional changes on the biosystem. As described further below in Example III, polymorphic enzymes having alterations in these G6PD activities can be distinguished in the methods of the invention as those mediating non-chronic and chronic hemolytic anemia.

Similarly, pyruvate kinase (PK) functions in glycolysis and is sensitive to changes in $V_{max}$ and the affinity for substrates such as phosphoenolpyruvate ($K_{PEP}$). Alterations in these activities result in changes in ATP concentration, and 2,3 DPG concentration. Sensitive indicators of $V_{max}$ and $K_{PEP}$ can include, for example, the concentration of ATP when the biosystem is under maximum energy loads or stress compared to normal conditions. As with G6PD, polymorphic PK enzymes having alterations in these activities show that anemic patients have a diminished ability to deviate from the normal homeostatic state.

For determining the effect on function, a reaction network specifying the activity of the polymorphic enzyme is constructed and the system is stressed as described above. Sensitivity to the stressed condition compared to that of the normal or native reaction network can then be determined using a variety of indicators. Those described above for G6PD and PK are exemplary indicators for enzyme activity. Those skilled in the art will understand, given the teachings and guidance provided herein that other indicators of biochemical or physiological activity of the particular enzyme or polypeptide being assessed can be used in the methods of the invention. For example, essentially any measure of substrate, product, cofactor, or other metabolite can be used as an indicator of polypeptide activity. Such indicators can be assessed directly or indirectly such as by measuring the products of downstream reactions and the like. Moreover, ratios of such indicators or of general indicators of a particular biochemical or physiological state can similarly be used. For example, ATP, and energy cofactors such as NADPH and NADP are general indicators of the oxidative state and energy charge, respectively, of a biosystem.

Changes in activity under stressed conditions of such biochemical or physiological indicators will identify the change in function of the biosystem due to the altered activity as well as show the phenotypic consequences of the polymorphic enzyme. For example, the inability of a biosystem to respond to excess oxidative or energy requirements can show, for example, that the polymorphic enzyme is unable to adequately produce components within its assigned subsystem to handle the increased work requirements caused by the stress. A functional biosystem change can correspond to, for example, altered demands and products that are produced as well as changes in flux or pathways which compensate the deficient enzyme activity. A phenotypic outcome can be, for example, inhibition of biosystem proliferation, decrease in biosystem mass or even biosystem lysis and death.

The methods of the invention also can be used for diagnosis of a genetic polymorphism-mediated pathology. The methods described above can be used to generate a biosystem reaction network representing activities of suspected genetic polymorphism. The biosystem reaction network can be stressed as described above and the reaction network containing the suspected polymorphic enzyme activity compared to that of a normal reaction network. A change in function or phenotype of the suspected polymorphic network compared to the normal will indicate that the genetic alteration is linked to the enzyme deficiency. Those skilled in the art will understand that a plurality of suspected enzyme defects can be identified and linked to a particular disease given the teachings and guidance provided herein. For example, those skilled in the art can use activity measurements from a suspected patient in the creation of a plurality of reaction networks. Comparison of the function or phenotype of the networks harboring suspect activities with normal networks will identify the differences in function or phenotype and whether any of such identified differences are sufficient to result in a pathological condition.

Therefore, the invention provides a method of diagnosing a genetic polymorphism-mediated pathology. The method consists of: (a) applying a biochemical or physiological condition stressing a physiological state of a reaction network representing a biosystem with a genetic polymorphism-mediated pathology, the applied biochemical or physiological condition correlating with the genetic polymorphism-mediated pathology, and (b) measuring one or more biochemical or physiological indicators of the pathology within the reaction network, wherein a change in the one or more biochemical or physiological indicators in the stressed state compared to an unstressed physiological state indicates the presence of a genetic polymorphism corresponding to the pathology.

The invention further provides a method of reconciling biosystem data sets. The method consists of: (a) providing a first regulatory network reconstructed from legacy data comprising a plurality of hierarchical regulatory events; (b) providing a second regulatory network obtained from empirical data, and (c) determining a consistency measure between the hierarchical regulatory events in the first regulatory network and elements in the second regulatory network, wherein a high degree of the consistency measure for the hierarchical regulatory events indicates the validity of the first regulatory network or a subcomponent thereof.

The method of the invention for reconciling data sets is useful for determining the accuracy of a biosystem model as well as for identifying new components, linkages, networks and subnetwork of a biosystem model. The model can be based on scientifically proven data, mathematical interpretations as well as on pure computational analysis or even theoretical prediction. Regardless of the source of a biosystem model, the method for reconciling data sets compares the model or a data set representation thereof to another source of data to identify the consistency between one model or data set and that of the comparison model or data set. The degree of consistency between the two models or data sets thereof will show how accurate the initial model is to its corresponding natural biosystem.

Data sets representing whole biosystems can be reconciled using the methods of the invention as well as any substructure thereof. Substructures can consist of subnetworks or modules of the biosystem reaction network. While the exact boundaries of subnetworks and boundaries can vary depending on the assessment criteria used, one feature is that such substructures can be evaluated, analyzed or identified as a unit in itself. Criteria for boundary determination can include, for example, functional attributes, structural attributes and graphical or mathematical separateness, for example. Specific examples of subnetworks or modules of a biosystem have been described above and below and are further shown in FIG. 16 and its associated Example IV. Other examples are well known to those skilled in the art and can be employed in the methods of the invention given the teachings provided herein.

Data sets applicable for comparison can include a broad range of different types and sizes. For example, the data sets can contain a large and complex number of diverse data elements or components of the reaction network. Alternatively, the data sets can be small and relatively simple such as when comparing subnetworks or modules of the reaction network. Those skilled in the art will appreciate that the more inclusive each data set for comparison is with respect to its system components, the more accurate and reliable will be the consistency measure. However, those skilled in the art will know, or can determine, a reliable means to compensate for inherent differences based on the character of one or both of the initial data sets. Therefore, the method of the invention can be used for reconciling data sets where the pair of data sets for comparison can be either large or small, or diverse or simple, as well as for comparison where the data sets within the pair are either large or small, or diverse or simple with respect to each other.

As used herein, the term "legacy" or "legacy data" is intended to refer to known information or data such as that obtainable from literature, other reports, computational data, databases or a combination thereof. The information can be obtained from the public domain or previously known by the user's own investigations. The term therefore is intended to include secondary data that has received the benefit of scientific evaluation and considerations toward the system to which it pertains, the scientific authenticity or the theory which it promotes. Legacy data in essentially any obtainable form can be used in the methods of the invention and can include, for example, literary, graphical, electronic, mathematical or computational forms as well as functional equivalents and transformations thereof. Given the teachings and guidance provided herein, those skilled in the art will known how to use a particular format either directly or following transformation into a useful format for representing a reaction network of the invention. A variety of such useful formats have been described above and below and others are well known to those skilled in the art.

As used herein, the term "empirical" or "empirical data" refers to data based on primary factual information, observation, or direct sense experience. Empirical data is therefore intended to refer to raw data or primary data that has not received the benefit of scientific evaluation and considerations toward the system to which it pertains, the scientific authenticity or the theory which it promotes. The term is intended to include, for example, data, data sets or equivalent transformational forms thereof corresponding to gene expression data, protein activity data and the like. It can include, for example, large, high throughput datasets such as that obtainable by genomic, proteomic, transcriptomic, metabolic and fluxomic data acquisition as well as small data sets obtainable by a variety of research methods well known to those skilled in the art. Other forms of primary data well known to those skilled in the art can similarly be employed in the methods of the invention.

Useful attributes of reconciling data sets include, for example, both validation of known reaction network and subnetwork models as well as the identification or discovery of new subnetworks or modules thereof. Validation of an existing model is useful in itself because it authenticates previous scientific theories as well as subsequent discoveries based on the original model. Similarly, invalidation of a network model can be useful, for example, because it informs the user that components, links or scientific premises may be omitted from the network model as a whole. Moreover, reconciliation of data sets can identify subnetworks or modules of the biosystem reaction network model by showing differential validation of a particular subsystem or of several subsystems within the whole. For example, discovery of new subnetworks or identification of valid subnetworks within the whole can occur when some, but not all, modules within the biosystem network are reconciled. Identifications are particularly striking where the subnetwork or module thereof constitute relatively independent entities within the biosystem reaction network or are relatively decoupled from the body of the biosystem network. Finally, information gained from reconciliation of data sets and validation of whole networks, subnetworks or modules thereof can be used to refine the network or subnetworks by altering the model determining whether the altered model reconciles with the comparative data set.

Validation and discovery methods of the invention are applicable to essentially any form or format of the reaction network. For example, data sets can be reconciled where a reaction network is represented by an in silico model, a mathematical representation thereof, a statistical representation, computational representation, graphical representation or any of a variety of other formats well known to those skilled in the art.

Reconciliation of data sets allows for the validation of essentially any causal relationships within the compared biosystem networks. For example, the method for reconciliation of data sets can be employed on data sets specifying all types of reaction networks described herein. Therefore, the method is applicable to reaction networks corresponding to a metabolic reaction network, a regulatory reaction network, a transcriptional reaction network or a genome-scale reaction network, or any combination thereof. To perform the method of reconciliation, a first reaction network can be provided that is reconstructed from legacy data. As described previously, the legacy data can be obtained from a secondary source that has assembled primary data into a working model of the biosystem network components. The first reaction network is compared with a second reaction network obtained from empirical data. The empirical data can consist of, for example, any primary data representing an activity or other attribute of the components within the biosystem.

A comparison of data sets can be accomplished by, for example, any method known to those skilled in the art that provides a measure of consistency between the network representation and the empirical data. In one embodiment a consistency measure is determined between the empirical data and the legacy data, or the legacy-derived network model by, for example, grouping the network components into hierarchical organization of reaction categories. The reaction categories are useful for determining consistency measurements between the data sets to be reconciled. The reaction categories can include, for example, reactants and products, reaction fluxes, metabolic reactions, regulatory reactions and regulatory events. Moreover, the reaction categories can be arbitrary, or based on, for example, functional criteria, statistical criteria, or molecular associations so long as the categories provide an acceptable framework for obtaining a consistency measure between the legacy-derived network and the empirical data set.

Exemplary reaction categories for the specific embodiment of a regulatory reaction network are described further below in Example IV. Briefly, elements of a regulatory network can be separated into, for example, three categories based on functional interactions. These categories include, for example, pair-wise regulatory interactions, target-regulator units and regulons. Given the teachings and guidance provided herein, categories other than these for regulatory networks as well as categories for other types of reaction networks can be identified or generated by those skilled in the art. For example, other types of categories can include anabolic or catabolic reactions or cell signaling functions. The particular type of category will depend on the type of reaction network to be reconciled and the measure of consistency selected to be used in the method of the invention.

Consistency of the data sets to be reconciled can be determined by a variety of methods well known to those skilled in the art. Such methods can be employed to generate a value for each of category or element within a network that can be analyzed for significance. For example, in the above exemplary reaction categories, consistency measurements for pairwise interactions can be obtained, for example, by Pearson correlation coefficients whereas consistency measurements for target-regulator units can be determined by, for example, multiple correlation coefficients. Further, consistency measurements for regulons can be determined by, for example, the average within regulon correlation. Other methods well known in the art also can be employed and include, for example, mutual information-based measures (Cover T M & Thomas J. A., *Elements of Information Theory*, Wiley (1991)), or nonlinear regression methods (Hastie T, Thibshirani R & Friedman J., *The Elements of Statistical Learning*, Springer (2001)). The mutual information measures require discretization of the original data, but allow incorporating nonlinear dependencies that are not accounted for by Pearson or multiple correlation coefficients. Similarly non-linear correlation measures can be used as consistency metrics, but their added flexibility compared to linear correlation may result in overestimating the consistency between empirical data and a proposed network structure. The statistical significance of particular values of a consistency measure can be determined to assess whether the legacy data and empirical data constitute a good fit. A high degree of consistency measure, such as those that are statistically significant, indicate that the two networks, subnetworks or subcomonents reconcile. Further, those data sets that reconcile either as to the whole network or a subnetwork thereof indicate a validation of the legacy model whereas those that are inconsistent indicate a divergence between the legacy-derived model and the empirical data.

The invention further provides a method of refining a biosystem reaction network. The method consists of: (a) providing a mathematical representation of a biosystem; (b) determining differences between observed behavior of a biosystem and in silico behavior of the mathematical representation of the biosystem under similar conditions; (c) modifying a structure of the mathematical representation of the biosystem; (d) determining differences between the observed behavior of the biosystem and in silico behavior of the modified mathematical representation of the biosystem under similar conditions, and (e) repeating steps (d) and (e) until behavioral differences are minimized, wherein satisfaction of a predetermined accuracy criteria indicates an improvement in the biosystem reaction network.

The method can further include the steps of: (f) determining a behavior of the biosystem under different conditions, and (g) repeating steps (b) through (e) of the method for refining a biosystem reaction network under the different conditions. The method for refining a biosystem reaction network can additionally include repeating steps (f) and (g) until the minimized behavioral differences are exhausted, wherein the improved biosystem reaction network representing an optimal biosystem reaction network.

Figure 2B:
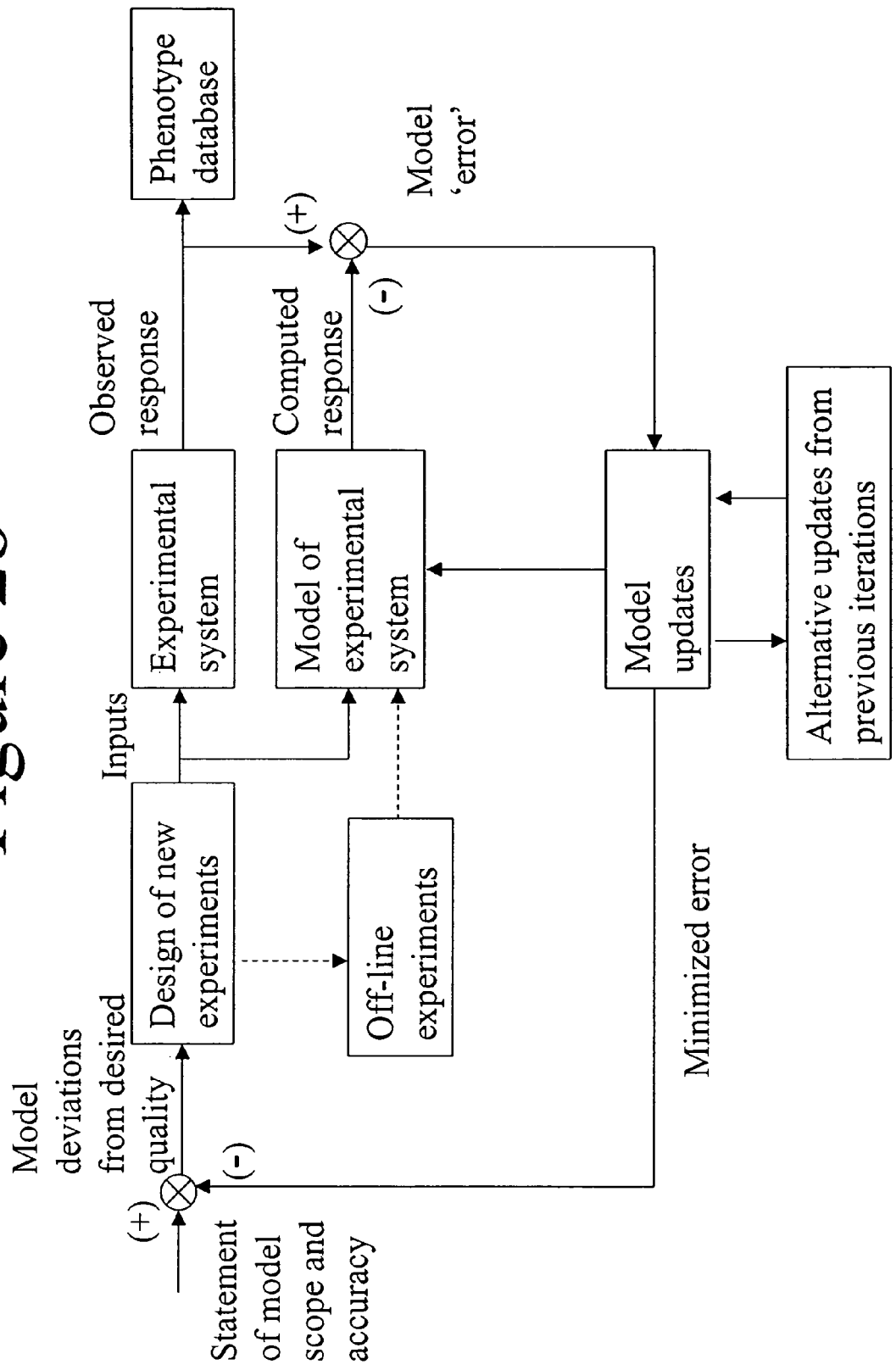
FIG. 2B shows a process by which mathematical representations of biosystems can be improved in an iterative fashion using algorithmic approaches and targeted experimentation.

The methods of the invention can also be applied in a general process by which mathematical representations of biosystems can be improved in an iterative fashion using algorithmic approaches and targeted experimentation. Many biological systems are incompletely characterized and additional experimentation can be required to reconstruct a reaction network of these systems. For such a process to converge quickly on an optimal model, an iterative experimentation can be systematized. FIG. 2B exemplifies such a procedure, which is further described in Example V.

The model building process can begin with a statement of model scope and accuracy. Alternatively, the model building process can proceed in the absence of such a predetermined assessment of scope or accuracy but terminated once a desired scope or accuracy is ultimately obtained.

The purpose for building the model leads to specification of expected accuracy and the scope of capabilities that the model is to have. The scope of a model can range from, for example, describing a single pathway to a genome-scale description of a wild type strain of an organism. An even broader scope would be to include sequence variations and thus insist that a model describes all the variants of the wild type strain.

The accuracy can be based on, for example, qualitative or quantitative criteria. A useful model can be qualitative and be able to make statements that predict, for example, that the growth rate of an organism is reduced when a particular gene product is inhibited under a particular growth condition. A quantitative model can insist, within measurement error, on predicting the percent reduction in growth rate of inhibition of all the gene products under one or more growth conditions. The extent of the iterative model-building process is therefore dictated and predetermined by the user who can specify a required scope and accuracy of the model to be generated.

A reconstructed biochemical reaction network can be envisioned as a model of an experimental system. In this regard, it is a duplicate of an actual organism that is capable of flexible manipulation and study under any conditions that is desirable to subject the actual organism to. One advantage of a reconstructed biosystem reaction network, or an in silico version thereof, is that it is capable of generating an immense amount of information that characterizes the function and phenotype of the organism. The accuracy of the in silico model can also be determined by, for example, using the methods described above for reconciliation and determining the consistency of the reconstructed network with that of empirical data obtained from the actual organism. The availability of both an actual organism and a reconstructed model of the organism that is readily manipulable can be used synergistically to harness the power of in silico models for reliable and accurate predictions of organism behavior and function.

An approach to reconstructing an in silico model of a biosystem is through iterative refinement of a biochemical reaction network. The refinement of a model can be accomplished by assessing a particular function of the actual organism and incorporating into the model new information gained from that particular study. Because the model is an duplicate of the organism, deviations in performance from the model compared to the actual organism when performed under similar conditions will yield data indicating that additions, omissions or revisions to the in silico that can account for the deviations. By successive iterations of studies duplicating conditions that the actual and in silico organisms are subjected to, altering the model structure to correct and be consistent with the empirical data obtained from the actual organism and repeating the condition or subjecting the pair to different conditions, the accuracy of the model to predict function and phenotype of the actual organism will successively increase.

Briefly, studies can be performed with the actual organism under defined conditions prescribed by an experiment design algorithm. Similarly, the in silico model that describes the actual organism can be used to simulate the behavior of the actual organism under the same conditions. Based on the available data at any given time, if the model fails to meet the desired scope or accuracy requirements, further studies can be performed to improve the model. These studies can be designed using, for example, a systematic procedure to stepwise or incrementally probe network function. One approach to probe network function can be, for example, to incrementally move from a robust or validated subsystem of the network to less validated parts. Another approach can be, for example, to target different types functions or different types of methods for probing function. Particular examples of such targeted methods of study include, for example, genomic knock-outs, expression profiling, protein-protein interactions, and the like. Therefore, the content and capabilities of the in silico model are subject to iterative updates.

The decision on what experiments to perform can be determined, for example, based on the nature of the deviation and the requirements in an accuracy specification. Deviations can include a gene expression array that is not predicted correctly by the model, a set of calculated flux values which does not match the experimentally-determined fluxome under given conditions, or a set of phenotypes, for example, growth, secretion and/or uptake rates, which shows discrepancy from model predictions. Experiments which could be performed to resolve such discrepancies include perturbation analysis wherein one or more genes thought to be responsible for the discrepancy are knocked out, upon which the resulting organism is characterized using transcriptomics, fluxomics and the like, or environmental analysis wherein one or more component of the extracellular environment thought to contribute to model deviations is removed and the system is re-characterized.

Algorithms can be devised that design such experiments automatically. An algorithm which can be used in the case of gene expression can be, for example (1) determine the gene(s) which exhibit a discrepancy from the predictions of the model, (2) use the regulatory network model to identify the regulatory protein(s) which control the gene(s) in step (1), (3) knockout one or more genes in the organism which encode one or more regulatory proteins (4) perform the same transcriptome experiment under the same environmental conditions but with the new knockout strain. A second such algorithm which could be used in the case of a high-throughput phenotype study with a reconstructed metabolic network could be (1) determine the phenotype(s) which exhibit discrepancy (e.g., growth rates do not correlate), (2) systematically add all biochemical reactions, one or more at a time, until the model prediction matches the observed phenotype(s), (3) identify gene locus/loci with significant sequence similarity to identified enzymes which catalyze the reaction(s) in step (2), (4) clone and characterize the gene in step (3) to verify whether it can catalyze the predicted reaction(s). The inputs algorithm are several, including the present model, the data that it has been tested against, the magnitude and nature of deviations, and so forth. The output from the algorithm can be component experiments of whole organism experiments.

An algorithm can identify, for example, missing components in the model and request that specific biochemical, protein-DNA binding, protein-protein interaction, or enzyme kinetic activity experiments be performed. As described above, the missing components in the two above examples would be regulatory interactions and identified enzymes. If these studies reveal missing components of the model appropriate model updates are performed.

An algorithm can be facilitated by, for example, the inclusion of additional data from whole cell behavior. It may request that growth, transcription profiling, metabolic profiling, DNA-transcription factor binding state, or proteomic experiments be performed under one or more environmental conditions in order to obtain sufficient information to allow model updating.

Given a set of inputs such as gene deletions or environmental inputs, the response of the biochemical reaction network can be examined both actually and computationally. The actual system will yield an observed response characterized through phenomenological pathways of the system, while the model of the actual system will predict a response characterized by the systemic pathways of the system. The observed and computed responses can be compared to identify operational pathways as described previously. The difference in the measured and computed cellular functions under the defined conditions where the experiment is performed can be characterized, for example, as an "error". This difference corresponds to those systemic pathways that are not operational. The error can then be used to update the model.

Model update also can be accomplished by, for example, using an algorithm for updating parameters in the model so that the model error is minimized. As identified in Example VI, an algorithm for characterization of a regulatory network can be, for example, (1) obtain the activity of each protein as predicted by the model, (2) for each protein, generate a rule based on the activity of the given protein which results in the correct expression value for T5a, (3) recalculate the overall expression array for the regulated genes, (4) evaluate the difference between the criterion for model accuracy by determining the new model error, and (5) choose the model(s) with the lowest error as the new model for future iterations. Following optimal model updates are implemented, the remaining "error" between corrected model predictions and actual responses can be used to design new studies to further probe the system. The process can be repeated, for example, one or more times to further update the model based on these new studies and until a desired scope or accuracy is obtained.

Model updates that can minimize error on a round of the iterative reconstruction process can be non-unique or very similar to each other in generating optimal model updates. To preserve the availability of such data and increase the efficiency of subsequent rounds, alternative model updates can be stored, for example, so that they capable of being retrieved and available for subsequent use on further rounds of iterative model building. Additionally, a collection of experimental outcomes can be stored as a historic record of the behavioral data or phenotypic data that has been obtained on a particular organism. Model updates and design algorithms can be optionally capable of querying this database during execution. Various other records and system data can be alternatively stored for later efficient utilization in one or more steps of the iterative process. Such computational approaches are well known in the art and can be routinely implemented given the teachings and guidance provided herein.

Further, combinations and permutations of the various methods of the invention can be combined in any desired fashion to facilitate the model building process or to augment a purpose or implementation of the method. Additionally, single or other "off-line" studies can be performed and the information generated used in any of the methods of the invention to facilitate, augment or optimize results or implementation. For example, in addition to studies designed for the iterative process, in some cases specific pair-wise interactions among molecules can be probed in separate off-line studies to further characterize individual molecular components.

Advantageous properties of the iterative model-building procedure include convergence of system components into an operative and optimal representation of the actual organism and efficiency of constructing such a model. Efficiency in convergence is important since it will minimize the number of studies that need to be performed.

It is understood that modifications which do not substantially affect the activity of the various embodiments of this invention are also included within the definition of the invention provided herein. Accordingly, the following examples are intended to illustrate but not limit the present invention.

EXAMPLE I

Decomposing a Set of Phenomenological Flux Distributions for the *E. coli* Core Metabolic Network in Order to Identify Operational Extreme Pathways This example shows how a set of phenomenological pathways (flux distributions) can be decomposed into dominant modes these modes can be compared with a set of systemic pathways (extreme pathways) to identify operational reaction pathways of a metabolic reaction network (*E. coli* core metabolism).

An in silico-generated metabolic flux profile of core metabolism in *E. coli* was prepared. The reactions were taken from table 6.3 of Schilling, "On Systems Biology and the Pathway Analysis of Metabolic Networks," Department of Bioengineering, University of California, San Diego: La Jolla. p. 198-241 (2000), with the exception that reaction pntAB was not included, and instead of T3P2 in reaction tktA2, T3P1 was used. The reaction list is tabulated in Table 1.

Figure 3:
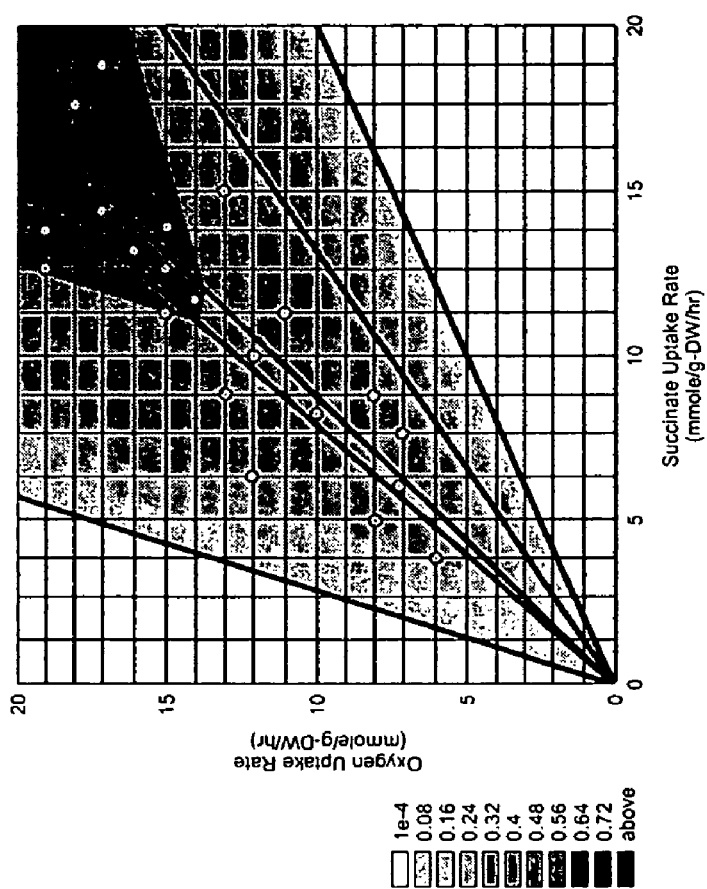
FIG. 3 shows a phase plane for succinate for an in silico-generated metabolic flux profile of core metabolism in E. coli was prepared.

The flux profile, which is the input matrix for Singular Value Decomposition (SVD) analysis, consists of 57 fluxes (rows) and 7 conditions in each phase (columns). The phase plane for succinate for this system is presented in FIG. 3; generation of Phase Planes is described in (Edwards J S, Ramakrishna R, Palsson B O. Characterizing the metabolic phenotype: a phenotype phase plane analysis. Biotechnol Bioeng. Jan. 5, 2002; 77(1):27-36). The points on FIG. 3 were chosen to define the upper limit of oxygen and succinate available to the system. Each point, therefore, represents a different condition (or column of the flux matrix) in constructing the flux profile.

SVD analysis was performed on each phase (each of the 7 conditions) separately. The decomposition of the flux matrix, A, results in three distinct matrices U (the left singular matrix), $\epsilon$ (singular value matrix), and V (right singular matrix):

$$A = U \epsilon V^T$$

Figure 4:
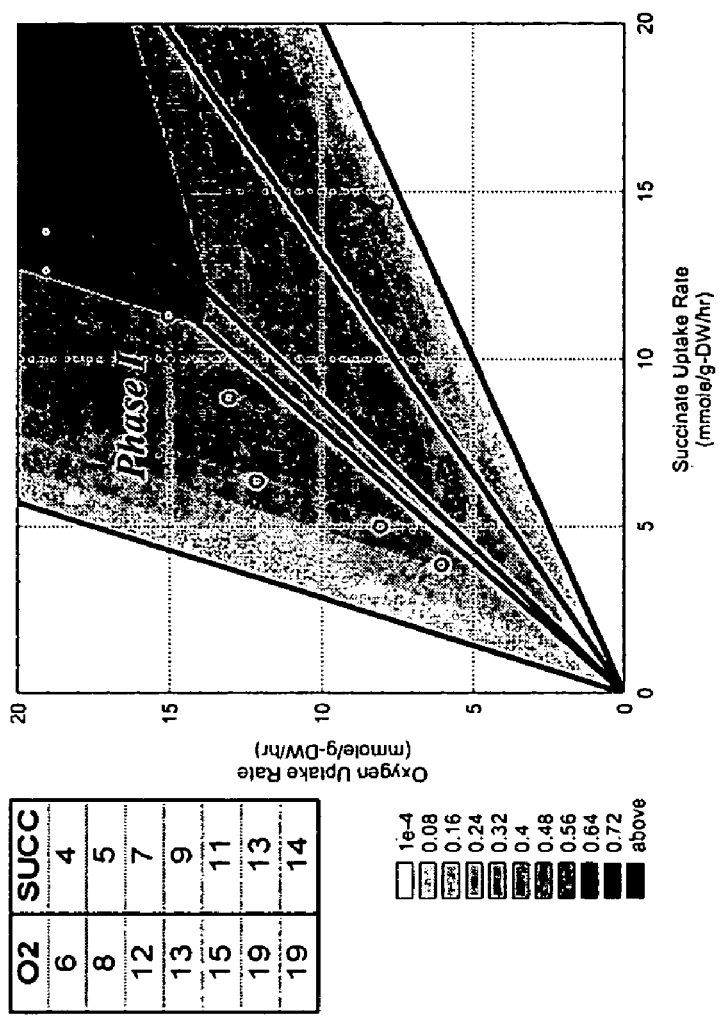
FIG. 4 shows phase I of a phase plane for a flux distribution matrix generated with the E. coli core metabolism using the oxygen and succinate input values show next to the figure.

For phase I of the phase plane, the flux distribution matrix was generated with the *E. coli* core metabolism using the oxygen and succinate input values that are tabulated next to FIG. 4. The points lie on phase I as shown.

Figure 5:
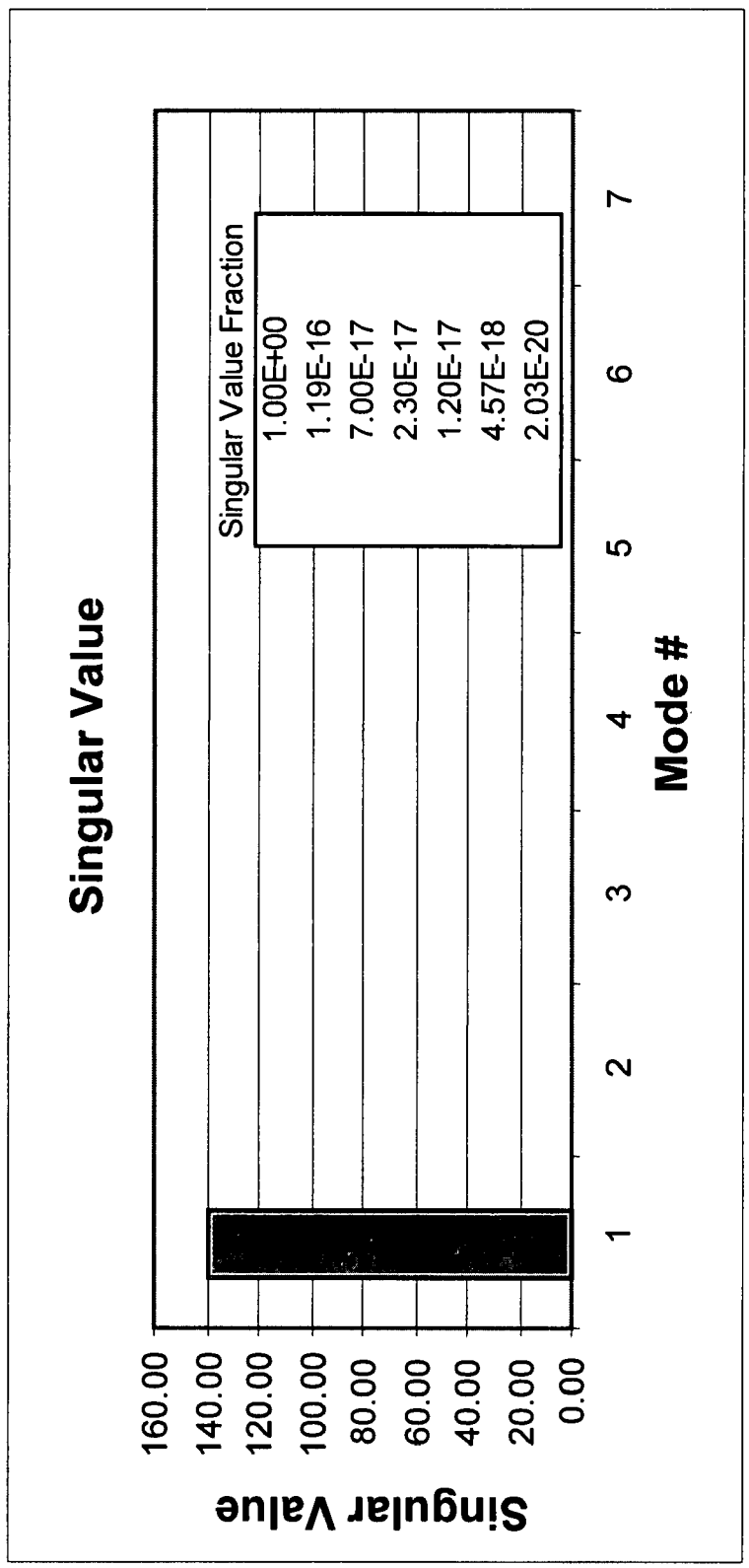
FIG. 5 shows an Singular Value Decomposition (SVD) analysis on the flux matrix shown in FIG. 4.

SVD analysis on the flux matrix revealed that there is only one dominant mode in phase I as demonstrated by the singular value fractions shown in FIG. 5. Therefore, there is a common expression that dominates nearly all of the system's behavior in this phenotypic phase, which can be called a phase invariant singular value.

Figure 6:
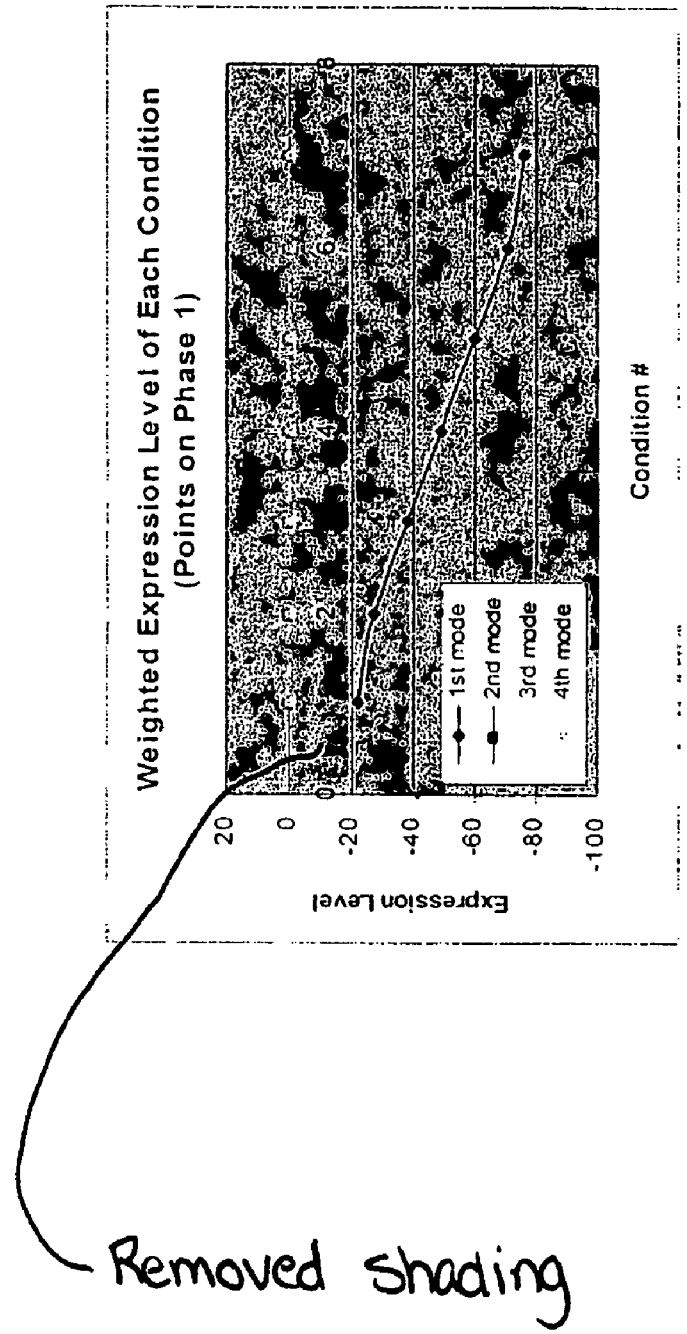
FIG. 6 shows the contribution level of each condition, or point shown in phase I of the FIG. 4 phase plane, for various modes obtained from SVD.
Figure 7:
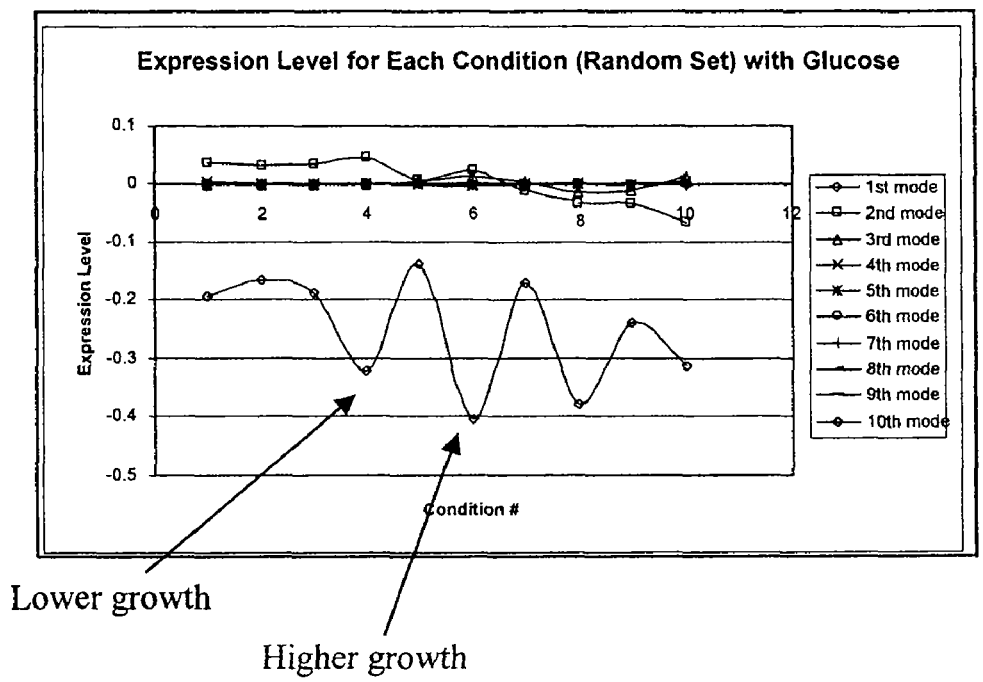
FIG. 7 shows the contribution level of each condition, or point shown in phase I of the FIG. 4 phase plane, for various modes obtained from SVD.

The contribution level of each condition (i.e. each point shown in Phase I of the phase plane) is shown in FIGS. 6 and 7 for various modes obtained from SVD. The weight that each mode has on the overall contribution of a pathway is seen by how far the curve of that mode is from the zero contribution level (horizontal zero level). Also, for each mode, the expression level increases with the condition number which shows how fluxes increase in the pathway represented by that mode. These representations provide information regarding where on the phase plane the point lies relative to other points (i.e. at a higher or lower growth rate). Thus, not only is information provided about the dominant modes, but also additional information is provided on biomass production rate. The slope of the first dominant mode ("first mode") should correspond to the slope of growth rate. The first mode captures nearly 100% of the overall contribution.

Figure 8:
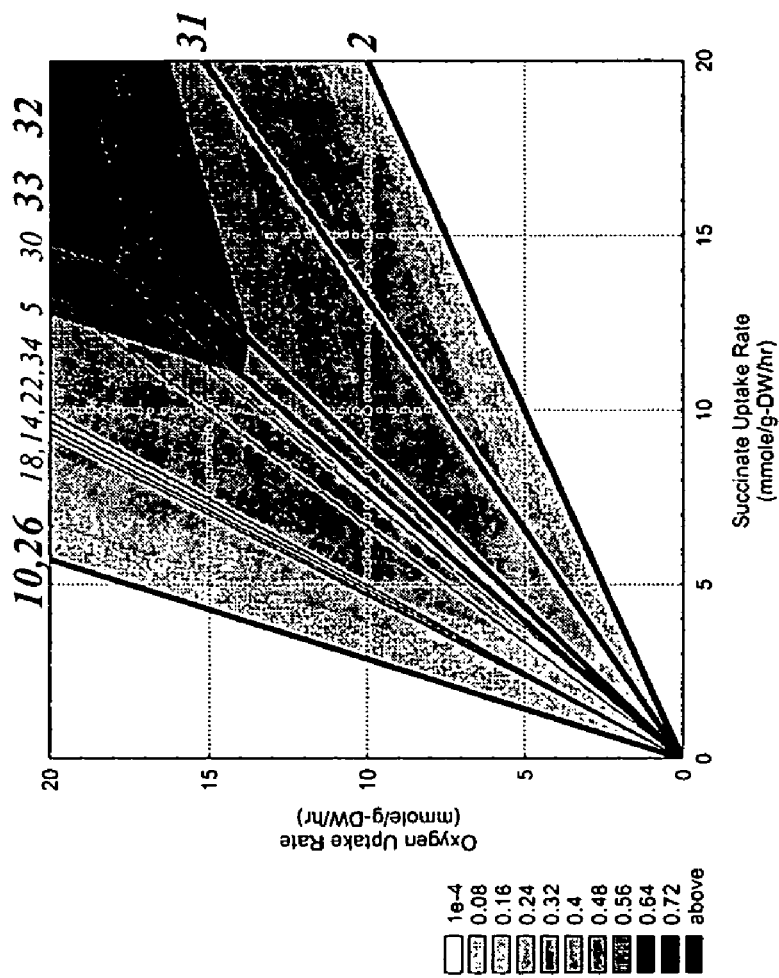
FIG. 8 shows the reduced set of extreme pathways for succinate that is presented in Table 2.
Figure 9:
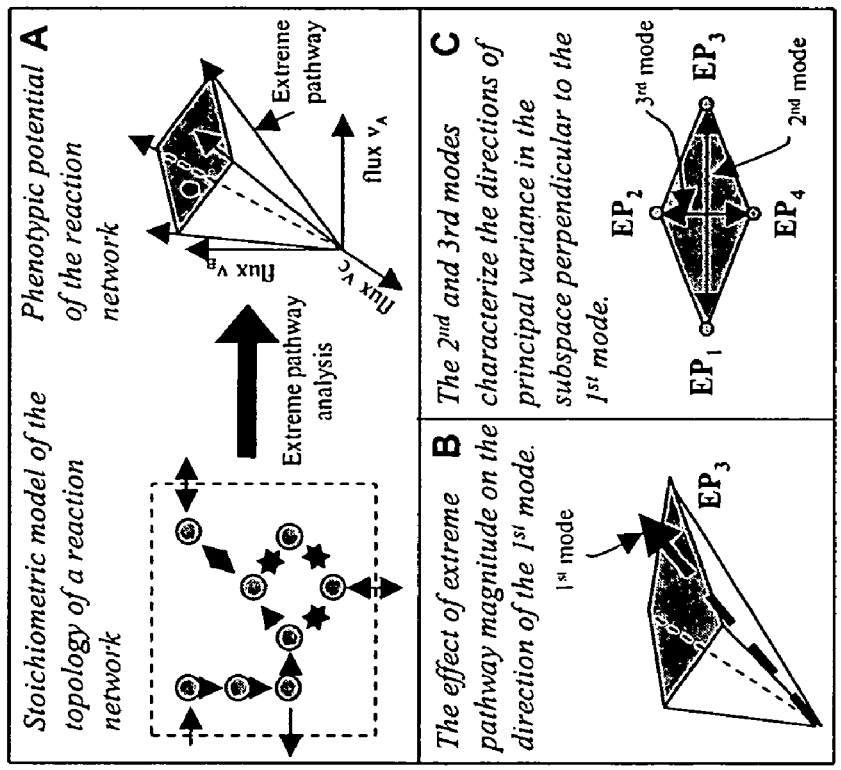
FIG. 9 shows a schematic diagram of flux balance analysis (FBA) and convex analysis to identify extreme and operational pathways of the invention.

To compare the results from SVD and with the results from pathway analysis, extreme pathways of the core *E. coli* system were calculated, using succinate as the sole carbon source. The reduced set of extreme pathways for succinate is presented in Table 2 (adopted from Schilling, supra (2000), Table 6.6) and shown in FIG. 8.

For the Phase I analysis described above, to compare the extreme pathways with the 1st mode, the genes were arranged in the same order and fluxes were normalized by succinate uptake rate. The angles between the I st mode and each of the 12 extreme pathways were calculated and sorted in descending order. Also, the number of different fluxes (i.e. fluxes that are zero in one case and non-zero in the other case or have opposite signs) and the net flux difference between the first mode and each pathway were calculated and sorted in the same fashion. Table 3 provides the results of this analysis.

This analysis shows that the first mode in phase I is exactly equivalent to the line of optimality (i.e. P_33). It also shows that following this pathway, the first mode is the closest to pathways 32, 30, and so on. Therefore, column angle not only shows what pathways best describe flux distribution in phase I in the order of similarity, but it also shows how similar they are amongst themselves.

The analysis was repeated for Phases II and III, and for all phases together. When all phases were analyzed by SVD together, again a single dominant mode was identified (FIG. 14), with relatively low entropy (4.80E-3). The angle between this mode and each of the 12 extreme pathways was calculated. Table 4 provides the results of this analysis. By this analysis, the dominant mode was closest to extreme pathways 33 and 32 shown in Table 2.

EXAMPLE II

Identifying Human Red Blood Cell Extreme Pathways Corresponding to Physiologically Relevant Flux Distributions This example shows how a set of phenomenological pathways (flux distributions) generated by a kinetic model can be compared with the modal decomposition of a set of systemic pathways (extreme pathways) to identify dominant regulatory modes of a metabolic reaction network (human red blood cell metabolism).

The extreme pathways of the red blood cell (RBC) metabolic network have been computed (Wiback, S. J. & Palsson, B. O. Biophysical Journal 83, 808-818 (2002)). Here, SVD analysis was applied to the extreme pathway matrix, P, formed by these pathways. A full kinetic model of the entire metabolic network of the RBC has been developed (Jamshidi, N., Edwards, J. S., Fahland, T., Church, G. M., Palsson, B. O.

Bioinformatics 17, 286-7 (2001); Joshi, A. & Palsson, B. O. Journal of Theoretical Biology 141, 515-28 (1991)), and was used to generate flux vectors (v) for physiologically relevant states. These flux vectors were decomposed using the modes obtained from SVD of P.

The rank of the $V_{max}$-scaled RBC extreme pathway matrix, P, was 23. The first mode represents 47% of the variance (FIG. 10F). Combined, the first five modes capture 86% of the variance of the solution space, while the first nine modes capture 95% of its variance.

Figure 10:
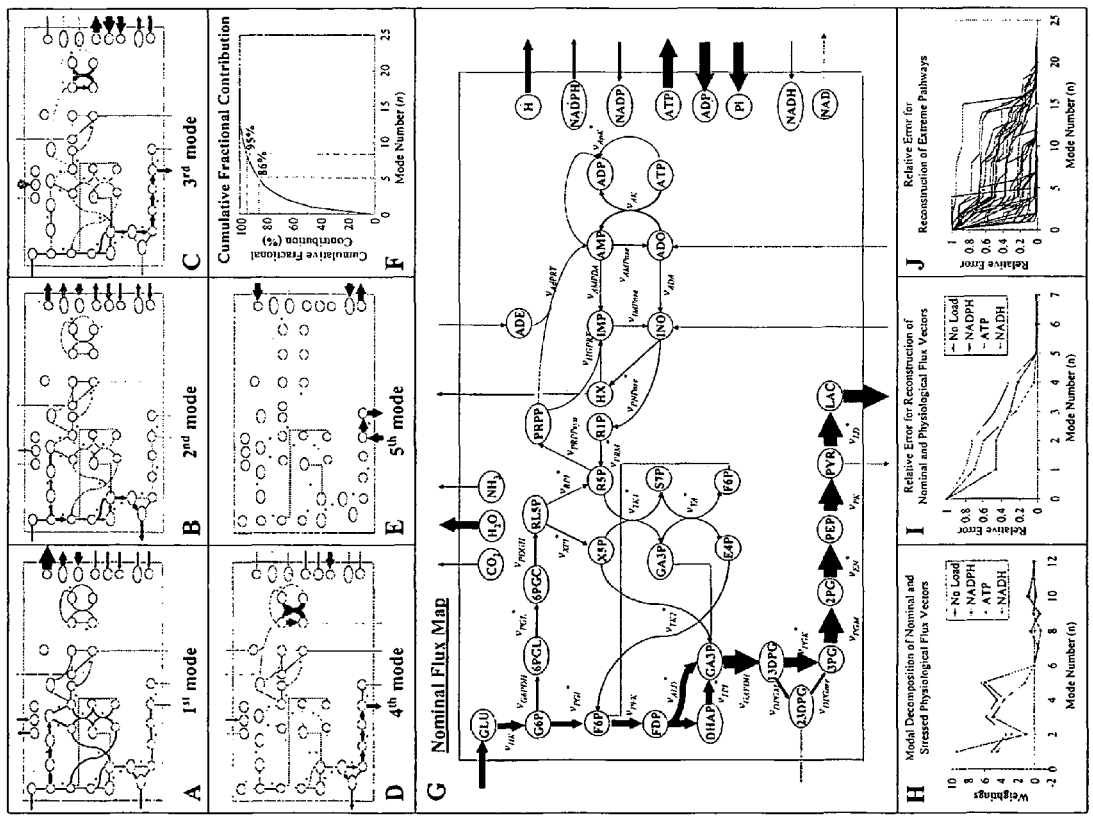
FIG. 10 shows decomposed flux vectors using the modes obtained from SVD of P for the extreme pathways of the red blood cell (RBC) metabolic network.
Figure 11:
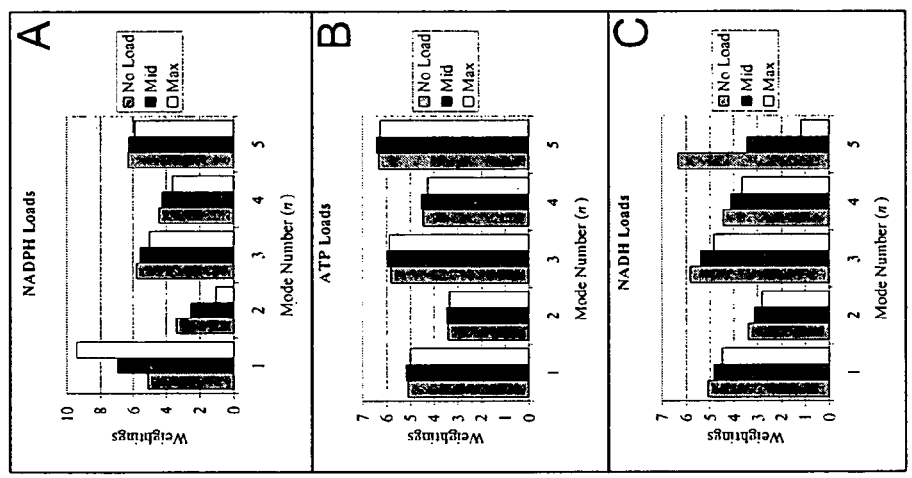
FIG. 11 shows a histogram of the first five modes of the SVD analysis shown in FIG. 10 under maximum (Max), moderate (Mid) and nominal state (no load) oxidative and energy loads.

The first five modes of P are shown on the metabolic maps in FIG. 10(A-E). The first mode shows low flux values though the adenosine reactions, higher fluxes through the glycolytic reactions, with an exit through the R/L shunt, and the highest flux levels through the pentose phosphate pathway. This map describes the principal variance of the steady-state solution space. The subsequent modes describe the next directions of greatest variance in the steady-state solution space (FIG. 10). Movement along a mode in the positive direction corresponds to increasing the fluxes shown in red and decreasing those shown in green. Since the modes are required to be orthogonal, they specifically describe the directions of variance in the cone that are independent from each other. The subsequent modes can be interpreted biochemically as follows:

The second mode describes the flux split between glycolysis and the pentose phosphate pathway. If the contribution of this mode is added to the first mode it would lead to decreased flux through the pentose phosphate pathway and reduced production of NADPH. The increased glycolytic flux exits through the Rapoport-Leubering (R/L) shunt leading to decreased ATP production since ATP is used in upper glycolysis and not recovered in lower glycolysis. The production of NADH increases.

The third mode describes the glycolytic pathway down to pyruvate with production of ATP and NADH. It also describes lowered dissipation of ATP as a consequence of AMP dissipation by AMPase. This mode has a significant ATP production.

The fourth mode describes the flux split between lower glycolysis and the R/L shunt. It thus naturally interacts biochemically with the second mode. The fourth mode further describes an increase in ATP dissipation via the AMPase-AK cycle leading to little net production of ATP, and interacts with mode three.

The fifth mode is actually one of the extreme pathways. It describes importing pyruvate and converting it to lactate, thus dissipating one NADH. It thus will be important in balancing NADH redox metabolism.

As shown below the first five modes account for most of the RBC's physiological states.

The nominal state (no additional metabolic load) of the red blood cell metabolic network was calculated using a full kinetic model and is shown on the RBC metabolic map (FIG. 10G). This nominal physiologic steady state of the RBC was decomposed into 23 modes (FIG. 10H). The relative error remaining in the reconstructed solution after the addition of each mode to the reconstruction of the nominal steady state fell sharply (FIG. 10H). After the contribution of the first five modes, the reconstructed nominal state had a relative error of 0.013 (RE(5)=0.013).

An inspection of the first five modes (FIG. 10A-E) demonstrates how they reconstruct the physiologic steady state solution. Relative to the first mode (FIG. 10A), adding the second mode (FIG. 10B) increases the flux through the first half of glycolysis, decreases the flux through the pentose phosphate reaction, and decreases NADPH production, all of which moves the reconstructed solution significantly towards the physiologic steady state (FIG. 10G). Adding the third mode (FIG. 10C) increases the flux through all of glycolysis, particularly through lower glycolysis. The addition of the fourth mode (FIG. 10D) appropriately decreases the amount of 23DPG that is produced and instead sends that flux through lower glycolysis. Finally, the addition of the fifth mode increases the flux from pyruvate to lactate, which leads essentially to the steady state solution where lactate is the primary output of glycolysis. Thus, the significant features of the physiologic steady state are captured within the first five modes. A regulatory structure that can move the solution along these five independent directions in the solution space will be able to generate the desired physiological state.

Steady-state flux distributions for two load levels of NADPH, ATP, and NADH were calculated using the RBC kinetic model. These pairs of load levels each represented the maximum load the in silico RBC could withstand, as well as one value chosen within the tolerated load range. NADPH loads simulate physiologic states corresponding to the red blood cell's response to oxidative free radicals. The maximum NADPH load is 2.5 mM/hr. The ATP loads simulate conditions of increased energy loads, such as in hyperosmotic media. The maximum ATP load is 0.37 mM/hr. Two NADH loads, important for methemoglobin reduction in the RBC, were also applied. These six computed flux vectors thus represent extreme physiological states of the RBC, and help designate the region of physiologically meaningful states within the steady-state solution space.

The modal composition of each of the six "stressed" steady state flux solutions gives significant weighting to the first five modes (FIG. 10H). In addition, some "fine tuning" appears in modes 7 to 11. All of the other modes are essentially insignificant in reconstructing these solutions to the RBC kinetic model.

The application of metabolic loads changed the weighting of the first five modes to reconstruct the appropriate metabolic flux distribution (FIG. 10H,I). Increases in the NADPH load resulted in a substantial increase of the weighting on the first mode, increasing the flux through the pentose phosphate reactions and thus elevating the production of NADPH. The weightings on the second, third, fourth, and fifth modes decrease with the application of higher NADPH loads largely because as NADPH production is maximized the flux distribution approaches that of the first mode. The reduction in the weighting of the second mode, however, is the most dramatic. The application of increasing ATP loads resulted in little change in the values of the weightings on all of the first five modes. The application of ATP load is handled in the RBC by a decrease in an ATP-consuming futile cycle, with the ATP generated instead being used instead to satisfy the load imposed upon the cell. Thus, the usage of an ATP-dissipiating futile cycle in the unstressed state of the RBC acts to dampen the effects of changing ATP loads, allowing the RBC to respond to changing ATP loads with little change in the overall flux distribution in the cell. Related experimental findings have demonstrated that the concentration of ATP in the RBC does not change much as environmental conditions change within specified limits, as a result of this buffer, but then changes dramatically when the ATP load is pushed beyond those limits. The application of the NADH loads resulted in a significant decrease of all the mode weightings because the length of the flux vector decreases. The weighting on the fifth mode decreased most dramatically since it consumes NADH when utilized in the positive direction and thus had needed to be scaled down.

After the inclusion of the first five modes, the relative error (RE(5)) of all the reconstructed solutions ranged from 0.005 to 0.018. In all six cases, the first five modes reconstructed at least 98% of the steady state solutions. Thus, the physiologically relevant portion of the steady-state solution space appears to be only 5 dimensional, and therefore there are effectively only five degrees of freedom to the problem of regulating red cell metabolism.

Decomposition of the extreme pathway vectors into the modes shows that the most important mode, in the reconstruction, is often not one of the first five modes (FIG. 10J). Thus, many portions of the allowable solution space, as defined by the extreme pathways, are poorly characterized by the first five modes, which effectively reconstruct each solution to the full RBC kinetic model. Thus, many of the extreme pathways are physiologically irrelevant and they can be identified using SVD of P, if the approximate location of physiologically meaningful solutions is known.

Study of regulation of metabolism has historically focused on the identification and characterization of individual regulatory events. Now that we can reconstruct full metabolic reaction networks we can address the need for regulation from a network-based perspective. This study has focused on interpreting regulation from a network-based perspective using singular value decomposition of the extreme pathway matrix for human red blood cell metabolism. Two main results were obtained. First, the dominant modes obtained by SVD interpret RBC metabolic physiology well. Second, the first five modes effectively characterize all the relevant physiological states of the red cell.

RBC metabolic physiology is well interpreted by the dominant modes obtained for SVD. Using the calculated modes, seven physiologically relevant solutions to the full RBC kinetic model were reconstructed. The RE(5) for these solutions was within 0.017. Thus, the first five modes can be used to essentially completely recapture each of the physiologically relevant kinetic solutions. However, most of the extreme pathways could not be reconstructed to such a high degree by the first five modes. Thus, the first five modes represented the space relevant to solutions to the full kinetic model better than they did to the space as a whole, even though they were calculated to optimize their description of the entire space. This fact suggests that developing constraints-based methods that take into account kinetics and metabolomics will result in defining a solution space that is much smaller than the space circumscribed by the extreme pathways.

The results obtained herein were based on the topology of the metabolic network and knowledge of some $V_{max}$ values. The next step to bridge the gap between the network-based results and the study of individual regulatory events is to find the best ways to pair candidate regulatory molecules and the systemic regulatory needs. In control theory this is known as the 'loop-pairing' problem (Seborg, D. E., Edgar, T. F. & Mellichamp, D. A. Process dynamics and control (Wiley, N.Y., 1989)). As a part of its solution we may have to relax the need for strict orthonormality of the modes and look for oblique modal bases that are more in line with the underlying biochemistry of the network.

Taken together, this study presents a network-based approach to studying regulatory networks and defines the degrees of freedom of the regulatory problem. This method calculates the modalities needed to enable the metabolic network to navigate its solution space and thus could be used to infer candidate regulatory loops of metabolic systems for which the regulation is largely unknown. Further, based upon their contribution to the steady-state solution space, these regulatory loops can potentially be ordered in terms of their importance to the reconstruction of the space. Network-based approaches to studying regulation, such as the one offered herein, complement component-based studies and provide a potential framework to better understand the interaction of regulatory components needed to achieve the regulatory demands of the cell.

EXAMPLE III

In Silico Assessment of the Phenotypic Consequences of Red Blood Cell Single Nucleotide Polymorphisms The following example illustrates the application of the described methods to analysis of phenomenological pathways defined through pathological data.

Figure 12:
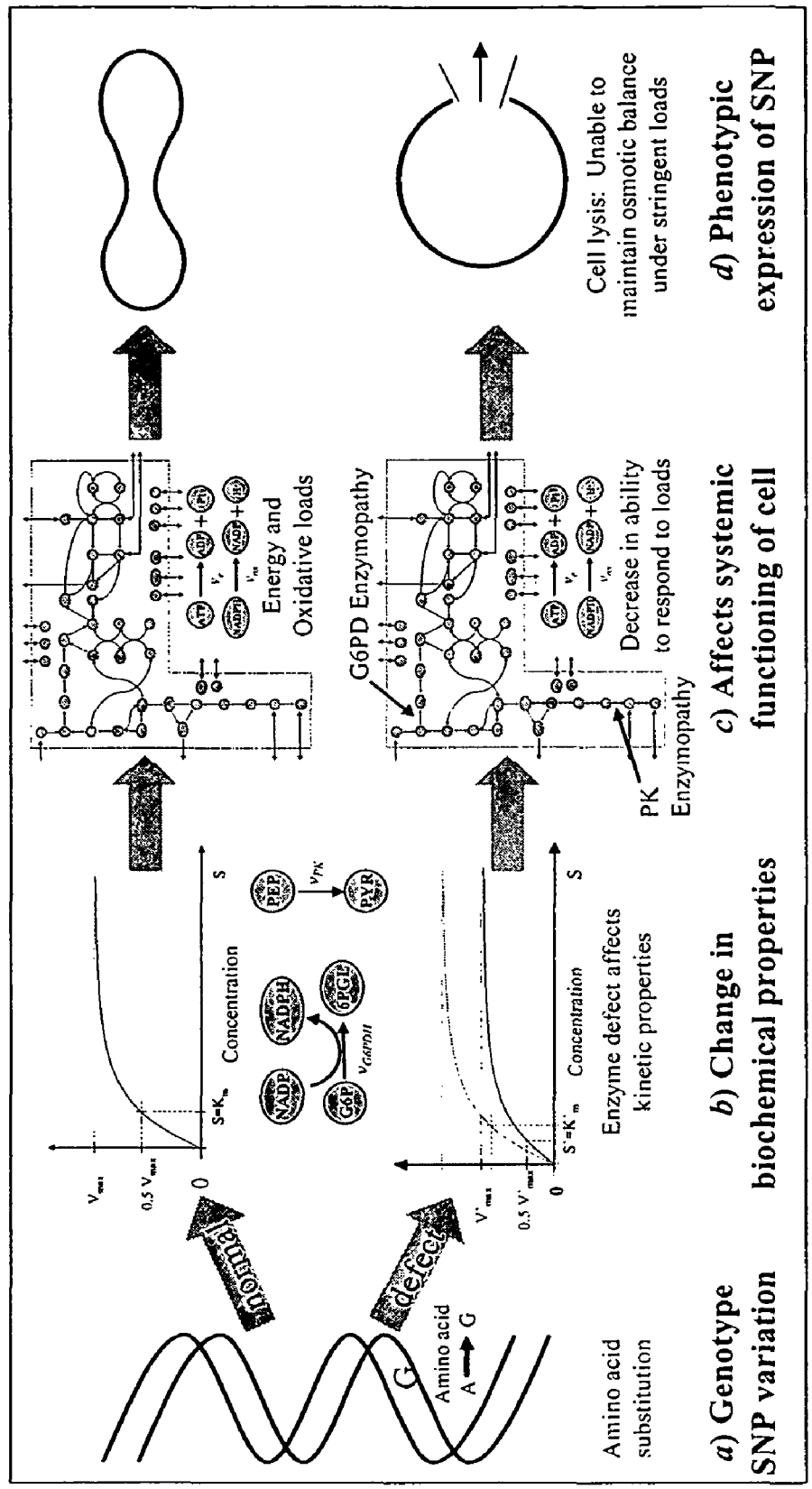
FIG. 12 shows a schematic diagram for building large-scale in silico models of complex biological processes.

The Human Genome Project (HGP) is now essentially complete. One result of the HGP is the definition of single nucleotide polymorphisms (SNPs) and their effects on the development of human disease. Although the number of SNPs in the human genome is expected to be a few million, it is estimated that only 100,000 to 200,000 will effectively define a unique human genotype. A subset of these SNPs are believed to be "informative" with respect to human disease (Syvanen, A., 2001. Accessing genetic variation: Genotyping single nucleotide polymorphisms. Nat Rev Genet 2: 930-942). Many of these SNPs will fall into coding regions while others will be found in regulatory regions. The human genotype-phenotype relationship is very complex and it will be hard to determine the causal relationship between sequence variation and physiological function. One way to deal with this intricate relationship is to build large-scale in silico models of complex biological processes (FIG. 12). Defects or alterations in the properties of a single component in complex biological processes can be put into context of the rest by using an in silico model. In this work, recent data on SNPs in key red blood cell enzymes (FIG. 12a) and corresponding alterations in their kinetic properties (FIG. 12b) were used in an in silico red blood cell model (FIG. 12c) to calculate the overall effect of SNPs on whole cell function (FIG. 12d).

The study of variations in the kinetic properties of red blood cell enzymes is not merely an academic study of the quality of a mathematical model, but has real utility in the clinical diagnosis and treatment of enzymopathies and can provide a link to the underlying sequence variation (FIG. 12). Here, an in silico model is used to study SNPs in two of the most frequent red blood cell enzymopathies: glucose-6-phosphate dehydrogenase (G6PD) and pyruvate kinase (PK).

For both enzyme deficiencies, clinical data was obtained from the published literature to determine measured values for the various kinetic parameters ($V_{max}$'s, Km's, Ki's) associated with each clinically diagnosed variant. These numerical values were then used in the iii silico model (Jamshidi, N., Edwards, J. S., Fahland, T., Church, G. M., Palsson, B. O. Bioinformatics 17, 286-7 (2001)) and sensitivities to various oxidative and energy loads (above normal, baseline values) were simulated. The results are interpreted with respect to the genetic basis of the enzymopatby in an attempt to establish a direct link between the genotype and phenotype (FIG. 12).

Glucose-6-phosphate dehydrogenase (G6PD) catalyzes the first step in the oxidative branch of the pentose pathway (FIG. 12c) and is thus of critical importance in maintaining the red blood cell's resistance to oxidative stresses. G6PD is the most common erythrocyte enzymopathy, affecting approximately 400 million people worldwide.

G6PD from normal patients and patients with hemolytic anemia have been characterized on the molecular level. A total of 61 G6PD class I variants have been described at the molecular level. Of the 61 class I chronic variants, 55 are the result of SNPs involving amino acid changes, 5 result from frame deletions and one results from a splicing defect (Fiorelli, G., F. M. d. Montemuros and M. D. Cappellini, Bailliere's Clinical Haematology 13: 35-55 (2000)).

Figure 13:
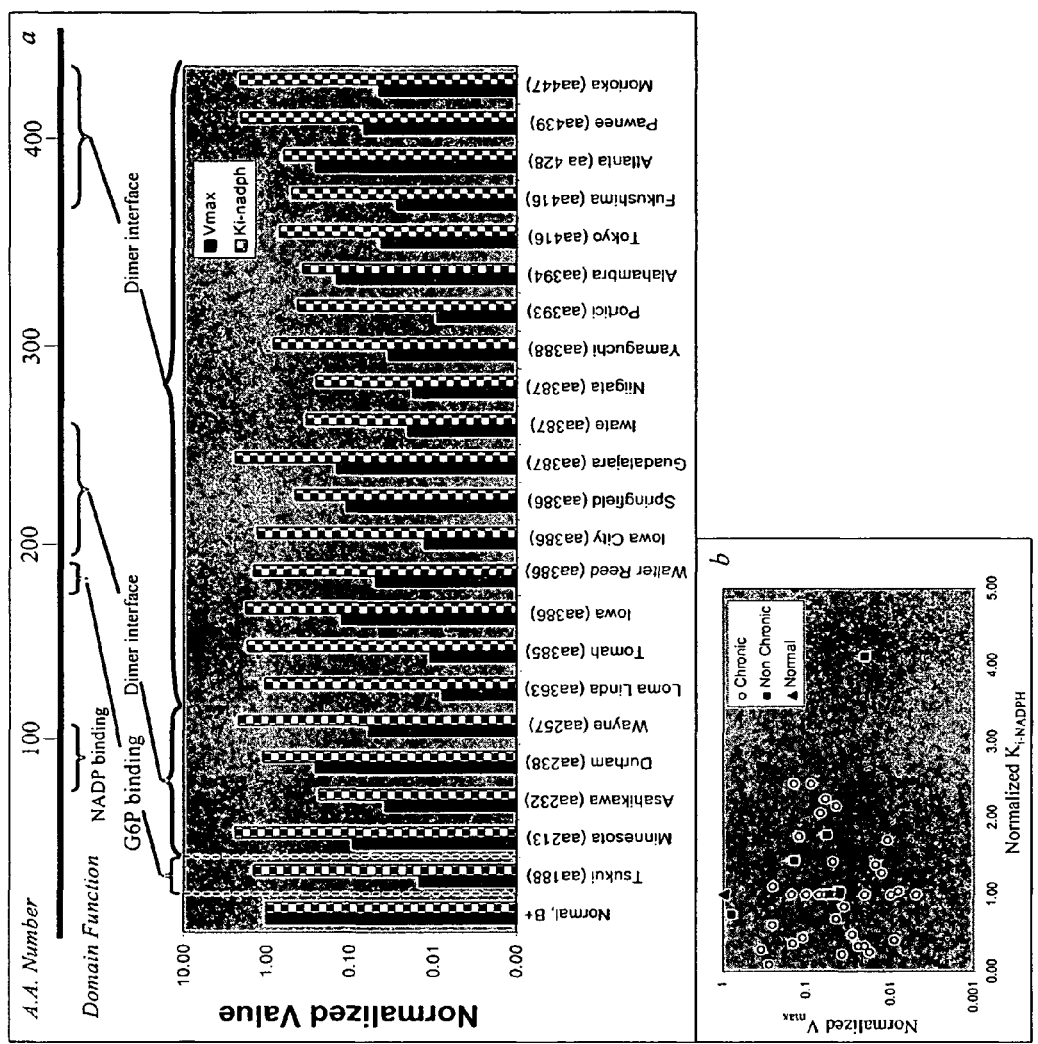
FIG. 13 shows the localization of single nucleotide polymorphism clusters found in clinically diagnosed glucose-6-phosphate dehydrogenase (G6PD) patients.

Clinically diagnosed SNPs cluster around important, active regions of G6PD enzyme including the dimer interface and substrate binding sites (FIG. 13a). Numerical values of G6PD kinetic parameters were varied in silico to determine the sensitivity of red blood cell metabolic functions to these changes in enzyme function. The most sensitive parameters were found to be $V_{max}$ and Ki-NADPH. The NADPH/NADP ratio proved to be the most informative indicator of metabolic status as it was the most sensitive to changes in these two parameters and it gives an indication as to the oxidative state of the cell (Kirkman, H. N., G. D. Gaetani, E. H. Clemons and C. Mareni, Journal of Clinical Investigation 55: 875-8 (1975)). For each documented variant there appears to be no direct correlation between $V_{max}$ and Ki-NADPH (FIG. 13b). Clinically, G6PD deficiencies are broken down into two main categories: chronic and non-chronic hemolytic anemia. Chronic cases show clinical symptoms and are very sensitive to the environment. Non-chronic cases appear normal under homeostatic conditions but can experience problems when subjected to large oxidative stresses (Jacobasch, G., and S. M. Rapoport, in Molecular Aspects of Medicine (1995)). For this study, kinetic data for 12 chronic and 8 non-chronic cases from Yoshida and 19 chronic cases from Fiorelli were used (Fiorelli, G., F. M. d. Montemuros and M. D. Cappellini, Bailliere's Clinical Haematology 13: 35-55 (2000); Yoshida, A., pp. 493-502 in Glucose-6-Phosphate Dehydrogenase. Academic Press 1995).

Figure 14:
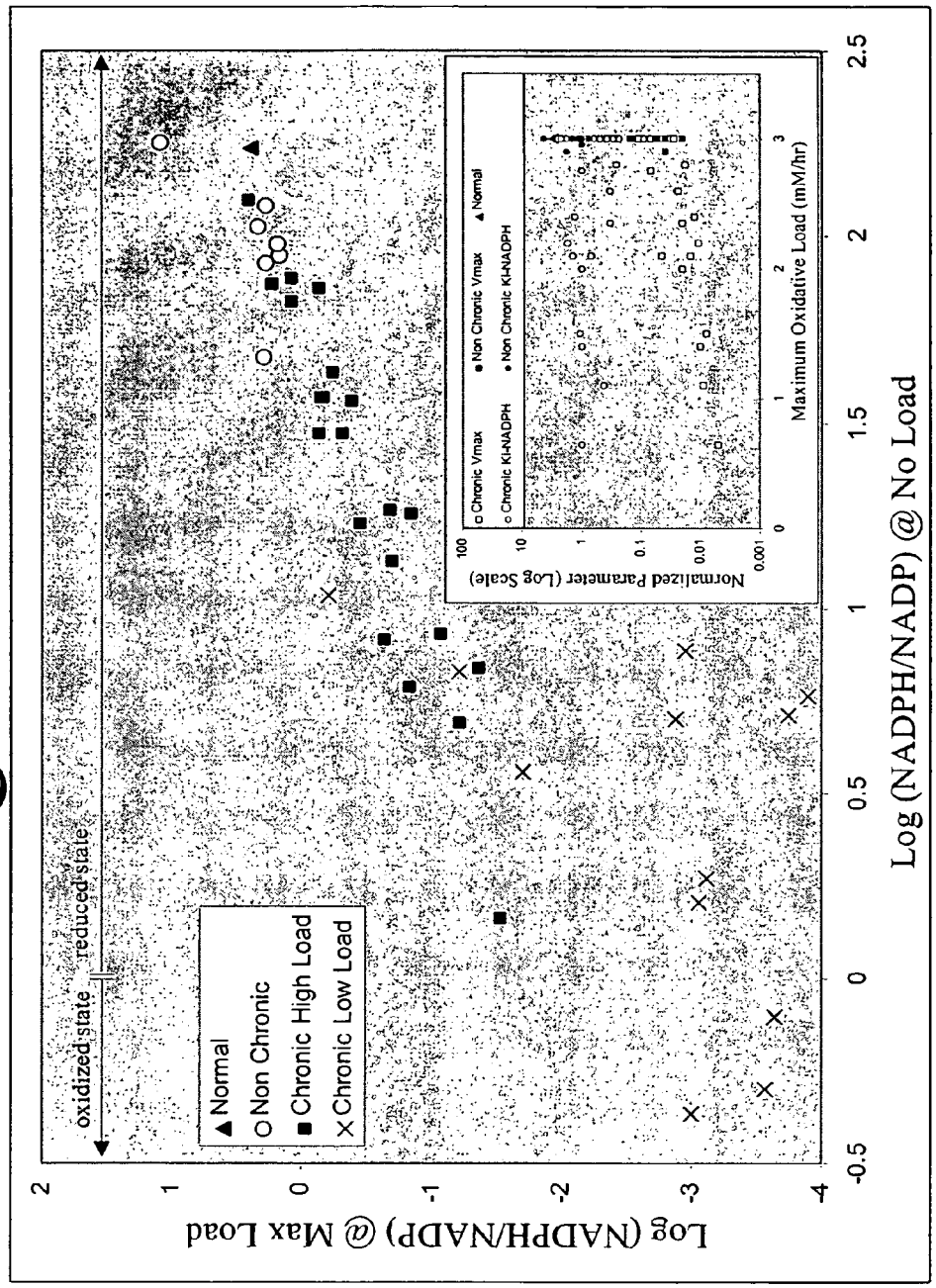
FIG. 14 shows the toleration of oxidative load between chronic and non-chronic hemolytic anemia states having G6PD SNPs.

Under normal conditions (i.e. oxidative load, $V_{ox}=0$) there are differences between the chronic and non-chronic groups with the chronic group having a somewhat lower homeostatic steady state NADPH/NADP ratio than the non-chronic group. When subjected to an oxidative load ($V_{ox}>0$), noticeable differences between the two groups (chronic and non-chronic) appear (FIG. 14). The NADPH/NADP ratio at the maximum tolerated oxidative load ($V_{ox}$=max value) correlates with this ratio in the un-stressed situation ($V_{ox}=0$). The group of chronic hemolytic anemia patients are clearly separated from the normal and non-chronic group. A number of the chronic cases can only withstand a very modest oxidative load. Of the variant cases studied, a handful have been characterized at the molecular (amino acid) level (Table 5). Of the cases considered, most of the single base changes in the chronic (class I) variants occur at or near the dimer interface (exons 10,11 and 6,7) or near the NADP binding site, leading to an impaired ability to respond to systemic oxidative challenges.

Pyruvate kinase (PK) is a key glycolytic regulatory enzyme. There have only been about 400 documented variants since PK's first description in 1961 (Jacobasch, G., and S. M. Rapoport, in Molecular Aspects of Medicine (1996); Tanaka, K. R., and C. R. Zerez, Seminars in Hematology 27: 165-185 (1990); Zanella, A., and P. Bianchi, Balliere's Clinical Hematology 13: 57-81 (2000)). PK accounts for 90% of the enzyme deficiencies found in red blood cell glycolysis. It is autosomal recessive where clinical manifestations appear only in compound heterozygotes (2 mutant alleles). There are four isozymes: L, R, M1, and M2, with the R type being exclusive to the red blood cells. PK is encoded by the PK-LR gene on chromosome 1q21. The kinetics of the enzyme have been extensively studied (Otto, M., R. Heinrich, B. Kuhn and G. Jacobasch, European Journal of Biochemistry 49: 169-178 (1974)). PK activity is regulated by F6P, ATP, Mg, and MgATP. Anemic heterozygotes have 5-40% of normal PK activity.

A summary of the PK variants is presented in Table 6. The Sassari variant only has a SNP (cDNA nt 514) transversion of a G to a C resulting in a change of Glu to Gin at aa 172 which is in between the β1 and β2 in the B domain. Here a basic (negatively charged amino acid) is replaced by a polar uncharge amino acid. Parma has 2 SNPs, one at aa 331 or 332 and another at aa 486 or 487, neither of whose amino acid changes have been elucidated yet. Soresina and Milano share the amino acid change Arg to Trp at aa 486 (positively charged to non-polar). Brescia has a deletion of Lys at aa 348 and another change at aa 486 or 487 that has not been defined yet. Mantova has an exchange at amino acid 390 Asp to Asn (negatively charged to polar uncharged). (Bianchi, P., and A. Zanella, 2000 Hematologically important mutations: red cell pyruvate kinase. Blood Cells, Molecules, and Diseases 15: 47-53; Zanella, A., and P. Bianchi, Balliere's Clinical Hematology 13: 57-81 (2000)).

Figure 15:
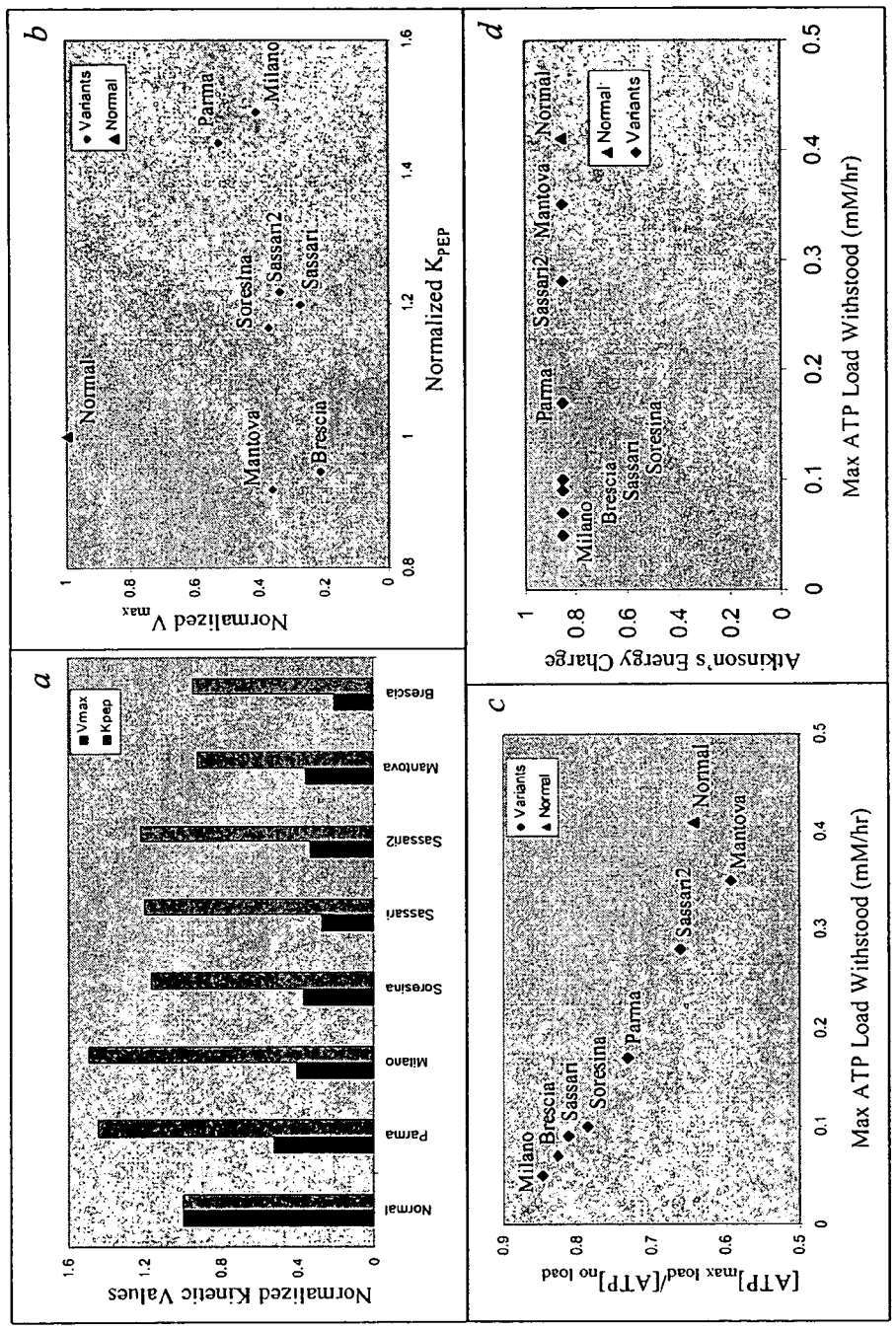
FIG. 15 shows the characterization and toleration of energy loads for glycolytic states harboring different pyruvate kinase (PK) SNP variants.

Unlike for G6PD, the characterized PK SNPs are scattered throughout the protein coding region and do not appear to cluster near the corresponding active site of the enzyme. The documented kinetic values for the main kinetic parameters $V_{max}$ and KPEP are shown (FIG. 15a). Similar to the G6PD variants, there is not a clear correlation between changes in the numerical $V_{max}$ and KPEP amongst the PK variants (FIG. 15b). Although changes in KADP are also documented for each variant and accounted for in the simulations, increases or decreases in its value did not significantly affect the red blood cell's steady state metabolite concentrations or its ability to withstand energy loads (data not shown). Changes in KPEP and $V_{max}$ influence the concentration of ATP and 2,3DPG most significantly. When increased energy loads ($V_e>0$) are applied in silico, differences between the variants are observed. The ratio between the ATP concentration at maximum tolerated load (ve=max value) and the ATP concentration in the unchallenged state ($V_e=0$) varies approximately linearly with the maximum tolerated load when all the variants are evaluated (FIG. 15c). Thus the variants that tolerated the lowest maximum load have a [ATP]max/[ATP]no load ratio close to unity indicating their sharply diminished ability to deviate from the nominal homeostatic state. Interestingly, the computed energy charge (EC=(ATP+1/2ADP)/(ATP+ADP+AMP)) (Atkinson, D. E., 1977 Cellular energy metabolism and its regulation. Academic Press, New York) stays relatively constant (FIG. 15d). This result indicates that red blood cell metabolism strives to maintain its EC within the tolerated load range, thus allowing for an energetically consistent metabolic function.

Sequence variations in coding regions for metabolic enzymes can lead to altered kinetic properties. The kinetic properties of enzymes are described by many parameters and a single SNP can alter one or many of these parameters. For the variants of G6PD and PK considered here, there appears to be no clear relationship between their kinetic parameters as a function of sequence variation. Thus consequences of sequence variations on the function of a gene product must be fully evaluated to get a comprehensive assessment of the altered biochemical function.

The consequences of many simultaneously altered enzyme properties must in turn be evaluated in terms of the function of the enzyme in the context of the reaction network in which it participates. The assessment of sequence variation on biochemical and kinetic properties of enzymes may seem difficult and this challenge is currently being addressed (Yamada, K., Z. Chen, R. Rozen and R. G. Matthews, *Proc Natl Acad Sci U SA* 98: 14853-14858 (2001)), but the assessment of sequence variation on entire network function is even more complicated. This highly complex and intricate relationship between sequence variation and network function can be studied through the use of a computer model. Here we have shown that a large number of variants in red blood cell G6PD and PK can be systematically analyzed using an in silico model of the red blood cell. Correlation between sequence variation and predicted overall cell behavior is established, and in the case of G6PD, it in turn correlates with the severity of the clinical conditions.

EXAMPLE IV

Consistency Between Known Regulatory Network Structures and Transcriptomics Data The following example illustrates the use of the described methods to validate and expand known regulatory network structures by reconciling these structures with large-scale gene expression data sets.

The availability of large genome-scale expression data sets has initiated the development of methods that use these data sets to infer large-scale regulatory networks (D'Haeseleer, P., Liang, S. & Somogyi, R, Bioinformatics 16:707-26 (2000); de Jong, H. J. Comput. Biol. 9:67-103 (2002); Yeung, M. K., Tegner, J. & Collins, J. J. Proc. Natl. Acad. Sci. USA 99:6163-8 (2002)). Alternatively, such regulatory network structures can be reconstructed based on annotated genome information, well-curated databases, and primary research literature (Guelzim, N., Bottani, S., Bourgine, P. & Kepes, F. Nat. Genet. 31, 60-3. (2002); Shen-Orr, S. S., Milo, R., Mangan, S. & Alon, U. Nat. Genet. 31, 64-8 (2002)). Here we examine how consistent existing large-scale gene expression data sets are with known genome-wide regulatory network structures in Echerichia coli and Saccharomyces cerevisiae. We find that approximately 10% of the known pair-wise regulatory interactions between transcription factors and their target genes are consistent with gene expression data in both organisms. We show that accounting for combinatorial effects due to multiple transcription factors acting on the same gene can improve the agreement between gene expression data and regulatory network structures. We also find that regulatory network elements involving repressors are typically less consistent with the data than ones involving activators. Taken together these results allow us to define regulatory network modules with high degree of consistency between the network structure and gene expression data. The results suggest that targeted gene expression profiling data can be used to refine and expand particular subcomponents of known regulatory networks that are sufficiently decoupled from the rest of the network.

The known genome-scale transcriptional regulatory network structures for yeast (Guelzim, N., Bottani, S., Bourgine, P. & Kepes, F. Nat. Genet. 31, 60-3. (2002)) and E. coli (Shen-Orr, S. S., Milo, R., Mangan, S. & Alon, U. Nat. Genet. 31, 64-8 (2002)) were obtained and pre-processed to remove autoregulation. These structures were represented as graphs with directed regulatory interaction edges between a regulator node (typically a transcription factor) and a target gene node, with the mode of regulation (activation, repression, or both) indicated for each interaction. The yeast network has 108 regulatory genes regulating 414 target genes through 931 regulatory interactions, whereas the E. coli network has 123 regulatory genes regulating 721 target genes through 1367 regulatory interactions. We used data from a total of 641 diverse gene expression profiling experiments organized into five separate data sets for yeast and 108 experiments organized into three separate data sets for E. coli.

There were three basic types of regulatory network elements analyzed in this study: 1) pair-wise regulatory interactions, 2) target-regulator units, and 3) regulons. A target-regulator unit (TRU) is defined as a single target gene together with all of its transcriptional regulators. A regulon is defined as the set of all target genes for a single transcriptional regulator. For each instance of the individual network elements present in the network, we computed a consistency measure between a particular gene expression data set and the network element structure. The particular measures we used were Pearson correlation coefficients for pairwise interactions, multiple coefficients of determination for TRUs, and average within regulon correlation for regulons. The statistical significance of a particular value of a consistency measure was determined by a randomization procedure.

The simplest elements in the regulatory network are pair-wise regulator-target interactions. Overall only a relatively small fraction (less than 10% at P<0.01) of pairwise interactions are in agreement with the gene expression data given the criteria stated above. In particular, virtually none of the repressor-target interactions are supported by any of the gene expression data sets examined. Most repressors actually have positive correlation with the expression of their target genes—not negative as would be expected for a repressor. These results for repressing pair-wise interactions highlights the problems associated with detecting transcripts expressed at a low level as a result of a transcriptional repressor bound to the promoter of the target gene.

Analysis of pair-wise correlations could overestimate correlations between transcription factor and target gene expression levels in the presence of transcriptional feed-forward loops. In such cases two or more transcription factors act on the same gene, but some of them (primary regulators) also regulate another (secondary) regulator directly. Feed-forward loops can lead to an indirect effect by which the secondary regulator-target correlation is solely due the influence of the primary regulators. In the framework used here, this effect can be accounted for by replacing standard correlation coefficients with partial correlation coefficients for secondary regulator-target interactions. Although there is a significant number of feed-forward loops in both networks (240 in yeast, 206 in E. coli), the overall effect of accounting for feed-forward loops is small (0-3 percentage points).

Target-regulator units represent more complex combinatorial effects than feed-forward loops. The percentage of TRUs consistent with gene expression data is higher than the percentage of consistent pair-wise interactions for E. coli at all confidence levels. This result indicates that combinatorial effects between transcription factors play a significant role in many cases. Conversely for TRUs in yeast, we do not observe a significant change in the percentage of units in agreement with expression data compared to the calculations that considered only pairwise interactions.

TRUs can be categorized by the number of regulators that act on the target gene. In yeast, the TRUs with four regulators are in general best supported by the gene expression data. These four-regulator TRUs include genes participating in diverse cellular functions including nitrogen utilization, oxygen regulation, and stress response. Hence the high degree of consistency observed for four-regulator TRUs does not appear to be solely due to a particular subcomponent of the network, but is a more general feature of the network structure. In E. coli, no clear dependence between the number of regulators and the fraction of consistent TRUs can be detected.

In order to investigate the agreement between regulatory network structures and gene expression data from a different perspective that does not assume correlation between the expression levels of transcription factors and their target genes, we studied the coherence of gene expression within known regulons. A large fraction of regulons (over 40%) have coherent gene expression in both yeast and *E. coli* even for the most stringent confidence level (P<0.001) in at least one data set. This result indicates that a clustering-like approach to analyzing gene expression data can indeed be expected to be successful in detecting truly co-regulated genes. The most interesting feature of this calculation is the relatively low level of regulon coherence for regulons regulated by transcriptional repressors in yeast. In contrast, *E. coli* regulons controlled by repressors tend to be more coherent than those controlled by activators.

Figure 16:
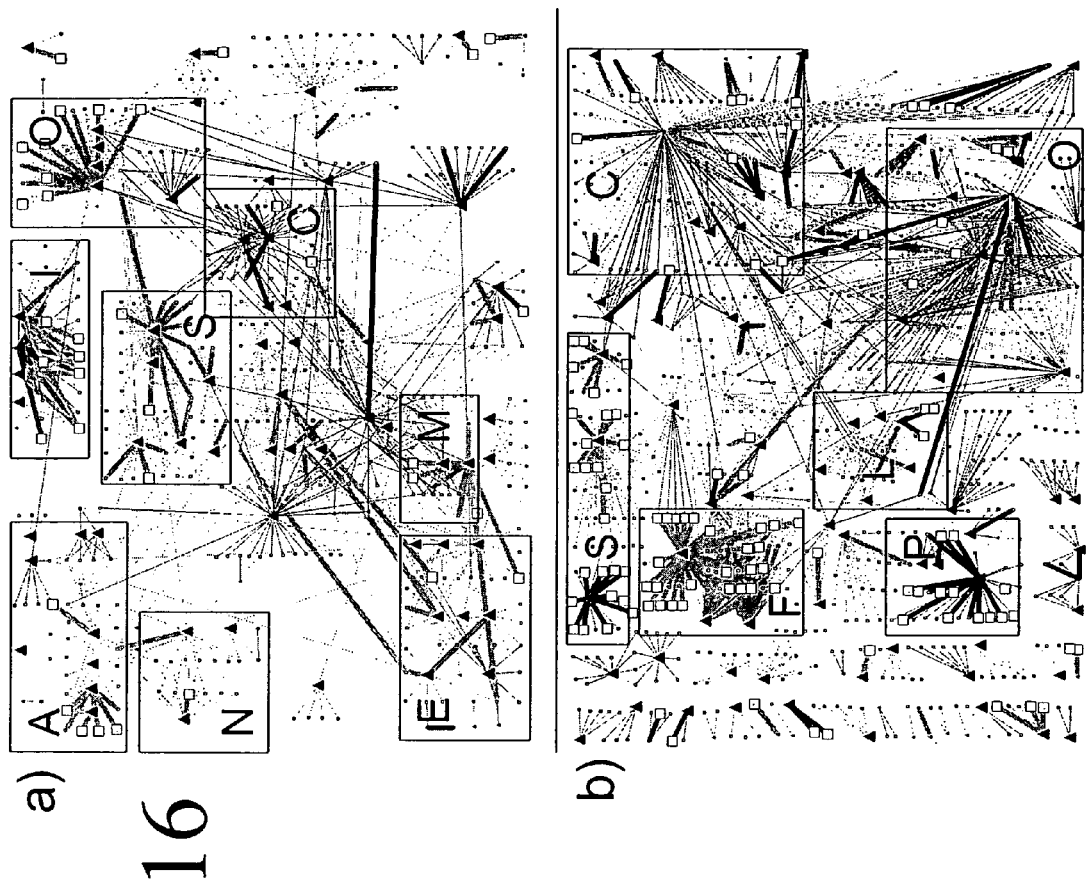
FIG. 16 shows the reconciliation of legacy and empirical data sets for regulatory networks of yeast and E. coli.
Figure 17:
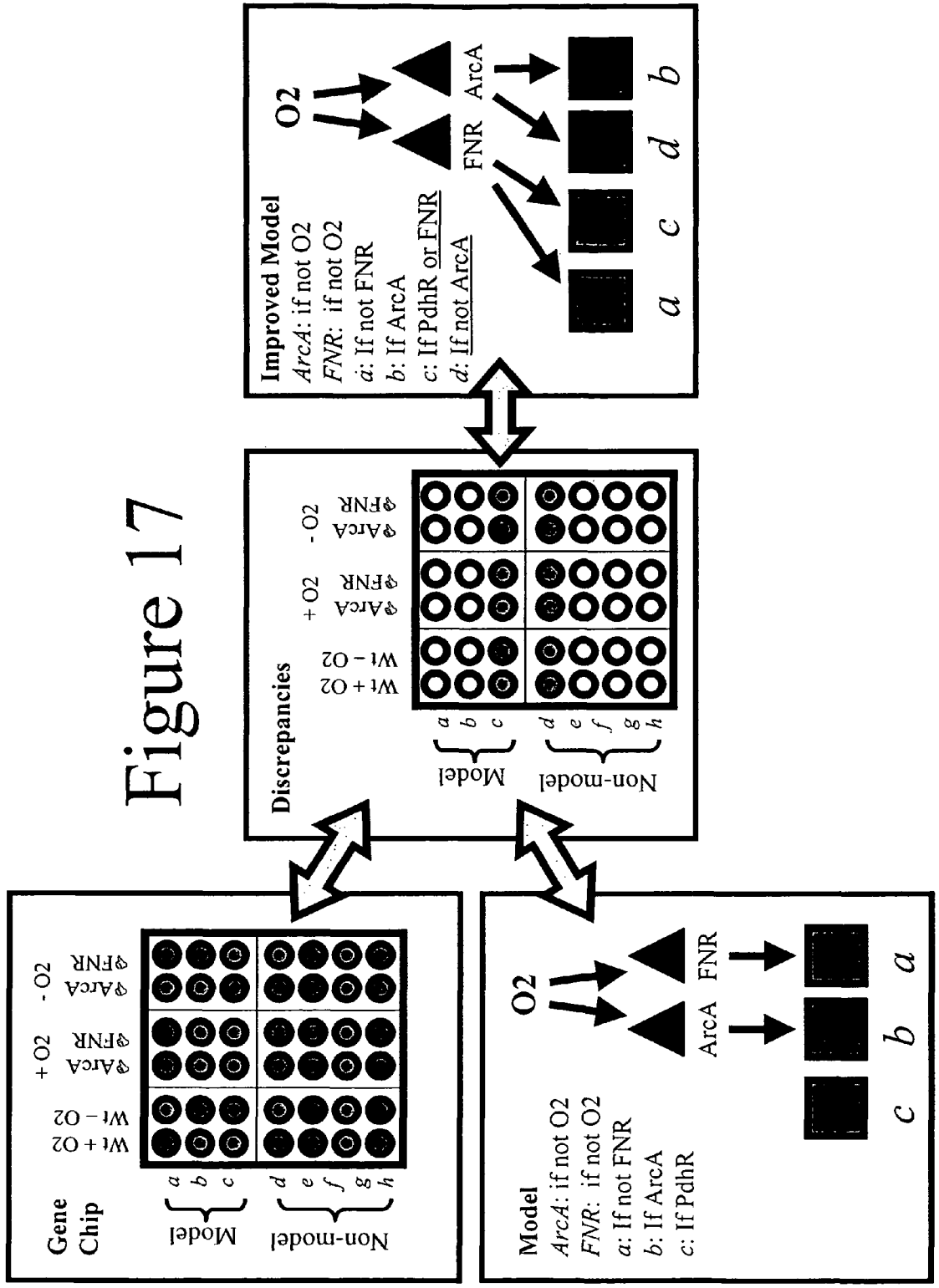
FIG. 17 shows a schematic diagram of an algorithm for reconciliation of data sets and iterative improvement of a mathematical or in silico model.

All the results described above for both yeast and *E. coli* can be displayed on a map of the regulatory network (FIG. 16). This data display allows identifying subcomponents of the networks that have high degree of agreement with the gene expression data sets analyzed. For example in yeast the nitrogen utilization (I in FIG. 16*a*) and oxygen response (O) systems have many highly consistent elements, but the elements in the carbon utilization (C) network are generally not consistent with the gene expression data. Similarly in *E. coli* components such as the flagellar biosynthesis network (F in FIG. 16*b*) are highly consistent, but the carbon utilization (C) network again does not have many consistent network elements.

Some of the variability in consistency between regulatory network structures and gene expression data appears to be due to the types of data sets utilized in this work. For example, the DNA repair system in *E. coli* was specifically activated in one of the gene expression data sets and the response to nitrogen depletion was studied in one of the yeast data set. However, there are also general network structural features that appear to influence consistency. The most prominent feature is the tendency of relatively isolated subcomponents of the network such as flagellar biosynthesis in *E. coli* or nitrogen utilization in yeast to be consistent with gene expression data whereas highly interconnected components such as carbon utilization regulation are typically inconsistent. However, not every isolated sub-network is consistent indicating that the network reconstruction may be incomplete and these subnetworks may in fact be more strongly connected to other parts of the network than is currently known.

Taken together, the results shown here indicate that combining information on known regulatory network structures with gene expression data is a productive way to validate and expand regulatory networks structures. It is important to note that, because the overall level of consistency was generally found to be low, genome-scale reconstruction of regulatory networks based on gene expression data alone does not appear to be feasible, even if large quantities of data is available as is the case for yeast. The results show that different features of the network structure influence consistency. In particular, we observe that network elements involving repressors (pair-wise interactions, regulons) are typically less consistent than those involving activators indicating that reconstruction of these types of network components would pose a challenge. Further, in yeast TRUs with four regulators are generally more consistent than other types of TRUs indicating that in such cases the known network structure appears to be sufficiently complete whereas for the TRUs with fewer regulators there may be regulators missing. The discovery of highly consistent network subcomponents indicates that a gene expression data based reconstruction of regulatory networks can be a powerful strategy for particular subcomponents that are sufficiently isolated and for which sufficient quantities of relevant data is available. Future availability of other high-throughput data types such as genome-wide DNA-binding site occupancy data (Ren, B. et al. Science 290:2306-9. (2000)) will further improve the prospects of such reconstruction as additional data types can be used to resolve inconsistencies. The full utilization of all high-throughput data types, however, will require the combination prior biological knowledge extracted from databases and literature with the statistical analysis of the large-scale data sets. Thus, full reconstruction of regulatory networks will rely on a combination of 'bottom-up' and 'top-down' approaches with targeted prospective experimentation to successively resolve inconsistencies between the two. Ultimately, all such data types are expected to be reconciled in the context of genome-scale in silico models of regulatory networks that can be used to analyze, interpreted and ultimately predict their function.

EXAMPLE V

Iterative Refinement of a Regulatory Network Model

This example illustrates how the described methods can be used for regulatory network identification, improvement and the identification of regulatory states in regulatory or combined regulatory/metabolic models.

The "bottom-up" approach to genome-scale transcriptional regulatory network model reconstruction is initiated by incorporation of knowledge into a computational model to analyze, interpret and predict phenotype. The process begins with first pass reconstruction of metabolic and transcriptional regulatory networks for the organism of interest. Reconstruction of such genome-scale models has been described elsewhere in detail (Covert M W, Schilling C H, Famili I, Edwards J S, Goryanin II, Selkov E, Palsson B O. *Trends Biochem Sci.* 26:179-86 (2001); Covert M W, Schilling C H, Palsson B. *J Theor. Biol.* 213:73-88 (2001)) and leads to the representation of metabolic behavior as a linear programming problem, with a matrix describing all known metabolic reactions, and certain measured parameters (e.g., maximum uptake rates, biomass composition) defined as constraints on the metabolic system. Transcriptional regulatory behavior is represented as a set of regulatory rules written as Boolean logic statements. These rules are dependent on environmental and internal conditions and determine the expression and/or repression of various metabolic genes in the metabolic network.

The regulatory and metabolic models are integrated as the outcomes of the logic statements impose time-dependent constraints on the metabolic linear programming problem. The outcome of the linear programming problem is then used to recalculate environmental conditions (Varma A, Palsson B O, *Appl Environ Microbiol.* 60:3724-31 (1995); Covert M W, Schilling C H, Palsson B. *J Theor Biol.* 213:73-88 (2001)), and the Boolean logic equations are reevaluated.

The Boolean logic rules are derived from the primary literature to represent the conditions required for expression of a particular gene or set of genes. Experimental studies are examined to obtain a set of potential transcription factors for all known promoters of expression of a particular target gene. The presence of multiple promoters from which transcription may occur indicates an OR relationship, and the presence of two interacting transcription factors which effect one promoter indicates an AND relationship. For example, if gene A has two promoters, one of which is activated by transcription factor X and the other which is repressed by the integrated product of transcription factors Y and Z, then a rule may be derived which states that A is transcribed IF (X) OR NOT (Y AND Z).

Such a model is in process of being built for *E. coli*. For this organism, a genome-scale metabolic network model had already been reconstructed (Edwards J S, Palsson B O, *Proc Natl Acad Sci USA*. 97:5528-33 (2000)). The regulatory network model was first implemented for core metabolic processes. The first combined metabolic/regulatory model accounts for 149 genes, the products of which include 16 regulatory proteins and 73 enzymes. These enzymes catalyze 113 reactions, 45 of which are controlled by transcriptional regulation. The combined metabolic/regulatory model can predict the ability of mutant *E. coli* strains to grow on defined media, as well as time courses of cell growth, substrate uptake, metabolic by-product secretion and qualitative gene expression under various conditions, as indicated by comparison to experimental data under a variety of environmental conditions. The in silico model may also be used to interpret dynamic behaviors observed in cell cultures (Covert M W, Palsson B O. *J Biol Chem* 277:28058-64 (2002)).

When integrated as mentioned above, the regulatory/metabolic models represent a first-pass reconstruction and may be used for the generation of testable hypotheses (see FIG. 16). First, a phenotypic or behavioral shift of interest must be specified for a particular organism (e.g., glucose-lactose diauxie in *E. coli*), as well as important regulatory genes. The regulatory/metabolic model may then be used to simulate behavior of the wild type strain over the course of the shift, as well as behavior of knockout and/or mutant strains of the relevant regulatory genes. These simulations represent hypotheses about the growth behavior, substrate uptake, by-product secretion, and gene expression over the course of the shift for each strain.

Strains of the organism are then obtained and/or constructed to build a full complement of the wild type as well as all corresponding knockout strains. Each strain is then cultured to monitor experimentally the shift in question. Rates of growth, uptake and secretion as well as gene expression are monitored over the course of the shift using practices that are well known in the art (Ideker T, Thorsson V, Ranish J A, Christmas R, Buhler J, Eng J K, Bumgarner R, Goodlett D R, Aebersold R, Hood L. *Science* 294:929-34 (2001)).

Once the necessary experimental data has been obtained, the experimental outcomes are compared rigorously to the computationally-generated data. This comparison will lead to (1) validation of certain regulatory relationships described by the model; (2) the identification of regulatory relationships included in the model but for which the experimental results were contradictory; and (3) the identification of regulatory relationships which were not previously known which must be incorporated into the model. Both (2) and (3) represent areas where the model may be improved.

Many genes are regulated by more than one transcription factor in certain organisms. Such genes correspond to complex Boolean logic rules, which must obtained by further experimentation. Specifically, for genes which are shown by the process above to be regulated by more than one transcription factor, the multiple knockout strains may be constructed, in which to determine complex interactions. If two transcription factors are required to affect the regulation of a gene, they have an AND relationship; if only one factor is required they have an OR relationship.

The method is applied to the study of anaerobiosis in *E. coli* (FIG. 16). A large-scale model of metabolism and transcriptional regulation was generated for *E. coli* previously (Covert M W, Palsson B O, *J Biol Chem* 277:28058-64 (2002)). This model will be built up to the genome-scale and used to generate predictions about growth, uptake and secretion rates as well as gene expression of *E. coli* under conditions of aerobic and anaerobic growth in glucose minimal media. Six strains—the appY, soxS, oxyR, fnr and arcA knockout strains as well as the wild type—will be grown in batch culture as described above, with growth, uptake and secretion monitored continually. A sample will be taken at mid-log phase from which the mRNA will be extracted and analyzed using Affymetrix Gene Chip technology. From this data, the model will be evaluated both in terms of regulation (e.g., its ability to predict gene induction/repression) and metabolism (e.g., its ability to predict growth behavior of the wild type and mutant strains). This information will then be used to iteratively improve the model in terms of anaerobiosis prediction.

EXAMPLE VI

Iterative Refinement of a Regulatory Network Model Via a Systematic Model Improvement Algorithm The purpose of this example is to illustrate the importance of the systematic approach described above and depicted in FIG. 2B to converge quickly on the best model of a biological process. Although a hypothetical regulatory network is used here as an example, this process is equally applicable to metabolic networks, signaling pathways, protein interaction networks and any other biological processes.

Figure 18:
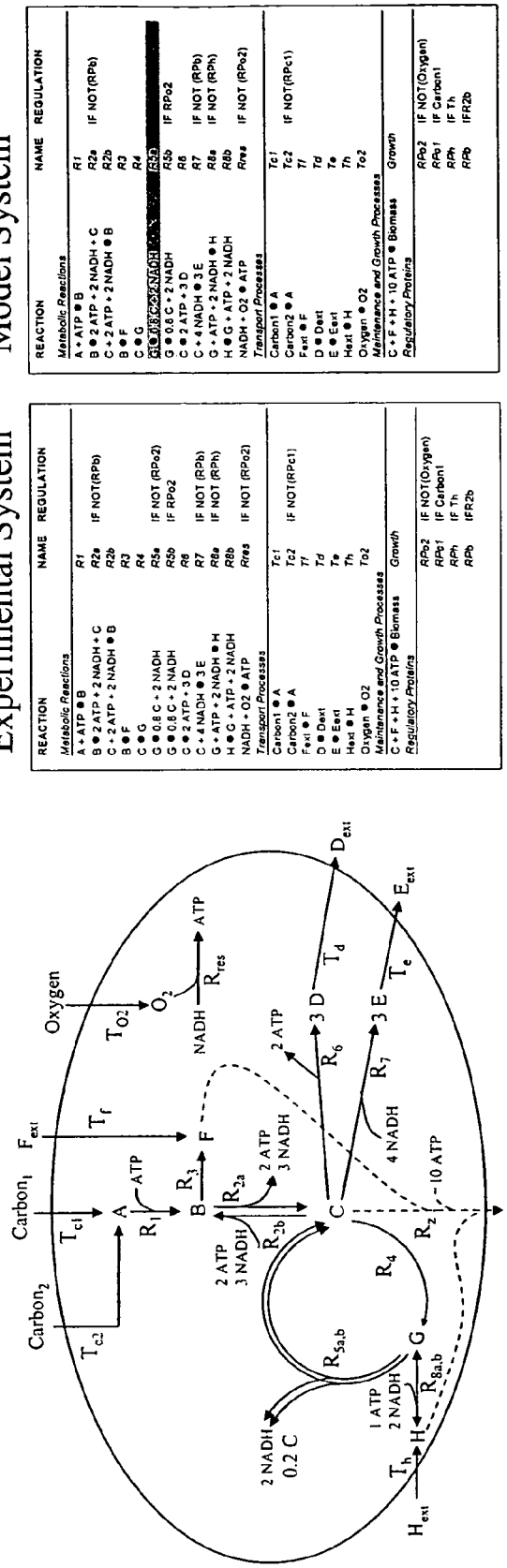
FIG. 18 shows a skeleton network of core metabolism and regulation, together with a table containing relevant chemical reactions and regulatory rules which govern the transcriptional regulation.

A skeleton network of core metabolism was formulated earlier (Covert M W, Schilling C H, Palsson B. *J Theor Biol.* 213:73-88 (2001)). It includes 20 reactions, 7 of which are governed by regulatory logic. This network is a highly simplified representation of core metabolic processes (e.g. glycolysis, the pentose phosphate pathway, TCA cycle, fermentation pathways, amino acid biosynthesis and cell growth), along with corresponding regulation (e.g. catabolite repression, aerobic/anaerobic regulation, amino acid biosynthesis regulation and carbon storage regulation). A schematic of this skeleton network is shown in FIG. 18, together with a table containing all of the relevant chemical reactions and regulatory rules which govern the transcriptional regulation. In terms of FIG. 2B, this network will be considered the actual experimental system which is to be characterized.

To the right of the experimental system in FIG. 18 is the model of the experimental system. The model is fairly complete, with one exception: the regulation of R5a in the model has not been correctly characterized, with no regulatory rule given (i.e., the reaction is expressed under all conditions).

A statement of scope and accuracy is determined for the model; namely, that the model will model the entire transcriptional regulatory component of the system qualitatively, using Boolean logic, where a "1" indicates that the gene corresponding to a given reaction has been expressed and a "0" indicates that the gene has been down-regulated. The experiments of interest are growth of the system on metabolite Carbon2 under aerobic and anaerobic conditions. For this example, the criterion for the desired accuracy of the model is that the model error, calculated as the sum of the squared difference between the observed and predicted expression of all regulated genes in the system, is equal to zero.

In Phase I of the process, an experiment is run with Carbon2 and Oxygen available to the system. The expression of the regulated genes in the experimental and model system are calculated and shown in FIG. 19. The model error is equal to zero in this case, indicating that the experimental data and the model predictions agree completely in this case.

Next, an experiment is run with Carbon2, but not Oxygen, available to the system. In this case, there is a discrepancy between the observed and calculated expression of T5a, resulting in an error of one. Because the model error is greater than allowed by the stated criterion, a procedure is implemented to alter the composition of the mathematical model in such a way that the model error is minimized under the given experimental conditions. The procedure used in this case is developed with the following assumption: the regulation of T5a depends on only one of the known regulatory proteins (RPc1, RPb, RPh, and RPO2) in the system. The procedure is therefore as follows: (1) Obtain the activity of each protein as predicted by the model, (2) for each protein, generate a rule based on the activity of the given protein which results in the correct expression value for T5a, (3) recalculate the overall expression array for the regulated genes, (4) evaluate the difference between the criterion for model accuracy by determining the new model error, and (5) choose the model(s) with the lowest error as the new model for future iterations.

Figure 19:
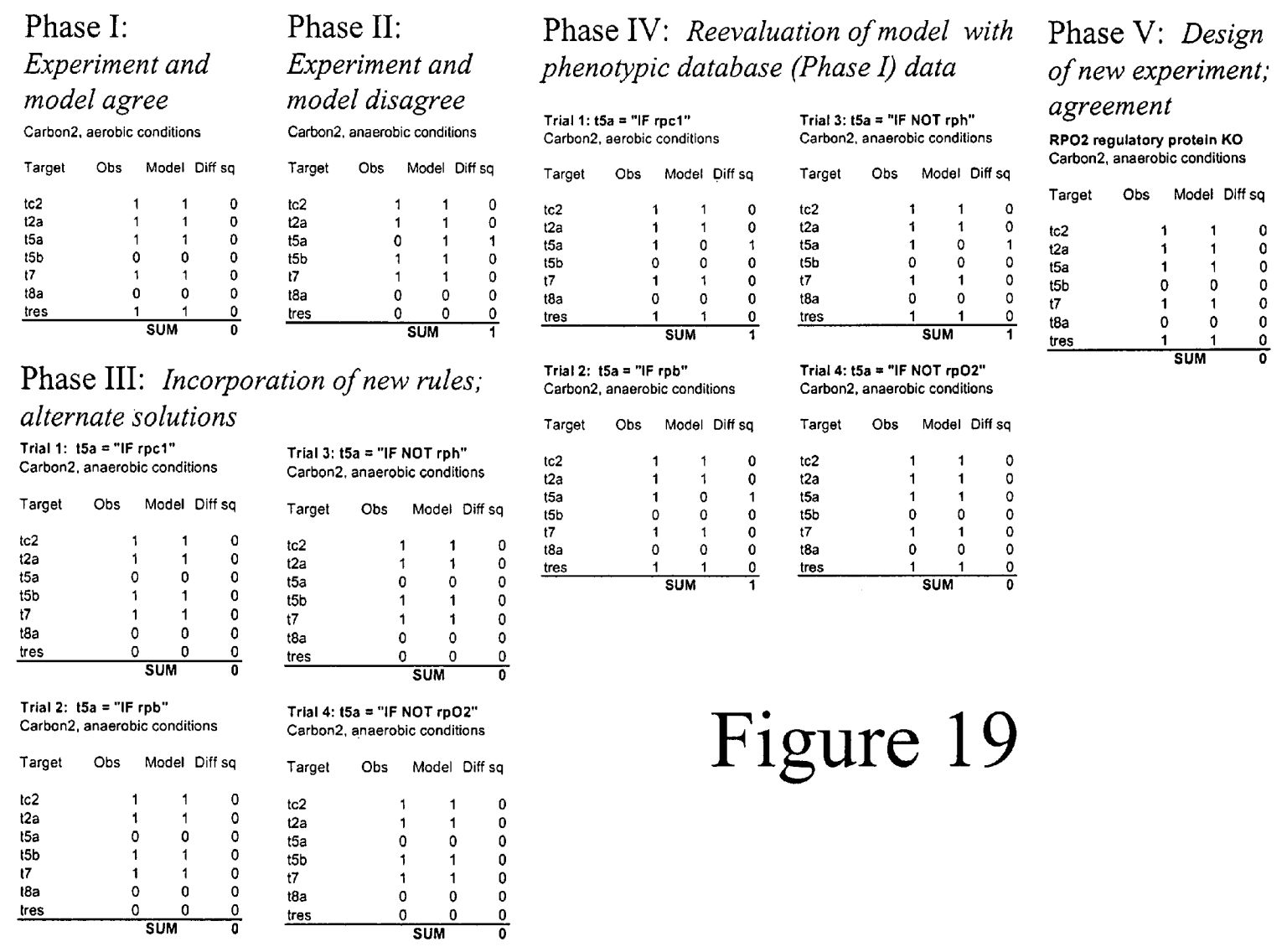

The activity of the regulatory proteins under the given conditions are: RPc1=0, RPb=0, RPh=1, RPO2=1. For T5a to have a value of zero, the rules which could be implemented are therefore: T5a=IF (RPc1), T5a=IF (RPb), T5a=IF NOT (RPh), and T5a=IF NOT (RPO2). The error of the model is calculated with each new rule; and the new models all have an error of zero, as shown in FIG. 19 (Phase III). As a result, one of the models (with new rule T5a=IF (RPc1), for example) is picked arbitrarily and the other equivalent solutions are stored.

The new model may then be reevaluated with data in the Phenotypic database. For this example, data from the experiment where Carbon2 and Oxygen were available to the system is compared to the predictions of the new model. The new model has an error with respect to these conditions (shown in Phase IV of FIG. 19); as the other alternative solutions are considered, only the model with new rule T5a=IF NOT (RPO2) fits the data with zero error. This model is kept for future iterations.

The process suggests a new experiment to further characterize the regulatory network: specifically, creating a RPO2 knockout strain of the system and testing the ability of the knockout strain to grow where Carbon2 is available but Oxygen is not. As shown in FIG. 19, the model predictions and experimental data are also in agreement for this experiment.

The model has therefore been used to drive an experimental process where new data has been generated to improve model predictions and better characterize the experimental system itself, as well to suggest a new round of experiments which can be performed to gain further knowledge and insight.

EXAMPLE VII

Decomposing Steady State Flux Distributions into Extreme Pathways Using the Alpha-Cone Method This example shows how an arbitrary steady state phenomenological flux distribution can be decomposed in a principled fashion into systemic pathways (here extreme pathways) to identify operational pathways in a biosystem. The alpha-cone decomposition method allows identifying the range of systemic pathway weightings for a given flux distribution as well as defining the minimal set of systemic pathways required to describe a phenomenological pathway. This minimal set of systemic pathways together with the range of possible weightings of these pathways defines the operational pathways of the biosystem.

The sample metabolic network used for this analysis has been published previously (Covert M W, Schilling C H, Palsson B. *J TheorBiol* 213:73-88 (2001)). The network consists of 20 reactions and 16 internal metabolites. The example network was designed to mirror some of the core metabolic processes such as glycolysis, the citric acid cycle, and respiration. The extreme pathways of this network were calculated previously (Covert M W & Palsson B O. *J Theor Biol* 216 (2003)). The network has 80 Type I extreme pathways that are included in this analysis. Each extreme pathway, pi, was scaled to its maximum possible flux based on the maximum value of the uptake reactions ($V_{max}$). A matrix P is then formed using $p_i$ (i=1 . . . n, where n is the number of extreme pathways for the system) as its columns.

To mimic phenomenological flux distributions produced by experimental measurements the steady state flux distributions for this network were calculated using the well-established technique of flux balance analysis (FBA). For the purposes of this study, unique steady state flux distributions were calculated for various environmental conditions.

For a given phenomenological flux distribution the decomposition weightings on the extreme pathways (denoted by a) are not usually unique. The rank of the P matrix determines the number of consistent equations and is usually smaller than the number of extreme pathways, resulting in extra degrees of freedom. This results in an "alpha space" of allowable extreme pathway weightings. In order to elucidate the range of possible alpha values that could contribute to the steady state solution, the alpha-spectrum was developed based on the equation $P.\alpha=v$ where P is a matrix of extreme pathway vectors (extreme pathways are the columns, reactions are the rows), $\alpha$ is a vector of alpha weightings on the pathways and v an arbitrary steady state flux distribution that is to be decomposed. For each individual extreme pathway defined for the network, the alpha weighting for that pathway was both maximized and minimized using linar programming while leaving all other extreme pathway alpha weightings free. This resulted in an allowable alpha range for each extreme pathway. The results were then plotted on a 2-dimensional graph with the extreme pathways on the x-axis and the range of alpha weightings on the y-axis. Since the pathways are normalized to $V_{max}$, the alpha weightings correspond to a percentage usage of each extreme pathway. Some extreme pathways are not used while others can have a range of alpha weightings.

In addition to defining the alpha-spectrum, mixed integer linear programming (MILP) (Williams, H P Model building in mathematical programming. Chichester; New York, Wiley (1990)) was used to find the minimum number of extreme pathways that were needed to describe a given phenomenological flux distribution in cases where multiple pathway combinations exist. The usage of a specific extreme pathway was represented by a Boolean variable ($\beta_j$ which was assumed to have a value of when the corresponding pathway is used and zero when the pathway is not used. The sum of all Boolean variables representing pathway usage was minimized to obtain the alpha weightings corresponding to the case where the least number of pathways was used. The corresponding optimization problem can be formally described as:

$$\text{Min} \sum_{i=1}^{N_P} \beta_i$$

$$P\alpha = v$$

$$0 \le \alpha_i \le \beta_i$$

where β is the vector of the Boolean variables corresponding to the pathway usage and α is the vector of the pathway weightings. The solution is a set of alpha weightings such that the minimum number of extreme pathways are used to obtain the decomposition of the desired phenomenological flux distribution.

Figure 20:
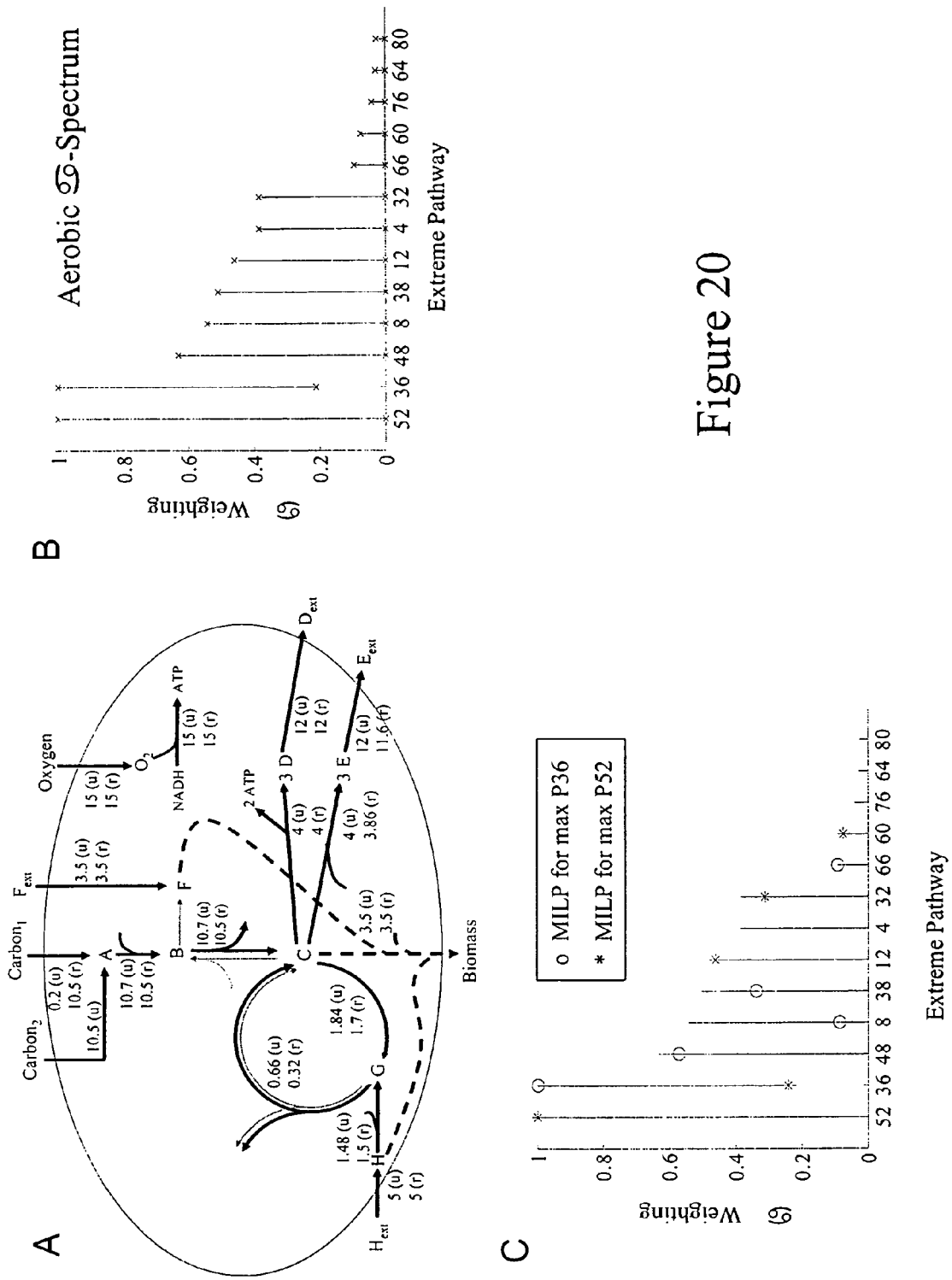
FIG. 20 shows computed flux distributions using flux balance analysis (FBA) for the aerobic growth without regulation using an in silico model of the invention.

The methods described above were applied to the case of aerobic growth with no regulation included. This case was essentially unrestricted as all possible substrates (Carbon 1, Carbon 2, F, H, and Oxygen) were provided to the network. The resulting flux distribution computed using FBA can be seen in FIG. 20A. The calculated alpha-spectrum shows that of the 80 Type I pathways, only 13 could be used in reconstructing the aerobic flux distribution (FIG. 20B). Pathway 52 can range from 0 to 1 (0 to 100% of its maximum possible usage). Pathway 36 must be used as indicated by the non-zero minimum alpha value. The remaining 11 pathways vary from 0 to various sub-maximum values. An MILP analysis was done to determine the minimum number of pathways needed to produce the aerobic steady state flux distribution. When the MILP was solved without additional constraints, P36 was used to its maximum capacity (100%) with sub-maximal contributions from pathways 48, 38, 66, and 8. Interestingly, when the network was forced to maximally use the pathway with the greatest alpha range (P52), pathway 36 was also used, albeit sub-maximally, along with pathways 12, 32, and 60. Note that with the exception of P36, which has a non-zero minimum possible weighting and thus has to be used in all possible solutions, there are no pathways in common between the two sets of MILP solutions (FIG. 20C).

While the alpha-cone method was demonstrated above for a flux distribution obtained through an FBA calculation, it is be possible to use experimentally determined metabolic flux data in the analysis as well. Even given partial or fragmented flux data, it will be possible to determine the candidate alpha-spectrum and hence obtain the operational pathways active in a cell in a given external condition.

EXAMPLE VIII

Integrating High-Throughput and Computational Data for the Elucidation of Bacterial Networks This example shows the reconciliation and single-iteration refinement of high-throughput data sets with a genome-scale computational model for identification and refinement of networks and expansion of a model of a cellular biosystem.

Briefly, an integrated genome-scale in silico model of a transcriptional regulatory and metabolic network was reconstructed based on literature and database derived information. The model accounts for 1,010 genes in *Escherichia coli*, including 104 regulatory genes, whose products together with other stimuli regulate the expression of 479 of the 906 genes in the reconstructed metabolic network. The in silico model was able to predict the outcomes of both high-throughput growth phenotyping and gene expression experiments as well as indicate knowledge gaps and identify previously unknown components and interactions in the regulatory and metabolic networks. These results further corroborate the methods described that genome-scale experimentation and computation information can be combined to accurate in silico models of biosystems.

Reconciliation and refinement of a genome-scale model was performed by validating a genome-scale model or in silico strain of *E. coli* such as that described in the previous Examples or such as the strain iJR904 reported by Reed et al., *Genome Biol.* 4, R54.1-R54.12 (2003). Reconciliation and refinement for this study was performed using the genome-scale model iMC1010$^{v1}$, constructed initially on legacy data. Validation of iMC1010$^{v1}$ was performed against a data set of 13,750 growth phenotypes (Bochner, B. R., *Nature Rev. Genet.* 4:309-314 (2003)) obtained from the ASAP database (Glasner et al., *Nucleic Acids Res.* 31:147-151 (2003)), and the validated model was subsequently used to select transcription factors for prospective gene knockout modifications.

The computational model of the *E. coli* metabolic and regulatory network was constructed by identifying network components, their functions, and interactions from the primary literature as described in the above Examples and also in, for example, Reed et al., (2003), supra; Covert and Palsson, (2002), supra, and Reed and Palsson, *J. Bacteriol.* 185, 2692-9 (2003). Growth and gene expression simulations were performed using regulated flux-balance analysis, which combines linear optimization to determine a growth-optimized metabolic flux distribution, and logic statements to simulate the effects of regulatory processes over time. Construction and simulation of the model was performed as described in the above Examples and in Covert et al., (2001), supra.

The parent strain for knockout strains in this study was K-12 MG1655, and all deletion strains were generated using the method described by Datsenko and Wanner, *Proc. Natl. Acad. Sci. USA* 97:6640-5 (2000). Growth experiments for the gene expression study were performed on M9 glucose medium (2 g/L) under aerobic and anaerobic conditions, as described by Edwards et al., *Nat. Biotechnol.* 19:125-130 (2001). The growth data contained in the ASAP database was obtained using high-throughput phenotype arrays (Biolog, Inc., Hayward, Calif.; Bochner, B. R., *Nature Rev. Genet.* 4:309-314 (2003). In certain cases, such as where the viability of a particular environment was unclear from the phenotype array data, cross-validation was performed on the ASAP phenotyping data by culturing the wild-type strain under the given conditions. A further description of these results is set forth below in Example IX.

For gene expression profiling and analysis, samples were RNA-stabilized using Qiagen RNAProtect Bacterial Reagent, and total RNA was isolated from exponentially growing cells using a Qiagen RNeasy mini kit as recommended by the manufacturer. Specific protocols for these procedures are available at www1.qiagen.com. The RNA (10 μg) was then used as the template for cDNA synthesis, the product of which was fragmented, labeled, and hybridized to an Affymetrix *E. coli* Antisense Genome Array (Affymetrix, Inc., Santa Clara, Calif.), which was washed and scanned to obtain an image. All of these steps were performed according to the manufactures recommendations (protocols are available at www.affymetrix.com). The image files were processed and expression values were normalized using dChip software (Li and Wong, *Proc. Natl. Acad. Sci. USA* 98:31-6 (2001)). Quantitative real time RT-PCR was used to validate expression changes for selected genes.

The statistical significance of expression changes for each gene and each strain between aerobic and anaerobic conditions was determined using a t-test (log-transformed data, equal variance). For each deletion strain two-way ANOVA (strain as the first factor and aerobic/anaerobic condition as the second factor) was used to determine whether the differential expression observed in the wild-type strain was significantly altered in the deletion strain by determining the statistical significance of the strain/condition interaction effect. For both the t-test and the ANOVA analysis correction for multiple testing was performed using the Benjamini-Hochberg false discovery rate procedure (Benjamini and Hochberg, J. Roy. Stat. Soc. Ser. B (Methodological) 57:289-300 (1995)), which determines the P-value cut-off for each test separately by estimating the false discovery rate (FDR) resulting from using a particular P-value cut-off. The false discovery rate refers to the fraction of true null tests out of all the tests called significant and an FDR of 5% was used for all the tests performed. A fuirther description of the gene expression data and other relevant information such as the MIAME checklist is provided below in Example IX.

Validity comparison of the genome-scale model with the growth phenotypes showed that experimental and computational outcomes agreed in 10,828 (78.7%) of the cases examined. This percentage of consistency corresponded to about the same measure of consistency observed with studies in *E. coli* and yeast that considered only a few hundred phenotypes (Forster et al., *Omics* 7:193-202 (2003); Edwards and Palsson, (2000), supra; Covert and Palsson, (2002), supra. In additionally, 18.3% of the cases were only predicted correctly when regulatory effects were incorporated with the metabolic model. A further description of these results is provided below in Example IX.

Figure 21A:
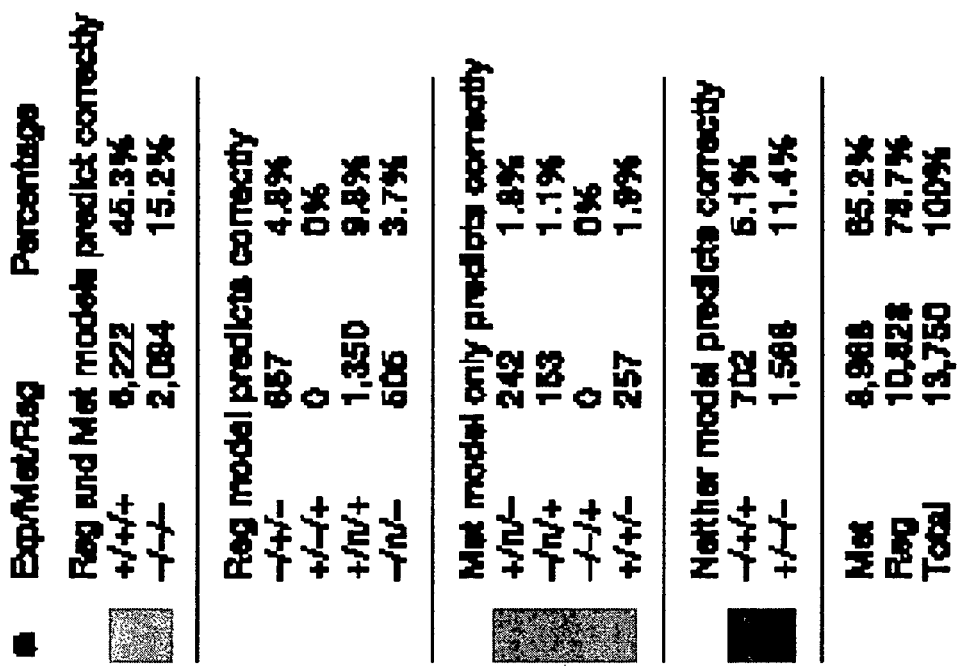
FIG. 21 shows the results of a growth phenotype study. Panel (a) is a comparison of high-throughput phenotyping array data with in silico predictions for an E. coli regulatory network. Panel (b) shows the results for individual knockout strains under each environmental condition whereas panel (c) summaries the environments or knockout strains for which the fraction of agreement between regulatory model determinations and observed phenotypes meet a threshold.
Figure 21B:
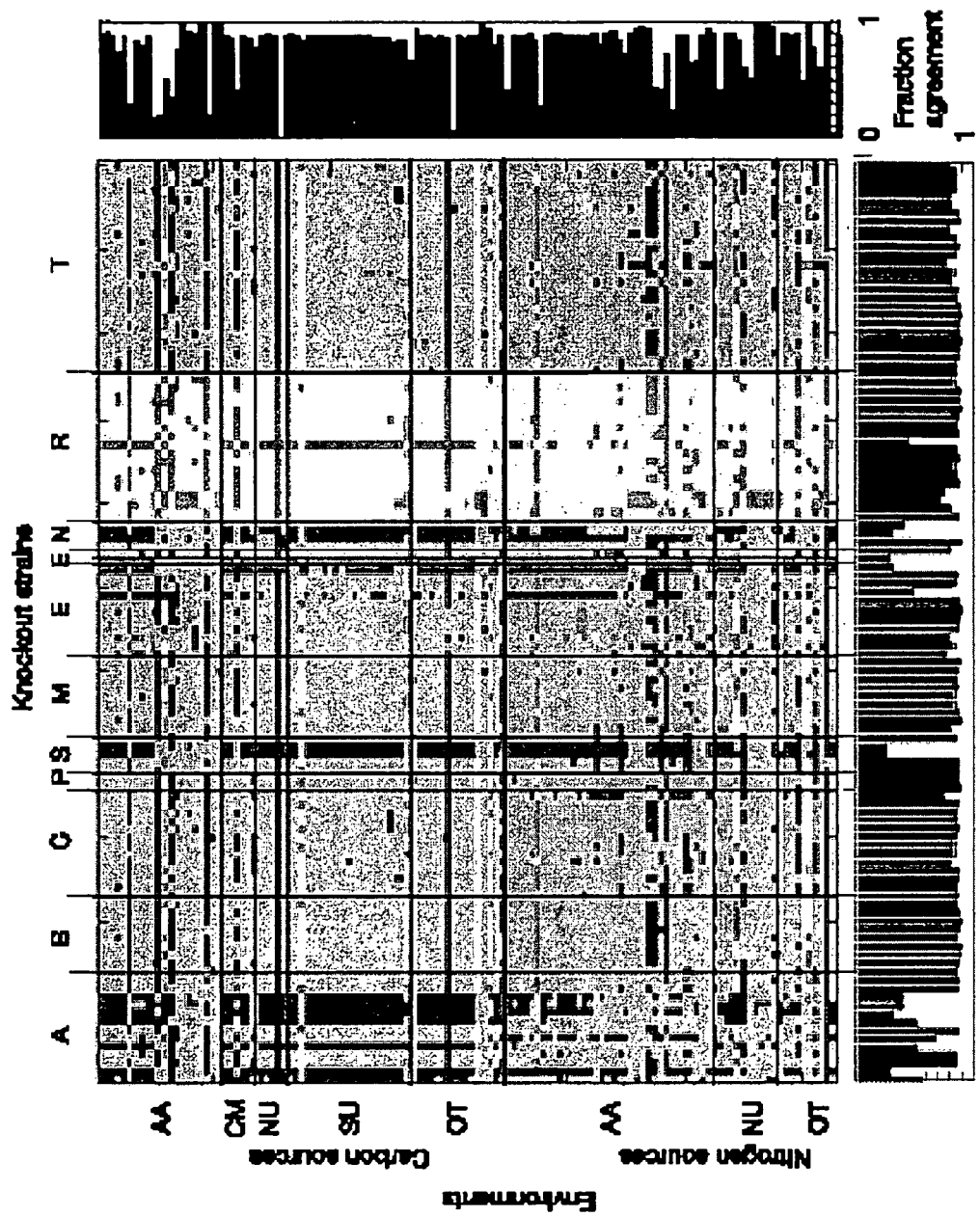
Figure 21C:
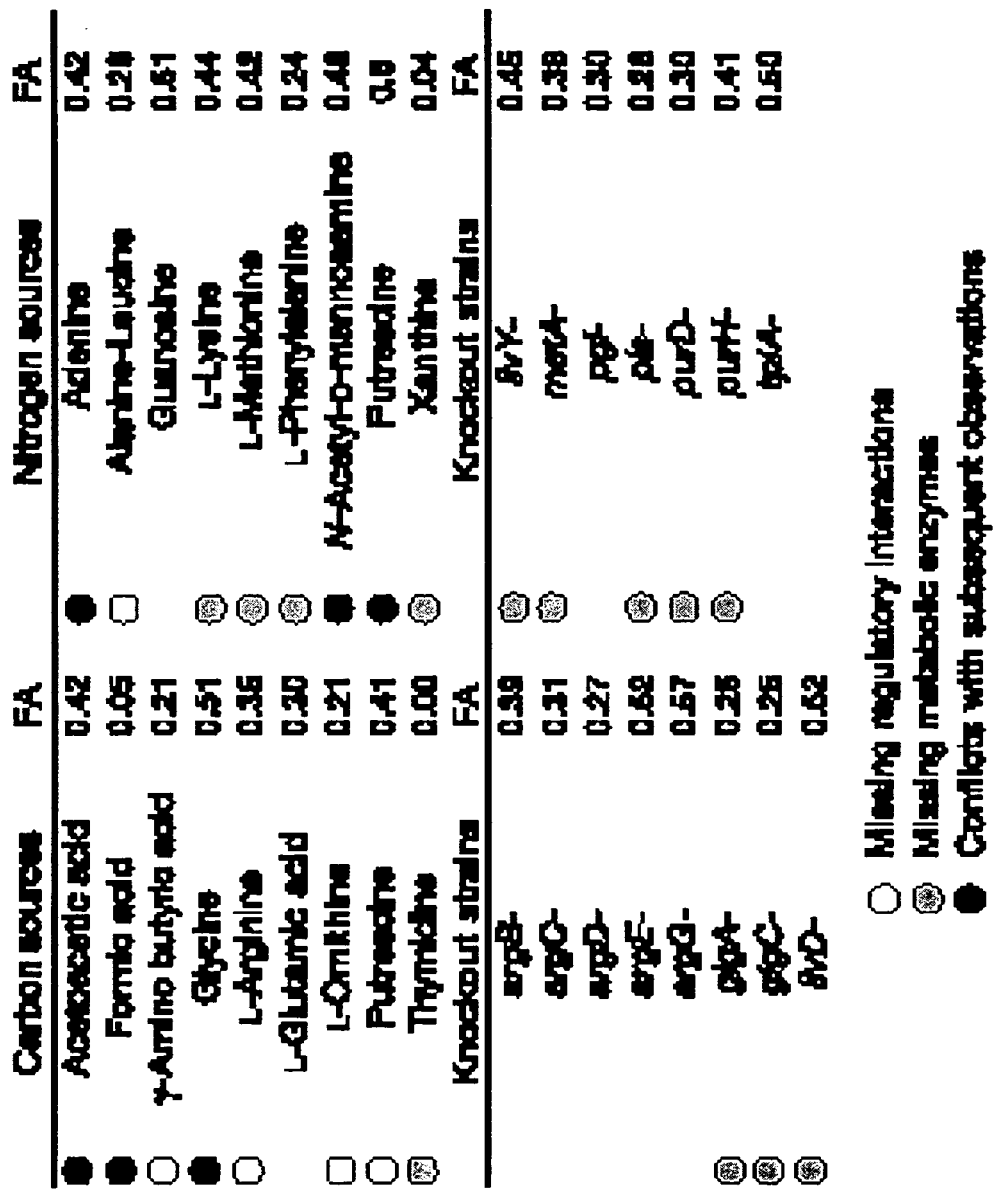

The comparisons of phenotypes with a genomic-scale in silico model and knockout modifications of the model identified several substrates and knockout strains whose growth behavior did not match predictions. The results of these growth phenotype comparisons are shown in FIG. 21. Panel (a) of FIG. 21 shows a comparison of high-throughput phenotyping array data (exp) with predictions for the *E. coli* network, both considering regulatory constraints (reg) and ignoring such constraints as a control (met). Each case is categorized by comparison type (exp/met/reg), where results are listed with a "+", indicating predicted or observed growth, "−" indicating no growth, or "n", for cases involving a regulatory gene knockout not predictable by the met model. The comparisons are further divided into four subgroups, represented by four colors as indicated in the table in FIG. 21(*a*).

FIG. 21(*b*) is a chart showing the individual results for each knockout under each environmental condition, the colors used match those defined by panel (a). The environments involve variation of a carbon source or nitrogen source and are further divided into subgroups (AA=amino acid or derivative(s), CM=central metabolic intermediate, NU=nucleotide/nucleoside, SU=sugar, OT=other). The knockout strains are also divided by functional group (A=amino acid biosynthesis and metabolism, B=biosynthesis of cofactors, prosthetic groups and carriers, C=carbon compound catabolism, P=cell processes (including adaptation, protection), S=cell structure, M=central intermediary metabolism, E=energy metabolism, F=fatty acid and phospholipid metabolism, N=nucleotide biosynthesis and metabolism, R=regulatory function, T=transport and binding proteins, U=unassigned). Each environment and knockout strain is associated with a fraction of agreement (FA) between regulatory model predictions and observed phenotypes, as shown in the bar charts to the right of and below the chart.

FIG. 21(*c*) is a table of the results containing all environments or knockout strains for which the FA<0.60. Eighteen of these substrates or knockout strains point to uncharacterized metabolic or regulatory capabilities in this organism, as indicated. A description of these results on a case-by-case basis is further provided in Example IX below.

Analysis of these conditions and strains led to identification of five environmental conditions where dominant, uncharacterized regulatory interactions actively contribute to the observed growth phenotype. Five environmental conditions as well as eight knockout strains also were identified which highlight uncharacterized enzymes or non-canonical pathways that are predicted to be used by the organism. A further description of these apparent discrepancies and analysis is provided below in Example IX.

Following reconciliation and validation as described above, the genome-scale model was further refined to elucidate additional transcriptional regulatory networks. The study described in Example IV, which evaluated the consistency between existing gene expression data sets and the known transcriptional regulatory network of *E. Coli*, identified the response to oxygen deprivation as a partially consistent module and was targeted as part of the transcriptional regulatory network for further network characterization. Six knockout strains involving key transcriptional regulators in the oxygen response (ΔarcA-, ΔappY-, Δfnr-, ΔoxyR-, ΔsoxS, and double knockout ΔarcA-fnr-) were constructed. These strains as well as the wild-type strain were mRNA expression profiled in aerobic and anaerobic glucose minimal medium conditions. The data was analyzed in the context of iMC1010$^{v1}$ predictions to identify new interactions in the regulatory network.

Figure 22A:
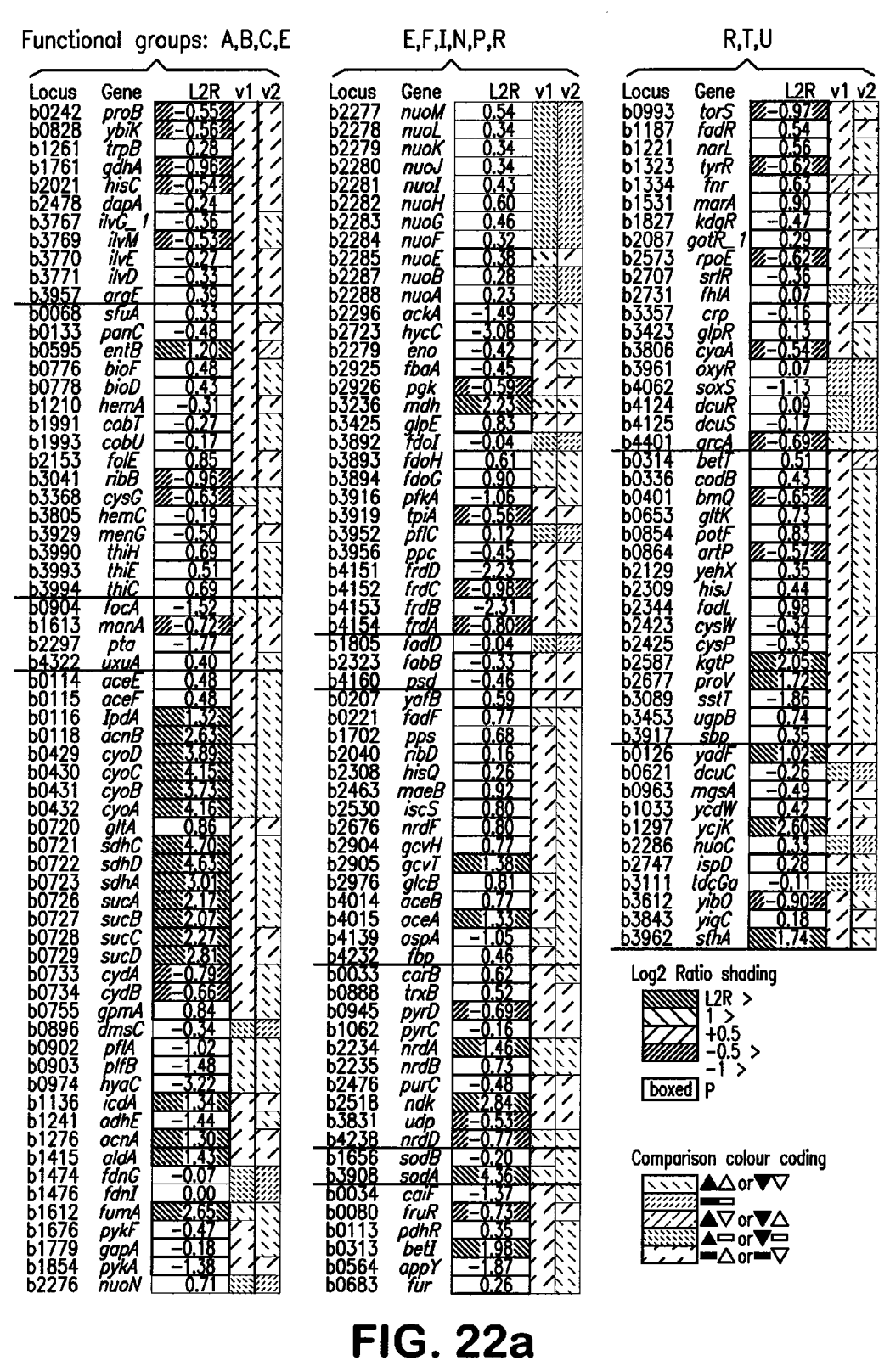

The results of the above analysis characterizing the regulatory network related to the aerobic-anaerobic shift are shown in FIG. 22. In panel (a) the locus numbers, gene names and the log2 ratio (L2R) of gene expression (aerobic to anaerobic) are shown for all model genes with either predicted or observed expression changes. Genes were divided into functional groups with the same abbreviations as shown in FIG. 21. The L2Rs are shaded depending on the magnitude of the expression shift, and L2Rs enclosed by a box indicate a statistically significant (P<0.007, FDR=5%) change in expression.

Comparisons between the experimental data and model predictions are also shown in FIG. 22(*a*), where v1 (iMC1010$^{v1}$) and v2 (iMC1010$^{v2}$) designate which model is used in the predictions. A legend for the results is shown in the lower right of panel (a). Briefly, filled and open symbols indicate model predictions and experimental data, respectively; rectangles indicate no change in gene expression while triangles are used to indicate a change in expression as well as the direction of change (upregulated or downregulated).

FIG. 22(*b*) shows a comparison of the predicted and observed expression changes for the v1 and v2 models. A question mark indicates either that the given gene was not included in the model or that no expression data were obtained for a given shift; other symbols are the same as in panel (a).

FIG. 22(*c*) shows the results where a systematic perturbation analysis was used to determine the transcription factors responsible for the expression change. The transcription factors knocked out in the six strains are shown on top. Each row indicates a pattern of knockout strains in which differential expression was abolished. The number of genes that show this pattern is indicated on the right. Thus, the first row indicates that for 73 of the 437 genes that showed differential expression in the wild-type strain (or 20 of the 151 genes accounted for by the model), the observed differential expression was abolished only in the ΔarcA$^-$fnr$^{--}$ knockout strain.

The results obtained from the above expression profiling of the wild-type strain identified 437 genes that experienced a significant change in transcription (t-test, multiple testing corrected to give false discovery rate, FDR<5%) in response to oxygen deprivation. Of these identified genes, 151 genes were included in iMC1010$^{v1}$. Computationally, 75 genes were predicted by iMC1010$^{v1}$ to show differential expression in response to oxygen deprivation. These 75 computationally predicted genes could be classified into three categories: 23 agreed with measured expression changes, 24 had a predicted expression change which was not found to be statistically significant in the experimental data (23 out of 24 cases) or was in the opposite, direction compared with the experimental data (1 out of 24 cases) and for 28 there were no expression data available (transcript abundance was determined to be "absent" for two or more of the replicates). Of the 47 differentially expressed genes that could be compared between the model computation and experiment, 23 (or 49% accuracy) agreed. Considering the overall number of genes in the model for which there was experimental data, the overlap (23) between the sets of predicted (47) and experimentally detected (151) differentially expressed genes is significant compared to a model that would randomly predict expression changes (P<0.005 based on a cumulative binomial distribution). A schematic diagram of the reconciliation, refinement and iteration steps and the obtained results are shown in FIG. 23.

Figure 23:
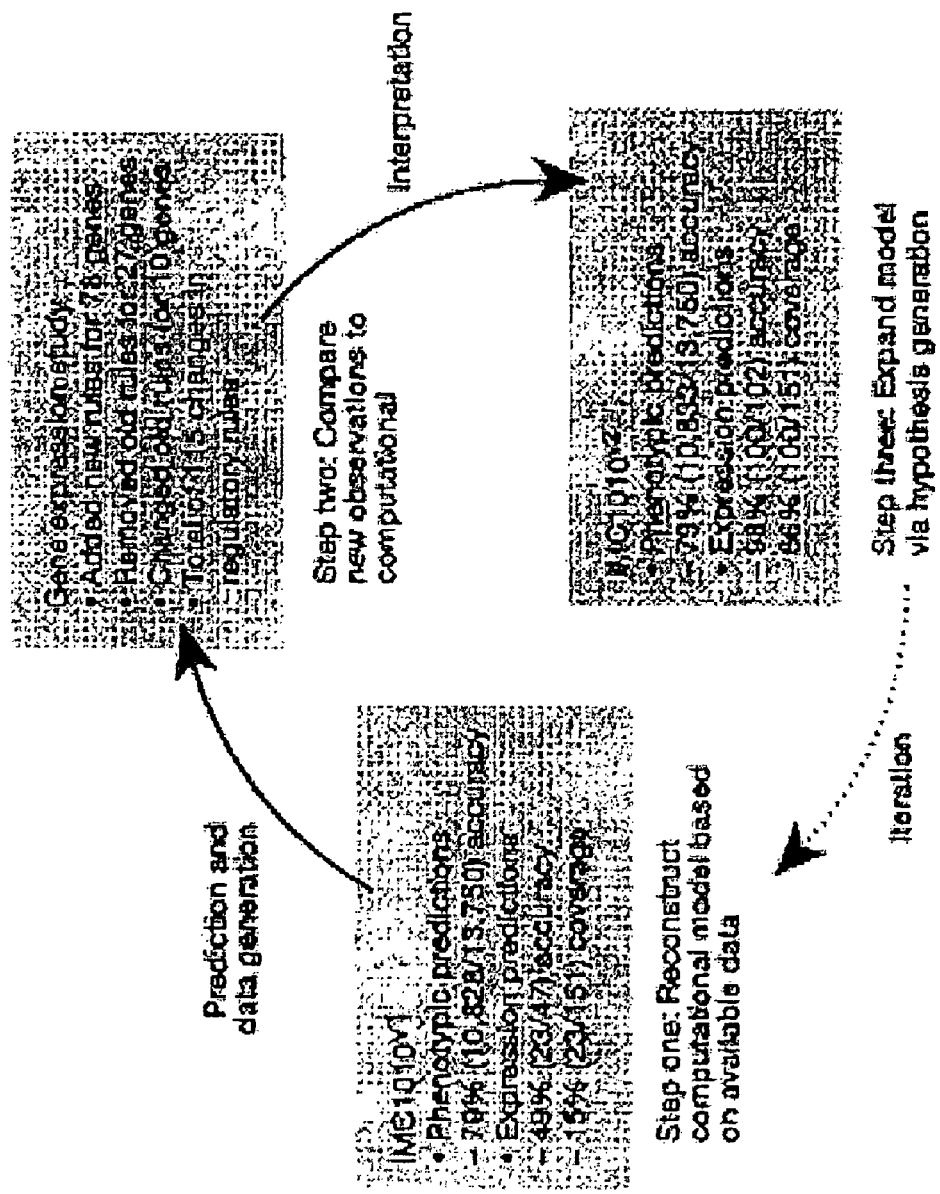
FIG. 23 shows biosystem network reconciliation and refinement for the expansion of multiple interrelated networks by applying phenotyping and gene expression data in connection with in silico model results.

Briefly, FIG. 23 shows that biosystem network reconciliation or refinement using the methods of the invention allow multiple interrelated networks, such as metabolic and regulatory networks, to be expanded and refined by applying phenotyping and gene expression data in connection with the predictions of a computational model. If model predictions are consistent with experimental observations, the network is adequately characterized. If consistency is less than desired, the model identifies a knowledge gap and can be used to update, validate and generate refinements about organism function. Accuracy refers to the percentage of model predictions that agree with experimental data, coverage indicates the percentage of experimental changes predicted correctly by the model.

Figure 22C:
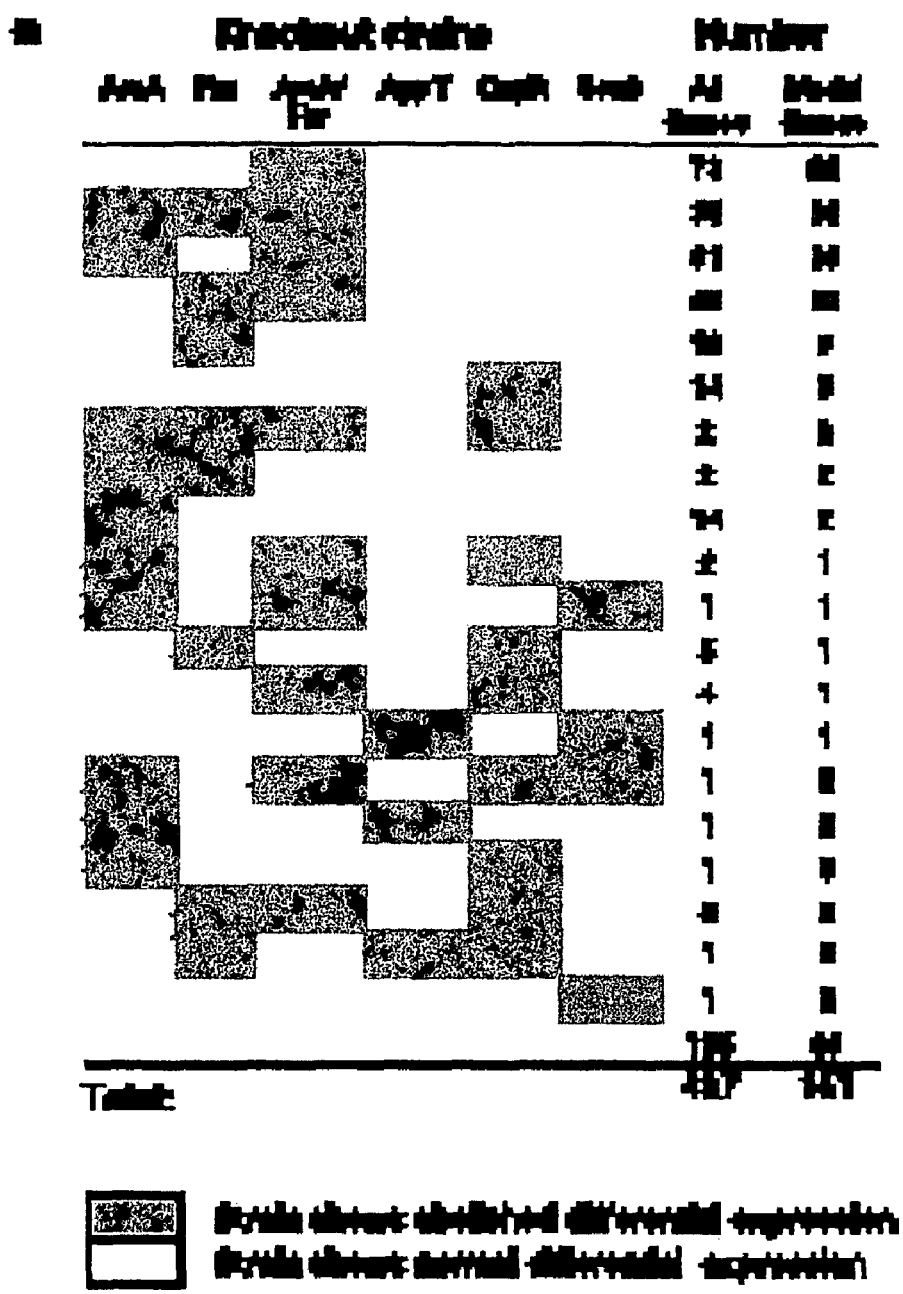
FIG. 22 shows (a) a characterization and accuracy of a regulatory network related to the aerobic-anaerobic shift; (b) a comparison of predicted and observed expression changes for a base in silico and a refinement of that model, and (c) the results of a perturbation analysis identifying transcription factors responsible for gene expression change.

The transcription factors involved in the regulation of the differentially expressed genes following oxygen deprivation identified above were identified by comparing the gene expression data for the wild-type and each knockout strain separately. Two-way analysis of variance (ANOVA) was used to determine whether the differential expression was significantly altered in the knockout strain compared to the wild-type. A large portion of the expression changes observed for the wild-type strain were not significantly affected in any of the knockout strains (195/437 or 44.6% of genes overall, 63/151 or 41.7% of genes in the model, FDR<5%), indicating that none of the five transcription factors studied here regulate their expression or that combinatorial interactions between multiple transcription factors are involved in regulation. The remainder of the genes exhibited abolished differential expression in one or more of the knockout strains as shown in FIG. 22c.

The ANOVA-based identification of transcription factors that influence differential expression of specific genes guided systematic modifications to the model to rewrite, relax or remove various regulatory rules which resolved the discrepancies between iMC1010v1 and the experimentally determined wild-type differential gene expression. For 81 of the cases, a regulatory rule already existed and was further reconciled with the obtained data to accommodate newly identified transcription factor dependencies. In cases where none of the knockouts abolished differential expression, a new regulatory rule was formulated on the presence of oxygen rather than a transcription factor, which occurred in 39 of the cases. Conversely, in cases where a change in expression was predicted but not observed, the oxygen dependency was removed from the existing regulatory rule, which occurred in 23 of the cases. There were also 12 cases where the predicted expression changes agreed with the observed expression in the wild-type, but our knockout perturbation analysis indicated that the transcription factors involved in the regulation were different than previously reported and the model needed to be changed. A further description of these new regulatory rules is provided below in Example IX.

The updated model, iMC1010$^{v2}$ was used to recalculate all of the predictions for both the aerobic/anaerobic expression data and the high-throughput phenotyping arrays. Model iMC1010$^{v2}$ accounts for the same genes as iMC1010$^{v1}$ but has different regulatory interactions amongst the gene products and oxygen as an environmental variable. Agreement between model predictions and the gene expression data was found to be substantially higher using the iMC1010$^{v2}$ model, which is shown in FIG. 22c. Specifically, 100 of the 151 expression changes were correctly computed with iMC1010$^{v2}$, and the number of false positive (yellow boxes in FIG. 22) predictions was reduced to zero. In resolving many of the unpredicted differential expression (orange boxes in FIG. 22), implementation of the ANOVA-derived rule resulted in the inability of the wild-type or knockout in silico strain to grow aerobically or anaerobically on glucose, or under other conditions where growth had been previously established (e.g., wild-type and knockout strain average growth rate under aerobic conditions: 0.68±0.04/hr; anaerobic: 0.43±0.07/hr). Such cases can be thought of as an "overfit" of the microarray data. Accordingly, we relaxed the regulatory rule in these cases (42 total) to allow for a more tailored phenotype prediction. Comparisons for the high-throughput phenotyping data revealed very little difference from FIG. 21, affecting only 11 out of the 13,750 cases. A further description of these results is provided below in Example IX.

Iterative modification of the regulatory rules led to several refinements. First, some of the results of the knockout perturbation analysis were sufficiently complex to indicate that substitution of alternative logic for the Boolean rule formulation used in the model can be appropriate, but that the Boolean logic was sufficient for the accurate functioning of the model. For example, the interplay of Fnr and ArcA can lead to complex behaviors where the expression change observed in wild-type is abolished in the ΔarcA$^-$ or the Δfnr$^-$ strains, but not the ΔarcA$^-$fnr$^-$ strain. Such complex interplay between transcription factors can lead to specialized expression changes, as has been observed in the cydAB response to anaerobic, microaerobic and aerobic conditions (Compan et al., *Mol. Microbiol.* 11:955-64 (1994); Cotter et al., *Mol. Microbiol.* 25:605-15 (1997)).

Second, in refining the regulatory rules for transcription factors, the results showed that in many cases, such as arca, expression of a regulatory protein correlates positively with its activity. However, in some cases, including fnr, betI, and fur, among others, the transcription of a regulatory gene was reduced when in fact, the protein is activated. For example, under anaerobic conditions, when Fnr is known to be active (Salmon et al. *J. Biol. Chem.* 278:29837-55 (2003)), its expression level is significantly reduced. Such behavior, also has been previously observed comparing mRNA transcript levels and corresponding protein product abundance in yeast (Griffin et al., *Mol. Cell Proteomics.* 1:323-33 (2002), indicating that identification of regulatory networks, and particularly transcription factors, can incorporate the assessment of factors additional to the determination of coregulated gene sets for increased accuracy of a model.

Third, many of these gene expression changes involve complex interactions and indirect effects. Transcription factors can be affected, for example, by the presence of fermentation by-products or the build-up of internal metabolites, indicating that such effects would be difficult to identify or account for without a computational model.

In summary, the results show that the reconciliation of high-throughput data sets with genome-scale computational model predictions enables systematic and effective identification of new components and interactions in microbial biological networks. In addition, the model refinement described here illustrates a high predictive accuracy with only a single round of an iteration where the initial model was based on literature derived information.

EXAMPLE IX

Methods and Analysis for Integrating High-Throughput and Computational Data for the Elucidation of Bacterial Networks This Example describes further details of the methods and analysis set forth above in Example VIII. Accordingly, the description of the in silico model, procedures and results described herein should be understood in reference with the teachings of Example VIII. The additional methods described below with respect to the model refinement of Example VIII have been divided into three main sections: network model reconstruction, phenotype data comparison, and microarray data comparison.

Network Model Reconstruction

The initial regulatory model was based on a previous model of metabolism in *Escherichia coli* (iJR904; Reed et al., (2003), supra). The differences between the previous network and that employed in the refinement of Example VIII are summarized below in Table 7.

The Regulation List shown below in Table 8 contains a list of all the genes in the model. Each gene is listed by B number and gene name, and the regulatory rules for expression or activity (in the case of transcription factors) are included with references listed by their PubMed Ids. Chapters from the book "*Escherichia coli* and *Salmonella*: cellular and molecular biology" edited by F. C. Neidhardt, are indicated first by an NH (e.g. chapter 22 is listed as NH 22).

Simulation Parameters are shown below in Table 9 and lists all the parameters used in the simulations, including time delays for transcription and translation, the biomass function, non-growth associated ATP maintenance flux, initial metabolite concentrations, and initial biomass concentrations. Concentrations highlighted in yellow in Table 9 are the ones that vary across the different experiments. This table also includes the lower limits (which correspond to maximal uptake rates) and upper limits for exchange fluxes of extracellular metabolites. Exchange fluxes include those listed in iJR09 with the addition of an h2s exchange flux as shown in Table 8. Exchange fluxes are written in the direction that external metabolites are depleted from the system, so a negative flux value corresponds to that metabolite entering the system. Condition dependent changes to lower limits on the exchange fluxes were also taken into account when running simulations, where the lower limit of an exchange flux is temporarily set to zero if that metabolite is not present in the medium.

The Abbreviations List shown below in Table 10 contains a list of the metabolite abbreviations, and their definitions, that are used in the previous worksheets. Those ending in "(e)" are external metabolites rather than intracellular metabolites. The metabolite list matches that reported in iJR904, with the exception of six additional extracellular metabolites: 5dglcn (e), btn(e), cbi(e), h2o2(e), ppa(e), and thym(e). These eight metabolites act as stimuli for the regulatory network.

Phenotype Data Comparison

Figure 24:
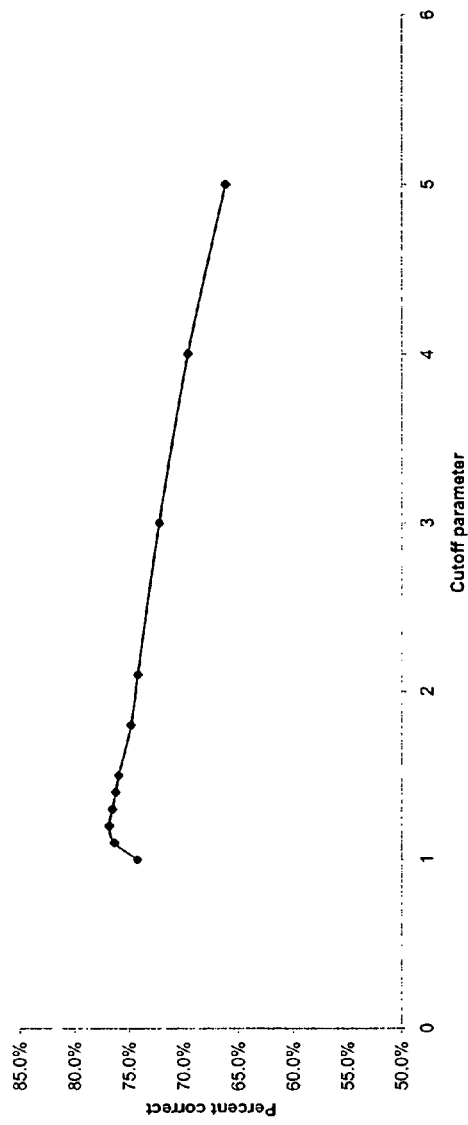
FIG. 24 shows a sensitivity analysis of the phenotype cutoff parameter used for data normalization.

A more detailed version of FIG. 22 also was generated where the predictions of both the regulated and unregulated models were compared with experimental data from the ASAP website (https://asap.ahabs.wisc.edu/annotation/php/logon.php). Plates PM1, PM2 and PM3 were considered for this comparison, and only used data where the knockout strain and the environmental condition could be simulated by the model (e.g., no knockout strains of non-metabolic or associated regulatory genes). The data was compiled as described in Example VIII and normalized by a cutoff parameter, which was taken as 1.2 times the negative control value. If this normalized Biolog growth value was greater than the cutoff parameter, the condition was assigned a qualitative value of "growth"; otherwise, the condition was assigned "no growth." As shown in FIG. 24, variation of this parameter can change some specific recommendations for model expansion or network identification, but does not affect the overall conclusions of the results.

As described in Example VIII, 18.3% of the cases were only predicted correctly when regulatory constraints were incorporated with the metabolic model. Table 11 below lists the carbon sources with significantly higher fractions of agreement between model prediction and experimental observations.

The regulatory effects which lead to these phenotypes are described below, beginning with the carbon sources. Growth on citrate as a carbon source depends on a transporter (encoded by citT) which is only expressed anaerobically. Part of the pathway for sucrose utilization involves xylose isomerase (encoded by xylA). Synthesis of this enzyme is induced by XylR, which is only active if xylose is present in sufficient concentration. 1,2-Propanediol utilization depends on an L-lactate dehydrogenase, whose expression depends on the presence of L-lactate. Several required genes in the pathway for butyric and tartaric acid utilization (atoB, atoD, atoE) are regulated by the activating protein AtoC, which is only active when stimulated by AtoS, which in turn is activated by acetoacetate. For the nitrogen sources, the presence of guanine downregulates a number of genes involved in pyrimidine and purine biosynthesis (purA, purB, pyrB, pyrF, prsA); prsA is also needed in histidine biosynthesis. Nitrate and nitrite environments require nitrate reductase for utilization, and the subunit for this enzyme encoded for by nirB is expressed only under anaerobic conditions, as mediated by Fnr. Similarly, allantoin utilization requires the allC gene product (allantoate amidohydrolase), which is downregulated under aerobic conditions.

A further treatment of the environments and knockouts incorrectly predicted by the model is described below. Finally, there were only 11 cases (out of 13,750) where the results of the comparison between model predictions and experimental observations shown in FIG. 22b differed when calculated using iMC1010$^{v2}$. For all 11 of these cases, iMC1010$^{v1}$ predicted no growth and iMC1010$^{v2}$ predicted growth, indicating that the changes are a result from the relaxation of regulatory rules. Most of the cases (8 out of 11) are now predicted more accurately with iMC1010$^{v2}$.

Briefly, the following sections analyze the apparent discrepancies and model predictions for carbon and nitrogen sources as well as for knockout strains. Some of the high discrepancy growth conditions were retested on a Bioscreen C (Helsinki, Finland) with five replicates; Bioscreen measures growth rates by monitoring OD. M-9 minimal media with 0.2% carbon source was used to test K-12 MG 1655 growth on different carbon sources; W-salts media (10.5 g of $K_2HPO_4$, 4.5 g of $KH_2PO_4$, and 0.241 ml of 1 M MgSO4 per liter) supplemented with 0.2% succinate and 0.2% nitrogen source was used to test wildtype growth on different nitrogen sources. Two controls were used: M-9 minimal media with no carbon source and 0.2% succinate W-salts media with no nitrogen source. Cells were precultured overnight in 0.2% succinate M-9 minimal media and transferred into the different media conditions Bioscreen was run over three days, and the relative growth rates (growth rate divided by the appropriate control growth rate) are set forth in Tables 12-14 below. MEME and MAST sequence alignment and comparison tools (Bailey and Elkan, *Proc Int Conf Intell Syst Mol Biol* 2:28-36 (1994); Bailey and Gribskov, *Bioinformatics* 14:48-54 (1998)), were used as reported previously (Reed et al., (2003), supra) to identify putative genes for some of the enzymes that could resolve model and reconcile discrepancies.

Formic Acid (+/−/−), Glycine (+/+/−) and Acetoacetic Acid (−/+/+)

The metabolic and regulatory models incorrectly predict growth phenotypes as measured on the Biolog plates with formate and acetoacetate as carbon sources, while only the regulatory model disagrees with experimental observations with glycine. According to the Biolog plates, *E. coli* grows with formate as a carbon source and does not grow with acetoacetate as a carbon source (Jenkins and Nunn, *J Bacteriol* 169:42-52 (1987)). Mixed Biolog results were observed for growth on glycine. Wildtype K-12 was retested for growth on all three carbon sources using the Bioscreen; in all cases the results are in agreement with the regulatory model predictions and disagree with the Biolog results.

Thymidine (+/−/−)

Both the regulated and unregulated models predict that thymidine can not be used as the sole carbon or nitrogen source. Thymidine can be converted to thymine by thymidine phosphorylase, this enzyme is already in the metabolic network. Older experimental studies have shown that thymine can be degraded by some strains of *E. coli* (Ban et al., *J Gen Microbiol* 73:267-72 (1972); Patel and West, *B. Microbios* 49:107-13 (1987)), and it has been proposed that *E. coli* B contains the reductive pathway involved in uracil and thymine degredation (EC numbers 1.3.1.2 or 1.3.1.1, 3.5.2.2, 3.5.1.6; Patel and West (1987), supra). Sequence comparisons using MEME and MAST indicate that 1.3.1.2 might be encoded by 2106 and 3.5.2.2 might be encoded by b2873 and b0512. Identification of this pathway in *E. coli* K-12 MG 1655 would explain the observed Biolog data. Incorporating the associated metabolic genes and knowledge on how they are regulated would increase the predictive ability of the model.

L-Glutamic Acid (−/+/+)

The inability to grow on glutamate as the sole carbon source is believed to be due to a low transport capacity (NH 20). If measured a maximum rate for the uptake of glutamate can be used to further constrain the solutions predicted by the models.

g-Amino Butyric Acid, L-arginine, Ornithine and Putrescine (−/+/+)

Both models predict growth on g-amino butyratate (GABA), arginine, ornithine and putrescine as a sole carbon source. This is in disagreement with the Biolog and Bioscreen data, which indicate that these substrates are not suitable carbon sources. The gab pathway, needed for the degradation of GABA and putrescine, is reported to be expressed at a low constitutive level that is not sufficient to support growth on GABA (McFall and Newman, E. B. in *Escherichia coli* and *Salmonella* (ed. Neidhardt, F. C.) 358-379 (ASM Press, Washington, D.C., 1996)) (strain W3110 is able to utilize GABA as a carbon source; Schneider et al., *J Bacteriol* 184: 6976-86 (2002)). In addition to the gab pathway arginine and ornithine, can also be degraded by enzymes in the ast pathway, but this latter pathway is only expressed under nitrogen limitation. The gabDPTC operon is induced under nitrogen limitation allowing these compounds to be used as a nitrogen sources (Schneider et al., (2002), supra). Constraining the maximum allowable fluxes through the gab pathway or including regulation of these genes in the model would explain the lack of growth and increase the predictive capabilities of the models.

Adenine, N-Acetyl-D-Mannosamine and Putrescine (−/+/+)

These three nitrogen sources do not support growth according to the Biolog data, but are predicted to support growth by the regulated and unregulated models. It has been shown previously that *E. coli* can use adenine as a sole nitrogen source (Schneider et al., (2002), supra), indicating that the Biolog results might be inaccurate. N-acetyl-D-mannosamine and putrescine were also tested as nitrogen sources using the Bioscreen—growth rates were significantly higher than the control indicating that the Biolog results are incorrectly measuring a lack of growth.

L-Lysine, L-Methionine, L-Phenylalanine and Xanthine (+/−/−)

Both the Biolog data and Bioscreen data indicate that lysine, methionine, phenylalanine, and xanthine can be used as an alternate nitrogen sources. Neither the regulated or unregulated model predicts growth with these substrates as nitrogen sources, indicating that the metabolic enzymes, which allow incorporation of nitrogen from these substrates, are missing from the metabolic network. For the case of lysine, we could not find any data on how nitrogen is removed from lysine. Proposed pathways for methionine, phenylalanine, and xanthine utilization are summarized below. Methionine aminotransferase activity has been observed in *E. coli* B, where methionine and a-ketoglutarate are converted to 2-oxo-4-methylthiobutyric acid and glutamate (Ince and Knowles, *Arch Microbiol* 146:151-8 (1986), 2-oxo-4-methylthiobutyric acid is then converted into ethylene (Shipston and Bunch, *J Gen Microbiol* 135 ( Pt 6), 1489-97 (1989)). The pathway and associated genes have not been found in K-12 and so have not yet been included in the models. Including the phenylpyruvate decarboxylase reaction, which converts phenylpyruvate to phenylacetate (EC 4.1.1.43), as well as the complete phenylacetate degradation pathway (which has not yet been fully characterized) would enable the model to use phenylalanine as a nitrogen source. A xanthine dehydrogenase activity has been assigned to the xdhA gene product, where xanthine would be converted to uric acid and then presumably to allantoin (Schneider et al., (2002), supra). Allantoin can not be used as a nitrogen source under aerobic conditions, so how nitrogen is removed from the base remains unclear biochemically.

Alanine-Leucine (+/+/−)

Leucine represses the synthesis of biosynthetic enzymes for isoleucine and valine, which is why the model predicts that *E. coli* won't grow on with leucine or alanine+leucine as the sole nitrogen source. Experimentally growth with just leucine as the nitrogen source does not permit growth, but growth with both alanine and leucine allows for growth. A lower concentration of leucine might allow for growth with alanine if the repression of the isoleucine and valine biosynthetic enzymes is relaxed.

Guanosine (−/+/+)

Biolog data indicates growth with guanosine in 64 knockouts and no growth with 46 knockouts. Performing more replicates of the Biolog data and possibly testing the knockout strains on the Bioscreen would provide more information as to whether the model or the Biolog data is more accurate.

All of the major failure modes between model predictions of knockouts and Biolog data, are the case where the regulated and unregulated models predict the knockout to be lethal but the experimental data seems to suggest that they are not lethal. Most of these discrepancies involve knockouts which prevent the production of a biomass component.

glgA-, glgC- (+/−/−)

These two genes are involved in the synthesis of glycogen. Three different hypotheseis can be made from the model and data discrepancies: (1) glycogen is not an essential biomass component, (2) glycogen phoshporylase is reversible, or (3) there is a new redundant pathway for glycogen synthesis. If incorporated into the model any of these possibilities could resolve the model and data disagreements.

arAB-, argC-, argD-, argE-, argG- (+/−/−)

The following genes involved in arginine biosynthesis: argB, argC, argD, argE, and argG, are all lethal deletions according to the model but not in the Biolog data. For argB, argC, argD, and argE the growth phenotype can be explained by making a few reactions reversible in the model (ABUTD, PTRCTA, and ORNDC); the backwards reactions allow for a new route converting glutamate into ornithine (and then arginine). No information could be found regarding the reversibility of these enzymes. For argG there must be another isozyme.

purD-, purH-, metA (+/−/−)

The genes, purD and purfH are responsible for the enzymes needed in the early and late steps of purine biosynthesis. One of the early reactions of methionine biosynthesis is carried out by the metA gene product. *E. coli* will obviously need to still make purines and methionine, so isozymes or alternate synthesis routes must be available.

pgi-, tpiA- (+/−/−)

Both pgi and tpiA are predicted to be lethal under most conditions by the model because with these knockouts there is no way of making glucose-6-phosphate from carbon sources that do not directly feed into upper glycolysis. Like with the arg knockouts, making some of the reactions in the model reversible (6-phosphogluconolactonase and either the entner doudoroff pathway or phosphogluconate dehydrogenase) would change the model predictions.

ilvD-, ilvY- (+/−/−, +/n/−)

Both the ilvD and ilvY are incorrectly predicted by the model to be lethal because both are needed to make the biomass components leucine, valine, and isoleucine. ilvD encodes an enzyme in the metabolic pathways and ilvY is an transcriptional activator for ilvC encoding another essential enzyme in the pathway (Rhee et al., *J Biol Chem* 273:11257-66 (1998)). This result indicates that there is another way of making these amino acids, either alternate isozymes exist for ilvD and ilvC or in the case of ilvY, the level of IlvC is still high enough to permit growth.

Microarray Data

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

TABLE 1

| Enzyme | Reaction/Gene Name | Reaction |
|---|---|---|
| Membrane Transport | | |
| Phosphotransferase system | pts | GLCxt + PEP • G6P + PYR |
| Succinate transport | SUCC trx | SUCCxt * SUCC |
| Acetate transport | AC trx | ACxt * AC |
| Ethanol transport | ETH trx | ETHxt * ETH |
| Oxygen transport | O2 trx | O2xt *O2 |
| Carbon dioxide transport | CO2 trx | CO2xt * CO2 |
| Phosphate transport | Pi trx | P1xt * P1 |
| Glycolysis | | |
| Phosphoglucose isomerase | pgi | G6P * F6P |
| Phosphofructokinase | pfkA | F6P + ATP • FDP + ADP |
| Fructose-1, 6-bisphosphatase | fbp | FDP • F6P + P1 |
| Fructose-1, 6-bisphosphatate aldolase | fba | FDP * T3P1 + T3P2 |
| Triosphosphate Isomerase | tpiA | T3P2 * T3P1 |
| Glyceraldehyde-3-phosphate dehydrogenase | gapA | T3P1 + P1 + NAD* NADH + 13PDG |
| Phosphoglycerate kinase | pgk | 13PDG + ADP* 3PG + ATP |
| Phosphoglycerate mutase 1 | gpmA | 3PG * 2PG |

TABLE 1-continued

| Enzyme | Reaction/Gene Name | Reaction |
|---|---|---|
| Enolase | eno | 2PG * PEP |
| Pyruvate Kinase II | pykA | PEP + ADP •YR + ATP |
| Phosphoenolpyruvate synthase | ppsA | PYR + ATP• PEP + AMP + P1 |
| Pyruvate dehydrogenase | aceE | PYR + COA + NAD• NADH + CO2 + ACCOA |
| Pentose Phosphate Shunt | | |
| Glucose 6-phosphate-1-dehydrogenase | zwf | G6P + NADP* D6PGL + NADPH |
| 6-Phosphogluconolactonase | pgl | D6PGL • D6PGC |
| 6-Phosphogluconate dehydrogenase | gnd | D6PGC + NADP *NADPH + CO2 + RL5P |
| Ribose-5-phosphate isomerase A | rpiA | RL5P * R5P |
| Ribulose phosphate 3-epimerase | rpe | RL5P * X5P |
| Transketolase I | tktA1 | R5P + X5P * T3P1 + S7P |
| Transaldolase B | talA | T3P1 + S7P * E4P + F6P |
| Transketolase II | tktA2 | X5P + E4P * F6P + T3P1 |
| TCA cycle | | |
| Citrate synthase | gltA | ACCOA + OA •OA + CIT |
| Aconitase A | acnA | CIT * ICIT |
| Isocitrate dehydrogenase | icdA | ICIT + NADP* CO2 + NADPH + AKG |
| 2-Ketoglutarate dehyrogenase | sucA | AKG + NAD + COA• CO2 + NADH + SUCCOA |
| Succinyl-CoA synthetase | sucC | SUCCOA + ADP + P1* ATP + COA + SUCC |
| Succinate dehydrogenase | sdhA1 | SUCC + FAD• FADH + FUM |
| Fumurate reductase | frdA | FUM + FADH• SUCC + FAD |
| Fumarase A | fumA | FUM *MAL |
| Malate dehydrogenase | mdh | MAL + NAD* NADH + OA |
| Dissimilation of Pyruvate | | |
| Acetaldehyde dehydrogenase | adhE | ACCOA + 2 NADH *ETH + 2 NAD + COA |
| Phosphotransacetylase | pta | ACCOA + P1* ACTP + COA |
| Acetate kinase A | ackA | ACTP + ADP* ATP + AC |
| Anapleurotic Reactions | | |
| Phosphoenolpyruvate carboxykinase | pckA | OA + ATP • PEP + CO2 + ADP |
| Phosphoenolpyruvate carboxylase | ppc | PEP + CO2 • OA + P1 |
| Energy/Redox Metabolism | | |
| NADH dehydrogenase 1 | nuoA | NADH + Q• NAD + QH2 + 2 HEXT |
| Cytochrome oxidase bo3 | cyoA | QH2 + 1/2 O2 • + 2 HEXT |
| Pyridine nucleotide transhydrogenase | pntA | NADPH + NAD •NADP + NADH |
| Succinate dehydrogenase complex | sdhA2 | FADH + Q •AD + QH2 |
| F0F1-ATPase | atpABCDEFGHI | ADP + P1 + 3 HEXT• ATP |
| Adenylate kinase | adk | ATP + AMP * ADP |
| ATP drain | ATP_dr | ATP • ADP + P1 |

TABLE 1-continued

| Enzyme | Reaction/Gene Name | Reaction |
|---|---|---|
| Growth Flux | | |
| Growth flux | GRO | 41.3 ATP + 3.5 NAD + 18.2 NADPH + 0.2 G6P + 0.1 F6P + 0.9 R5P + 0.4 E4P + 0.1 T3P1 + 1.5 3PG + 0.5 PEP + 2.8 PYR + 3.7 ACCOA + 1.8 OA + 1.1 AKG • 1.3 ADP + 41.3 P1 + 3.5 NADH + 18.2 NADP + 3.7 COA + 1.0 BIOMASS |
| Exchange Fluxes | | |
| Glucose external | GLCxt | GLCxt • |
| Succinate external | SUCCxt | SUCCxt • |
| Ethanol external | ETHxt | ETHxt • |
| Acetate external | ACxt | ACxt • |
| Biomass drain | BIOMASS | BIOMASS • |
| Phosphate external | P1xt | P1xt • |
| Carbon dioxide external | CO2xt | CO2xt • |
| Oxygen external | O2xt | O2xt • |

TABLE 2

| Pathway Number | Exchange Fluxes | | | | | | | Net Pathway Reaction Balance |
|---|---|---|---|---|---|---|---|---|
| | SUCCxt/ SUCCxt | ETHxt/ SUCCxt | ACxt/ SUCCxt | GRO/ SUCCxt | P1xt/ SUCCxt | CO2xt/ SUCCxt | O2xt/ SUCCxt | |
| 33 | −1.000 | 0 | 0 | 0.051 | −0.188 | 1.825 | −1.267 | SUCCxt + 0.188 P1xt + 1.267 O2xt ---> 0.051 GRO + 1.825 CO2xt |
| 30 | −1.000 | 0 | 0 | 0.034 | −0.125 | 2.553 | −2.014 | SUCCxt + 0.125 P1xt + 2.014 O2xt ---> 0.034 GRO + 2.553 CO2xt |
| 32 | −1.000 | 0 | 0 | 0.033 | −0.121 | 2.600 | −2.062 | SUCCxt + 0.121 P1xt + 2.062 O2xt ---> 0.033 GRO + 2.6 CO2xt |
| 34 | −1.000 | 0 | 0 | 0.049 | −0.182 | 1.895 | −1.338 | SUCCxt + 0.182 P1xt + 1.338 O2xt ---> 0.049 GRO + 1.895 CO2xt |
| 22 | −1.000 | 0 | 0 | 0.032 | −0.117 | 2.644 | −2.108 | SUCCxt + 0.117 P1xt + 2.108 O2xt ---> 0.032 GRO + 2.644 CO2xt |
| 14 | −1.000 | 0 | 0 | 0.031 | −0.114 | 2.679 | −2.144 | SUCCxt + 0.114 P1xt + 2.144 O2xt ---> 0.031 GRO + 2.679 CO2xt |
| 18 | −1.000 | 0.549 | 0 | 0.025 | −0.092 | 1.837 | −0.759 | SUCCxt + 0.092 P1xt + 0.759 O2xt ---> 0.025 GRO + 1.837 CO2xt + 0.549 ETHxt |
| 31 | −1.000 | 0 | 0.158 | 0.047 | −0.172 | 1.696 | −1.142 | SUCCxt + 0.172 P1xt + 1.142 O2xt ---> 0.047 GRO + 1.696 CO2xt + 0.158 ACxt |
| 10 | −1.000 | 0 | 0 | 0 | 0 | 4.000 | −3.500 | SUCCxt + 3.5 O2xt ---> 4.0 CO2xt |
| 5 | −1.000 | 0 | 1.000 | 0 | 0 | 2.000 | −1.500 | SUCCxt + 1.5 O2xt ---> 2.0 CO2xt + 1.0 ACxt |
| 2 | −1.000 | 1.000 | 0 | 0 | 0 | 2.000 | −0.500 | SUCCxt + 0.5 O2xt ---> 2.0 CO2xt + 1.0 ETHxt |
| 26 | −1.000 | 0 | 0 | 0 | 0 | 4.000 | −3.500 | SUCCxt + 3.5 O2xt ---> 4.0 CO2xt |

TABLE 3

| Angles (degree) | Pathway # | Diff Fluxes (%) | Pathway # | Net Diff (%) | Pathway # |
|---|---|---|---|---|---|
| 4.62E−05 | P_33 | 0 | P_33 | 5.84E−05 | P_33 |
| 4.9 | P_32 | 3.5 | P_34 | 11.3 | P_32 |
| 11.1 | P_30 | 5.3 | P_22 | 22.4 | P_30 |
| 22.6 | P_31 | 5.3 | P_30 | 36.8 | P_31 |
| 25.2 | P_34 | 8.8 | P_14 | 67.1 | P_2 |
| 26.1 | P_22 | 8.8 | P_31 | 67.8 | P_34 |
| 27.0 | P_14 | 10.5 | P_32 | 70.7 | P_5 |
| 27.7 | P_18 | 14.0 | P_18 | 72.2 | P_22 |
| 38.8 | P_10 | 22.8 | P_26 | 76.3 | P_14 |
| 40.1 | P_5 | 38.6 | P_10 | 79.6 | P_18 |
| 40.4 | P_26 | 52.6 | P_2 | 177.0 | P_10 |
| 41.5 | P_2 | 52.6 | P_5 | 233.1 | P_26 |

TABLE 4

| Angles (degree) | Pathway # | Diff Fluxes (%) | Pathway # | Net Diff (%) | Pathway # |
|---|---|---|---|---|---|
| 2.3 | P_32 | 3.5 | P_32 | 5.2 | P_32 |
| 2.6 | P_33 | 7.0 | P_33 | 6.4 | P_33 |
| 10.9 | P_30 | 10.5 | P_34 | 25.1 | P_30 |
| 21.9 | P_31 | 12.3 | P_22 | 35.8 | P_31 |
| 25.9 | P_34 | 12.3 | P_30 | 66.9 | P_2 |
| 26.9 | P_22 | 15.8 | P_14 | 71.4 | P_5 |
| 27.8 | P_14 | 15.8 | P_31 | 75.3 | P_34 |
| 28.4 | P_18 | 21.1 | P_18 | 79.9 | P_22 |
| 39.5 | P_10 | 29.8 | P_26 | 84.1 | P_14 |
| 39.5 | P_5 | 45.6 | P_10 | 87.5 | P_18 |
| 40.5 | P_26 | 45.6 | P_5 | 187.6 | P_10 |
| 41.0 | P_2 | 59.6 | P_2 | 241.7 | P_26 |

TABLE 5

| Variant | Type | Nucleotide Change | Amino Acid Change | Result |
|---|---|---|---|---|
| B+ | normal | none | none | |
| A+ | non-chronic | 376 A→G | Asn→Asp | polar to acidic |
| A− | non-chronic | 376 A→G | Asn→Asp | polar to acidic |
| | | 202* G→A | Val→Met | nonpolar to nonpolar |
| Mediterranean | non-chronic | 563 C→T | Ser→Phe | polar to nonpolar |
| Tsukui | chronic | 561-563 del | 188/189 del | |
| Minnesota | chronic | 637 G→T | 213 Val→Leu | nonpolar to nonpolar |
| Asahikawa | chronic | 695 G→A | 232 Cys→Tyr | slightly polar to nonpolar |
| Durham | chronic | 713 A→G | 238 Lys→Arg | basic to basic |
| Wayne | chronic | 769 C→G | 257 Arg→Gly | basic to nonpolar |
| Loma Linda | chronic | 1089 C→A | 363 Asn→Lys | polar to basic |
| Tomah | chronic | 1153 T→C | 385 Cys→Arg | slightly polar to basic |
| Iowa | chronic | 1156 A→G | 386 Lys→Glu | basic to acidic |
| Walter Reed | chronic | 1156 A→G | 386 Lys→Glu | basic to acidic |
| Iowa City | chronic | 1156 A→G | 386 Lys→Glu | basic to acidic |
| Springfield | chronic | 1156 A→G | 386 Lys→Glu | basic to acidic |
| Guadalajara | chronic | 1159 C→T | 387 Arg→Cys | basic to slightly polar |
| Iwate | chronic | 1160 G→A | 387 Arg→His | basic to acidic/basic |
| Niigata | chronic | 1160 G→A | 387 Arg→His | basic to acidic/basic |
| Yamaguchi | chronic | 1160 G→A | 387 Arg→His | basic to acidic/basic |
| Portici | chronic | 1178 G→A | 393 Arg→His | basic to acidic/basic |
| Alhambra | chronic | 1180 G→C | 394 Val→Leu | nonpolar to nonpolar |
| Tokyo | chronic | 1246 G→A | 416 Glu→Lys | acidic to basic |
| Fukushima | chronic | 1246 G→A | 416 Glu→Lys | acidic to basic |
| Atlanta | chronic | 1284 C→A | 428 Tyr→End | |
| Pawnee | chronic | 1316 G→C | 439 Arg→Pro | basic to nonpolar |
| Morioka | chronic | 1339 G→A | 447 Gly→Arg | nonpolar to basic |

TABLE 6

| Variant | Nucleotide Change | Amino Acid Change | Result |
|---|---|---|---|
| Sassari | 514 G→C | Glu→Gln | acidic to slightly polar |
| Parma | not characterized | — | — |
| | 1456 C→T | Arg→Trp | basic to nonpolar |
| Soresina | 1456 C→T | Arg→Trp | basic to nonpolar |
| | 1552 C→A | Arg→Ser | basic to slightly polar |
| Milano | 1456 C→T | Arg→Trp | basic to nonpolar |
| Brescia | 1042-1044 del | Lys deleted | basic deleted |
| | 1456 C→T | Arg→Trp | basic to nonpolar |
| Manatova | 1168 G→A | Asp→Asn | acidic to slightly polar |

TABLE 7

| | Changes to Regulatory Model | | |
|---|---|---|---|
| Rxn Abbr | Gene | Reaction | Comment |
| GALU | galU | [c]g1p + h + utp <==> ppi + udpg | Removed |
| ORNTA | ygjG | [c] : akg + orn --> glu-L + glu5sa | Removed |
| PTRCA | ygjG | [c] : akg + ptrc --> 4abutn + glu-L | Added GPR Assoc. |
| ABUTD | aldH | [c]4abutn + h2o + nad --> 4abut + (2) h + nadh | Added Isozyme |
| TRPAS1 | none | [c]cys-L + h2o --> h2s + nh4 + pyr | Added Isozyme |
| CYSabc | none | atp[c] + cys-L[e] + h2o[c] --> adp[c] + cys-L[c] + h[c] + pi[c] | Added Isozyme |
| CYSabc | none | atp[c] + cys-L[e] + h2o[c] --> adp[c] + cys-L[c] + h[c] + pi[c] | Added Isozyme |
| INDOLEt | acrEF | h[c] + indole[c] --> h[e] + indole[e] | Added Reaction |
| H2SO | none | [c] : h2s + (2) o2 --> (2) h + so4 | Added Reaction |
| H2St | none | h2s[c] --> h2s[e] | Added Reaction |
| EX_h2s(e) | none | [e]h2s <==> | Added Reaction |

TABLE 8

| bNum | Gene | Rule | Reference |
|---|---|---|---|
| b0002 | thrA | (NOT (thr-L(e) > 0 OR ile-L(e) > 0)) | NH 32 |
| b0003 | thrB | (NOT (thr-L(e) > 0 OR ile-L(e) > 0)) | NH 32 |
| b0004 | thrC | (NOT (thr-L(e) > 0 OR ile-L(e) > 0)) | NH 32 |
| b0007 | yaaJ | | |
| b0008 | talB | | |
| b0019 | nhaA | ((NhaR) OR (RpoS)) | PMID: 11133959 |
| b0020 | nhaR | (na1(e) > 0) | PMID: 11133959 |
| b0025 | ribF | | |
| b0029 | lytB | | |
| b0031 | dapB | (NOT lys-L(e) > 0) | NH 32 |
| b0032 | carA | (NOT ArgR) | NH 25; PMID: 9457878 |
| b0033 | carB | (NOT ArgR) | NH 25; PMID: 9457878 |
| b0034 | caiF | (Fnr AND Crp AND NOT NarL) | PMID: 10564497, 8631699 |
| b0036 | caiD | (Crp AND CaiF) | PMID: 10564497 |
| b0038 | caiB | (Crp AND CaiF) | PMID: 10564497 |
| b0040 | caiT | (Crp AND CaiF) | PMID: 10564497 |
| b0048 | folA | | |
| b0049 | apaH | | |
| b0052 | pdxA | (RpoE) | PMID: 11844765 |
| b0061 | araD | (AraC OR (AraC AND Crp)) | NH 20 |
| b0062 | araA | (AraC OR (AraC AND Crp)) | NH 20 |
| b0063 | araB | (AraC OR (AraC AND Crp)) | NH 20 |
| b0064 | araC | (arab-L(e) > 0) | NH 20 |
| b0066 | sfuC | | |
| b0067 | sfuB | | |
| b0068 | sfuA | | |
| b0071 | leuD | (NOT(leu-L(e) > 0) OR Lrp) | |
| b0072 | leuC | (NOT(leu-L(e) > 0) OR Lrp) | |
| b0073 | leuB | (NOT(leu-L(e) > 0) OR Lrp) | NH 27 |
| b0074 | leuA | (NOT(leu-L(e) > 0) OR Lrp) | NH 27 |
| b0077 | ilvI | (Lrp AND NOT (leu-L(e) > 0)) | NH 27; PMID: 12218014 |
| b0078 | ilvH | (Lrp AND NOT (leu-L(e) > 0)) | NH 27; PMID: 12218014 |
| b0080 | fruR | (NOT ("Surplus FDP")) | PMID: 8550429 |
| b0085 | murE | | |
| b0086 | murF | | |
| b0087 | mraY | | |
| b0088 | murD | | |
| b0090 | murG | | |
| b0091 | murC | | |
| b0092 | ddlB | | |
| b0096 | lpxC | | |
| b0099 | mutT | | |
| b0104 | guaC | (NOT((gln-L(e) > 0) OR (gua(e) > 0))) | NH 34; PMID: 2999079 |
| b0109 | nadC | | |
| b0112 | aroP | (NOT (TyrR AND ((phe-L(e) > 0) OR (tyr-L(e) > 0) OR (trp-L(e) > 0)))) | NH 22, 28; PMID: 9209035, 9765583 |
| b0113 | pdhR | (NOT "Surplus PYR") | PMID: 7783622 |
| b0114 | aceE | ((NOT(PdhR)) OR (Fis)) | NH 16; PMID: 7783622 |
| b0115 | aceF | ((NOT(PdhR)) OR (Fis)) | NH 16; PMID: 7783622 |
| b0116 | lpdA | (ON) | NH 16, NH 23; PMID: 7783622, 9209026, 9720032, 12101307 |
| b0118 | acnB | (ON) | PMID: 9421904 |
| b0120 | speD | | NH 25 |
| b0121 | speE | | NH 25 |
| b0124 | gcd | (NOT Crp) | PMID: 11810262 |
| b0125 | hpt | (Crp) | NH 34: PMID: 11810262 |
| b0126 | yadF | | |
| b0131 | panD | | |
| b0133 | panC | | |
| b0134 | panB | | |
| b0142 | folK | | |
| b0154 | hemL | | |
| b0158 | yadT | | |
| b0159 | mtn | | |
| b0160 | dgl | | PMID: 2157212 |
| b0162 | sdaR | ((glcr(e) > 0) OR (galct-D(e) > 0)) | PMID: 10762278 |
| b0166 | dapD | | NH 32 |
| b0167 | glnD | (Lrp) | NH 23 |
| b0171 | pyrH | | |
| b0173 | dxr | | |
| b0174 | uppS | | |
| b0175 | cdsA | | |
| b0179 | lpxD | | |
| b0180 | fabZ | ((NOT((Stringent > 0) OR (Stringent < 0))) OR CpxR OR RpoE OR FadR2) | NH 37; PMID: 11859088, 11566998, 864995 |
| b0181 | lpxA | | |
| b0182 | lpxB | | |

TABLE 8-continued

| | | | |
|---|---|---|---|
| b0185 | accA | | NH 37 |
| b0186 | ldcC | | PMID: 9339543 |
| b0197 | yaeC | (NOT MetJ) | PMID: 12218041 |
| b0198 | yaeE | (NOT MetJ) | PMID: 12218041 |
| b0199 | abc | (NOT MetJ) | PMID: 12218041 |
| b0200 | yaeD | | |
| b0207 | yafB | | |
| b0212 | gloB | | |
| b0221 | fadF | (NOT (FadR2) OR NOT (ArcA)) | NH 21 |
| b0222 | gmhA | | |
| b0238 | gpt | | NH 34 |
| b0242 | proB | | NH 25, 26 |
| b0243 | proA | | NH 25, 26 |
| b0273 | argF | (NOT ArgR) | NH 25 |
| b0312 | betB | (NOT (ArcA OR BetI)) | PMID: 8626294 |
| b0313 | betI | (chol(e) > 0) | PMID: 8626294 |
| b0314 | betT | (NOT (BetI)) | PMID: 8626294 |
| b0323 | yahI | | |
| b0331 | prpB | (ppa(e) > 0) | PMID: 12473114 |
| b0333 | prpC | (ppa(e) > 0) | PMID: 12473114 |
| b0334 | prpD | (ppa(e) > 0) | PMID: 12473114 |
| b0335 | prpE | (ppa(e) > 0) | PMID: 12473114 |
| b0336 | codB | (NOT (PurR) OR NRI_hi) | NH 35; PMID 7500333 |
| b0337 | codA | (NOT (PurR) OR NRI_hi) | PMID: 2673119 |
| b0338 | cynR | (cynt(e) > 0) | PMID: 7961413, 8253686 |
| b0339 | cynT | | PMID: 7961413, 8253686 |
| b0340 | cynS | (CynR) | PMID: 8083164, 7961413, 8253686 |
| b0341 | cynX | (cynt(e) > 0) | PMID: 2670891 |
| b0343 | lacY | ("CRP noGLC" AND NOT(LacI)) | Adhya, S. (1996) |
| b0344 | lacZ | ("CRP noGLC" AND NOT(LacI)) | Adhya, S. (1996) |
| b0345 | lacI | (NOT(lcts(e) > 0)) | PMID: 9104037 |
| b0346 | mhpR | (3hpppn(e) > 0) | PMID: 9098055 |
| b0347 | mhpA | (MhpR) | PMID: 9098055 |
| b0348 | mhpB | (MhpR) | PMID: 9098055 |
| b0349 | mhpC | (MhpR) | PMID: 9098055 |
| b0350 | mhpD | (MhpR) | PMID: 9098055 |
| b0351 | mhpF | (MhpR) | PMID: 9098055 |
| b0352 | mhpE | (MhpR) | PMID: 9098055 |
| b0353 | mhpT | | |
| b0356 | adhC | | |
| b0365 | tauA | (Cbl AND CysB) | |
| b0366 | tauB | (Cbl AND CysB) | |
| b0367 | tauC | (Cbl AND CysB) | |
| b0368 | tauD | (Cbl AND CysB) | PMID: 11479697, 9401024 |
| b0369 | hemB | | |
| b0381 | ddlA | | |
| b0386 | proC | | NH 25,26 |
| b0388 | aroL | (NOT((TyrR AND (tyr-L(e) > 0)) OR, (TyrR AND (tyr-L(e) > 0) AND TrpR))) | NH 28 |
| b0399 | phoB | (PhoR) | NH 87, PMID: 11489853 |
| b0400 | phoR | (pi(e) < 0.004E−6 M) | NH 87, PMID: 11489853 |
| b0401 | brnQ | | |
| b0403 | malZ | (MalT) | PMID: 11931562, 11867639, 9529892 |
| b0414 | ribD | | |
| b0415 | ribH | | |
| b0417 | thiL | | |
| b0418 | pgpA | | |
| b0420 | dxs | | |
| b0421 | ispA | | |
| b0423 | thiI | | |
| b0425 | panE | | |
| b0428 | cyoE | (NOT (ArcA OR Fnr)) | |
| b0429 | cyoD | (NOT (ArcA OR Fnr)) | PMID: 8576043 |
| b0430 | cyoC | (NOT (ArcA OR Fnr)) | PMID: 8576043 |
| b0431 | cyoB | (NOT (ArcA OR Fnr)) | PMID: 8576043 |
| b0432 | cyoA | (NOT (ArcA OR Fnr)) | PMID: 8576043 |
| b0451 | amtB | | |
| b0469 | apt | | |
| b0474 | adk | | NH 34 |
| b0475 | hemH | | |
| b0477 | gsk | | |
| b0480 | ushA | | |
| b0485 | ybaS | | NH 22 |
| b0504 | ybbS | (NOT(o2(e) > 0) AND NOT AllR AND NOT (nh4(e) > 0)) | PMID: 12460564 |
| b0505 | allA | (NOT AllR) | PMID: 12460564 |
| b0506 | allR | (OFF) /* glyoxalate is the inactivator */ | PMID: 12460564 |

TABLE 8-continued

| | | | |
|---|---|---|---|
| b0507 | gcl | (NOT AllR) | PMID: 12460564 |
| b0508 | hyi | | PMID: 10561547, 8440684 |
| b0509 | glxR | (NOT AllR) | PMID: 12460564 |
| b0511 | allP | | |
| b0512 | allB | (NOT AllR) | PMID: 12460564 |
| b0514 | glxK | (NOT AllR) | PMID: 12460564 |
| b0516 | allC | (AllS) | PMID: 12460564 |
| b0521 | arcC | | |
| b0522 | purK | (NOT (PurR)) | NH 34 |
| b0523 | purE | (NOT (PurR)) | NH 34 |
| b0529 | folD | | |
| b0564 | appY | (NOT CitB) | PMID 11889485, 9701802 |
| b0576 | pheP | | |
| b0583 | entD | (NOT (Fur)) | |
| b0586 | entF | | |
| b0593 | entC | (NOT (Fur)) | NH 39; PMID: 8655506 |
| b0594 | entE | (NOT (Fur)) | |
| b0595 | entB | (NOT (Fur)) | |
| b0596 | entA | (NOT (Fur)) | |
| b0612 | citT | (CitB AND (NOT (o2(e) > 0))) | PMID: 11889485 |
| b0615 | citF | (CitB) | PMID: 11889485, 9701802 |
| b0616 | citE | (CitB) | PMID: 11889485, 9701802 |
| b0617 | citD | (CitB) | PMID: 11889485, 9701802 |
| b0619 | dpiB | (cit(e) > 0) | PMID: 11889485 |
| b0620 | dpiA | (CitA) | PMID: 11889485 |
| b0621 | dcuC | (Fnr OR ArcA) | PMID: 8955408 |
| b0638 | phpB | | |
| b0639 | nadD | | |
| b0652 | gltL | (NOT (glc-D(e) > 0)) | NH 22 |
| b0653 | gltK | (NOT (glc-D(e) > 0)) | NH 22 |
| b0654 | glu | (NOT (glc-D(e) > 0)) | NH 22 |
| b0655 | gltI | (NOT (glc-D(e) > 0)) | NH 22 |
| b0662 | ubiF | | |
| b0674 | asnB | | NH 24 |
| b0676 | nagC | (NOT((acgam(e) > 0) OR AGDC > 0)) | NH 75 |
| b0677 | nagA | (NOT (NagC)) | NH 20; PMID 1766379, 11139621 |
| b0678 | nagB | (NOT (NagC) OR (gam(e) > 0)) | NH 20; PMID 1766379, 11139621 |
| b0679 | nagE | (NOT (NagC)) | PMID: 1766379, 11139621 |
| b0683 | fur | ((fe2(e) > 0) AND (OxyR OR SoxS)) | PMID: 10419964 |
| b0688 | pgm | | |
| b0692 | potE | | |
| b0693 | speF | | NH 22, 25 |
| b0694 | kdpE | (KdpD) | PMID: 12115059 |
| b0695 | kdpD | (NOT (k(e) > 1)) | PMID: 11248697 |
| b0696 | kdpC | (KdpE) | PMID: 8437514, 11248697 |
| b0697 | kdpB | (KdpE) | PMID: 8437514, 11248697 |
| b0698 | kdpA | (KdpE) | PMID: 8437514, 11248697 |
| b0720 | gltA | | PMID: 8051021 |
| b0721 | sdhC | (NOT((ArcA) OR (Fnr)) OR (Crp) OR (Fis)) | PMID: 9209026, 9720032 |
| b0722 | sdhD | (NOT((ArcA) OR (Fnr)) OR (Crp) OR (Fis)) | PMID: 9209026, 9720032 |
| b0723 | sdhA | (NOT((ArcA) OR (Fnr)) OR (Crp) OR (Fis)) | PMID: 9209026, 9720032 |
| b0724 | sdhB | (NOT((ArcA) OR (Fnr)) OR (Crp) OR (Fis)) | PMID: 9209026, 9720032 |
| b0726 | sucA | | PMID: 9209026, 9720032 |
| b0727 | sucB | | PMID: 9209026, 9720032 |
| b0728 | sucC | | NH 16; PMID: 9209026, 9720032, 7783622, 8057842 |
| b0729 | sucD | | NH 16; PMID: 9209026, 9720032, 7783622, 8057842 |
| b0733 | cydA | ((NOT Fnr) OR (ArcA)) | PMID: 8576043 |
| b0734 | cydB | ((NOT Fnr) OR (ArcA)) | PMID: 8576043 |
| b0750 | nadA | | NH 48 |
| b0751 | pnuC | | |
| b0754 | aroG | (NOT(((phe-L(e) > 0) OR (trp-L(e) > 0)) AND TyrR )) | NH 28 |
| b0755 | gpmA | | |
| b0757 | galK | (NOT(glc-D(e) > 0) AND (NOT(GalR OR GalS)) OR NOT (Rob)) | Adhya, S. (1996) |
| b0758 | galT | (NOT(glc-D(e) > 0) AND (NOT(GalR OR GalS)) OR NOT (Rob)) | PMID: 12101127; Adhya, S. (1996) |
| b0759 | galE | (NOT(glc-D(e) > 0) AND (NOT(GalR OR GalS)) OR NOT (Rob)) | Adhya, S. (1996) |
| b0774 | bioA | (NOT (BirA)) | NH 45; PMID: 12368242 |
| b0775 | bioB | (NOT (BirA)) | NH 45; PMID: 12368242 |

TABLE 8-continued

| | | | |
|---|---|---|---|
| b0776 | bioF | (NOT (BirA)) | NH 45; PMID: 12368242 |
| b0778 | bioD | (NOT (BirA)) | NH 45; PMID: 12368242 |
| b0809 | glnQ | | NH 22, 23, 24 |
| b0810 | glnP | | NH 22, 23, 24 |
| b0811 | glnH | | NH 22, 23, 24 |
| b0825 | fsa | | |
| b0828 | ybiK | | PMID: 12007658 |
| b0840 | deoR | (NOT((PPM2 > 0) OR (PPM2 < 0))) | NH 20 |
| b0854 | potF | | NH 25 |
| b0855 | potG | | NH 25 |
| b0856 | potH | | NH 25 |
| b0857 | potI | | NH 25 |
| b0860 | artJ | | NH 25 |
| b0861 | artM | | NH 25 |
| b0862 | artQ | | NH 25 |
| b0864 | artP | | NH 25 |
| b0870 | ltaA | | |
| b0871 | poxB | ((NOT (Growth > 0)) AND (RpoS)) | NH 93 |
| b0888 | trxB | | PMID: 10788450 |
| b0889 | lrp | (NOT leu-L(e) > 0) | NH 94 |
| b0894 | dmsA | (Fnr AND NOT NarL) | PMID: 12079504 |
| b0895 | dmsB | (Fnr AND NOT NarL) | PMID: 12079504 |
| b0896 | dmsC | (Fnr AND NOT NarL) | PMID: 12079504 |
| b0902 | pflA | (ArcA OR Fnr AND (Crp OR NOT(NarL))) | NH 95; PMID: 7934836 |
| b0903 | pflB | (ArcA OR Fnr AND (Crp OR NOT(NarL))) | NH 95; PMID: 7934836 |
| b0904 | focA | (ArcA OR Fnr AND (Crp OR NOT (NarL))) | NH 95; PMID: 7934836 |
| b0907 | serC | (Lrp OR (NOT (Crp))) | NH 30; PMID: 9171388 |
| b0908 | aroA | | NH 28 |
| b0910 | cmk | | |
| b0915 | lpxK | | |
| b0918 | kdsB | | PMID: 7543480 |
| b0928 | aspC | | NH 22, 24, 28 |
| b0931 | pncB | (NOT (NadR)) | NH 48 |
| b0945 | pyrD | ((NOT (csn(e) > 0)) OR (gua(e) > 0) OR NOT PurR) | NH 35 |
| b0954 | fabA | ((NOT((Stringent > 0) OR (Stringent < 0))) OR CpxR OR RpoE OR FadR2) | NH 37; PMID: 11859088, 11566998, 864995 |
| b0963 | mgsA | | |
| b0972 | hyaA | ((ArcA OR Fnr) AND (AppY)) | NH 17; PMID 10537212 |
| b0973 | hyaB | ((ArcA OR Fnr) AND (AppY)) | NH 17; PMID 10537212 |
| b0974 | hyaC | ((ArcA OR Fnr) AND (AppY)) | NH 17; PMID 10537212 |
| b0993 | torS | (tmao(e) > 0) | PMID: 9135110, 11004177 |
| b0995 | torR | (TorS) | PMID: 9135110, 11004177 |
| b0996 | torC | (TorR OR NOT (NarL)) | PMID: 9135110, 11004177 |
| b0997 | torA | (TorR OR NOT (NarL)) | PMID: 9135110, 11004177 |
| b1002 | agp | | NH 87 |
| b1006 | ycdG | | |
| b1014 | putA | ((pro-L(e) > 0) OR Crp OR Nac) | NH 22 |
| b1015 | putP | ((pro-L(e) > 0) OR Crp OR Nac) | NH 22; PMID: 2464125 |
| b1033 | ycdW | | PMID: 11237876 |
| b1054 | lpxL | | |
| b1062 | pyrC | ((NOT (csn(e) > 0)) OR (gua(e) > 0) OR NOT PurR) | NH 35 |
| b1091 | fabH | ((NOT((Stringent > 0) OR (Stringent < 0))) | PMID: 8649995 |
| b1092 | fabD | ((NOT((Stringent > 0) OR (Stringent < 0))) | PMID: 8649995 |
| b1093 | fabG | ((NOT((Stringent > 0) OR (Stringent < 0))) OR CpxR OR RpoE OR FadR2) | NH 37; PMID: 11859088, 11566998, 864995 |
| b1095 | fabF | ((NOT((Stringent > 0) OR (Stringent < 0))) OR CpxR OR RpoE OR FadR2) | |
| b1096 | pabC | | |
| b1098 | tmk | | |
| b1101 | ptsG | (NOT(Mlc) OR NOT(Cra)) | PMID: 10469172, 8106445, 7518773, 1324322, 11931562, 11867639, 9529892, 9148912 |
| b1109 | ndh | (NOT (Fnr)) | |
| b1123 | potD | | NH 25 |
| b1124 | potC | | NH 25 |
| b1125 | potB | | NH 25 |
| b1126 | potA | | NH 25 |
| b1131 | purB | (NOT (PurR)) | NH 34 |
| b1136 | icdA | | PMID: 9209047, 9922253 |
| b1186 | nhaB | | PMID: 11779554 |
| b1187 | fadR | (glc-D(e) > 0 OR NOT (ac(e) > 0 ) ) | PMID: 8755903 |
| b1189 | dadA | (ala-L(e) > 0 AND NOT Crp) | NH 22 |
| b1190 | dadX | (((ala-L(e) > 0) OR (ala-D(e) > 0)) AND Crp) | NH 22, 24 |
| b1197 | treA | (RpoS) | PMID: 9148912, 8892826 |
| b1198 | dhaH | | PMID: 11021910 |
| b1199 | dhaK2 | | PMID: 11021910 |

TABLE 8-continued

| | | | |
|---|---|---|---|
| b1200 | dhaK1 | | PMID: 11021910 |
| b1207 | prsA | (NOT PurR) | PMID: 8388874 |
| b1208 | ispE | | |
| b1210 | hemA | | PMID: 8997718 |
| b1215 | kdsA | | PMID: 7543480 |
| b1216 | chaA | | PMID: 11779554, 9518629 |
| b1221 | narL | ((no3(e) > 0) OR (no2(e) > 0)) | NH 17 |
| b1223 | narK | (Fnr OR NarL) | PMID: 1474901 |
| b1224 | narG | (Fnr AND NarL) | NH 17; PMID: 8736541, 10464201 |
| b1225 | narH | (Fnr AND NarL) | NH 17; PMID: 8736541, 10464201 |
| b1226 | narJ | (Fnr AND NarL) | NH 17; PMID: 8736541, 10464201 |
| b1227 | narI | (Fnr AND NarL) | NH 17; PMID: 8736541, 10464201 |
| b1232 | purU | | |
| b1236 | galU | | |
| b1238 | tdk | | |
| b1241 | adhE | (NOT (o2(e) > 0) OR (NOT ((o2(e) > 0) AND (Cra))) OR (Fis) OR NOT (NarL) OR (RpoS)) | PMID: 10601216, 9371462 |
| b1249 | cls | | |
| b1260 | trpA | (NOT TrpR) | NH 28 |
| b1261 | trpB | (NOT TrpR) | NH 28 |
| b1262 | trpC | (NOT TrpR) | NH 28 |
| b1263 | trpD | (NOT TrpR) | NH 28 |
| b1264 | trpE | (NOT TrpR) | NH 28 |
| b1270 | btuR | | |
| b1275 | cysB | (NOT (cys-L(e) > 0)) | NH 31 |
| b1276 | acnA | (SoxS) | PMID: 9421904 |
| b1277 | ribA | | PMID: 8709966 |
| b1278 | pgpB | | |
| b1281 | pyrF | | NH 35 |
| b1288 | fabI | ((NOT((Stringent > 0) OR (Stringent < 0))) OR CpxR OR RpoE OR FadR2) | NH 37; PMID: 11859088, 11566998, 864995 |
| b1297 | ycjK | | |
| b1300 | aldH | | |
| b1302 | goaG | | |
| b1323 | tyrR | ((trp-L(e) > 0) OR (tyr-L(e) > 0) OR (phe-L(e) > 0)) | NH 28 |
| b1334 | fnr | (NOT (o2(e) > 0) ) | PMID: 2964639, NH 95 |
| b1363 | trkG | | NH 72 |
| b1380 | ldhA | | PMID: 11535784 |
| b1384 | feaR | (Crp) | PMID: 8631685 |
| b1385 | feaB | (FeaR) | PMID: 8631685 |
| b1386 | tynA | (MaoB) | PMID: 8631685 |
| b1398 | paaK | | PMID: 9748275 |
| b1415 | aldA | | PMID: 9202484 |
| b1416 | gapC_2 | | |
| b1417 | gapC_1 | | |
| b1440 | ydcS | | |
| b1441 | ydcT | | |
| b1442 | ydcU | | |
| b1443 | ydcV | | |
| b1469 | narU | | PMID: 7747940 |
| b1474 | fdnG | (Fnr OR NarL) | PMID: 1629153, 8736541 |
| b1475 | fdnH | (Fnr OR NarL) | PMID: 1629153, 8736541 |
| b1476 | fdnI | (Fnr OR NarL) | PMID: 1629153, 8736541 |
| b1479 | sfcA | | |
| b1492 | xasA | | |
| b1493 | gadB | ((NOT (Growth > 0)) OR (pH < 4)) | NH 22; PMID: 11976288 |
| b1519 | tam | (NOT (Growth > 0)) | PMID: 10224113 |
| b1521 | uxaB | (NOT ExuR) | NH 20 |
| b1524 | yneH | ((NOT (glc-D(e) > 0) OR ((nh4(e) > 0) AND NOT Crp))) | NH 22 |
| b1531 | marA | (Salicylate > 0) | PMID: 8522515 |
| b1584 | speG | | PMID: 10986239 |
| b1594 | mlc | (NOT (glc-D(e) > 0)) | PMID: 10469172 |
| b1602 | pntB | | |
| b1603 | pntA | | |
| b1605 | arcD | | |
| b1611 | fumC | (MarA OR Rob OR SoxS AND (NOT(ArcA))) | PMID: 7592392 |
| b1612 | fumA | (NOT(ArcAORFnr)) | PMID: 7592392 |
| b1613 | manA | | NH 20 |
| b1620 | malI | (NOT (malt(e) > 0)) | PMID: 2670898 |
| b1621 | malX | ((MalT AND Crp) OR MalT) | PMID: 1856179 |
| b1622 | malY | (NOT (MalI)) | PMID: 11931562, 11867639, 9529892 |

TABLE 8-continued

| | | | |
|---|---|---|---|
| b1623 | add | ((ade(e) > 0) OR (hxan(e) > 0)) | NH 34 |
| b1636 | pdxY | | |
| b1638 | pdxH | | NH 32 |
| b1646 | sodC | (NOT(Growth > 0) AND NOT Fnr) | PMID: 8626323, 10216871 |
| b1651 | gloA | | |
| b1656 | sodB | | PMID: 11782507 |
| b1658 | purR | ((hxan(e) > 0) OR (gua(e) > 0)) | NH 34 |
| b1662 | ribE | | |
| b1676 | pykF | (NOT(Cra)) | PMID: 8550429 |
| b1692 | ydiB | | |
| b1693 | aroD | | NH 28 |
| b1702 | pps | (Cra) | PMID: 9512708 |
| b1704 | aroH | (NOT TrpR) | NH 28 |
| b1709 | btuD | | |
| b1711 | btuC | | |
| b1723 | pfkB | | |
| b1732 | katE | (NOT(Growth > 0)) | PMID: 12589799 |
| b1740 | nadE | | |
| b1744 | astE | ((NOT(Growth > 0) AND RpoS) OR (NRI_hi AND RpoN)) | PMID: 12003934 |
| b1745 | astB | ((NOT(Growth > 0) AND RpoS) OR (NRI_hi AND RpoN)) | PMID: 12003934 |
| b1746 | astD | ((NOT(Growth > 0) AND RpoS) OR (NRI_hi AND RpoN)) | PMID: 12003934 |
| b1747 | astA | ((NOT(Growth > 0) AND RpoS) OR (NRI_hi AND RpoN)) | PMID: 12003934 |
| b1748 | astC | ((NOT(Growth > 0) AND RpoS) OR (NRI_hi AND RpoN)) | PMID: 12003934 |
| b1761 | gdhA | (NOT ((Nac) OR (glu-L(e) > 0)) ) | NH 22, 24; PMID: 9785451 |
| b1764 | selD | | PMID: 1650339 |
| b1767 | ansA | | NH 22 |
| b1768 | pncA | | |
| b1773 | b1773 | | |
| b1779 | gapA | | PMID: 9851989 |
| b1801 | yeaV | | |
| b1805 | fadD | (NOT (FadR2) OR NOT (ArcA)) | NH 21 |
| b1812 | pabB | | |
| b1814 | sdaA | ((gly(e) > 0 OR leu-L(e) > 0 OR NOT (o2(e) > 0)) AND ((NOT Lrp) OR (Lrp AND leu-L(e) > 0))) | NH 22 |
| b1817 | manX | (("CRP noLAC") OR (NOT (Mlc))) | NH 20; PMID: 9484892, 11934616 |
| b1818 | manY | (("CRP noLAC") OR (NOT (Mlc))) | NH 20; PMID: 9484892, 11934616 |
| b1819 | manZ | (("CRP noLAC") OR (NOT (Mlc))) | NH 20; PMID: 9484892, 11934616 |
| b1827 | kdgR | (NOT(2ddglcn(e) > 0) AND NOT (MNNH > 0) AND NOT(ALTRH > 0)) | NH 20 |
| b1849 | purT | (NOT (PurR)) | NH 34 |
| b1850 | eda | (ON) /* GntR represser also /* | PMID: 1624451, 8655507 |
| b1851 | edd | (NOT (GntR)) | PMID: 1624451, 8655507 |
| b1852 | zwf | | |
| b1854 | pykA | | |
| b1855 | msbB | | |
| b1865 | ntpA | | |
| b1872 | torZ | | PMID: 11004177 |
| b1873 | torY | | PMID: 11004177 |
| b1896 | otsA | (RpoS) | PMID: 9148912, 12105274 |
| b1897 | otsB | (RpoS) | PMID: 9148912, 12105274 |
| b1898 | araH_2 | (AraC OR (AraC AND Crp)) | NH 20 |
| b1899 | araH_1 | (AraC OR (AraC AND Crp)) | NH 20 |
| b1900 | araG | (AraC OR (AraC AND Crp)) | NH 20 |
| b1901 | araF | (AraC OR (AraC AND Crp)) | NH 20 |
| b1907 | tyrP | (NOT(TyrR AND (tyr-L(e) > 0))) | NH 22, 28 |
| b1912 | pgsA | | |
| b1982 | amn | | NH 34 |
| b1987 | cbl | (NOT ((so4(e) > 0) OR (cys-L(e) > 0 )) AND CysB ) | PMID: 10506196 |
| b1988 | nac | (NRI_low AND RpoN) | NH 23 |
| b1991 | cobT | (cbi(e) > 0) | PMID: 7592411 |
| b1992 | cobS | (cbi(e) > 0) | PMID: 7592411 |
| b1993 | cobU | (cbi(e) > 0) | PMID: 7592411 |
| b2019 | hisG | | NH 29 |
| b2020 | hisD | | NH 29 |
| b2021 | hisC | | NH 29 |
| b2022 | hisB | | NH 29 |
| b2023 | hisH | | NH 29 |
| b2024 | hisA | | NH 29 |
| b2025 | hisF | | NH 29 |

TABLE 8-continued

| | | | |
|---|---|---|---|
| b2026 | hisI | | NH 29 |
| b2028 | ugd | | |
| b2029 | gnd | | |
| b2036 | gif | | |
| b2038 | rfbC | | |
| b2039 | rfbA | | |
| b2040 | rfbD | | |
| b2041 | rfbB | | |
| b2042 | galF | | |
| b2045 | wcaK | | |
| b2048 | cpsG | | |
| b2049 | manC | | |
| b2052 | fcl | | |
| b2053 | gmd | | |
| b2065 | dcd | | |
| b2066 | udk | (NOT ((thym(e) > 0) OR (csn(e) > 0) OR (ura(e) > 0))) | NH 35 |
| b2087 | gatR_1 | (NOT (galt(e) > 0)) | PMID: 7772602 |
| b2090 | gatR_2 | (NOT (galt(e) > 0)) | PMID: 7772602 |
| b2091 | gatD | (NOT (GatR)) | N20; PMID: 8955298 |
| b2092 | gatC | (NOT (GatR)) | N20; PMID: 8955298 |
| b2093 | gatB | (NOT (GatR)) | N20; PMID: 8955298 |
| b2094 | gatA | (NOT (GatR)) | N20; PMID: 8955298 |
| b2095 | gatZ | (NOT (GatR)) | N20; PMID: 8955298 |
| b2096 | gatY | (NOT (GatR)) | N20; PMID: 8955298 |
| b2097 | fbaB | ((pyr(e) > 0) OR (lac-D(e) > 0) AND NOT(glc-D(e) > 0)) | PMID: 9531482 |
| b2103 | thiD | | |
| b2104 | thiM | | |
| b2128 | yehW | | |
| b2129 | yehX | | |
| b2130 | yehY | | |
| b2131 | yehZ | | |
| b2132 | bglX | | PMID: 8757730 |
| b2133 | did | | |
| b2143 | cdd | (Crp AND NOT (CytR)) | PMID: 2575702 |
| b2148 | mglC | (Crp AND NOT (GalS)) | PMID: 12101127 |
| b2149 | mglA | (Crp AND NOT (GalS)) | PMID: 12101127 |
| b2150 | mglB | (Crp AND NOT (GalS)) | PMID: 12101127 |
| b2151 | galS | (NOT (lcts(e) > 0) OR NOT (gal(e) > 0)) | PMID: 8982002 |
| b2153 | folE | | |
| b2156 | lysP | | |
| b2167 | fruA | (NOT (Cra)) | PMID: 7852310 |
| b2168 | fruK | (NOT (Cra)) | PMID: 7852310 |
| b2169 | fruB | (NOT (Cra)) | PMID: 7852310 |
| b2210 | mqo | (NOT ArcA) | PMID: 11092847 |
| b2219 | atoS | (acac(e) > 0) | NH 21 |
| b2220 | atoC | (AtoS) | NH 21 |
| b2221 | atoD | (AtoC) | NH 21 |
| b2222 | atoA | (AtoC) | NH 21 |
| b2223 | atoE | (AtoC) | |
| b2224 | atoB | (AtoC) | NH 21 |
| b2232 | ubiG | ((o2(e) > 0) AND Crp) | NH 39; PMID: 2830238 |
| b2234 | nrdA | (NOT (ArcA)) | NH 34; PMID: PMID: 9680219, 8954104 |
| b2235 | nrdB | (NOT (ArcA)) | NH 34; PMID: PMID: 9680219, 8954104 |
| b2239 | glpQ | ((NOT GlpR OR Fnr) AND Crp) | PMID: 9179845, 1521763 |
| b2240 | glpT | (NOT (GlpR) AND Crp) | PMID: 9179845 |
| b2241 | glpA | ("CRP noRIB" AND (Fnr OR ArcA) AND (NOT(GlpR))) | NH 20; PMID: 2403539; Paigen K. (1970) |
| b2242 | glpB | ("CRP noRIB" AND (Fnr OR ArcA) AND (NOT(GlpR))) | NH 20; PMID: 2403539; |
| b2243 | glpC | ("CRP noRIB" AND (Fnr OR ArcA) AND (NOT(GlpR))) | NH 20; PMID: 2403539; Paigen K. (1970) |
| b2260 | menE | | |
| b2261 | menC | | |
| b2262 | menB | | |
| b2264 | menD | | |
| b2265 | menF | | |
| b2276 | nuoN | (NOT (ArcA OR Fnr) OR NarL) | PMID: 10628873 |
| b2277 | nuoM | (NOT (ArcA OR Fnr) OR NarL) | PMID: 10628873 |
| b2278 | nuoL | (NOT (ArcA OR Fnr) OR NarL) | PMID: 10628873 |
| b2279 | nuoK | (NOT (ArcA OR Fnr) OR NarL) | PMID: 10628873 |
| b2280 | nuoJ | (NOT (ArcA OR Fnr) OR NarL) | PMID: 10628873 |
| b2281 | nuoI | (NOT (ArcA OR Fnr) OR NarL) | PMID: 10628873 |
| b2282 | nuoH | (NOT (ArcA OR Fnr) OR NarL) | PMID: 10628873 |
| b2283 | nuoG | (NOT (ArcA OR Fnr) OR NarL) | PMID: 10628873 |
| b2284 | nuoF | (NOT (ArcA OR Fnr) OR NarL) | PMID: 10628873 |

TABLE 8-continued

| | | | |
|---|---|---|---|
| b2285 | nuoE | (NOT (ArcA OR Fnr) OR NarL) | PMID: 10628873 |
| b2286 | nuoC | (NOT (ArcA OR Fnr) OR NarL) | PMID: 10628873 |
| b2287 | nuoB | (NOT (ArcA OR Fnr) OR NarL) | PMID: 10628873 |
| b2288 | nuoA | (NOT (ArcA OR Fnr) OR NarL) | PMID: 10628873 |
| b2296 | ackA | | |
| b2297 | pta | | |
| b2306 | hisP | (NOT (lys-L(e) > 0)) | NH 22 |
| b2307 | hisM | (NOT (lys-L(e) > 0)) | NH 22 |
| b2308 | hisQ | (NOT (lys-L(e) > 0)) | NH 22 |
| b2309 | hisJ | (NOT (lys-L(e) > 0)) | NH 22 |
| b2310 | argT | (NOT (lys-L(e) > 0)) | NH 22 |
| b2311 | ubiX | (NOT (PurR)) | |
| b2312 | purF | (NOT (PurR)) | NH 34 |
| b2315 | folC | | |
| b2316 | accD | | NH 37 |
| b2320 | pdxB | | PMID: 11844765 |
| b2323 | fabB | ((NOT((Stringent > 0) OR (Stringent < 0))) OR CpxR OR RpoE OR FadR2) | PMID: 11859088, 11566998 |
| b2329 | aroC | | NH 28 |
| b2344 | fadL | ((NOT (Crp OR FadR OR OmpR))) | NH 21; |
| b2364 | dsdC | (ser-D(e) > 0) | PMID: 7592420 |
| b2366 | dsdA | ((Crp AND DsdC) OR DsdC) | NH 22 |
| b2378 | lpxP | | PMID: 10092655 |
| b2388 | glk | | |
| b2393 | nupC | (Crp OR NOT (CytR)) | NH 35 |
| b2400 | gitX | | |
| b2405 | xapR | (xtsn(e) > 0) | PMID: 7559336 |
| b2406 | xapB | (XapR) | PMID: 7559336 |
| b2407 | xapA | (XapR) | PMID: 7559336 |
| b2411 | lig | | |
| b2413 | cysZ | (CysB) | NH 31 |
| b2414 | cysK | (CysB) | NH 31 |
| b2415 | ptsH | (ON) | PMID: 10469172, 8106445, 7518773, 1324322, 11931562, 11867639, 9529892, 9148912 |
| b2416 | ptsI | (ON) | PMID: 10469172, 8106445, 7518773, 1324322, 11931562, 11867639, 9529892, 9148912 |
| b2417 | crr | (ON) | PMID: 10469172, 8106445, 7518773, 1324322, 11931562, 11867639, 9529892, 9148912 |
| b2418 | pdxK | | |
| b2421 | cysM | (CysB) | NH 31 |
| b2422 | cysA | (CysB) | NH 31 |
| b2423 | cysW | (CysB) | NH 31 |
| b2424 | cysU | (CysB) | NH 31 |
| b2425 | cysP | (CysB) | NH 31 |
| b2429 | yfeV | | |
| b2436 | hemF | | PMID: 8990283 |
| b2440 | eutC | | |
| b2441 | eutB | | |
| b2458 | eutD | | |
| b2463 | maeB | | |
| b2464 | talA | | |
| b2465 | tktB | | |
| b2472 | dapE | | NH 32 |
| b2476 | purC | (NOT (PurR)) | NH 34 |
| b2478 | dapA | | NH 32 |
| b2479 | gcvR | (NOT (gly(e) > 0)) | PMID: 12101307 |
| b2492 | focB | (ArcA OR Fnr AND (Crp OR NOT (NarL))) | PMID: 12426353 |
| b2497 | uraA | | NH 35 |
| b2498 | upp | | NH 35 |
| b2499 | purM | (NOT (PurR)) | NH 34 |
| b2500 | purN | (NOT (PurR)) | NH 34 |
| b2507 | guaA | (NOT (PurR AND Crp)) | NH 34; PMID: 10856643 |
| b2508 | guaB | (NOT (PurR AND Crp)) | NH 34; PMID: 10856643 |
| b2515 | gcpE | | |
| b2518 | ndk | | NH 34 |
| b2530 | iscS | | |
| b2533 | suhB | | PMID: 8831954 |
| b2536 | hcaT | | PMID: 9603882 |
| b2537 | hcaR | (pppn(e) > 0) | PMID: 9603882 |
| b2538 | hcaE | (HcaR AND (NOT((LBMedia > 0) OR (LBMedia < 0)))) | PMID: 9603882 |
| b2539 | hcaF | (HcaR AND (NOT((LBMedia > 0) OR (LBMedia < 0)))) | PMID: 9603882 |
| b2540 | hcaC | (HcaR AND (NOT((LBMedia > 0) OR (LBMedia < 0)))) | PMID: 9603882 |

TABLE 8-continued

| | | | |
|---|---|---|---|
| b2541 | hcaB | (HcaR AND (NOT((LBMedia > 0) OR (LBMedia < 0)))) | PMID: 9603882 |
| b2542 | hcaD | (HcaR AND (NOT((LBMedia > 0) OR (LBMedia < 0)))) | PMID: 9603882 |
| b2551 | glyA | (NOT (gly(e) > 0) OR MetR OR NOT (PurR)) | NH 22, 30; PMID 8900067 |
| b2553 | glnB | (Lrp) | NH 23 |
| b2557 | purL | (NOT (PurR)) | NH 34 |
| b2563 | acpS | | |
| b2564 | pdxJ | (RpoE) | PMID: 11844765 |
| b2573 | rpoE | ("heat shock") | PMID: 7751307 |
| b2574 | nadB | (NOT (NadR)) | NH 48 |
| b2585 | pssA | | |
| b2587 | kgtP | | PMID: 1556144 |
| b2599 | pheA | (NOT (phe-L(e) > 0) ) | NH 28 |
| b2600 | tyrA | (NOT(((phe-L(e) > 10) OR (tyr-L(e) > 0)) AND TyrR)) | NH 28 |
| b2601 | aroF | (NOT(((phe-L(e) > 10) OR (tyr-L(e) > 0)) AND TyrR)) | NH 28 |
| b2615 | yfjB | | |
| b2661 | gabD | | NH 22, 23 |
| b2662 | gabT | | NH 22, 23; PMID: 12446648 |
| b2663 | gabP | | PMID: 9829938 |
| b2675 | nrdE | | PMID: 11278973 |
| b2676 | nrdF | | PMID: 11278973 |
| b2677 | proV | | NH 25, 26 |
| b2678 | proW | | NH 25, 26 |
| b2679 | proX | | NH 25, 26 |
| b2687 | luxS | | |
| b2688 | gshA | | |
| b2690 | yqaB | | |
| b2702 | srlA | ((NOT GutR) AND "CRP noGL") | NH 20 |
| b2703 | srlE | ((NOT GutR) AND "CRP noGL") | NH 20 |
| b2704 | srlB | ((NOT GutR) AND "CRP noGL") | NH 20 |
| b2705 | srlD | (GutM AND (NOT GutR) AND "CRP noGL") | NH 20 |
| b2706 | gutM | (ON) | PMID: 3062173 |
| b2707 | srlR | (NOT (sbt-D(e) > 0)) | EcoCyc and N20 |
| b2719 | hycG | (FhlA AND RpoN AND (NOT (o2(e) > 0))) | NH 18 |
| b2720 | hycF | (FhlA AND RpoN AND (NOT (o2(e) > 0))) | NH 18 |
| b2721 | hycE | (FhlA AND RpoN AND (NOT (o2(e) > 0))) | NH 18 |
| b2722 | hycD | (FhlA AND RpoN AND (NOT (o2(e) > 0))) | NH 18 |
| b2723 | hycC | (FhlA AND RpoN AND (NOT (o2(e) > 0))) | NH 18 |
| b2724 | hycB | (FhlA AND RpoN AND (NOT (o2(e) > 0))) | NH 18 |
| b2731 | fhlA | ((NOT (o2(e) > 0)) AND (NOT (no3(e) > 0)) AND (NOT (no2(e) > 0)) AND (NOT (tmao(e) > 0)) AND (NOT (dmso(e) > 0)) AND (for(e) > 0)) | NH 18 |
| b2738 | ygbL | | |
| b2741 | rpoS | (NOT (Growth > 0)) | NH 93 |
| b2746 | ispF | | |
| b2747 | ispD | | |
| b2750 | cysC | (CysB) | NH 31 |
| b2751 | cysN | (CysB) | NH 31 |
| b2752 | cysD | (CysB) | NH 31 |
| b2762 | cysH | (CysB) | NH 31 |
| b2763 | cysI | (CysB) | NH 31 |
| b2764 | cysJ | (CysB) | NH 31 |
| b2779 | eno | | |
| b2780 | pyrG | | NH 35 |
| b2781 | mazG | | |
| b2787 | gudD | (SdaR) | PMID: 10762278 |
| b2788 | ygcY | | |
| b2789 | gudP | | |
| b2796 | sdaC | (Crp OR (NOT (Lrp) AND (leu-L(e) > 0) AND Crp)) | NH 22 |
| b2797 | sdaB | (ON) | NH 22 |
| b2799 | fucO | (((((FucR) OR (rmn(e) > 0)) AND (NOT (o2(e) > 0))) AND Crp) OR (((FucR) OR (rmn(e) > 0)) AND (NOT (o2(e) > 0)))) | PMID: 3325779 |
| b2800 | fucA | ((FucR AND Crp) OR FucR) | PMID: 3325779 |
| b2801 | fucP | ((FucR AND Crp) OR FucR) | PMID: 3325779 |
| b2802 | fucI | ((FucR AND Crp) OR FucR) | PMID: 3325779 |
| b2803 | fucK | ((FucR AND Crp) OR FucR) | PMID: 3325779 |
| b2805 | fucR | (fuc-L(e) > 0) | PMID: 3325779 |
| b2808 | gcvA | (NOT GcvR) | PMID: 12101307 |
| b2818 | argA | (NOT ArgR) | NH 25 |
| b2827 | thyA | | |
| b2836 | aas | | |
| b2837 | galR | (NOT (lcts(e) > 0) OR NOT (gal(e) > 0)) | PMID: 8982002 |
| b2838 | lysA | (LysR AND NOT lys-L(e) > 0) | NH 32 |
| b2839 | lysR | (NOT (lys-L(e) > 0)) | NH 32 |

TABLE 8-continued

| | | | |
|---|---|---|---|
| b2841 | araE | (Crp) | NH 20 |
| b2874 | yqeA | | |
| b2883 | ygfP | | |
| b2889 | idi | | |
| b2901 | bglA | | |
| b2903 | gcvP | ((Fis AND NOT PdhR) AND ((NOT(GcvR) AND GcvA) OR Lrp OR NOT PurR)) | NH 23; PMID: 12101307 |
| b2904 | gcvH | ((Fis AND NOT PdhR) AND ((NOT(GcvR) AND GcvA) OR Lrp OR NOT PurR)) | NH 23; PMID: 12101307 |
| b2905 | gcvT | ((Fis AND NOT PdhR) AND ((NOT(GcvR) AND GcvA) OR Lrp OR NOT PurR)) | NH 23; PMID: 12101307 |
| b2907 | ubiH | | |
| b2913 | serA | | NH 30 |
| b2914 | rpiA | | |
| b2917 | sbm | | |
| b2919 | ygfG | | |
| b2920 | ygfH | | |
| b2925 | fbaA | | |
| b2926 | pgk | (ON) | PMID: 9851989 |
| b2927 | epd | (Crp) | |
| b2935 | tktA | | |
| b2937 | speB | | NH 22 |
| b2938 | speA | (NOT (PurR)) | NH 25; PMID: 8388874 |
| b2942 | metK | | NH 33 |
| b2943 | galP | ((NOT (GalR)) OR (GalS) AND (Crp OR NOT (Crp))) | PMID: 8703508, 8982002, 1970645, 12101127 |
| b2947 | gshB | | |
| b2957 | ansB | (Fnr AND Crp) | NH 22 |
| b2964 | nupG | (Crp OR NOT (CytR) OR NOT (DeoR)) | PMID: 8596434, 2115441 |
| b2965 | speC | (NOT (Crp)) | NH 22; PMID 3021588 |
| b2975 | glcA | (NOT ArcA AND GlcC) | PMID: 8606183, 9880556 |
| b2976 | glcB | (NOT (ArcA) AND (GlcC)) | PMID: 8606183, 9880556 |
| b2978 | glcF | | PMID: 9880556 |
| b2979 | glcD | | PMID: 9880556 |
| b2980 | glcC | ((ac(e) > 0) OR (glyclt(e) > 0))) | PMID 9880556 |
| b2987 | pitB | (NOT (PhoB)) | PMID: 11489853 |
| b2988 | gsp | | |
| b2994 | hybC | (FhlA AND RpoN AND (NOT (o2(e) > 0))) | PMID 10537212 |
| b2997 | hybO | (FhlA AND RpoN AND (NOT (o2(e) > 0))) | PMID 10537212 |
| b3008 | metC | (NOT MetJ) | NH 33 |
| b3012 | yqhE | | |
| b3018 | plsC | | |
| b3041 | ribB | | |
| b3052 | rfaE | | NH 69 |
| b3058 | folB | | |
| b3061 | ttdA | (NOT(o2(e) > 0) AND (tartr-L(e) > 0)) | PMID: 8371115 |
| b3062 | ttdB | (NOT(o2(e) > 0) AND (tartr-L(e) > 0)) | PMID: 8371115 |
| b3063 | ygjE | | |
| b3073 | ygjG | | |
| b3089 | sstT | | PMID: 12097162 |
| b3091 | uxaA | (NOT ExuR) | NH 20 |
| b3092 | uxaC | (NOT ExuR) | NH 20 |
| b3093 | exuT | (NOT ExuR) | NH 20 |
| b3094 | exuR | (NOT(GUI1 > 0) AND NOT(GUI2 > 0) AND NOT (MANAO > 0) AND NOT(TAGURr > 0) AND NOT (GUI1 < 0) AND NOT(GUI2 < 0) AND NOT(MANAO < 0) AND NOT(TAGURr < 0)) | NH 20 |
| b3111 | tdcGa | (Crp OR NOT(o2(e) > 0)) | PMID: 11251844 |
| b3112 | tdcGb | (Crp OR NOT(o2(e) > 0)) | PMID: 11251844 |
| b3114 | tdcE | (Crp OR Fnr OR LysR OR TdcA OR NOT TdcR) | PMID: 11251844 |
| b3115 | tdcD | (Crp OR Fnr OR LysR OR TdcA OR NOT TdcR) | PMID: 11251844 |
| b3116 | tdcC | (Crp OR Fnr OR LysR OR TdcA OR NOT TdcR) | PMID: 7928991, 8413189 |
| b3117 | tdcB | (Crp OR Fnr OR LysR OR TdcA OR NOT TdcR) | NH 22 |
| b3118 | tdcA | ((thr-L(e) > 0) AND (ser-L(e) > 0) AND (val-L(e) > 0) AND (ile-L(e) > 0) AND NOT (o2(e) > 0)) | PMID: 7928991, 2573820, 8413189 |
| b3119 | tdcR | ((thr-L(e) > 0) AND (ser-L(e) > 0) AND (val-L(e) > 0) AND (ile-L(e) > 0) AND NOT (o2(e) > 0)) | PMID: 7928991, 2573820, 8413189 |
| b3124 | garK | (SdaR) | PMID: 10762278 |
| b3125 | garR | (SdaR) | PMID: 10762278 |
| b3126 | garL | (SdaR) | PMID: 10762278 |
| b3127 | garP | | |
| b3128 | garD | (SdaR) | PMID: 10762278 |
| b3132 | agaZ | | |
| b3137 | agaY | | |
| b3161 | mtr | (NOT TrpR OR (TyrR AND ((phe-L(e) > 0) OR (tyr-L(e) > 0)))) | NH 28 |
| b3172 | argG | | NH 25 |

TABLE 8-continued

| | | | |
|---|---|---|---|
| b3176 | mrsA | | |
| b3177 | folP | | |
| b3187 | ispB | | |
| b3189 | murA | | |
| b3202 | rpoN | (ON) | NH 24 |
| b3212 | gltB | ((Lrp AND NOT (leu-L(e) > 0)) OR NOT (NRI_hi AND ((glu-L(e) > 0) OR (arg-L(e) > 0) OR (asp-L(e) > 0) OR (his-L(e) > 0) OR (pro-L(e) > 0)))) | NH 22, 23, 24 |
| b3213 | gltD | ((Lrp AND NOT (leu-L(e) > 0)) OR NOT (NRI_hi AND ((glu-L(e) > 0) OR (arg-L(e) > 0) OR (asp-L(e) > 0) OR (his-L(e) > 0) OR (pro-L(e) > 0)))) | NH 22, 23, 24 |
| b3222 | nanK | | PMID: 9864311 |
| b3223 | nanE | | PMID: 9864311 |
| b3224 | nanT | | |
| b3225 | nanA | | |
| b3236 | mdh | (NOT(ArcA)) | |
| b3237 | argR | (arg-L(e) > 0) | PMID: 3116542, 12003934, NH 25 |
| b3255 | accB | | NH 37 |
| b3256 | accC | | NH 37 |
| b3258 | panF | | PMID: 8226664 |
| b3261 | fis | (Growth > 0) | NH 90 |
| b3265 | acrE | | |
| b3266 | acrF | | |
| b3281 | aroE | | NH 28 |
| b3357 | crp | ("CRP noGLC") | PMID: 5337847 |
| b3359 | argD | (NOT ArgR) | NH 25 |
| b3360 | pabA | | PMID: 2050628 |
| b3365 | nirB | (Fnr AND NarL) | PMID: 11004182 |
| b3366 | nirD | (Fnr AND NarL) | PMID: 11004182 |
| b3367 | nirC | (Fnr AND NarL) | PMID: 11004182 |
| b3368 | cysG | (Fnr OR NarL) | |
| b3380 | yhfW | | |
| b3385 | gph | | PMID: 10572959 |
| b3386 | rpe | | |
| b3389 | aroB | | NH 28 |
| b3390 | aroK | | NH 28 |
| b3403 | pckA | | |
| b3405 | ompR | ("high osmolarity") | PMID: 7932717 |
| b3409 | feoB | | NH 71 |
| b3415 | gntT | (NOT (GntR) AND "CRP GLCN") | PMID: 9537375 |
| b3416 | malQ | (MalT) | PMID: 11931562, 11867639, 9529892 |
| b3417 | malP | (MalT) | PMID: 11931562, 11867639, 9529892 |
| b3418 | malT | ((malt(e) > 0) OR (malttr(e) > 0) OR (maltttr(e) > 0) OR (malthx(e) > 0) OR (maltpt(e) >0) | PMID: 10973069 |
| b3423 | glpR | (NOT (glyc(e) > 0)) | PMID: 1372899, 9524241 |
| b3425 | glpE | (Crp) | PMID: 1846566, 9524241 |
| b3426 | glpD | ("CRP noMAL" AND NOT(ArcA OR GlpR)) | NH 20; PMID: 2403539, 8955388; Paigen K. (1970) |
| b3428 | glgP | (Crp) | NH 67; |
| b3429 | glgA | | NH 67; PMID: 8576033 |
| b3430 | glgC | | PMID: 12067347 |
| b3433 | asd | | NH 32 |
| b3437 | gntK | (NOT (GntR) AND "CRP GLCN") | PMID: 8655507 |
| b3438 | gntR | (NOT (glcn(e) > 0)) | PMID 9537375 |
| b3450 | ugpC | (Crp OR PhoB) | PMID: 1987150, 1745236 |
| b3451 | ugpE | (Crp OR PhoB) | PMID: 1987150, 1745236 |
| b3452 | ugpA | (Crp OR PhoB) | PMID: 1987150, 1745236 |
| b3453 | ugpB | (Crp OR PhoB) | PMID: 1987150, 1745236 |
| b3454 | livF | (NOT(leu-L(e) > 0) OR Lrp) | NH 22; PMID: 1729203 |
| b3455 | livG | (NOT(leu-L(e) > 0) OR Lrp) | NH 22; PMID: 1729203 |
| b3456 | livM | (NOT(leu-L(e) > 0) OR Lrp) | NH 22; PMID: 1729203 |
| b3457 | livH | (NOT(leu-L(e) > 0) OR Lrp) | NH 22; PMID: 1729203 |
| b3458 | livK | (NOT(leu-L(e) > 0) OR Lrp) | NH 22; PMID: 1729203 |
| b3460 | livJ | (NOT(leu-L(e) > 0) OR Lrp) | NH 22; PMID: 1729203 |
| b3493 | pitA | | PMID: 11489853 |
| b3500 | gor | (OxyR OR RpoS) | PMID: 8593953 |
| b3517 | gadA | ((NOT (Growth > 0 ) AND NOT Crp) OR (pH < 4)) | NH 22; PMID: 11976288 |
| b3519 | treF | (RpoS) | PMID: 9148912, 8892826 |
| b3526 | kdgK | (NOT KdgR) | NH 20 |
| b3528 | dctA | ((("CRP noMAN") AND NOT(ArcA) AND (DcuR)) AND RpoN) | PMID: 10482502 |
| b3551 | bisC | | |
| b3553 | yiaE | | PMID: 11237876, 9811658 |

TABLE 8-continued

| | | | |
|---|---|---|---|
| b3564 | xylB | ((XylR AND Crp) OR XylR) | PMID: 9371449 |
| b3565 | xylA | ((XylR AND Crp) OR XylR) | PMID: 9371449 |
| b3566 | xylF | ((XylR AND Crp) OR XylR) | PMID: 9371449 |
| b3567 | xylG | ((XylR AND Crp) OR XylR) | PMID: 9371449 |
| b3568 | xylH | ((XylR AND Crp) OR XylR) | PMID: 9371449 |
| b3569 | xylR | (xyl-D(e) > 0) | PMID: 9371449 |
| b3572 | avtA | (NOT (ala-L(e) > 0 OR leu-L(e) > 0 )) | NH 24, 27; PMID: 6373721 |
| b3574 | yiaJ | (NOT (fuc-L(e) > 0)) | PMID: 10913096 |
| b3575 | yiaK | ((NOT YiaJ) AND Crp) | PMID: 10913096 |
| b3579 | yiaO | (Crp OR YiaJ) | |
| b3581 | sgbH | (NOT YiaJ) | PMID: 10913096 |
| b3583 | sgbE | (NOT YiaJ) | PMID: 10913096 |
| b3588 | aldB | (RpoS AND (Crp)) | PMID: 7768815 |
| b3599 | mtlA | (NOT (MtlR)) | NH 20 |
| b3600 | mtlD | (NOT MtlR) | NH 20 |
| b3601 | mtlR | (NOT(mnl(e) > 0)) | PMID: 8300537 |
| b3603 | lldP | (NOT (ArcA)) | PMID: 8892825 |
| b3605 | lldD | (LLACxt > 0 AND O2xt > 0) | PMID: 8407843 |
| b3607 | cysE | (CysB) | NH 31 |
| b3608 | gpsA | | |
| b3612 | yibO | | |
| b3616 | tdh | (NOT (Lrp) AND (leu-L(e) > 0)) | NH 22 |
| b3617 | kbl | (NOT (Lrp) AND (leu-L(e) > 0)) | NH 22 |
| b3619 | rfaD | | NH 69 |
| b3620 | rfaF | | NH 69 |
| b3621 | rfaC | | NH 69 |
| b3622 | rfaL | | NH 69 |
| b3626 | rfaJ | | NH 69 |
| b3627 | rfaI | | NH 69 |
| b3631 | rfaG | | NH 69 |
| b3633 | kdtA | | |
| b3634 | coaD | | |
| b3640 | dut | | |
| b3642 | pyrE | (NOT (ura(e) > 0 OR gua(e) > 0)) | NH 35 |
| b3648 | gmk | | NH 34 |
| b3653 | gltS | (asp-L(e) > 0) | NH 22 |
| b3654 | yicE | | |
| b3665 | yicP | | |
| b3666 | uhpT | (Crp OR UhpA) | PMID: 11702079 |
| b3668 | uhpB | (g6p(e) > 0) | PMID: 11702079 |
| b3669 | uhpA | (UhpB) | PMID: 7596290 |
| b3670 | ilvN | (NOT(leu-L(e) > 0 OR val-L(e) > 0) AND Crp) | NH 27 |
| b3671 | ilvB | (NOT(leu-L(e) > 0 OR val-L(e) > 0) AND Crp) | NH 27 |
| b3691 | dgoT | (galctn-D(e) > 0) | NH 20 |
| b3692 | dgoA | (galctn-D(e) > 0) | NH 20 |
| b3693 | dgoK | (galctn-D(e) > 0) | NH 20 |
| b3708 | tnaA | (Crp AND (trp-L(e) > 0 OR cys-L(e) > 0)) | NH 22 |
| b3709 | tnaB | (Crp AND (trp-L(e) > 0)) | NH 22, 28 |
| b3725 | pstB | (PhoB) | PMID: 2651888, 3054125 |
| b3726 | pstA | (PhoB) | PMID: 2651888, 3054125 |
| b3727 | pstC | (PhoB) | PMID: 2651888, 3054125 |
| b3728 | pstS | (PhoB) | PMID: 2651888, 3054125 |
| b3729 | glmS | | PMID: 11139621 |
| b3730 | glmU | (NagC) | PMID: 11139621 |
| b3731 | atpC | | |
| b3732 | atpD | | |
| b3733 | atpG | | |
| b3734 | atpA | | |
| b3735 | atpH | | |
| b3736 | atpF | | |
| b3737 | atpE | | |
| b3738 | atpB | | |
| b3739 | atpI | | |
| b3743 | asnC | (NOT (asn-L(e) > 0) AND NRI_hi) | NH 24 |
| b3744 | asnA | (NOT (asn-L(e) > 0) AND AsnC) | NH 24 |
| b3748 | rbsD | ("CRP noXYL" AND NOT(RbsR)) | PMID: 9666469, 9673030, 6327616 |
| b3749 | rbsA | ("CRP noXYL" AND NOT(RbsR)) | PMID: 9666469, 9673030, 6327616 |
| b3750 | rbsC | ("CRP noXYL" AND NOT(RbsR)) | PMID: 9666469, 9673030, 6327616 |
| b3751 | rbsB | ("CRP noXYL" AND NOT(RbsR)) | PMID: 9666469, 9673030, 6327616 |

TABLE 8-continued

| | | | |
|---|---|---|---|
| b3752 | rbsK | ("CRP noXYL" AND NOT(RbsR)) | PMID: 9666469, 9673030, 6327616 |
| b3753 | rbsR | (NOT (rib-D(e) > 0)) | PMID: 9673030, 9666469, 6327616 |
| b3767 | ilvG_1 | (NOT(leu-L(e) > 0 OR ile-L(e) > 0 OR val-L(e) > 0) AND Lrp) | NH 27 |
| b3768 | ilvG_2 | (NOT(leu-L(e) > 0 OR ile-L(e) > 0 OR val-L(e) > 0) AND Lrp) | NH 27 |
| b3769 | ilvM | (NOT(leu-L(e) > 0 OR ile-L(e) > 0 OR val-L(e) > 0) AND Lrp) | NH 27 |
| b3770 | ilvE | | NH 27 |
| b3771 | ilvD | | NH 27 |
| b3772 | ilvA | | NH 27 |
| b3773 | ilvY | (NOT val-L(e) > 0) | NH 27, PMID: 10588699 |
| b3774 | ilvC | (ilvY) | NH 27; PMID: 10588699 |
| b3784 | wecA | | |
| b3786 | wecB | | |
| b3787 | wecC | | |
| b3788 | rffG | | |
| b3789 | rffH | | |
| b3790 | wecD | | |
| b3791 | wecE | | |
| b3793 | wecF | | |
| b3794 | wecG | | |
| b3803 | hemX | | |
| b3804 | hemD | | PMID: 8997718 |
| b3805 | hemC | | PMID: 8997718 |
| b3806 | cyaA | (NOT Crp) | |
| b3809 | dapF | | NH 32 |
| b3821 | pldA | | |
| b3825 | pldB | | |
| b3828 | metR | (NOT (met-L(e) > 0)) | NH 33 |
| b3829 | metE | ((NOT MetJ) AND MetR) | NH 33 |
| b3831 | udp | (NOT (CytR) OR Crp) | NH 35 |
| b3833 | ubiE | | |
| b3835 | ubiB | | |
| b3843 | yigC | | |
| b3845 | fadA | (NOT (FadR2) OR NOT (ArcA)) | NH 21 |
| b3846 | fadB | (NOT (FadR2) OR NOT (ArcA)) | NH 21 |
| b3849 | trkH | | NH 72 |
| b3850 | hemG | | |
| b3868 | glnG | (NOT(nh4(e) > 2)) | NH 23, NH 24 |
| b3869 | glnL | (ON) | NH 24 |
| b3870 | glnA | (Crp AND RpoN) | NH 24; PMID: 12218022 |
| b3892 | fdoI | ((o2(e) > 0) OR ((NOT (o2(e) > 0) AND (no3(e) > 0)))) | PMID: 8522521 |
| b3893 | fdoH | ((o2(e) > 0) OR ((NOT (o2(e) > 0) AND (no3(e) > 0)))) | PMID: 8522521 |
| b3894 | fdoG | ((o2(e) > 0) OR ((NOT (o2(e) > 0) AND (no3(e) > 0)))) | PMID: 8522521 |
| b3902 | rhaD | (RhaS OR (RhaS AND Crp)) | PMID: 10852886 |
| b3903 | rhaA | (RhaS OR (RhaS AND Crp)) | PMID: 10852886 |
| b3904 | rhaB | (RhaS OR (RhaS AND Crp)) | PMID: 10852886 |
| b3905 | rhaS | (RhaR) | PMID: 10852886 |
| b3906 | rhaR | (rmn(e) > 0) | PMID: 10852886 |
| b3907 | rhaT | (RhaS OR (RhaS AND Crp)) | PMID: 8757746 |
| b3908 | sodA | (NOT (ArcA OR Fur) OR (MarA OR Rob OR SoxS)) | PMID: 8412671 |
| b3909 | kdgT | (NOT KdgR) | NH 20 |
| b3912 | cpxR | (Stress > 0) | PMID: 10671468 |
| b3916 | pfkA | | |
| b3917 | sbp | (CysB) | NH 31 |
| b3918 | cdh | | |
| b3919 | ipiA | | |
| b3926 | glpK | ("CRP noMAL" AND (NOT(GlpR))) | NH 20; PMID: 1372899; Paigen K. (1970) |
| b3927 | glpF | | PMID: 1372899 |
| b3929 | menG | | |
| b3930 | menA | | |
| b3934 | cytR | (cytd(e) > 0) | PMID: 8626289 |
| b3938 | metJ | (met-L(e) > 0) | PMID: 12218041 |
| b3939 | metB | (NOT MetJ) | NH 32, 33 |
| b3940 | metL | (NOT MetJ) | NH 32, 33 |
| b3941 | metF | | NH 36 |
| b3942 | katG | ((Growth > 0) AND OxyR AND RpoS) | PMID: 12589799 |
| b3945 | gldA | | PMID: 8132480 |
| b3946 | talC | | |
| b3951 | pflD | (ArcA OR Fnr) | NH 95; PMID: 7934836 |
| b3952 | pflC | (ArcA OR Fnr) | NH 95; PMID: 7934836 |

TABLE 8-continued

| | | | |
|---|---|---|---|
| b3956 | ppc | | |
| b3957 | argE | (NOT ArgR) | NH 25 |
| b3958 | argC | (NOT ArgR) | NH 25 |
| b3959 | argB | (NOT ArgR) | NH 25 |
| b3960 | argH | (NOT ArgR) | NH 25 |
| b3961 | oxyR | (h2o2(e) > 0) | PMID: 12589799 |
| b3962 | sthA | | |
| b3966 | btuB | | |
| b3967 | murI | | |
| b3972 | murB | | |
| b3973 | birA | (btn(e) > 0) | PMID 12368242, NH 46 |
| b3974 | coaA | | |
| b3990 | thiH | | |
| b3991 | thiG | | |
| b3992 | thiF | | |
| b3993 | thiE | | |
| b3994 | thiC | | |
| b3997 | hemE | | |
| b4005 | purD | (NOT (PurR)) | NH 34 |
| b4006 | purH | | NH 34 |
| b4013 | metA | (NOT (MetJ) OR MetR) | NH 33 |
| b4014 | aceB | (NOT (IclR) AND (NOT (ArcA) OR NOT (Cra))) | NH 16, 95; PMID: 8755903, 2001680 |
| b4015 | aceA | (NOT (IclR) AND (NOT (ArcA) OR NOT (Cra))) | NH 16; PMID: 8755903, 2001680 |
| b4018 | iclR | (FadR) | PMID: 2001680, 8755903 |
| b4019 | metH | (MetR) | NH 33 |
| b4024 | lysC | (NOT lys-L(e) > 0) | NH 32 |
| b4025 | pgi | | |
| b4031 | xylE | (XylR) | PMID: 9371449 |
| b4032 | malG | ((MalT AND Crp) OR MalT) | PMID: 11931562, 11867639, 9529892 |
| b4033 | malF | ((MalT AND Crp) OR MalT) | PMID: 11931562, 11867639, 9529892 |
| b4034 | malE | ((MalT AND Crp) OR MalT) | PMID: 11931562, 11867639, 9529892 |
| b4035 | malK | ((MalT AND Crp) OR MalT) | PMID: 11931562, 11867639, 9529892 |
| b4036 | lamB | ((MalT AND Crp) OR MalT) | PMID: 11931562, 11867639, 9529892 |
| b4039 | ubiC | ((NOT Fnr) AND Crp) | PMID: 9315722 |
| b4040 | ubiA | ((NOT Fnr) AND Crp) | PMID: 9315722, 7765507 |
| b4041 | plsB | | |
| b4042 | dgkA | | |
| b4053 | alr | | NH 22, 24 |
| b4054 | tyrB | (NOT(((phe-L(e) > 0) OR (tyr-L(e) > 0)) AND TyrR)) | NH 24: PMID: 12207706 |
| b4062 | soxS | (SoxR) | NH 95 |
| b4063 | soxR | ((h2o2(e) > 0) OR ("Oxidative Stress" > 0)) | NH 95 |
| b4069 | acs | (RpoS OR Fnr OR ((NOT IclR) AND ("CRP noSUCC"))) | PMID: 10894724 |
| b4077 | gltP | | NH 22 |
| b4079 | fdhF | (FhlA AND RpoN AND (NOT (o2(e) > 0))) | NH 18 |
| b4089 | rpiR | (NOT (rib-D(e) > 0)) | PMID: 8576032 |
| b4090 | rpiB | (NOT(RpiR)) | PMID: 8572885, 8576032 |
| b4111 | proP | (NOT (Crp) AND Fis AND RpoS) | NH 22; PMID: 9079929 |
| b4116 | adiY | ((pH < 7) AND (NOT (o2(e) > 0)) AND NOT ("Rich Medium" > 0)) | PMID: 8704970 |
| b4117 | adiA | (AdiY) | NH 22; PMID 8704970 |
| b4118 | melR | ((melib(e) > 0) OR (melib(e) > 0 AND Crp)) | PID: 10747919, 10760178 |
| b4119 | melA | ((MelR) OR (MelR AND Crp)) | PMID: 10747919, 10760178 |
| b4120 | melB | ((MelR) OR (MelR AND Crp)) | PMID: 10747919, 10760178 |
| b4122 | fumB | ((Fnr) OR NOT (Crp) OR (DcuR) OR NOT(NarL)) | PMID: 9418241 |
| b4123 | dcuB | ((("CRP noMAN") AND (Fnr) AND (DcuR)) AND NOT (NarL)) | PMID: 9852003, 9973351 |
| b4124 | dcuR | (DcuS) | PMID: 9973351 |
| b4125 | dcuS | ((succ(e) > 0) OR (asp-L(e) > 0) OR (fum(e) > 0) OR (mal-L(e) > 0)) | PMID: 9973351 |
| b4131 | cadA | (ArcA OR CadC) | PMID: 9075621, 7830562 |
| b4132 | cadB | (ArcA OR CadC) | PMID: 7830562, 9075621 |
| b4133 | cadC | (lys-L(e) > 0) | NH 33, PMID: 7830562 |
| b4138 | dcuA | | PMID: 9852003 |
| b4139 | aspA | ((Crp AND NOT (Fnr)) OR Fnr) | NH 22 |
| b4151 | frdD | (Fnr OR DcuR OR NOT (NarL)) | PMID: 9973351, 8576043 |
| b4152 | frdC | (Fnr OR DcuR OR NOT (NarL)) | PMID: 9973351, 8576043 |
| b4153 | frdB | (Fnr OR DcuR OR NOT (NarL)) | PMID: 9973351, 8576043 |
| b4154 | frdA | (Fnr OR DcuR OR NOT (NarL)) | PMID: 9973351, 8576043 |
| b4160 | psd | | |

TABLE 8-continued

| | | | |
|---|---|---|---|
| b4177 | purA | (NOT (PurR) OR RpoE) | NH 34 |
| b4196 | sgaH | | no rule |
| b4197 | sgaU | | |
| b4198 | sgaE | | |
| b4208 | cycA | | |
| b4226 | ppa | | |
| b4227 | ytfQ | | |
| b4228 | ytfR | | |
| b4229 | ytfS | | |
| b4230 | ytfT | | |
| b4231 | yjfF | | |
| b4232 | fbp | | |
| b4238 | nrdD | (Fnr) | PMID: 8954104 |
| b4239 | treC | (((NOT TreR) AND Crp) OR (NOT TreR)) | PMID: 9148912 |
| b4240 | treB | (((NOT TreR) AND Crp) OR (NOT TreR)) | PMID: 9148912 |
| b4241 | treR | (NOT (tre(e) > 0)) | PMID: 9148912 |
| b4244 | pyrI | (NOT (ura(e) > 0 OR gua(e) > 0)) | NH 35 |
| b4245 | pyrB | (NOT (ura(e) > 0 OR gua(e) > 0)) | NH 35 |
| b4254 | argI | (NOT ArgR) | NH 25 |
| b4264 | idnR | ((idon-L(e) > 0) OR (5dglcn(e) > 0)) | PMID: 9658018 |
| b4265 | idnT | (IdnR) | PMID: 9658018 |
| b4266 | idnO | (IdnR) | PMID: 9658018 |
| b4267 | idnD | (IdnR) | PMID: 9658018 |
| b4268 | idnK | | PMID: 9658018 |
| b4301 | sgcE | | |
| b4321 | gntP | (Crp AND NOT (glcn(e) > 0)) | PMID: 8550444 |
| b4322 | uxuA | (NOT ExuR AND NOT UxuR) | NH 20; PMID: 3083215 |
| b4323 | uxuB | (NOT ExuR AND NOT UxuR) | NH 20; PMID: 3083215 |
| b4324 | uxuR | (NOT(MANAO > 0) AND NOT(GUI1 > 0) AND NOT (MANAO < 0) AND NOT(GUI1 < 0)) | NH 20 |
| b4381 | deoC | ((NOT DeoR) OR ((NOT DeoR) AND (Crp) AND (NOT CytR))) | NH 20 |
| b4382 | deoA | (NOT (DeoR OR CytR) AND Crp) | NH 35 |
| b4383 | deoB | ((NOT DeoR) OR ((NOT DeoR) AND (Crp) AND (NOT CytR)) OR ((ins(e) > 0) OR (gua(e) > 0))) | NH 20 |
| b4384 | deoD | ((NOT DeoR) OR ((NOT DeoR) AND (NOT CytR)) OR (ins(e) > 0) OR (gua(e) > 0)) | NH 34 |
| b4388 | serB | | NH 30 |
| b4390 | nadR | ("high NAD") | PMID: 10464228 |
| b4393 | trpR | (trp-Me) > 0) | NH 28 |
| b4395 | gpmB | | |
| b4396 | rob | (dipyridyl > 0) | PMID: 11844771 |
| b4401 | arcA | (NOT (o2(e) > 0)) | PMID: 2964639, NH 95 |
| b4407 | thiS | | |

Additional Comments on the Regulatory Rules
Note: Crp
Crp has complex regulation based on the level of cAMP in the cell. To describe this using Boolean logic, we divided the responses into categories based on the data of PMID: 5337847 and assuming that repression by a "higher" level substrate was complete until the substrate was exhausted. Additionally, because most Crp testing involved only glucose, we have a more general Crp statement which depends on glucose only.
The resulting statements are shown below:

| | |
|---|---|
| CRP GLCN | (glcn(e) > 0) |
| CRPnoARAB | (NOT((glcn(e) > 0) OR (glc-D(e) > 0) OR (arab-L(e) > 0))) |
| CRP noGL | (NOT((glcn(e) > 0) OR (glc-D(e) > 0) OR (arab-L(e) > 0) OR (xyl-D(e) > 0) OR (rib-D(e) > 0) OR (mal-L(e) > 0) OR (glyc(e) > 0))) |
| CRP noGLC | (NOT((glcn(e) > 0) OR (glc-D(e) > 0))) |
| CRP noGLCN | (NOT((glcn(e) > 0))) |
| CRP noGLT | (NOT((glcn(e) > 0) OR (glc-D(e) > 0) OR (arab-L(e) > 0) OR (xyl-D(e) > 0) OR (rib-D(e) > 0) OR (mal-L(e) > 0) OR (glyc(e) > 0) OR (sbt-D(e) > 0))) |
| CRP noLAC | (NOT((glcn(e) > 0) OR (glc-D(e) > 0) OR (arab-L(e) > 0) OR (xyl-D(e) > 0) OR (rib-D(e) > 0) OR (mal-L(e) > 0) OR (glyc(e) > 0) OR (sbt-D(e) > 0) OR (lac-D(e) > 0))) |
| CRP noMAL | (NOT((glcn(e) > 0) OR (glc-D(e) > 0) OR (arab-L(e) > 0) OR (xyl-D(e) > 0) OR (rib-D(e) > 0) OR (mal-L(e) > 0))) |
| CRP noMAN | (NOT((glcn(e) > 0) OR (glc-D(e) > 0) OR (arab-L(e) > 0) OR (xyl-D(e) > 0) OR (rib-D(e) > 0) OR (mal-L(e) > 0) OR (glyc(e) > 0) OR (sbt-D(e) > 0) OR (lac-D(e) > 0) OR (man(e) > 0))) |
| CRP noRIB | (NOT((glcn(e) > 0) OR (glc-D(e) > 0) OR (arab-L(e) > 0) OR (xyl-D(e) > 0) OR (rib-D(e) > 0))) |

TABLE 8-continued

| | |
|---|---|
| CRP noSUCC | (NOT((glcn(e) > 0) OR (glc-D(e) > 0) OR (arab-L(e) > 0) OR (xyl-D(e) > 0) OR (rib-D(e) > 0) OR (mal-L(e) > 0) OR (glyc(e) > 0) OR (sbt-D(e) > 0) OR (lac-D(e) > 0) OR (man(e) > 0) OR (succ(e) > 0))) |
| CRP noXYL | (NOT((glcn(e) > 0) OR (glc-D(e) > 0) OR (arab-L(e) > 0) OR (xyl-D(e) > 0))) |

Note: "Surplus" internal metabolites.
The method we describe does not currently allow for the calculation of internal metabolite concentrations. For most cases where internal metabolite concentrations are involved in activation/repression, we simply use concentration of related external metabolites as an approximation (e.g., for induction of the lac operon, we consider external lactose, rather than internal allolactose, the inducer). However, in the case of important central metabolites, we use the values of connected fluxes to approximate concentration qualitatively, as shown below:

| | |
|---|---|
| Surplus FDP | ((NOT (FBP > 0) AND NOT (TKT2 > 0 OR TALA > 0 OR PGI > 0)) OR fru(e) > 0) |
| Surplus PYR | (NOT ((ME2 > 0 OR ME1 > 0) AND NOT (GLCpts > 0 OR PYK > 0 OR PFK > 0 OR LDH_D < 0 OR LDH_D2 > 0 OR SUCCt2_2 > 0 OR SUCCt2_3 > 0))) |

Note: FadR
FadR seems to respond to two different stimuli and regulates different sets of genes accordingly. A second rule was written for FadR activity to accomodate this action:

| | |
|---|---|
| FadR2 | (NOT (ttdca(e) > 0 OR hdca(e) > 0 OR ocdca(e) > 0)) |

Note: NRI
The nitrogen response has a fast (low-level) and a slow (high-level) response, which we describe using two rules.

| | |
|---|---|
| NRI_hi | (NRI_low AND RpoN) |
| NRI_low | (GlnG AND GlnB AND GlnD) |

The following stimuli were recorded in the literature and therefore included in the model but are not yet defined or accounted for strictly:

| | | |
|---|---|---|
| Dipyridyl | High Osmolarity | Salicylate |
| Heat shock | LB Media/Rich media | Stress |
| High NAD | Oxidative Stress | Stringent response |

Two References without PMIDs:
Adhya, S. (1996) The lac and gal operons today. In Regulation of Gene Expression in *Escherichia coli*, edited by E. C. C. Lin and A. Simon Lynch. R. G. Landes Company, pages 181-200
Paigen K., Williams, B. (1970) Catabolite repression and other control mechanisms in carbohydrate utilization. Adv Microbiol Physiol 4: 251-324

TABLE 9

| | |
|---|---|
| Time Delay | 30 minutes |
| Biomass Function | (0.05) 5mthf + (5.0E−5) accoa + (0.488) ala-L + (0.0010) amp + (0.281) arg-L + (0.229) asn-L + (0.229) asp-L + (45.7318) atp + (1.29E−4) clpn_EC + (6.0E−6) coa + (0.126) ctp + (0.087) cys-L + (0.0247) datp + (0.0254) dctp + (0.0254) dgtp + (0.0247) dttp + (1.0E−5) fad + (0.25) gln-L + (0.25) glu-L + (0.582) gly + (0.154) glycogen + (0.203) gtp + (45.5608) h2o + (0.09) his-L + (0.276) ile-L + (0.428) leu-L + (0.0084) lps_EC + (0.326) lys-L + (0.146) met-L + (0.00215) nad + (5.0E−5) nadh + (1.3E−4) nadp + (4.0E−4) nadph + (0.001935) pe_EC + (0.0276) peptido_EC + (4.64E−4) pg_EC + (0.176) phe-L + (0.21) pro-L + (5.2E−5) ps_EC + (0.035) ptrc + (0.205) ser-L + (0.0070) spmd + (3.0E−6) succoa + (0.241) thr-L + (0.054) trp-L + (0.131) tyr-L + (0.0030) udpg + (0.136) utp + (0.402) val-L --> (45.5608) adp + (45.56035) h + (45.5628) pi + (0.7302) ppi |
| ATPmaintenance | 7.6 mmol/gDW/hr |
| Inital Biomass Concentration | 0.003 |

Metabolite concentrations used in simulations depend on the medium conditions and are listed below (units are mmol)
Metabolites not listed below always had a concentration of 0.

| | [Carbon Source] | [succ(e)] | [nh4(e)] | [o2(e)] | [co2(e)] |
|---|---|---|---|---|---|
| Gene Expression Simulations | | | | | |
| Wild-type or knockout strain, aerobic | glc(e) | 10 | 0 | 10 | 10 | 15 |
| Wild-type or knockout strain, anaerobic | glc(e) | 10 | 0 | 10 | 0 | 15 |
| Biolog Plate PM1 | | | | | |
| OD600 growth on 1,2-Propanediol | 12ppd-S(e) | 10 | 0 | 10 | 10 | 15 |
| OD600 growth on 2-Deoxy Adenosine | dad-2(e) | 10 | 0 | 10 | 10 | 15 |
| OD600 growth on a-D-Glucose | glc-D(e) | 10 | 0 | 10 | 10 | 15 |
| OD600 growth on a-D-Lactose | lcts(e) | 10 | 0 | 10 | 10 | 15 |
| OD600 growth on a-Keto-Glutaric Acid | akg(e) | 10 | 0 | 10 | 10 | 15 |
| OD600 growth on Acetic Acid | ac(e) | 10 | 0 | 10 | 10 | 15 |
| OD600 growth on Acetoacetic Acid | acac(e) | 10 | 0 | 10 | 10 | 15 |

TABLE 9-continued

| | | | | | | |
|---|---|---|---|---|---|---|
| OD600 growth on Adenosine | adn(e) | 10 | 0 | 10 | 10 | 15 |
| OD600 growth on Citric Acid | cit(e) | 10 | 0 | 10 | 10 | 15 |
| OD600 growth on D,L-Malic Acid | mal-L(e) | 10 | 0 | 10 | 10 | 15 |
| OD600 growth on D-Alanine | ala-D(e) | 10 | 0 | 10 | 10 | 15 |
| OD600 growth on D-Fructose | fru(e) | 10 | 0 | 10 | 10 | 15 |
| OD600 growth on D-Galactose | gal(e) | 10 | 0 | 10 | 10 | 15 |
| OD600 growth on D-Galacturonic Acid | galur(e) | 10 | 0 | 10 | 10 | 15 |
| OD600 growth on D-Gluconic Acid | glcn(e) | 10 | 0 | 10 | 10 | 15 |
| OD600 growth on D-Glucose-6-Phosphate | g6p(e) | 10 | 0 | 10 | 10 | 15 |
| OD600 growth on D-Glucuronic Acid | glcur(e) | 10 | 0 | 10 | 10 | 15 |
| OD600 growth on D-Mannitol | mnl(e) | 10 | 0 | 10 | 10 | 15 |
| OD600 growth on D-Mannose | man(e) | 10 | 0 | 10 | 10 | 15 |
| OD600 growth on D-Melibiose | melib(e) | 10 | 0 | 10 | 10 | 15 |
| OD600 growth on D-Ribose | rib-D(e) | 10 | 0 | 10 | 10 | 15 |
| OD600 growth on D-Serine | ser-D(e) | 10 | 0 | 10 | 10 | 15 |
| OD600 growth on D-Sorbitol | sbt-D(e) | 10 | 0 | 10 | 10 | 15 |
| OD600 growth on D-Trehalose | tre(e) | 10 | 0 | 10 | 10 | 15 |
| OD600 growth on D-Xylose | xyl-D(e) | 10 | 0 | 10 | 10 | 15 |
| OD600 growth on Formic Acid | for(e) | 10 | 0 | 10 | 10 | 15 |
| OD600 growth on Fumaric Acid | fum(e) | 10 | 0 | 10 | 10 | 15 |
| OD600 growth on Glycerol | glyc(e) | 10 | 0 | 10 | 10 | 15 |
| OD600 growth on Glycolic Acid | glyclt(e) | 10 | 0 | 10 | 10 | 15 |
| OD600 growth on Inosine | ins(e) | 10 | 0 | 10 | 10 | 15 |
| OD600 growth on L-Alanine | ala-L(e) | 10 | 0 | 10 | 10 | 15 |
| OD600 growth on L-Arabinose | arab-L(e) | 10 | 0 | 10 | 10 | 15 |
| OD600 growth on L-Asparagine | asn-L(e) | 10 | 0 | 10 | 10 | 15 |
| OD600 growth on L-Aspartic Acid | asp-L(e) | 10 | 0 | 10 | 10 | 15 |
| OD600 growth on L-Fucose | fuc-L(e) | 10 | 0 | 10 | 10 | 15 |
| OD600 growth on L-Glutamic Acid | glu-L(e) | 10 | 0 | 10 | 10 | 15 |
| OD600 growth on L-Glutamine | gln-L(e) | 10 | 0 | 10 | 10 | 15 |
| OD600 growth on L-Lactic Acid | lac-L(e) | 10 | 0 | 10 | 10 | 15 |
| OD600 growth on L-Malic Acid | mal-L(e) | 10 | 0 | 10 | 10 | 15 |
| OD600 growth on L-Proline | pro-L(e) | 10 | 0 | 10 | 10 | 15 |
| OD600 growth on L-Rhamnose | rmn(e) | 10 | 0 | 10 | 10 | 15 |
| OD600 growth on L-Serine | ser-L(e) | 10 | 0 | 10 | 10 | 15 |
| OD600 growth on L-Threonine | thr-L(e) | 10 | 0 | 10 | 10 | 15 |
| OD600 growth on Maltose | malt(e) | 10 | 0 | 10 | 10 | 15 |
| OD600 growth on Maltotriose | malttr(e) | 10 | 0 | 10 | 10 | 15 |
| OD600 growth on N-Acetyl-b-D-Mannosamine | acmana(e) | 10 | 0 | 10 | 10 | 15 |
| OD600 growth on N-Acetyl-D-Glucosamine | acgam(e) | 10 | 0 | 10 | 10 | 15 |
| OD600 growth on Pyruvic Acid | pyr(e) | 10 | 0 | 10 | 10 | 15 |
| OD600 growth on Succinic Acid | succ(e) | 10 | 0 | 10 | 10 | 15 |
| OD600 growth on Sucrose | sucr(e) | 10 | 0 | 10 | 10 | 15 |
| OD600 growth on Thymidine | thymd(e) | 10 | 0 | 10 | 10 | 15 |
| OD600 growth on Uridine | uri(e) | 10 | 0 | 10 | 10 | 15 |
| Biolog Plate PM2 | | | | | | |
| OD600 growth on Butyric Acid | but(e) | 10 | 0 | 10 | 10 | 15 |
| OD600 growth on D,L-Carnitine | crn(e) | 10 | 0 | 10 | 10 | 15 |
| OD600 growth on Dihydroxy Acetone | dha(e) | 10 | 0 | 10 | 10 | 15 |
| OD600 growth on g-Amino Butyric Acid | 4abut(e) | 10 | 0 | 10 | 10 | 15 |
| OD600 growth on Glycine | gly(e) | 10 | 0 | 10 | 10 | 15 |
| OD600 growth on L-Arginine | arg-L(e) | 10 | 0 | 10 | 10 | 15 |
| OD600 growth on L-Histidine | his-L(e) | 10 | 0 | 10 | 10 | 15 |
| OD600 growth on L-Isoleucine | ile-L(e) | 10 | 0 | 10 | 10 | 15 |
| OD600 growth on L-Leucine | leu-L(e) | 10 | 0 | 10 | 10 | 15 |
| OD600 growth on L-Lysine | lys-L(e) | 10 | 0 | 10 | 10 | 15 |
| OD600 growth on L-Methionine | met-L(e) | 10 | 0 | 10 | 10 | 15 |
| OD600 growth on L-Ornithine | orn(e) | 10 | 0 | 10 | 10 | 15 |
| OD600 growth on L-Phenylalanine | phe-L(e) | 10 | 0 | 10 | 10 | 15 |
| OD600 growth on L-Tartaric Acid | tartr-L(e) | 10 | 0 | 10 | 10 | 15 |
| OD600 growth on L-Valine | val-L(e) | 10 | 0 | 10 | 10 | 15 |
| OD600 growth on N-Acetyl-Neuraminic Acid | acnam(e) | 10 | 0 | 10 | 10 | 15 |
| OD600 growth on Putrescine | ptrc(e) | 10 | 0 | 10 | 10 | 15 |

| | [Carbon Source] | [pi(e)] | [so4(e)] | [h(e)] | [h2o(e)] |
|---|---|---|---|---|---|
| Gene Expression Simulations | | | | | |
| Wild-type or knockout strain, aerobic | glc(e) | 10 | 15 | 10 | 10 | 55 |
| Wild-type or knockout strain, anaerobic | glc(e) | 10 | 15 | 10 | 10 | 55 |
| Biolog Plate PM1 | | | | | |
| OD600 growth on 1,2-Propanediol | 12ppd-S(e) | 10 | 15 | 10 | 10 | 55 |
| OD600 growth on 2-Deoxy Adenosine | dad-2(e) | 10 | 15 | 10 | 10 | 55 |
| OD600 growth on a-D-Glucose | glc-D(e) | 10 | 15 | 10 | 10 | 55 |
| OD600 growth on a-D-Lactose | lcts(e) | 10 | 15 | 10 | 10 | 55 |
| OD600 growth on a-Keto-Glutaric Acid | akg(e) | 10 | 15 | 10 | 10 | 55 |
| OD600 growth on Acetic Acid | ac(e) | 10 | 15 | 10 | 10 | 55 |

TABLE 9-continued

| | | | | | | |
|---|---|---|---|---|---|---|
| OD600 growth on Acetoacetic Acid | acac(e) | 10 | 15 | 10 | 10 | 55 |
| OD600 growth on Adenosine | adn(e) | 10 | 15 | 10 | 10 | 55 |
| OD600 growth on Citric Acid | cit(e) | 10 | 15 | 10 | 10 | 55 |
| OD600 growth on D,L-Malic Acid | mal-L(e) | 10 | 15 | 10 | 10 | 55 |
| OD600 growth on D-Alanine | ala-D(e) | 10 | 15 | 10 | 10 | 55 |
| OD600 growth on D-Fructose | fru(e) | 10 | 15 | 10 | 10 | 55 |
| OD600 growth on D-Galactose | gal(e) | 10 | 15 | 10 | 10 | 55 |
| OD600 growth on D-Galacturonic Acid | galur(e) | 10 | 15 | 10 | 10 | 55 |
| OD600 growth on D-Gluconic Acid | glcn(e) | 10 | 15 | 10 | 10 | 55 |
| OD600 growth on D-Glucose-6-Phosphate | g6p(e) | 10 | 15 | 10 | 10 | 55 |
| OD600 growth on D-Glucuronic Acid | glcur(e) | 10 | 15 | 10 | 10 | 55 |
| OD600 growth on D-Mannitol | mnl(e) | 10 | 15 | 10 | 10 | 55 |
| OD600 growth on D-Mannose | man(e) | 10 | 15 | 10 | 10 | 55 |
| OD600 growth on D-Melibiose | melib(e) | 10 | 15 | 10 | 10 | 55 |
| OD600 growth on D-Ribose | rib-D(e) | 10 | 15 | 10 | 10 | 55 |
| OD600 growth on D-Serine | ser-D(e) | 10 | 15 | 10 | 10 | 55 |
| OD600 growth on D-Sorbitol | sbt-D(e) | 10 | 15 | 10 | 10 | 55 |
| OD600 growth on D-Trehalose | tre(e) | 10 | 15 | 10 | 10 | 55 |
| OD600 growth on D-Xylose | xyl-D(e) | 10 | 15 | 10 | 10 | 55 |
| OD600 growth on Formic Acid | for(e) | 10 | 15 | 10 | 10 | 55 |
| OD600 growth on Fumaric Acid | fum(e) | 10 | 15 | 10 | 10 | 55 |
| OD600 growth on Glycerol | glyc(e) | 10 | 15 | 10 | 10 | 55 |
| OD600 growth on Glycolic Acid | glyclt(e) | 10 | 15 | 10 | 10 | 55 |
| OD600 growth on Inosine | ins(e) | 10 | 15 | 10 | 10 | 55 |
| OD600 growth on L-Alanine | ala-L(e) | 10 | 15 | 10 | 10 | 55 |
| OD600 growth on L-Arabinose | arab-L(e) | 10 | 15 | 10 | 10 | 55 |
| OD600 growth on L-Asparagine | asn-L(e) | 10 | 15 | 10 | 10 | 55 |
| OD600 growth on L-Aspartic Acid | asp-L(e) | 10 | 15 | 10 | 10 | 55 |
| OD600 growth on L-Fucose | fuc-L(e) | 10 | 15 | 10 | 10 | 55 |
| OD600 growth on L-Glutamic Acid | glu-L(e) | 10 | 15 | 10 | 10 | 55 |
| OD600 growth on L-Glutamine | gln-L(e) | 10 | 15 | 10 | 10 | 55 |
| OD600 growth on L-Lactic Acid | lac-L(e) | 10 | 15 | 10 | 10 | 55 |
| OD600 growth on L-Malic Acid | mal-L(e) | 10 | 15 | 10 | 10 | 55 |
| OD600 growth on L-Proline | pro-L(e) | 10 | 15 | 10 | 10 | 55 |
| OD600 growth on L-Rhamnose | rmn(e) | 10 | 15 | 10 | 10 | 55 |
| OD600 growth on L-Serine | ser-L(e) | 10 | 15 | 10 | 10 | 55 |
| OD600 growth on L-Threonine | thr-L(e) | 10 | 15 | 10 | 10 | 55 |
| OD600 growth on Maltose | malt(e) | 10 | 15 | 10 | 10 | 55 |
| OD600 growth on Maltotriose | malttr(e) | 10 | 15 | 10 | 10 | 55 |
| OD600 growth on N-Acetyl-b-D-Mannosamine | acmana(e) | 10 | 15 | 10 | 10 | 55 |
| OD600 growth on N-Acetyl-D-Glucosamine | acgam(e) | 10 | 15 | 10 | 10 | 55 |
| OD600 growth on Pyruvic Acid | pyr(e) | 10 | 15 | 10 | 10 | 55 |
| OD600 growth on Succinic Acid | succ(e) | 10 | 15 | 10 | 10 | 55 |
| OD600 growth on Sucrose | sucr(e) | 10 | 15 | 10 | 10 | 55 |
| OD600 growth on Thymidine | thymd(e) | 10 | 15 | 10 | 10 | 55 |
| OD600 growth on Uridine | uri(e) | 10 | 15 | 10 | 10 | 55 |
| Biolog Plate PM2 | | | | | | |
| OD600 growth on Butyric Acid | but(e) | 10 | 15 | 10 | 10 | 55 |
| OD600 growth on D,L-Carnitine | crn(e) | 10 | 15 | 10 | 10 | 55 |
| OD600 growth on Dihydroxy Acetone | dha(e) | 10 | 15 | 10 | 10 | 55 |
| OD600 growth on g-Amino Butyric Acid | 4abut(e) | 10 | 15 | 10 | 10 | 55 |
| OD600 growth on Glycine | gly(e) | 10 | 15 | 10 | 10 | 55 |
| OD600 growth on L-Arginine | arg-L(e) | 10 | 15 | 10 | 10 | 55 |
| OD600 growth on L-Histidine | his-L(e) | 10 | 15 | 10 | 10 | 55 |
| OD600 growth on L-Isoleucine | ile-L(e) | 10 | 15 | 10 | 10 | 55 |
| OD600 growth on L-Leucine | leu-L(e) | 10 | 15 | 10 | 10 | 55 |
| OD600 growth on L-Lysine | lys-L(e) | 10 | 15 | 10 | 10 | 55 |
| OD600 growth on L-Methionine | met-L(e) | 10 | 15 | 10 | 10 | 55 |
| OD600 growth on L-Ornithine | orn(e) | 10 | 15 | 10 | 10 | 55 |
| OD600 growth on L-Phenylalanine | phe-L(e) | 10 | 15 | 10 | 10 | 55 |
| OD600 growth on L-Tartaric Acid | tartr-L(e) | 10 | 15 | 10 | 10 | 55 |
| OD600 growth on L-Valine | val-L(e) | 10 | 15 | 10 | 10 | 55 |
| OD600 growth on N-Acetyl-Neuraminic Acid | acnam(e) | 10 | 15 | 10 | 10 | 55 |
| OD600 growth on Putrescine | ptrc(e) | 10 | 15 | 10 | 10 | 55 |

| Biolog Plate PM3 | | [Nitrogen Source] | [succ(e)] | [nh4(e)] | [o2(e)] | [co2(e)] |
|---|---|---|---|---|---|---|
| OD600 growth on Adenine | ade(e) | 10 | 10 | 0 | 10 | 15 |
| OD600 growth on Adenosine | adn(e) | 10 | 10 | 0 | 10 | 15 |
| OD600 growth on Ala-Asp | ala-L(e); asp-L(e) | 10 | 10 | 0 | 10 | 15 |
| OD600 growth on Ala-Gln | ala-L(e); gln-L(e) | 10 | 10 | 0 | 10 | 15 |
| OD600 growth on Ala-Glu | ala-L(e); glu-L(e) | 10 | 10 | 0 | 10 | 15 |
| OD600 growth on Ala-Gly | ala-L(e); gly(e) | 10 | 10 | 0 | 10 | 15 |
| OD600 growth on Ala-His | ala-L(e); his-L(e) | 10 | 10 | 0 | 10 | 15 |
| OD600 growth on Ala-Leu | ala-L(e); leu-L(e) | 10 | 10 | 0 | 10 | 15 |
| OD600 growth on Ala-Thr | ala-L(e); thr-L(e) | 10 | 10 | 0 | 10 | 15 |
| OD600 growth on Allantoin | alltn(e) | 10 | 10 | 0 | 10 | 15 |
| OD600 growth on Ammonia | nh4(e) | 10 | 10 | 0 | 10 | 15 |

TABLE 9-continued

| | | | | | | |
|---|---|---|---|---|---|---|
| OD600 growth on Cytidine | cytd(e) | 10 | 10 | 0 | 10 | 15 |
| OD600 growth on Cytosine | csn(e) | 10 | 10 | 0 | 10 | 15 |
| OD600 growth on D-Alanine | ala-D(e) | 10 | 10 | 0 | 10 | 15 |
| OD600 growth on D-Glucosamine | gam(e) | 10 | 10 | 0 | 10 | 15 |
| OD600 growth on D-Serine | ser-D(e) | 10 | 10 | 0 | 10 | 15 |
| OD600 growth on Gly-Asn | gly(e); asn-L(e) | 10 | 10 | 0 | 10 | 15 |
| OD600 growth on Gly-Gln | gly(e); gln-L(e) | 10 | 10 | 0 | 10 | 15 |
| OD600 growth on Gly-Glu | gly(e); glu-L(e) | 10 | 10 | 0 | 10 | 15 |
| OD600 growth on Gly-Met | gly(e); met-L(e) | 10 | 10 | 0 | 10 | 15 |
| OD600 growth on Glycine | gly(e) | 10 | 10 | 0 | 10 | 15 |
| OD600 growth on Guanine | gua(e) | 10 | 10 | 0 | 10 | 15 |
| OD600 growth on Guanosine | gsn(e) | 10 | 10 | 0 | 10 | 15 |
| OD600 growth on Inosine | ins(e) | 10 | 10 | 0 | 10 | 15 |
| OD600 growth on L-Alanine | ala-L(e) | 10 | 10 | 0 | 10 | 15 |
| OD600 growth on L-Arginine | arg-L(e) | 10 | 10 | 0 | 10 | 15 |
| OD600 growth on L-Asparagine | asn-L(e) | 10 | 10 | 0 | 10 | 15 |
| OD600 growth on L-Aspartic Acid | asp-L(e) | 10 | 10 | 0 | 10 | 15 |
| OD600 growth on L-Cysteine | cys-L(e) | 10 | 10 | 0 | 10 | 15 |
| OD600 growth on L-Glutamic Acid | glu-L(e) | 10 | 10 | 0 | 10 | 15 |
| OD600 growth on L-Glutamine | gln-L(e) | 10 | 10 | 0 | 10 | 15 |
| OD600 growth on L-Histidine | his-L(e) | 10 | 10 | 0 | 10 | 15 |
| OD600 growth on L-Isoleucine | ile-L(e) | 10 | 10 | 0 | 10 | 15 |
| OD600 growth on L-Leucine | leu-L(e) | 10 | 10 | 0 | 10 | 15 |
| OD600 growth on L-Lysine | lys-L(e) | 10 | 10 | 0 | 10 | 15 |
| OD600 growth on L-Methionine | met-L(e) | 10 | 10 | 0 | 10 | 15 |
| OD600 growth on L-Ornithine | orn(e) | 10 | 10 | 0 | 10 | 15 |
| OD600 growth on L-Phenylalanine | phe-L(e) | 10 | 10 | 0 | 10 | 15 |
| OD600 growth on L-Proline | pro-L(e) | 10 | 10 | 0 | 10 | 15 |
| OD600 growth on L-Serine | ser-L(e) | 10 | 10 | 0 | 10 | 15 |
| OD600 growth on L-Threonine | thr-L(e) | 10 | 10 | 0 | 10 | 15 |
| OD600 growth on L-Tryptophan | trp-L(e) | 10 | 10 | 0 | 10 | 15 |
| OD600 growth on L-Tyrosine | tyr-L(e) | 10 | 10 | 0 | 10 | 15 |
| OD600 growth on L-Valine | val-L(e) | 10 | 10 | 0 | 10 | 15 |
| OD600 growth on Met-Ala | met-L(e); ala-L(e) | 10 | 10 | 0 | 10 | 15 |
| OD600 growth on N-Acetyl-D-Glucosamine | acgam(e) | 10 | 10 | 0 | 10 | 15 |
| OD600 growth on N-Acetyl-D-Mannosamine | acmana(e) | 10 | 10 | 0 | 10 | 15 |
| OD600 growth on Nitrate | no3(e) | 10 | 10 | 0 | 10 | 15 |
| OD600 growth on Nitrite | no2(e) | 10 | 10 | 0 | 10 | 15 |
| OD600 growth on Putrescine | ptrc(e) | 10 | 10 | 0 | 10 | 15 |
| OD600 growth on Thymidine | thymd(e) | 10 | 10 | 0 | 10 | 15 |
| OD600 growth on Uracil | ura(e) | 10 | 10 | 0 | 10 | 15 |
| OD600 growth on Urea | urea(e) | 10 | 10 | 0 | 10 | 15 |
| OD600 growth on Uridine | uri(e) | 10 | 10 | 0 | 10 | 15 |
| OD600 growth on Xanthine | xan(e) | 10 | 10 | 0 | 10 | 15 |
| OD600 growth on Xanthosine | xtsn(e) | 10 | 10 | 0 | 10 | 15 |

| | | [Nitrogen Source] | [pi(e)] | [so4(e)] | [h(e)] | [h2o(e)] |
|---|---|---|---|---|---|---|
| OD600 growth on Adenine | ade(e) | 10 | 15 | 10 | 10 | 55 |
| OD600 growth on Adenosine | adn(e) | 10 | 15 | 10 | 10 | 55 |
| OD600 growth on Ala-Asp | ala-L(e); asp-L(e) | 10 | 15 | 10 | 10 | 55 |
| OD600 growth on Ala-Gln | ala-L(e); gln-L(e) | 10 | 15 | 10 | 10 | 55 |
| OD600 growth on Ala-Glu | ala-L(e); glu-L(e) | 10 | 15 | 10 | 10 | 55 |
| OD600 growth on Ala-Gly | ala-L(e); gly(e) | 10 | 15 | 10 | 10 | 55 |
| OD600 growth on Ala-His | ala-L(e); his-L(e) | 10 | 15 | 10 | 10 | 55 |
| OD600 growth on Ala-Leu | ala-L(e); leu-L(e) | 10 | 15 | 10 | 10 | 55 |
| OD600 growth on Ala-Thr | ala-L(e); thr-L(e) | 10 | 15 | 10 | 10 | 55 |
| OD600 growth on Allantoin | alltn(e) | 10 | 15 | 10 | 10 | 55 |
| OD600 growth on Ammonia | nh4(e) | 10 | 15 | 10 | 10 | 55 |
| OD600 growth on Cytidine | cytd(e) | 10 | 15 | 10 | 10 | 55 |
| OD600 growth on Cytosine | csn(e) | 10 | 15 | 10 | 10 | 55 |
| OD600 growth on D-Alanine | ala-D(e) | 10 | 15 | 10 | 10 | 55 |
| OD600 growth on D-Glucosamine | gam(e) | 10 | 15 | 10 | 10 | 55 |
| OD600 growth on D-Serine | ser-D(e) | 10 | 15 | 10 | 10 | 55 |
| OD600 growth on Gly-Asn | gly(e); asn-L(e) | 10 | 15 | 10 | 10 | 55 |
| OD600 growth on Gly-Gln | gly(e); gln-L(e) | 10 | 15 | 10 | 10 | 55 |
| OD600 growth on Gly-Glu | gly(e); glu-L(e) | 10 | 15 | 10 | 10 | 55 |
| OD600 growth on Gly-Met | gly(e); met-L(e) | 10 | 15 | 10 | 10 | 55 |
| OD600 growth on Glycine | gly(e) | 10 | 15 | 10 | 10 | 55 |
| OD600 growth on Guanine | gua(e) | 10 | 15 | 10 | 10 | 55 |
| OD600 growth on Guanosine | gsn(e) | 10 | 15 | 10 | 10 | 55 |
| OD600 growth on Inosine | ins(e) | 10 | 15 | 10 | 10 | 55 |
| OD600 growth on L-Alanine | ala-L(e) | 10 | 15 | 10 | 10 | 55 |
| OD600 growth on L-Arginine | arg-L(e) | 10 | 15 | 10 | 10 | 55 |
| OD600 growth on L-Asparagine | asn-L(e) | 10 | 15 | 10 | 10 | 55 |
| OD600 growth on L-Aspartic Acid | asp-L(e) | 10 | 15 | 10 | 10 | 55 |
| OD600 growth on L-Cysteine | cys-L(e) | 10 | 15 | 10 | 10 | 55 |

TABLE 9-continued

| | | | | | | |
|---|---|---|---|---|---|---|
| OD600 growth on L-Glutamic Acid | glu-L(e) | 10 | 15 | 10 | 10 | 55 |
| OD600 growth on L-Glutamine | gln-L(e) | 10 | 15 | 10 | 10 | 55 |
| OD600 growth on L-Histidine | his-L(e) | 10 | 15 | 10 | 10 | 55 |
| OD600 growth on L-Isoleucine | ile-L(e) | 10 | 15 | 10 | 10 | 55 |
| OD600 growth on L-Leucine | leu-L(e) | 10 | 15 | 10 | 10 | 55 |
| OD600 growth on L-Lysine | lys-L(e) | 10 | 15 | 10 | 10 | 55 |
| OD600 growth on L-Methionine | met-L(e) | 10 | 15 | 10 | 10 | 55 |
| OD600 growth on L-Ornithine | orn(e) | 10 | 15 | 10 | 10 | 55 |
| OD600 growth on L-Phenylalanine | phe-L(e) | 10 | 15 | 10 | 10 | 55 |
| OD600 growth on L-Proline | pro-L(e) | 10 | 15 | 10 | 10 | 55 |
| OD600 growth on L-Serine | ser-L(e) | 10 | 15 | 10 | 10 | 55 |
| OD600 growth on L-Threonine | thr-L(e) | 10 | 15 | 10 | 10 | 55 |
| OD600 growth on L-Tryptophan | trp-L(e) | 10 | 15 | 10 | 10 | 55 |
| OD600 growth on L-Tyrosine | tyr-L(e) | 10 | 15 | 10 | 10 | 55 |
| OD600 growth on L-Valine | val-L(e) | 10 | 15 | 10 | 10 | 55 |
| OD600 growth on Met-Ala | met-L(e); ala-L(e) | 10 | 15 | 10 | 10 | 55 |
| OD600 growth on N-Acetyl-D-Glucosamine | acgam(e) | 10 | 15 | 10 | 10 | 55 |
| OD600 growth on N-Acetyl-D-Mannosamine | acmana(e) | 10 | 15 | 10 | 10 | 55 |
| OD600 growth on Nitrate | no3(e) | 10 | 15 | 10 | 10 | 55 |
| OD600 growth on Nitrite | no2(e) | 10 | 15 | 10 | 10 | 55 |
| OD600 growth on Putrescine | ptrc(e) | 10 | 15 | 10 | 10 | 55 |
| OD600 growth on Thymidine | thymd(e) | 10 | 15 | 10 | 10 | 55 |
| OD600 growth on Uracil | ura(e) | 10 | 15 | 10 | 10 | 55 |
| OD600 growth on Urea | urea(e) | 10 | 15 | 10 | 10 | 55 |
| OD600 growth on Uridine | uri(e) | 10 | 15 | 10 | 10 | 55 |
| OD600 growth on Xanthine | xan(e) | 10 | 15 | 10 | 10 | 55 |
| OD600 growth on Xanthosine | xtsn(e) | 10 | 15 | 10 | 10 | 55 |

Constraints on Exchange Fluxes

| Abbreviation | Equation | Lower Bound | Upper Bound |
|---|---|---|---|
| EX_12ppd-S(e) | [e]12ppd-S <==> | −10 | 10 |
| EX_15dap(e) | [e]15dap <==> | −10 | 10 |
| EX_26dap-M(e) | [e]26dap-M <==> | −10 | 10 |
| EX_2ddglcn(e) | [e]2ddglcn <==> | −10 | 10 |
| EX_3hcinnm(e) | [e]3hcinnm <==> | −10 | 10 |
| EX_3hpppn(e) | [e]3hpppn <==> | −10 | 10 |
| EX_4abut(e) | [e]4abut <==> | −10 | 10 |
| EX_ac(e) | [e]ac <==> | −2.5 | 1000 |
| EX_acac(e) | [e]acac <==> | −10 | 10 |
| EX_acald(e) | [e]acald <==> | −10 | 10 |
| EX_acgam(e) | [e]acgam <==> | −10 | 10 |
| EX_acmana(e) | [e]acmana <==> | −10 | 10 |
| EX_acnam(e) | [e]acnam <==> | −10 | 10 |
| EX_ade(e) | [e]ade <==> | −10 | 10 |
| EX_adn(e) | [e]adn <==> | −10 | 10 |
| EX_akg(e) | [e]akg <==> | −10 | 10 |
| EX_ala-D(e) | [e]ala-D <==> | −10 | 10 |
| EX_ala-L(e) | [e]ala-L <==> | −10 | 10 |
| EX_alltn(e) | [e]alltn <==> | −10 | 10 |
| EX_amp(e) | [e]amp <==> | −10 | 10 |
| EX_arab-L(e) | [e]arab-L <==> | −10 | 10 |
| EX_arg-L(e) | [e]arg-L <==> | −10 | 10 |
| EX_asn-L(e) | [e]asn-L <==> | −10 | 10 |
| EX_asp-L(e) | [e]asp-L <==> | −10 | 10 |
| EX_but(e) | [e]but <==> | −10 | 10 |
| EX_cbl1(e) | [e]cbl1 <==> | −10 | 10 |
| EX_chol(e) | [e]chol <==> | −10 | 10 |
| EX_cit(e) | [e]cit <==> | −10 | 10 |
| EX_co2(e) | [e]co2 <==> | −1000 | 10 |
| EX_crn(e) | [e]crn <==> | −10 | 10 |
| EX_csn(e) | [e]csn <==> | −10 | 10 |
| EX_cynt(e) | [e]cynt <==> | −10 | 10 |
| EX_cys-L(e) | [e]cys-L <==> | −10 | 10 |
| EX_cytd(e) | [e]cytd <==> | −10 | 10 |
| EX_dad-2(e) | [e]dad-2 <==> | −10 | 10 |
| EX_dcyt(e) | [e]dcyt <==> | −10 | 10 |
| EX_dgsn(e) | [e]dgsn <==> | −10 | 10 |
| EX_dha(e) | [e]dha <==> | −10 | 10 |
| EX_din(e) | [e]din <==> | −10 | 10 |
| EX_dms(e) | [e]dms <==> | −20 | 10 |
| EX_dmso(e) | [e]dmso <==> | −20 | 20 |
| EX_duri(e) | [e]duri <==> | −10 | 20 |
| EX_etoh(e) | [e]etoh <==> | −11.3 | 1000 |
| EX_fe2(e) | [e]fe2 <==> | −10 | 10 |
| EX_for(e) | [e]for <==> | −11.3 | 1000 |

TABLE 9-continued

| | | | |
|---|---|---|---|
| EX_fru(e) | [e]fru <==> | −10 | 10 |
| EX_fuc1p-L(e) | [e]fuc1p-L <==> | −10 | 10 |
| EX_fuc-L(e) | [e]fuc-L <==> | −10 | 10 |
| EX_fum(e) | [e]fum <==> | −10 | 10 |
| EX_g6p(e) | [e]g6p <==> | −10 | 10 |
| EX_gal(e) | [e]gal <==> | −10 | 10 |
| EX_galct-D(e) | [e]galct-D <==> | −10 | 10 |
| EX_galctn-D(e) | [e]galctn-D <==> | −10 | 10 |
| EX_galt(e) | [e]galt <==> | −10 | 10 |
| EX_galur(e) | [e]galur <==> | −10 | 10 |
| EX_gam(e) | [e]gam <==> | −10 | 10 |
| EX_gbbtn(e) | [e]gbbtn <==> | −10 | 10 |
| EX_glc(e) | [e]glc-D <==> | −10 | 1000 |
| EX_glcn(e) | [e]glcn <==> | −10 | 10 |
| EX_glcr(e) | [e]glcr <==> | −10 | 10 |
| EX_glcur(e) | [e]glcur <==> | −10 | 10 |
| EX_gln-L(e) | [e]gln-L <==> | −10 | 10 |
| EX_glu-L(e) | [e]glu-L <==> | −10 | 10 |
| EX_gly(e) | [e]gly <==> | −10 | 10 |
| EX_glyald(e) | [e]glyald <==> | −10 | 10 |
| EX_glyb(e) | [e]glyb <==> | −10 | 10 |
| EX_glyc(e) | [e]glyc <==> | −11.3 | 1000 |
| EX_glyc3p(e) | [e]glyc3p <==> | −10 | 10 |
| EX_glyclt(e) | [e]glyclt <==> | −10 | 10 |
| EX_gsn(e) | [e]gsn <==> | −10 | 10 |
| EX_gua(e) | [e]gua <==> | −10 | 10 |
| EX_h(e) | [e]h <==> | −1000 | 1000 |
| EX_h2o(e) | [e]h2o <==> | −1000 | 1000 |
| EX_h2s(e) | [e]h2s <==> | −10 | 10 |
| EX_hdca(e) | [e]hdca <==> | −10 | 10 |
| EX_his-L(e) | [e]his-L <==> | −10 | 10 |
| EX_hxan(e) | [e]hxan <==> | −10 | 10 |
| EX_idon-L(e) | [e]idon-L <==> | −10 | 10 |
| EX_ile-L(e) | [e]ile-L <==> | −10 | 10 |
| EX_indole(e) | [e]indole <==> | −10 | 10 |
| EX_ins(e) | [e]ins <==> | −10 | 10 |
| EX_k(e) | [e]k <==> | −10 | 10 |
| EX_lac-D(e) | [e]lac-D <==> | −11.3 | 1000 |
| EX_lac-L(e) | [e]lac-L <==> | −10 | 10 |
| EX_lcts(e) | [e]lcts <==> | −3 | 1000 |
| EX_leu-L(e) | [e]leu-L <==> | −10 | 10 |
| EX_lys-L(e) | [e]lys-L <==> | −10 | 10 |
| EX_mal-L(e) | [e]mal-L <==> | −10 | 10 |
| EX_malt(e) | [e]malt <==> | −10 | 10 |
| EX_malthx(e) | [e]malthx <==> | −10 | 10 |
| EX_maltpt(e) | [e]maltpt <==> | −10 | 10 |
| EX_malttr(e) | [e]malttr <==> | −10 | 10 |
| EX_maltttr(e) | [e]maltttr <==> | −10 | 10 |
| EX_man(e) | [e]man <==> | −10 | 10 |
| EX_man6p(e) | [e]man6p <==> | −10 | 10 |
| EX_melib(e) | [e]melib <==> | −10 | 10 |
| EX_met-D(e) | [e]met-D <==> | −10 | 10 |
| EX_met-L(e) | [e]met-L <==> | −10 | 10 |
| EX_mnl(e) | [e]mnl <==> | −10 | 10 |
| EX_na1(e) | [e]na1 <==> | −10 | 10 |
| EX_nac(e) | [e]nac <==> | −10 | 10 |
| EX_nad(e) | [e]nad <==> | −10 | 10 |
| EX_nh4(e) | [e]nh4 <==> | −10 | 10 |
| EX_nmn(e) | [e]nmn <==> | −10 | 10 |
| EX_no2(e) | [e]no2 <==> | −10 | 10 |
| EX_no3(e) | [e]no3 <==> | −10 | 10 |
| EX_o2(e) | [e]o2 <==> | −10 | 1000 |
| EX_ocdca(e) | [e]ocdca <==> | −10 | 10 |
| EX_orn(e) | [e]orn <==> | −10 | 10 |
| EX_phe-L(e) | [e]phe-L <==> | −10 | 10 |
| EX_pi(e) | [e]pi <==> | −10 | 1000 |
| EX_pnto-R(e) | [e]pnto-R <==> | −10 | 10 |
| EX_pppn(e) | [e]pppn <==> | −10 | 10 |
| EX_pro-L(e) | [e]pro-L <==> | −10 | 10 |
| EX_ptrc(e) | [e]ptrc <==> | −10 | 10 |
| EX_pyr(e) | [e]pyr <==> | −11.3 | 1000 |
| EX_rib-D(e) | [e]rib-D <==> | −11.3 | 1000 |
| EX_rmn(e) | [e]rmn <==> | −10 | 10 |
| EX_sbt-D(e) | [e]sbt-D <==> | −10 | 10 |
| EX_ser-D(e) | [e]ser-D <==> | −10 | 10 |
| EX_ser-L(e) | [e]ser-L <==> | −10 | 10 |
| EX_so4(e) | [e]so4 <==> | −10 | 10 |
| EX_spmd(e) | [e]spmd <==> | −10 | 10 |
| EX_succ(e) | [e]succ <==> | −11.3 | 1000 |

TABLE 9-continued

| | | | |
|---|---|---|---|
| EX_sucr(e) | [e]sucr <==> | −10 | 10 |
| EX_tartr-L(e) | [e]tartr-L <==> | −10 | 10 |
| EX_taur(e) | [e]taur <==> | −10 | 10 |
| EX_thm(e) | [e]thm <==> | −10 | 10 |
| EX_thr-L(e) | [e]thr-L <==> | −10 | 10 |
| EX_thymd(e) | [e]thymd <==> | −10 | 10 |
| EX_tma(e) | [e]tma <==> | −20 | 20 |
| EX_tmao(e) | [e]tmao <==> | −20 | 20 |
| EX_tre(e) | [e]tre <==> | −10 | 10 |
| EX_trp-L(e) | [e]trp-L <==> | −10 | 10 |
| EX_tsul(e) | [e]tsul <==> | −10 | 10 |
| EX_ttdca(e) | [e]ttdca <==> | −10 | 10 |
| EX_tyr-L(e) | [e]tyr-L <==> | −10 | 10 |
| EX_ura(e) | [e]ura <==> | −10 | 10 |
| EX_urea(e) | [e]urea <==> | −10 | 10 |
| EX_uri(e) | [e]uri <==> | −10 | 10 |
| EX_val-L(e) | [e]val-L <==> | −10 | 10 |
| EX_xan(e) | [e]xan <==> | −10 | 10 |
| EX_xtsn(e) | [e]xtsn <==> | −10 | 10 |
| EX_xyl-D(e) | [e]xyl-D <==> | −10 | 10 |

TABLE 10

Metabolite and Reaction Abbreviations used in this spreadsheet

| Metabolites Abbreviation | Name | Reactions Abbreviation | Reaction stoichiometry |
|---|---|---|---|
| 10fthf | 10-Formyltetrahydrofolate | AGDC | 1.0 ac -1.0 acgam6p 1.0 gam6p -1.0 h2o |
| 12dgr_EC | 1,2-Diacylglycerol (*E. coli*)** | ALTRH | 1.0 2ddglcn -1.0 altrn 1.0 h2o |
| 12ppd-S | (S)-Propane-1,2-diol | FBP | 1.0 f6p -1.0 fdp -1.0 h2o 1.0 pi |
| 12ppd-S(e) | (S)-Propane-1,2-diol (Extracellular) | GLCpts | 1.0 g6p - 1.0 pep 1.0 pyr - 1.0 glc(e) |
| 13dpg | 3-Phospho-D-glyceroyl phosphate | GUI1 | 1.0 fruur -1.0 glcur |
| 15dap | 1,5-Diaminopentane | GUI2 | −1.0 galur 1.0 tagur |
| 15dap(e) | 1,5-Diaminopentane (Extracellular) | LDH_D | 1.0 h -1.0 lac-D -1.0 nad 1.0 nadh 1.0 pyr |
| 1pyr5c | 1-Pyrroline-5-carboxylate | LDH_D2 | −1.0 lac-D 1.0 pyr -1.0 q8 1.0 q8h2 |
| 23ddhb | 2,3-Dihydro-2,3-dihydroxybenzoate | MANAO | 1.0 fruur 1.0 h -1.0 mana -1.0 nad 1.0 nadh |
| 23dhb | 2,3-Dihydroxybenzoate | ME1 | 1.0 co2 -1.0 mal-L -1.0 nad 1.0 nadh 1.0 pyr |
| 23dhba | (2,3-Dihydroxybenzoyl)adenylate | ME2 | 1.0 co2 -1.0 mal-L -1.0 nadp 1.0 nadph 1.0 pyr |
| 23dhdp | 2,3-Dihydrodipicolinate | MNNH | 1.0 2ddglcn 1.0 h2o -1.0 mana |
| 23dhmb | (R)-2,3-Dihydroxy-3-methylbutanoate | PFK | 1.0 adp -1.0 atp -1.0 f6p 1.0 fdp 1.0 h |
| 23dhmp | (R)-2,3-Dihydroxy-3-methylpentanoate | PGI | 1.0 f6p -1.0 g6p |
| 23doguln | 2,3-Dioxo-L-gulonate | PPM2 | −1.0 2dr1p 1.0 2dr5p |
| 25aics | (S)-2-[5-Amino-1-(5-phospho-D-ribosyl)imidazole-4-carboxamido]succinate | PYK | −1.0 adp 1.0 atp -1.0 h -1.0 pep 1.0 pyr |
| 25dkglcn | 2,5-diketo-D-gluconate | SUCCt2_2 | 2.0 h 1.0 succ -2.0 h(e) -1.0 succ(e) |
| 25drapp | 2,5-Diamino-6-(ribosylamino)-4-(3H)-pyrimidinone 5'-phosphate | SUCCt2_3 | 3.0 h 1.0 succ -3.0 h(e) -1.0 succ(e) |
| 26dap-LL | LL-2,6-Diaminoheptanedioate | TAGURr | 1.0 altrn 1.0 h -1.0 nad 1.0 nadh 1.0 tagur |
| 26dap-M | meso-2,6-Diaminoheptanedioate | TALA | 1.0 e4p 1.0 f6p -1.0 g3p -1.0 s7p |
| 26dap-M(e) | meso-2,6-Diaminoheptanedioate (Extracellular) | TKT2 | 1.0 e4p 1.0 f6p -1.0 g3p -1.0 xu5p-D |
| 2ahbut | (S)-2-Aceto-2-hydroxybutanoate | | |
| 2aobut | L-2-Amino-3-oxobutanoate | | |
| 2cpr5p | 1-(2-Carboxyphenylamino)-1-deoxy-D-ribulose 5-phosphate | | |
| 2dda7p | 2-Dehydro-3-deoxy-D-arabino-heptonate 7-phosphate | | |
| 2ddg6p | 2-Dehydro-3-deoxy-D-gluconate 6-phosphate | | |
| 2ddglcn | 2-Dehydro-3-deoxy-D-gluconate | | |
| 2ddglcn(e) | 2-Dehydro-3-deoxy-D-gluconate (Extracellular) | | |
| 2dh3dgal | 2-Dehydro-3-deoxy-D-galactonate | | |
| 2dh3dgal6p | 2-Dehydro-3-deoxy-D-galactonate 6-phosphate | | |
| 2dhglcn | 2-Dehydro-D-gluconate | | |
| 2dhguln | 2-Dehydro-L-gulonate | | |
| 2dhp | 2-Dehydropantoate | | |
| 2dmmq8 | 2-Demethylmenaquinone 8 | | |
| 2dmmql8 | 2-Demethylmenaquinol 8 | | |
| 2dr1p | 2-Deoxy-D-ribose 1-phosphate | | |
| 2dr5p | 2-Deoxy-D-ribose 5-phosphate | | |
| 2h3oppan | 2-Hydroxy-3-oxopropanoate | | |
| 2ippm | 2-Isopropylmaleate | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| 2kmb | 2-keto-4-methylthiobutyrate | | |
| 2mahmp | 2-Methyl-4-amino-5-hydroxymethylpyrimidine diphosphate | | |
| 2mcacn | cis-2-Methylaconitate | | |
| 2mcit | 2-Methylcitrate | | |
| 2me4p | 2-C-methyl-D-erythritol 4-phosphate | | |
| 2mecdp | 2-C-methyl-D-erythritol 2,4-cyclodiphosphate | | |
| 2obut | 2-Oxobutanoate | | |
| 2ohph | 2-Octaprenyl-6-hydroxyphenol | | |
| 2ombzl | 2-Octaprenyl-6-methoxy-1,4-benzoquinol | | |
| 2omhmbl | 2-Octaprenyl-3-methyl-5-hydroxy-6-methoxy-1,4-benzoquinol | | |
| 2ommbl | 2-Octaprenyl3-methyl-6-methoxy-1,4-benzoquinol | | |
| 2omph | 2-Octaprenyl-6-methoxyphenol | | |
| 2oph | 2-Octaprenylphenol | | |
| 2p4c2me | 2-phospho-4-(cytidine 5'-diphospho)-2-C-methyl-D-erythritol | | |
| 2pg | D-Glycerate 2-phosphate | | |
| 2pglyc | 2-Phosphoglycolate | | |
| 2shchc | 2-Succinyl-6-hydroxy-2,4-cyclohexadiene-1-carboxylate | | |
| 34hpp | 3-(4-Hydroxyphenyl)pyruvate | | |
| 3c2hmp | 3-Carboxy-2-hydroxy-4-methylpentanoate | | |
| 3c3hmp | 3-Carboxy-3-hydroxy-4-methylpentanoate | | |
| 3c4mop | 3-Carboxy-4-methyl-2-oxopentanoate | | |
| 3dgulnp | 3-keto-L-gulonate-6-phosphate | | |
| 3dhguln | 3-Dehydro-L-gulonate | | |
| 3dhq | 3-Dehydroquinate | | |
| 3dhsk | 3-Dehydroshikimate | | |
| 3hcinnm | 3-hydroxycinnamic acid | | |
| 3hcinnm(e) | 3-hydroxycinnamic acid (Extracellular) | | |
| 3hmrsACP | R-3-hydroxy-myristoyl-ACP | | |
| 3hpppn | 3-(3-hydroxy-phenyl)propionate | | |
| 3hpppn(e) | 3-(3-hydroxy-phenyl)propionate (Extracellular) | | |
| 3ig3p | C'-(3-Indolyl)-glycerol 3-phosphate | | |
| 3mob | 3-Methyl-2-oxobutanoate | | |
| 3mop | (S)-3-Methyl-2-oxopentanoate | | |
| 3ophb | 3-Octaprenyl-4-hydroxybenzoate | | |
| 3pg | 3-Phospho-D-glycerate | | |
| 3php | 3-Phosphohydroxypyruvate | | |
| 3psme | 5-O-(1-Carboxyvinyl)-3-phosphoshikimate | | |
| 4abut | 4-Aminobutanoate | | |
| 4abut(e) | 4-Aminobutanoate (Extracellular) | | |
| 4abutn | 4-Aminobutanal | | |
| 4abz | 4-Aminobenzoate | | |
| 4adcho | 4-amino-4-deoxychorismate | | |
| 4ahmmp | 4-Amino-5-hydroxymethyl-2-methylpyrimidine | | |
| 4ampm | 4-Amino-2-methyl-5-phosphomethylpyrimidine | | |
| 4c2me | 4-(cytidine 5'-diphospho)-2-C-methyl-D-erythritol | | |
| 4h2opntn | 4-Hydroxy-2-oxopentanoate | | |
| 4hba | 4-Hydroxy-benzyl alcohol | | |
| 4hbz | 4-Hydroxybenzoate | | |
| 4hthr | 4-Hydroxy-L-threonine | | |
| 4mhetz | 4-Methyl-5-(2-hydroxyethyl)-thiazole | | |
| 4mop | 4-Methyl-2-oxopentanoate | | |
| 4mpetz | 4-Methyl-5-(2-phosphoethyl)-thiazole | | |
| 4pasp | 4-Phospho-L-aspartate | | |
| 4per | 4-Phospho-D-erythronate | | |
| 4ppan | D-4'-Phosphopantothenate | | |
| 4ppcys | N-((R)-4-Phosphopantothenoyl)-L-cysteine | | |
| 4r5au | 4-(1-D-Ribitylamino)-5-aminouracil | | |
| 5aizc | 5-amino-1-(5-phospho-D-ribosyl)imidazole-4-carboxylate | | |
| 5aop | 5-Amino-4-oxopentanoate | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| 5aprbu | 5-Amino-6-(5'-phosphoribitylamino)uracil | | |
| 5apru | 5-Amino-6-(5'-phosphoribosylamino)uracil | | |
| 5caiz | 5-phosphoribosyl-5-carboxyaminoimidazole | | |
| 5dglcn | 5-Dehydro-D-gluconate | | |
| 5dglcn(e) | 5-Dehydro-D-gluconate (Extracellular) | | |
| 5dh4dglc | 5-Dehydro-4-deoxy-D-glucarate | | |
| 5mdr1p | 5-Methylthio-5-deoxy-D-ribose 1-phosphate | | |
| 5mdru1p | 5-Methylthio-5-deoxy-D-ribulose 1-phosphate | | |
| 5mta | 5-Methylthioadenosine | | |
| 5mthf | 5-Methyltetrahydrofolate | | |
| 5mtr | 5-Methylthio-D-ribose | | |
| 5prdmbz | N1-(5-Phospho-alpha-D-ribosyl)-5,6-dimethylbenzimidazole | | |
| 6hmhpt | 6-hydroxymethyl dihydropterin | | |
| 6hmhptpp | 6-hydroxymethyl-dihydropterin pyrophosphate | | |
| 6pgc | 6-Phospho-D-gluconate | | |
| 6pgl | 6-phospho-D-glucono-1,5-lactone | | |
| 8aonn | 8-Amino-7-oxononanoate | | |
| aacald | Aminoacetaldehyde | | |
| aacoa | Acetoacetyl-CoA | | |
| ac | Acetate | | |
| ac(e) | Acetate (Extracellular) | | |
| acac | Acetoacetate | | |
| acac(e) | Acetoacetate (Extracellular) | | |
| acACP | Acetyl-ACP | | |
| acald | Acetaldehyde | | |
| acald(e) | Acetaldehyde (Extracellular) | | |
| accoa | Acetyl-CoA | | |
| acg5p | N-Acetyl-L-glutamyl 5-phosphate | | |
| acg5sa | N-Acetyl-L-glutamate 5-semialdehyde | | |
| acgam(e) | N-Acetyl-D-glucosamine (Extracellular) | | |
| acgam1p | N-Acetyl-D-glucosamine 1-phosphate | | |
| acgam6p | N-Acetyl-D-glucosamine 6-phosphate | | |
| acglu | N-Acetyl-L-glutamate | | |
| acmana | N-Acetyl-D-mannosamine | | |
| acmana(e) | N-Acetyl-D-mannosamine (Extra cellular) | | |
| acmanap | N-Acetyl-D-mannosamine 6-phosphate | | |
| acnam | N-Acetylneuraminate | | |
| acnam(e) | N-Acetylneuraminate (Extracellular) | | |
| aconm | E-3-carboxy-2-pentenedioate 6-methyl ester | | |
| acon-T | trans-Aconitate | | |
| acorn | N2-Acetyl-L-ornithine | | |
| ACP | acyl carrier protein | | |
| acser | O-Acetyl-L-serine | | |
| actACP | Acetoacetyl-ACP | | |
| actp | Acetyl phosphate | | |
| ade | Adenine | | |
| ade(e) | Adenine (Extracellular) | | |
| adn | Adenosine | | |
| adn(e) | Adenosine (Extracellular) | | |
| adocbi | Adenosyl cobinamide | | |
| adocbip | Adenosyl cobinamide phosphate | | |
| adocbl | Adenosylcobalamin | | |
| adp | ADP | | |
| adpglc | ADPglucose | | |
| adphep-D,D | ADP-D-glycero-D-manno-heptose | | |
| adphep-L,D | ADP-L-glycero-D-manno-heptose | | |
| agdpcbi | Adenosine-GDP-cobinamide | | |
| agm | Agmatine | | |
| agpc_EC | acyl-glycerophosphocholine (*E. coli*) ** | | |
| agpe_EC | acyl-glycerophosphoethanolamine (*E. coli*) ** | | |
| agpg_EC | acyl-glycerophosphoglycerol (*E. coli*) ** | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| ahcys | S-Adenosyl-L-homocysteine | | |
| ahdt | 2-Amino-4-hydroxy-6-(erythro-1,2,3-trihydroxypropyl)dihydropteridine triphosphate | | |
| aicar | 5-Amino-1-(5-Phospho-D-ribosyl)imidazole-4-carboxamide | | |
| air | 5-amino-1-(5-phospho-D-ribosyl)imidazole | | |
| akg | 2-Oxoglutarate | | |
| akg(e) | 2-Oxoglutarate (Extracellular) | | |
| alaala | D-Alanyl-D-alanine | | |
| ala-B | beta-Alanine | | |
| alac-S | (S)-2-Acetolactate | | |
| ala-D | D-Alanine | | |
| ala-D(e) | D-Alanine (Extracellular) | | |
| ala-L | L-Alanine | | |
| ala-L(e) | L-Alanine (Extracellular) | | |
| alltn | Allantoin | | |
| alltn(e) | Allantoin (Extracellular) | | |
| alltt | Allantoate | | |
| altrn | D-Altronate | | |
| amet | S-Adenosyl-L-methionine | | |
| ametam | S-Adenosylmethioninamine | | |
| amob | S-Adenosyl-4-methylthio-2-oxobutanoate | | |
| amp | AMP | | |
| amp(e) | AMP (Extracellular) | | |
| anth | Anthranilate | | |
| ap4a | P1,P4-Bis(5'-adenosyl)tetraphosphate | | |
| ap5a | P1, P5-Bis(5'-adenosyl) pentaphosphate | | |
| apg_EC | acyl phosphatidylglycerol (*E. coli*) ** | | |
| apoACP | apoprotein [acyl carrier protein] | | |
| aps | Adenosine 5'-phosphosulfate | | |
| ara5p | D-Arabinose 5-phosphate | | |
| arab-L | L-Arabinose | | |
| arab-L(e) | L-Arabinose (Extracellular) | | |
| arbt6p | Arbutin 6-phosphate | | |
| arg-L | L-Arginine | | |
| arg-L(e) | L-Arginine (Extracellular) | | |
| argsuc | N(omega)-(L-Arginino)succinate | | |
| asn-L | L-Asparagine | | |
| asn-L(e) | L-Asparagine (Extracellular) | | |
| asp-L | L-Aspartate | | |
| asp-L(e) | L-Aspartate (Extracellular) | | |
| aspsa | L-Aspartate 4-semialdehyde | | |
| atp | ATP | | |
| bbtcoa | gamma-butyrobetainyl-CoA | | |
| betald | Betaine aldehyde | | |
| btcoa | Butanoyl-CoA | | |
| btn | Biotin | | |
| btn(e) | Biotin (Extracellular) | | |
| btnso | d-biotin d-sulfoxide | | |
| but | Butyrate (n-C4:0) | | |
| but(e) | Butyrate (n-C4:0) (Extracellular) | | |
| camp | cAMP | | |
| cbasp | N-Carbamoyl-L-aspartate | | |
| cbi | Cobinamide | | |
| cbi(e) | Cobinamide (Extracellular) | | |
| cbl1 | Cob(l)alamin | | |
| cbl1(e) | Cob(l)alamin (Extracellular) | | |
| cbp | Carbamoyl phosphate | | |
| cdp | CDP | | |
| cdpdag1 | CDPdiacylglycerol (*E coli*) ** | | |
| cdpea | CDPethanolamine | | |
| cechddd | cis-3-(3-carboxyethyl)-3,5-cyclohexadiene-1,2-diol | | |
| cenchddd | cis-3-(3-carboxyethenyl)-3,5-cyclohexadiene-1,2-diol | | |
| chol | Choline | | |
| chol(e) | Choline (Extracellular) | | |
| chor | Chorismate | | |
| cinnm | trans-Cinnamate | | |
| cit | Citrate | | |
| cit(e) | Citrate (Extracellular) | | |
| citr-L | L-Citrulline | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| ckdo | CMP-3-deoxy-D-manno-octulosonate | | |
| clpn_EC | Cardiolipin (*E coli*) ** | | |
| cmp | CMP | | |
| co2 | CO2 | | |
| co2(e) | CO2 (Extracellular) | | |
| coa | Coenzyme A | | |
| cpppg3 | Coproporphyrinogen III | | |
| crn | L-Carnitine | | |
| crn(e) | L-Carnitine (Extracellular) | | |
| crncoa | Carnitinyl-CoA | | |
| csn | Cytosine | | |
| csn(e) | Cytosine (Extracellular) | | |
| ctbt | crotonobetaine | | |
| ctbtcoa | crotonobetainyl-CoA | | |
| ctp | CTP | | |
| cyan | Cyanide | | |
| cynt | Cyanate | | |
| cynt(e) | Cyanate (Extracellular) | | |
| cys-L | L-Cysteine | | |
| cys-L(e) | L-Cysteine (Extracellular) | | |
| cyst-L | L-Cystathionine | | |
| cytd | Cytidine | | |
| cytd(e) | Cytidine (Extracellular) | | |
| dad-2 | Deoxyadenosine | | |
| dad-2(e) | Deoxyadenosine (Extracellular) | | |
| dadp | dADP | | |
| damp | dAMP | | |
| dann | 7,8-Diaminononanoate | | |
| datp | dATP | | |
| db4p | 3,4-dihydroxy-2-butanone 4-phosphate | | |
| dcamp | N6-(1,2-Dicarboxyethyl)-AMP | | |
| dcdp | dCDP | | |
| dcmp | dCMP | | |
| dctp | dCTP | | |
| dcyt | Deoxycytidine | | |
| dcyt(e) | Deoxycytidine (Extracellular) | | |
| ddcaACP | Dodecanoyl-ACP (n-C12:0ACP) | | |
| dgdp | dGDP | | |
| dgmp | dGMP | | |
| dgsn | Deoxyguanosine | | |
| dgsn(e) | Deoxyguanosine (Extracellular) | | |
| dgtp | dGTP | | |
| dha | Dihydroxyacetone | | |
| dha(e) | Dihydroxyacetone (Extracellular) | | |
| dhap | Dihydroxyacetone phosphate | | |
| dhcinnm | 2,3-dihydroxicinnamic acid | | |
| dhf | 7,8-Dihydrofolate | | |
| dhna | 1,4-Dihydroxy-2-naphthoate | | |
| dhnpt | 2-Amino-4-hydroxy-6-(D-erythro-1,2,3-trihydroxypropyl)-7,8-dihydropteridine | | |
| dhor-S | (S)-Dihydroorotate | | |
| dhpmp | Dihydroneopterin monophosphate | | |
| dhpppn | 3-(2,3-Dihydroxyphenyl)propanoate | | |
| dhpt | Dihydropteroate | | |
| dhptd | 4,5-dihydroxy-2,3-pentanedione | | |
| din | Deoxyinosine | | |
| din(e) | Deoxyinosine (Extracellular) | | |
| dkmpp | 2,3-diketo5-methylthio-1-phosphopentane | | |
| dmbzid | 5,6-Dimethylbenzimidazole | | |
| dmlz | 6,7-Dimethyl-8-(1-D-ribityl)lumazine | | |
| dmpp | Dimethylallyl diphosphate | | |
| dms | Dimethyl sulfide | | |
| dms(e) | Dimethyl sulfide (Extracellular) | | |
| dmso | Dimethyl sulfoxide | | |
| dmso(e) | Dimethyl sulfoxide (Extracellular) | | |
| dnad | Deamino-NAD+ | | |
| dpcoa | Dephospho-CoA | | |
| dtbt | Dethiobiotin | | |
| dtdp | dTDP | | |
| dtdp4aaddg | dTDP-4-acetamido-4,6-dideoxy-D-galactose | | |
| dtdp4addg | dTDP-4-amino-4,6-dideoxy-D-glucose | | |
| dtdp4d6dg | dTDP-4-dehydro-6-deoxy-D-glucose | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| dtdp4d6dm | dTDP-4-dehydro-6-deoxy-L-mannose | | |
| dtdpglu | dTDPglucose | | |
| dtdprmn | dTDP-L-rhamnose | | |
| dtmp | dTMP | | |
| dttp | dTTP | | |
| dudp | dUDP | | |
| dump | dUMP | | |
| duri | Deoxyuridine | | |
| duri(e) | Deoxyuridine (Extracellular) | | |
| dutp | dUTP | | |
| dxyl | 1-deoxy-D-xylulose | | |
| dxyl5p | 1-deoxy-D-xylulose 5-phosphate | | |
| e4p | D-Erythrose 4-phosphate | | |
| eca_EC | Enterobacterial common antigen polysaccharide (E coli) | | |
| eig3p | D-erythro-1-(Imidazol-4-yl)glycerol 3-phosphate | | |
| enter | Enterochelin | | |
| etha | Ethanolamine | | |
| etoh | Ethanol | | |
| etoh(e) | Ethanol (Extracellular) | | |
| f1p | D-Fructose 1-phosphate | | |
| f6p | D-Fructose 6-phosphate | | |
| fad | FAD | | |
| fadh2 | FADH2 | | |
| fc1p | L-Fuculose 1-phosphate | | |
| fcl-L | L-fuculose | | |
| fdp | D-Fructose 1,6-bisphosphate | | |
| fe2 | Fe2+ | | |
| fe2(e) | Fe2+ (Extracellular) | | |
| fgam | N2-Formyl-N1-(5-phospho-D-ribosyl)glycinamide | | |
| fmn | FMN | | |
| for | Formate | | |
| for(e) | Formate (Extracellular) | | |
| fpram | 2-(Formamido)-N1-(5-phospho-D-ribosyl)acetamidine | | |
| fprica | 5-Formamido-1-(5-phospho-D-ribosyl)imidazole-4-carboxamide | | |
| frdp | Farnesyl diphosphate | | |
| fru | D-Fructose | | |
| fru(e) | D-Fructose (Extracellular) | | |
| fruur | D-Fructuronate | | |
| fruur(e) | D-Fructuronate (Extracellular) | | |
| fuc1p-L | L-Fucose 1-phosphate | | |
| fuc1p-L(e) | L-Fucose 1-phosphate (Extracellular) | | |
| fuc-L | L-Fucose | | |
| fuc-L(e) | L-Fucose (Extracellular) | | |
| fum | Fumarate | | |
| fum(e) | Fumarate (Extracellular) | | |
| g1p | D-Glucose 1-phosphate | | |
| g3p | Glyceraldehyde 3-phosphate | | |
| g3pc | sn-Glycero-3-phosphocholine | | |
| g3pe | sn-Glycero-3-phosphoethanolamine | | |
| g3pg | Glycerophosphoglycerol | | |
| g3pi | sn-Glycero-3-phospho-1-inositol | | |
| g3ps | Glycerophosphoserine | | |
| g6p | D-Glucose 6-phosphate | | |
| g6p(e) | D-Glucose 6-phosphate (Extracellular) | | |
| gal | D-Galactose | | |
| gal(e) | D-Galactose (Extracellular) | | |
| gal1p | alpha-D-Galactose 1-phosphate | | |
| galct-D | D-Galactarate | | |
| galct-D(e) | D-Galactarate (Extracellular) | | |
| galctn-D | D-Galactonate | | |
| galctn-D(e) | D-Galactonate (Extracellular) | | |
| galt(e) | Galactitol (Extracellular) | | |
| galt1p | Galactitol 1-phosphate | | |
| galur | D-Galacturonate | | |
| galur(e) | D-Galacturonate (Extracellular) | | |
| gam(e) | D-Glucosamine (Extracellular) | | |
| gam1p | D-Glucosamine 1-phosphate | | |
| gam6p | D-Glucosamine 6-phosphate | | |
| gar | N1-(5-Phospho-D-ribosyl)glycinamide | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| gbbtn | gamma-butyrobetaine | | |
| gbbtn(e) | gamma-butyrobetaine (Extracellular) | | |
| gcald | Glycolaldehyde | | |
| gdp | GDP | | |
| gdpddman | GDP-4-dehydro-6-deoxy-D-mannose | | |
| gdpfuc | GDP-L-fucose | | |
| gdpmann | GDP-D-mannose | | |
| gdpofuc | GDP-4-oxo-L-fucose | | |
| glc-D | D-Glucose | | |
| glc-D(e) | D-Glucose (Extracellular) | | |
| glcn | D-Gluconate | | |
| glcn(e) | D-Gluconate (Extracellular) | | |
| glcr | D-Glucarate | | |
| glcr(e) | D-Glucarate (Extracellular) | | |
| glcur | D-Glucuronate | | |
| glcur(e) | D-Glucuronate (Extracellular) | | |
| gln-L | L-Glutamine | | |
| gln-L(e) | L-Glutamine (Extracellular) | | |
| glu1sa | L-Glutamate 1-semialdehyde | | |
| glu5p | L-Glutamate 5-phosphate | | |
| glu5sa | L-Glutamate 5-semialdehyde | | |
| glucys | gamma-L-Glutamyl-L-cysteine | | |
| glu-D | D-Glutamate | | |
| glu-L | L-Glutamate | | |
| glu-L(e) | L-Glutamate (Extracellular) | | |
| glutrna | L-Glutamyl-tRNA(Glu) | | |
| glx | Glyoxylate | | |
| gly | Glycine | | |
| gly(e) | Glycine (Extracellular) | | |
| glyald | D-Glyceraldehyde | | |
| glyald(e) | D-Glyceraldehyde (Extracellular) | | |
| glyb | Glycine betaine | | |
| glyb(e) | Glycine betaine (Extracellular) | | |
| glyc | Glycerol | | |
| glyc(e) | Glycerol (Extracellular) | | |
| glyc3p | Glycerol 3-phosphate | | |
| glyc3p(e) | Glycerol 3-phosphate (Extracellular) | | |
| glyclt | Glycolate | | |
| glyclt(e) | Glycolate (Extracellular) | | |
| glycogen | glycogen | | |
| glyc-R | (R)-Glycerate | | |
| gmhep17bp | D-Glycero-D-manno-heptose 1,7-bisphosphate | | |
| gmhep1p | D-Glycero-D-manno-heptose 1-phosphate | | |
| gmhep7p | D-Glycero-D-manno-heptose 7-phosphate | | |
| gmp | GMP | | |
| gp4g | P1,P4-Bis(5'-guanosyl)tetraphosphate | | |
| grdp | Geranyl diphosphate | | |
| gsn | Guanosine | | |
| gsn(e) | Guanosine (Extracellular) | | |
| gthox | Oxidized glutathione | | |
| gthrd | Reduced glutathione | | |
| gtp | GTP | | |
| gtspmd | Glutathionylspermidine | | |
| gua | Guanine | | |
| gua(e) | Guanine (Extracellular) | | |
| h | H+ | | |
| h(e) | H+ (Extracellular) | | |
| h2 | H2 | | |
| h2mb4p | 1-hydroxy-2-methyl-2-(E)-butenyl 4-diphosphate | | |
| h2o | H2O | | |
| h2o(e) | H2O (Extracellular) | | |
| h2o2 | Hydrogen peroxide | | |
| h2o2(e) | Hydrogen peroxide (Extracellular) | | |
| h2s | Hydrogen sulfide | | |
| hco3 | Bicarbonate | | |
| hcys-L | L-Homocysteine | | |
| hdca | Hexadecanoate (n-C16:0) | | |
| hdca(e) | Hexadecanoate (n-C16:0) (Extracellular) | | |
| hdcea | hexadecenoate (n-C16:1) | | |
| hdeACP | Hexadecenoyl-ACP (n-C16:1ACP) | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| hemeO | Heme O | | |
| his-L | L-Histidine | | |
| his-L(e) | L-Histidine (Extracellular) | | |
| hisp | L-Histidinol phosphate | | |
| histd | L-Histidinol | | |
| hkndd | 2-Hydroxy-6-oxonona-2,4-diene-1,9-dioate | | |
| hkntd | 2-hydroxy-6-ketononatrienedioate | | |
| hmbil | Hydroxymethylbilane | | |
| hmfurn | 4-hydroxy-5-methyl-3(2H)-furanone | | |
| hom-L | L-Homoserine | | |
| hpyr | Hydroxypyruvate | | |
| hqn | Hydroquinone | | |
| hxan | Hypoxanthine | | |
| hxan(e) | Hypoxanthine (Extracellular) | | |
| iasp | Iminoaspartate | | |
| ichor | Isochorismate | | |
| icit | Isocitrate | | |
| idon-L | L-Idonate | | |
| idon-L(e) | L-Idonate (Extracellular) | | |
| idp | IDP | | |
| ile-L | L-Isoleucine | | |
| ile-L(e) | L-Isoleucine (Extracellular) | | |
| imacp | 3-(Imidazol-4-yl)-2-oxopropyl phosphate | | |
| imp | IMP | | |
| indole | Indole | | |
| indole(e) | Indole (Extracellular) | | |
| inost | myo-Inositol | | |
| ins | Inosine | | |
| ins(e) | Inosine (Extracellular) | | |
| ipdp | Isopentenyl diphosphate | | |
| itp | ITP | | |
| k | K+ | | |
| k(e) | K+ (Extracellular) | | |
| kdo | 3-Deoxy-D-manno-2-octulosonate | | |
| kdo2lipid4 | KDO(2)-lipid IV(A) | | |
| kdo2lipid4L | KDO(2)-lipid IV(A) with laurate | | |
| kdo2lipid4p | KDO(2)-lipid IV(A) with palmitoleoyl | | |
| kdo8p | 3-Deoxy-D-manno-octulosonate 8-phosphate | | |
| kdolipid4 | KDO-lipid IV(A) | | |
| lac-D | D-Lactate | | |
| lac-D(e) | D-Lactate (Extracellular) | | |
| lac-L | L-Lactate | | |
| lac-L(e) | L-Lactate (Extracellular) | | |
| lald-L | L-Lactaldehyde | | |
| lcts | Lactose | | |
| lcts(e) | Lactose (Extracellular) | | |
| leu-L | L-Leucine | | |
| leu-L(e) | L-Leucine (Extracellular) | | |
| lgt-S | (R)-S-Lactoylglutathione | | |
| lipa | KDO(2)-lipid (A) | | |
| lipa_cold | cold adapted KDO(2)-lipid (A) | | |
| lipidA | 2,3-Bis(3-hydroxytetradecanoyl)-D-glucosaminyl-1,6-beta-D-2,3-bis(3-hydroxytetradecanoyl)-beta-D-glucosaminyl 1-phosphate | | |
| lipidAds | Lipid A Disaccharide | | |
| lipidX | 2,3-Bis(3-hydroxytetradecanoyl)-beta-D-glucosaminyl 1-phosphate | | |
| lps_EC | lipopolysaccharide (*E coli*) | | |
| lys-L | L-Lysine | | |
| lys-L(e) | L-Lysine (Extracellular) | | |
| malACP | Malonyl-[acyl-carrier protein] | | |
| malcoa | Malonyl-CoA | | |
| mal-L | L-Malate | | |
| mal-L(e) | L-Malate (Extracellular) | | |
| malt | Maltose | | |
| malt(e) | Maltose (Extracellular) | | |
| malt6p | Maltose 6'-phosphate | | |
| malthp | Maltoheptaose | | |
| malthx | Maltohexaose | | |
| malthx(e) | Maltohexaose (Extracellular) | | |
| maltpt | Maltopentaose | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| maltpt(e) | Maltopentaose (Extracellular) | | |
| malttr | Maltotriose | | |
| malttr(e) | Maltotriose (Extracellular) | | |
| maltttr | Maltotetraose | | |
| maltttr(e) | Maltotetraose (Extracellular) | | |
| man(e) | D-Mannose (Extracellular) | | |
| man1p | D-Mannose 1-phosphate | | |
| man6p | D-Mannose 6-phosphate | | |
| man6p(e) | D-Mannose 6-phosphate (Extracellular) | | |
| mana | D-Mannonate | | |
| melib | Melibiose | | |
| melib(e) | Melibiose (Extracellular) | | |
| met-D | D-Methionine | | |
| met-D(e) | D-Methionine (Extracellular) | | |
| methf | 5,10-Methenyltetrahydrofolate | | |
| met-L | L-Methionine | | |
| met-L(e) | L-Methionine (Extracellular) | | |
| mi1p-D | 1D-myo-Inositol 1-phosphate | | |
| micit | methylisocitrate | | |
| mlthf | 5,10-Methylenetetrahydrofolate | | |
| mmcoa-R | (R)-Methylmalonyl-CoA | | |
| mmcoa-S | (S)-Methylmalonyl-CoA | | |
| mnl(e) | D-Mannitol (Extracellular) | | |
| mnl1p | D-Mannitol 1-phosphate | | |
| mql8 | Menaquinol 8 | | |
| mqn8 | Menaquinone 8 | | |
| mthgxl | Methylglyoxal | | |
| myrsACP | Myristoyl-ACP (n-C14:0ACP) | | |
| N1aspmd | N1-Acetylspermidine | | |
| n8aspmd | N8-Acetylspermidine | | |
| na1 | Sodium | | |
| na1(e) | Sodium (Extracellular) | | |
| nac | Nicotinate | | |
| nac(e) | Nicotinate (Extracellular) | | |
| nad | Nicotinamide adenine dinucleotide | | |
| nad(e) | Nicotinamide adenine dinucleotide (Extracellular) | | |
| nadh | Nicotinamide adenine dinucleotide - reduced | | |
| nadp | Nicotinamide adenine dinucleotide phosphate | | |
| nadph | Nicotinamide adenine dinucleotide phosphate - reduced | | |
| ncam | Nicotinamide | | |
| nh4 | ammonium | | |
| nh4(e) | ammonium (Extracellular) | | |
| nicrnt | Nicotinate D-ribonucleotide | | |
| nmn | NMN | | |
| nmn(e) | NMN (Extracellular) | | |
| no2 | Nitrite | | |
| no2(e) | Nitrite (Extracellular) | | |
| no3 | Nitrate | | |
| no3(e) | Nitrate (Extracellular) | | |
| o2 | O2 | | |
| o2- | Superoxide anion | | |
| o2(e) | O2 (Extracellular) | | |
| oaa | Oxaloacetate | | |
| ocdca | octadecanoate (n-C18:0) | | |
| ocdca(e) | octadecanoate (n-C18:0) (Extracellular) | | |
| ocdcea | octadecenoate (n-C18:1) | | |
| octdp | all-trans-Octaprenyl diphosphate | | |
| octeACP | Octadecenoyl-ACP (n-C18:1ACP) | | |
| ohpb | 2-Oxo-3-hydroxy-4-phosphobutanoate | | |
| op4en | 2-Oxopent-4-enoate | | |
| orn | Ornithine | | |
| orn(e) | Ornithine (Extracellular) | | |
| orot | Orotate | | |
| orot5p | Orotidine 5'-phosphate | | |
| pa_EC | phosphatidate (*E. coli*) ** | | |
| pac | Phenylacetic acid | | |
| pacald | Phenylacetaldehyde | | |
| palmACP | Palmitoyl-ACP (n-C16:0ACP) | | |
| pan4p | Pantetheine 4'-phosphate | | |
| pant-R | (R)-Pantoate | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| pap | Adenosine 3',5'-bisphosphate | | |
| paps | 3'-Phosphoadenylyl sulfate | | |
| pc_EC | Phosphatidylcholine (*E. coli*) ** | | |
| pdx5p | Pyridoxine 5'-phosphate | | |
| pe_EC | Phosphatidylethanolamine (*E coli*) ** | | |
| peamn | Phenethylamine | | |
| pep | Phosphoenolpyruvate | | |
| peptido_EC | Peptidoglycan subunit of *Escherichia coli* | | |
| pg_EC | Phospatidylglycerol (*E coli*) ** | | |
| pgp_EC | Phosphatidylglycerophosphate (*E coli*) ** | | |
| phaccoa | Phenylacetyl-CoA | | |
| phe-L | L-Phenylalanine | | |
| phe-L(e) | L-Phenylalanine (Extracellular) | | |
| pheme | Protoheme | | |
| phom | O-Phospho-L-homoserine | | |
| phpyr | Phenylpyruvate | | |
| phthr | O-Phospho-4-hydroxy-L-threonine | | |
| pi | Phosphate | | |
| pi(e) | Phosphate (Extracellular) | | |
| pmcoa | Pimeloyl-CoA | | |
| pnto-R | (R)-Pantothenate | | |
| pnto-R(e) | (R)-Pantothenate (Extracellular) | | |
| ppa | Propionate | | |
| ppa(e) | Propionate (Extracellular) | | |
| ppap | Propanoyl phosphate | | |
| ppbng | Porphobilinogen | | |
| ppcoa | Propanoyl-CoA | | |
| pphn | Prephenate | | |
| ppi | Diphosphate | | |
| ppp9 | Protoporphyrin | | |
| pppg9 | Protoporphyrinogen IX | | |
| pppi | Inorganic triphosphate | | |
| pppn | Phenylpropanoate | | |
| pppn(e) | Phenylpropanoate (Extracellular) | | |
| pram | 5-Phospho-beta-D-ribosylamine | | |
| pran | N-(5-Phospho-D-ribosyl)anthranilate | | |
| prbamp | 1-(5-Phosphoribosyl)-AMP | | |
| prbatp | 1-(5-Phosphoribosyl)-ATP | | |
| prfp | 1-(5-Phosphoribosyl)-5-[(5-phosphoribosylamino)methylideneamino]imidazole-4-carboxamide | | |
| prlp | 5-[(5-phospho-1-deoxyribulos-1-ylamino)methylideneamino]-1-(5-phosphoribosyl)imidazole-4-carboxamide | | |
| pro-L | L-Proline | | |
| pro-L(e) | L-Proline (Extracellular) | | |
| prpp | 5-Phospho-alpha-D-ribose 1-diphosphate | | |
| ps_EC | phosphatidylserine (*E coli*) ** | | |
| pser-L | O-Phospho-L-serine | | |
| ptrc | Putrescine | | |
| ptrc(e) | Putrescine (Extracellular) | | |
| pyam5p | Pyridoxamine 5'-phosphate | | |
| pydam | Pyridoxamine | | |
| pydx | Pyridoxal | | |
| pydx5p | Pyridoxal 5'-phosphate | | |
| pydxn | Pyridoxine | | |
| pyr | Pyruvate | | |
| pyr(e) | Pyruvate (Extracellular) | | |
| q8 | Ubiquinone-8 | | |
| q8h2 | Ubiquinol-8 | | |
| quln | Quinolinate | | |
| r1p | alpha-D-Ribose 1-phosphate | | |
| r5p | alpha-D-Ribose 5-phosphate | | |
| rbl-L | L-Ribulose | | |
| rdmbzi | N1-(alpha-D-ribosyl)-5,6-dimethylbenzimidazole | | |
| rhcys | S-Ribosyl-L-homocysleine | | |
| rib-D | D-Ribose | | |
| rib-D(e) | D-Ribose (Extracellular) | | |
| ribflv | Riboflavin | | |
| rml | L-Rhamnulose | | |
| rml1p | L-Rhamnulose 1-phosphate | | |
| rmn | L-Rhamnose | | |
| rmn(e) | L-Rhamnose (Extracellular) | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| ru5p-D | D-Ribulose 5-phosphate | | |
| ru5p-L | L-Ribulose 5-phosphate | | |
| s7p | Sedoheptulose 7-phosphate | | |
| sbt6p | D-Sorbitol 6-phosphate | | |
| sbt-D(e) | D-Sorbitol (Extracellular) | | |
| sbzcoa | O-Succinylbenzoyl-CoA | | |
| seln | Selenide | | |
| selnp | Selenophosphate | | |
| seramp | L-seryl-AMP | | |
| ser-D | D-Serine | | |
| ser-D(e) | D-Serine (Extracellular) | | |
| ser-L | L-Serine | | |
| ser-L(e) | L-Serine (Extracellular) | | |
| shcl | Sirohydrochlorin | | |
| sheme | Siroheme | | |
| skm | Shikimate | | |
| skm5p | Shikimate 5-phosphate | | |
| sl26da | N-Succinyl-LL-2,6-diaminoheptanedioate | | |
| Sl2a6o | N-Succinyl-2-L-amino-6-oxoheptanedioate | | |
| so3 | Sulfite | | |
| so4 | Sulfate | | |
| so4(e) | Sulfate (Extracellular) | | |
| spmd | Spermidine | | |
| spmd(e) | Spermidine (Extracellular) | | |
| srch | Sirochlorin | | |
| ssaltpp | Succinate semialdehyde-thiamin diphosphate anion | | |
| suc6p | Sucrose 6-phosphate | | |
| sucarg | N2-Succinyl-L-arginine | | |
| sucbz | o-Succinylbenzoate | | |
| succ | Succinate | | |
| succ(e) | Succinate (Extracellular) | | |
| succoa | Succinyl-CoA | | |
| sucglu | N2-Succinyl-L-glutamate | | |
| sucgsa | N2-Succinyl-L-glutamate 5-semialdehyde | | |
| suchms | O-Succinyl-L-homoserine | | |
| sucorn | N2-Succinyl-L-ornithine | | |
| sucr(e) | Sucrose (Extracellular) | | |
| sucsal | Succinic semialdehyde | | |
| tag6p-D | D-Tagatose 6-phosphate | | |
| tagdp-D | D-Tagatose 1,6-biphosphate | | |
| tagur | D-Tagaturonate | | |
| tagur(e) | D-Tagaturonate (Extracellular) | | |
| tartr-L | L-tartrate | | |
| tartr-L(e) | L-tartrate (Extracellular) | | |
| taur | Taurine | | |
| taur(e) | Taurine (Extracellular) | | |
| tcynt | Thiocyanate | | |
| tdeACP | Tetradecenoyl-ACP (n-C14:1ACP) | | |
| thdp | 2,3,4,5-Tetrahydrodipicolinate | | |
| thf | 5,6,7,8-Tetrahydrofolate | | |
| thm | Thiamin | | |
| thm(e) | Thiamin (Extracellular) | | |
| thmmp | Thiamin monophosphate | | |
| thmpp | Thiamine diphosphate | | |
| thr-L | L-Threonine | | |
| thr-L(e) | L-Threonine (Extracellular) | | |
| thym | Thymine | | |
| thym(e) | Thymine (Extracellular) | | |
| thymd | Thymidine | | |
| thymd(e) | Thymidine (Extracellular) | | |
| tma | Trimethylamine | | |
| tma(e) | Trimethylamine (Extracellular) | | |
| tmao | Trimethylamine N-oxide | | |
| tmao(e) | Trimethylamine N-oxide (Extracellular) | | |
| trdox | Oxidized thioredoxin | | |
| trdrd | Reduced thioredoxin | | |
| tre | Trehalose | | |
| tre(e) | Trehalose (Extracellular) | | |
| tre6p | alpha, alpha'-Trehalose 6-phosphate | | |
| trnaglu | tRNA (Glu) | | |
| trp-L | L-Tryptophan | | |
| trp-L(e) | L-Tryptophan (Extracellular) | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| tsul | Thiosulfate | | |
| tsul(e) | Thiosulfate (Extracellular) | | |
| ttdca | tetradecanoate (n-C14:0) | | |
| ttdca(e) | tetradecanoate (n-C14:0) (Extracellular) | | |
| ttdcea | tetradecenoate (n-C14:1) | | |
| tyr-L | L-Tyrosine | | |
| tyr-L(e) | L-Tyrosine (Extracellular) | | |
| u23ga | UDP-2,3-bis(3-hydroxytetradecanoyl)glucosamine | | |
| u3aga | UDP-3-O-(3-hydroxytetradecanoyl)-N-acetylglucosamine | | |
| u3hga | UDP-3-O-(3-hydroxytetradecanoyl)-D-glucosamine | | |
| uaagmda | Undecaprenyl-diphospho-N-acetylmuramoyl-(N-acetylglucosamine)-L-ala-D-glu-meso-2,6-diaminopimeloyl-D-ala-D-ala | | |
| uaccg | UDP-N-acetyl-3-O-(1-carboxyvinyl)-D-glucosamine | | |
| uacgam | UDP-N-acetyl-D-glucosamine | | |
| uacmam | UDP-N-acetyl-D-mannosamine | | |
| uacmamu | UDP-N-acetyl-D-mannosaminouronate | | |
| uagmda | Undecaprenyl-diphospho-N-acetylmuramoyl-L-alanyl-D-glutamyl-meso-2,6-diaminopimeloyl-D-alanyl-D-alanine | | |
| uama | UDP-N-acetylmuramoyl-L-alanine | | |
| uamag | UDP-N-acetylmuramoyl-L-alanyl-D-glutamate | | |
| uamr | UDP-N-acetylmuramate | | |
| udcpdp | Undecaprenyl diphosphate | | |
| udcpp | Undecaprenyl phosphate | | |
| udp | UDP | | |
| udpg | UDPglucose | | |
| udpgal | UDPgalaclose | | |
| udpgalfur | UDP-D-galacto-1,4-furanose | | |
| udpglcur | UDP-D-glucuronate | | |
| ugmd | UDP-N-acetylmuramoyl-L-alanyl-D-gamma-glutamyl-meso-2,6-diaminopimelate | | |
| ugmda | UDP-N-acetylmuramoyl-L-alanyl-D-glutamyl-meso-2,6-diaminopimeloyl-D-alanyl-D-alanine | | |
| ump | UMP | | |
| unaga | Undecaprenyl diphospho N-acetyl-glucosamine | | |
| unagamu | Undecaprenyl-diphospho-N-acetylglucosamine-N-acetylmannosaminuronate | | |
| unagamuf | Undecaprenyl-diphospho N-acetylglucosamine-N-acetylmannosaminuronate-N-acetamido-4,6-dideoxy-D-galactose | | |
| uppg3 | Uroporphyrinogen III | | |
| ura | Uracil | | |
| ura(e) | Uracil (Extracellular) | | |
| urdglyc | (-)-Ureidoglycolate | | |
| urea | Urea | | |
| urea(e) | Urea (Extracellular) | | |
| uri | Uridine | | |
| uri(e) | Uridine (Extracellular) | | |
| utp | UTP | | |
| val-L | L-Valine | | |
| val-L(e) | L-Valine (Extracellular) | | |
| xan | Xanthine | | |
| xan(e) | Xanthine (Extracellular) | | |
| xmp | Xanthosine 5'-phosphate | | |
| xtsn | Xanthosine | | |
| xtsn(e) | Xanthosine (Extracellular) | | |
| xu5p-D | D-Xylulose 5-phosphate | | |

TABLE 10-continued

Metabolite and Reaction Abbreviations used in this spreadsheet

| Metabolites Abbreviation | Name | Reactions Abbreviation | Reaction stoichiometry |
|---|---|---|---|
| xu5p-L | L-Xylulose 5-phosphate | | |
| xyl-D | D-Xylose | | |
| xyl-D(e) | D-Xylose (Extracellular) | | |
| xylu-D | D-Xylulose | | |

TABLE 11

| Carbon sources | Reg | Met only |
|---|---|---|
| Citric acid | 0.85 | 0.26 |
| Sucrose | 0.67 | 0.34 |
| 1,2-Propanediol | 0.93 | 0.19 |
| Butryic acid | 0.97 | 0.16 |
| Tartaric acid | 0.81 | 0.25 |
| 1. Nitrogen sources | | |
| Guanine | 0.61 | 0.35 |
| Allantoin | 0.90 | 0.15 |
| NO$_3$ | 0.99 | 0.14 |
| NO$_2$ | 0.77 | 0.30 |

TABLE 12

Carbon Sources

| Carbon Sources | Fractional Agreement[1] | Biolog Results Growth/ No-Growth[2] | BioScreen Data for WT Strain[3] |
|---|---|---|---|
| Acetoacetic Acid | 0.42 | 43/67 | 2.7 |
| Formic Acid | 0.05 | 104/6 | 0.8 |
| Glycine | 0.51 | 54/56 | 1 |
| Thymidine | 0.00 | 110/0 | NA |
| g-Amino Butyric Acid | 0.21 | 13/97 | 0.9 |
| L-Arginine | 0.35 | 37/73 | NA |
| L-Ornithine | 0.21 | 15/95 | 1 |
| Putrescine | 0.41 | 43/67 | 0.9 |
| L-Glutamic Acid | 0.30 | 22/88 | NA |

[1]Fractional agreement tells what fraction of the 110 cases the regulatory model predicts the Biolog results.
[2]Biolog results report for the 110 knockouts, how many grow and do not grow on the media
[3]Relative growth rate is with respect to the control. NA indicates that this source was not tested.

TABLE 13

Nitrogen Sources (Succinate medium)

| Nitrogen Sources | Fractional Agreement[1] | Biolog Results Growth/ No-Growth[2] | BioScreen Data for WT Strain[3] |
|---|---|---|---|
| Adenine | 0.42 | 44/66 | NA |
| N-Acetyl-D-Mannosamine | 0.48 | 52/58 | 1.8 |
| Putrescine | 0.60 | 64/46 | 3.5 |
| L-Lysine | 0.44 | 62/48 | 2.4 |
| L-Methionine | 0.42 | 64/46 | 2.1 |
| L-Phenylalanine | 0.24 | 84/26 | 1.5 |
| Xanthine | 0.04 | 106/4 | NA |
| Guanosine | 0.51 | 64/46 | NA |
| Alanine-Leucine | 0.28 | 79/31 | NA |

[1]Fractional agreement tells what fraction of the 110 cases the regulatory model predicts the Biolog results.
[2]Biolog results report for the 110 knockouts, how many grow and do not grow on the media
[3]Relative growth rate is with respect to the control. NA indicates that this source was not tested.

TABLE 14

Knockout strains

| Knockout strains | Affected Enzymes | Fractional Agreement | Biolog Results Growth/ No-Growth |
|---|---|---|---|
| argB(b3959) - | acetylglutamate kinase | 0.39 | 76\34 |
| argC(b3958) - | N-acetyl-g-glutamyl-phosphate reductase | 0.31 | 86\24 |
| argD(b3359) - | acetylornithine transaminase | 0.27 | 91\19 |
| argE(b3957) - | acetylornithine deacetylase | 0.52 | 64\46 |
| argG(b3172) - | argininosuccinate synthase | 0.57 | 54\56 |
| glgA(b3429) - | glycogen synthase | 0.25 | 94\16 |
| glgC(b3430) - | glucose-1-phosphate adenylyltransferase | 0.25 | 94\16 |
| ilvD(b3771) - | dihydroxy-acid dehydratase | 0.52 | 60\50 |
| ilvY(b3773) - | transcriptional activator for isoleucine and valine synthesis | 0.45 | 69\41 |
| metA(b4013) - | homoserine O-succinyltransferase | 0.39 | 77\33 |
| pgi(b4025) - | glucose-6-phosphate isomerase | 0.30 | 95\15 |
| pls(b4041) - | glycerolphosphate acyltransferase | 0.28 | 90\20 |
| purD(b4005) - | phosphoribosylglycinamide synthase | 0.30 | 92\18 |
| purH(b4006) - | phosphoribosylamino-imidazolecarboxamide formyltransferase and IMP cyclohydrolase | 0.41 | 74\36 |
| tpiA(b3919) - | triose-phosphate isomerase | 0.50 | 91\19 |

TABLE 15

| Phenotype Data Culture | GR | st dev | SUR | st dev | OUR | st dev | Acetate | Ethanol | Formate | Succinate | Lactate |
|---|---|---|---|---|---|---|---|---|---|---|---|
| WT + O2 | 0.71 | 0.01 | 9.02 | 0.23 | 14.93 | 0.48 | 4.15 | 0.15 | 0.00 | 0.44 | 0.17 |
| WT − O2 | 0.485 | 0.003 | 17.27 | 0.20 | | | 8.00 | 5.76 | 13.34 | 0.44 | 0.50 |
| arcA + O2 | 0.686 | 0.011 | 9.56 | 0.32 | 15.62 | 0.28 | 0.32 | 0.15 | 0.13 | 0.39 | 0.17 |
| arcA − O2 | 0.377 | 0.012 | 14.98 | 1.06 | | | 6.70 | 3.71 | 11.64 | 0.93 | 1.00 |
| fnr + O2 | 0.635 | 0.007 | 8.38 | 0.29 | 14.73 | 0.77 | 0.45 | 0.19 | 0.13 | 0.35 | 0.16 |
| fnr − O2 | 0.410 | 0.011 | 13.15 | 1.24 | | | 7.50 | 4.87 | 12.69 | 1.46 | 0.70 |
| fnr/arcA + O2 | 0.648 | 0.018 | 9.29 | 0.59 | 17.52 | 1.65 | 4.00 | 0.00 | 0.78 | 0.34 | 0.30 |
| fnr/arcA − O2 | 0.301 | 0.005 | 12.56 | 0.38 | | | 4.90 | 4.61 | 13.60 | 7.68 | 0.95 |
| appY + O2 | 0.636 | 0.036 | 8.45 | 0.61 | 14.92 | 1.02 | 4.20 | 0.26 | 0.00 | 0.38 | 0.25 |
| appY − O2 | 0.476 | 0.002 | 15.19 | 1.25 | | | 8.20 | 7.81 | 16.61 | 0.32 | 1.20 |
| oxyR + O2 | 0.637 | 0.007 | 9.60 | 0.40 | 15.76 | 1.27 | 5.60 | 0.32 | 0.26 | 0.32 | 0.19 |
| oxyR − O2 | 0.481 | 0.000 | 15.63 | 0.34 | | | 8.20 | 8.07 | 17.66 | 0.33 | 1.34 |
| soxS + O2 | 0.724 | 0.001 | 9.28 | 0.39 | 15.57 | 0.21 | 4.00 | 0.17 | 0.72 | 0.30 | 0.24 |
| soxS − O2 | 0.465 | 0.002 | 17.05 | 1.90 | | | 7.80 | 6.40 | 16.48 | 0.28 | 1.00 |

Growth rates (GR)[1/hr]
Substrate uptake rate (SUR) [mmol/gDCW/hr]
Oxygen uptake rate (OUR) [mmol/gDCW/hr]
Byproducts (final recorded concentration) [mM]

TABLE 16

| Fxn | Bnum | Gene | L2R | Old | New | Old Rule | New Rule | Comments |
|---|---|---|---|---|---|---|---|---|
| A | b0242 | proB | −0.55 | 5 | 5 | none | (ON) | Essential for growth on Arginine |
| A | b0828 | ybiK | −0.56 | 5 | 5 | none | (ON) | Essential for WT growth |
| A | b1261 | trpB | | 5 | 5 | (NOT TrpR) | ((NOT TrpR)) | Essential for WT growth |
| A | b1761 | gdhA | −0.96 | 5 | 5 | (NOT ((Nac) OR (GLUxt > 0)) ) | (NOT ((Nac) OR (GLUxt > 0))) | Essential for WT growth |
| A | b2021 | hisC | −0.54 | 5 | 5 | none | (ON) | Essential for WT growth |
| A | b2478 | dapA | | 5 | 5 | none | none | Very small shift: ANOVA: (ArcA and Fnr) or OxyR |
| A | b3767 | ilvG_1 | | 5 | 1 | (NOT(LEUxt > 0 ORILExt > 0 OR VALxt > 0) AND Lrp) | ((NOT(LEUxt > 0 OR ILExt > 0 OR VALxt > 0) AND Lrp) AND NOT (OxyR)) | — |
| A | b3769 | ilvM | −0.53 | 5 | 1 | (NOT(LEUxt > 0 OR ILExt > 0 OR VALxt > 0) AND Lrp) | ((NOT(LEUxt > 0 OR ILExt > 0 OR VALxt > 0) AND Lrp) AND (Fnr)) | — |
| A | b3770 | ilvE | | 5 | 5 | none | (ON) | Essential for WT growth |
| A | b3771 | ilvD | | 5 | 5 | none | (ON) | Essential for WT growth |
| A | b3957 | argE | | 5 | 5 | (NOT ArgR) | (NOT ArgR) | Essential for WT growth |
| B | b0068 | sfuA | | 5 | 1 | none | (O2xt > 0) | No knockout exhibited abolished shift |
| B | b0133 | panC | | 5 | 5 | none | (ON) | Essential for WT growth |
| B | b0595 | entB | | 5 | 3 | (NOT (Fur)) | (NOT (Fur)) | Fur transcription is directly opposite to activity |
| B | b0776 | bioF | | 5 | 1 | (NOT (BirA)) | (NOT (BirA) AND (O2xt > 0)) | No knockout exhibited abolished shift |
| B | b0778 | bioD | | 5 | 1 | (NOT (BirA)) | (NOT (BirA) AND (O2xt > 0)) | No knockout exhibited abolished shift |
| B | b1210 | hemA | | 5 | 5 | none | (ON) | Essential for WT growth |
| B | b1991 | cobT | | 5 | 1 | (CBIxt > 0) | ((CBIxt > 0) OR (Fnr)) | — |
| B | b1993 | cobU | | 5 | 1 | (CBIxt > 0) | ((CBIxt > 0) OR (Fnr)) | — |
| B | b2153 | folE | | 5 | 5 | none | (ON) | Essential for WT growth |
| B | b3041 | ribB | −0.96 | 5 | 5 | none | (ON) | Essential for WT growth |
| B | b3368 | cysG | −0.63 | 1 | 1 | (Fnr OR NarL) | (AppY OR SoxS OR NarL) | Correct |
| B | b3805 | hemC | | 5 | 1 | none | (NOT (O2xt > 0)) | No knockout exhibited abolished shift |
| B | b3929 | menG | | 5 | 5 | none | none | Complex rule - ANOVA: Fnr and not ArcA |
| B | b3990 | thiH | | 5 | 1 | none | (O2xt > 0) | No knockout exhibited abolished shift |
| B | b3993 | thiE | | 5 | 1 | none | (NOT (Fnr OR ArcA)) | — |
| B | b3994 | thiC | | 5 | 1 | none | (NOT (Fnr OR ArcA)) | — |
| C | b0904 | focA | −1.52 | 1 | 1 | (ArcA OR Fnr AND (Crp OR NOT (NarL))) | (NOT (O2xt > 0) AND (Crp OR NOT (NarL))) | Correct |

TABLE 16-continued

| | | | | | | | |
|---|---|---|---|---|---|---|---|
| C | b1613 | manA | −0.72 | 5 | 5 | none | (ON) | Essential for WT growth |
| C | b2297 | pta | −1.77 | 5 | 5 | none | (ON) | Essential for WT growth |
| C | b4322 | uxuA | | 5 | 1 | (NOT ExuR AND NOT UxuR) | ((NOT ExuR AND NOT UxuR) OR (O2xt > 0)) | No knockout exhibited abolished shift |
| E | b0114 | aceE | | 5 | 1 | ((NOT(PdhR)) OR (Fis)) | (((NOT(PdhR)) OR (Fis)) AND (NOT (ArcA AND Fnr))) | — |
| E | b0115 | aceF | | 5 | 1 | ((NOT(PdhR)) OR (FiS)) | (((NOT(PdhR)) OR (Fis)) AND (NOT (ArcA AND Fnr))) | — |
| E | b0116 | lpdA | | 5 | 1 | (ON) | (NOT (ArcA AND Fnr)) | — |
| E | b0118 | acnB | | 5 | 1 | (NOT (TIME < 0 HRS)) | (NOT (ArcA)) | — |
| E | b0429 | cyoD | | 1 | 1 | (NOT (ArcA OR Fnr)) | (NOT (ArcA OR Fnr)) | Correct |
| E | b0430 | cyoC | | 1 | 1 | (NOT (ArcA OR For)) | (NOT (ArcA OR Fnr)) | Correct |
| E | b0431 | cyoB | | 1 | 1 | (NOT (ArcA OR Fnr)) | (NOT (ArcA OR Fnr)) | Correct |
| E | b0432 | cyoA | | 1 | 1 | (NOT (ArcA OR FNR)) | (NOT (ArcA OR Fnr)) | Correct |
| E | b0720 | gltA | | 5 | 5 | none | (ON) | Essential for WT growth |
| E | b0721 | sdhC | | 5 | 1 | (NOT((ArcA) OR (Fnr)) OR (Crp) OR (Fis)) | (NOT((ArcA) AND (Fnr)) AND ((Crp) OR (Fis))) | AND, OR change |
| E | b0722 | sdhD | | 5 | 1 | (NOT((ArcA) OR (Fnr)) OR (Crp) OR (Fis)) | (NOT((ArcA) AND (Fnr)) AND ((Crp) OR (Fis))) | AND, OR change |
| E | b0723 | sdhA | | 5 | 1 | (NOT((ArcA) OR (Fnr)) OR (Crp) OR (Fis)) | (NOT((ArcA) AND (Fnr)) AND ((Crp) OR (Fis))) | AND, OR change |
| E | b0726 | sucA | | 5 | 1 | none | (NOT ArcA) | — |
| E | b0727 | sucB | | 5 | 1 | none | (NOT ArcA) | — |
| E | b0728 | sucC | | 5 | 5 | none | (ON) | Essential for WT growth |
| E | b0729 | sucD | | 5 | 5 | none | (ON) | Essential for WT growth |
| E | b0733 | cydA | −0.79 | 5 | 1 | ((NOT Fnr) OR (ArcA)) | (NOT (O2xt > 0)) | No knockout exhibited abolished shift |
| E | b0734 | cydB | −0.66 | 5 | 1 | ((NOT Fnr) OR (ArcA)) | (NOT (O2xt > 0)) | No knockout exhibited abolished shift |
| E | b0755 | gpmA | | 5 | 1 | none | (NOT (ArcA AND Fnr)) | — |
| E | b0896 | dmsC | | 4 | 2 | (Fnr AND NOT NarL) | (NOT NarL) | No shift |
| E | b0902 | pflA | −1.02 | 1 | 1 | (ArcA OR Fnr AND (Crp OR NOT(NarL))) | (NOT (O2xt > 0) AND (Crp OR NOT (NarL))) | Correct |
| E | b0903 | pflB | −1.48 | 1 | 1 | (ArcA OR Fnr AND (Crp OR NOT(NarL))) | (NOT (O2xt > 0) AND (Crp OR NOT (NarL))) | Correct |
| E | b0974 | hyaC | −3.22 | 1 | 1 | ((ArcA OR Fnr) AND (AppY)) | (NOT (O2xt > 0)) | Correct |
| E | b1136 | icdA | | 5 | 5 | none | (ON) | Essential for WT growth |
| E | b1241 | adhE | −1.44 | 5 | 1 | (NOT (O2xt > 0) OR (NOT ((O2xt > 0) AND (Cra))) OR (Fis) OR NOT (NarL) OR (RpoS)) | (NOT (O2xt > 0) AND (NOT ((O2xt > 0) AND (Cra))) AND ((Fis) OR NOT (NarL) OR (RpoS))) | AND, OR change |
| E | b1276 | acnA | | 5 | 5 | (SoxS) | (ON) | Essential - ANOVA: ArcA |
| E | b1415 | aldA | | 5 | 5 | none | (ON) | Essential for WT growth |
| E | b1474 | fdnG | | 4 | 2 | (Fnr OR NarL) | (NarL) | No shift |
| E | b1476 | fdnI | | 4 | 2 | (Fnr OR NarL) | (NarL) | No shift |
| E | b1612 | fumA | | 1 | 1 | (NOT(ArcA OR Fnr)) | (NOT)ArcA OR Fnr)) | Correct |
| E | b1676 | pykF | | 5 | 1 | (NOT(Cra)) | (NOT(Cra) OR NOT (O2xt > 0)) | No knockout exhibited abolished shift |
| E | b1779 | gapA | | 5 | 1 | none | (NOT (O2xt > 0)) | No knockout exhibited abolished shift |
| E | b1854 | pykA | −1.38 | 5 | 5 | none | none | Complex rule - ANOVA: Fnr and not ArcA |
| E | b2276 | nuoN | | 4 | 2 | (NOT (ArcA OR Fnr) OR NarL) | (ON) | Essential for growth on acetate |
| E | b2277 | nuoM | | 4 | 2 | (NOT (ArcA OR Fnr) OR NarL) | (ON) | Essential for growth on acetate |
| E | b2278 | nuoL | | 4 | 2 | (NOT (ArcA OR Fnr) OR NarL) | (ON) | Essential for growth on acetate |
| E | b2279 | nuoK | | 4 | 2 | (NOT (ArcA OR Fnr) OR NarL) | (ON) | Essential for growth on acetate |
| E | b2280 | nuoJ | | 4 | 2 | (NOT (ArcA OR Fnr) OR NarL) | (ON) | Essential for growth on acetate |

TABLE 16-continued

| | | | | | | | |
|---|---|---|---|---|---|---|---|
| E | b2281 | nuoI | | 4 | 2 | (NOT (ArcA OR Fnr) OR NarL) | (ON) | Essential for growth on acetate |
| E | b2282 | nuoH | | 4 | 2 | (NOT (ArcA OR Fnr) OR NarL) | (ON) | Essential for growth on acetate |
| E | b2283 | nuoG | | 4 | 2 | (NOT (ArcA OR Fnr) OR NarL) | (ON) | Essential for growth on acetate |
| E | b2284 | nuoF | | 4 | 2 | (NOT (ArcA OR Fnr) OR NarL) | (ON) | Essential for growth on acetate |
| E | b2285 | nuoE | | 1 | 5 | (NOT (ArcA OR Fnr) OR NarL) | (ON) | Essential for growth on acetate |
| E | b2287 | nuoB | | 4 | 2 | (NOT (ArcA OR Fnr) OR NarL) | (ON) | Essential for growth on acetate |
| E | b2288 | nuoA | | 4 | 2 | (NOT (ArcA OR Fnr) OR NarL) | (ON) | Essential for growth on acetate |
| E | b2296 | ackA | −1.49 | 5 | 1 | none | (Fnr AND ArcA) | — |
| E | b2723 | hycC | −3.08 | 1 | 1 | (FhlA AND RpoN AND (NOT (O2xt > 0))) | (FhlA AND RpoN OR (NOT (O2xt > 0))) | AND, OR change |
| E | b2779 | eno | | 5 | 5 | none | (ON) | Essential for WT growth |
| E | b2925 | fbaA | | 5 | 1 | none | (NOT (O2xt > 0)) | No knockout exhibited abolished shift |
| E | b2926 | Pgk | −0.59 | 5 | 5 | (NOT(TIME < 0 HRS)) | (ON) | Essential for WT growth |
| E | b3236 | mdh | | 1 | 1 | (NOT(ArcA)) | (NOT(ArcA)) | Correct |
| E | b3425 | glpE | | 5 | 5 | (Crp) | (Crp) | Essential for WT growth |
| E | b3892 | fdoI | | 4 | 2 | ((O2xt > 0) OR ((NOT (O2xt > 0) AND (NO3xt > 0)))) | (NO3xt > 0) | No shift |
| E | b3893 | fdoH | | 1 | 1 | ((O2xt > 0) OR ((NOT (O2xt > 0) AND (NO3xt > 0)))) | ((NOT (ArcA) OR SoxS) OR ((ArcA AND (NO3xt > 0))) | Correct |
| E | b3894 | fdoG | | 1 | 1 | ((O2xt > 0) OR ((NOT (O2xt > 0) AND (NO3xt > 0)))) | ((NOT (ArcA) OR NOT (Fnr)) OR ((ArcA AND Fnr AND (NO3xt > 0)))) | Correct |
| E | b3916 | pfkA | −1.06 | 5 | 1 | none | (NOT (O2xt > 0)) | No knockout exhibited abolished shift |
| E | b3919 | tpiA | −0.56 | 5 | 5 | none | (ON) | Essential for WT growth |
| E | b3952 | pflC | | 4 | 2 | (ArcA OR Fnr) | (ON) | Essential for WT growth |
| E | b3956 | ppc | | 5 | 5 | none | (ON) | Essential for WT growth |
| E | b4151 | frdD | −2.23 | 5 | 1 | (Fnr OR DcuR OR NOT (NarL)) | (NOT (O2xt > 0) AND (DcuR OR NOT (NarL))) | No knockout exhibited abolished shift |
| E | b4152 | frdC | −0.98 | 5 | 1 | (Fnr OR DcuR OR NOT (NarL)) | (NOT (O2xt > 0) AND (DcuR OR NOT (NarL))) | No knockout exhibited abolished shift |
| E | b4153 | frdB | −2.31 | 5 | 1 | (Fnr OR DcuR OR NOT (NarL)) | (NOT (O2xt > 0) AND (DcuR OR NOT (NarL))) | No knockout exhibited abolished shift |
| E | b4154 | frdA | −0.80 | 5 | 1 | (Fnr OR DcuR OR NOT (NarL)) | (NOT (O2xt > 0) AND (DcuR OR NOT (NarL))) | No knockout exhibited abolished shift |
| F | b1805 | fadD | | 4 | 2 | (NOT (FadR2) OR NOT (ArcA)) | (NOT (FadR2)) | No shift |
| F | b2323 | fabB | | 5 | 5 | ((NOT((Stringent > 0) OR (Stringent < 0))) OR CpxR OR RpoE OR FadR2) | (((NOT((Stringent > 0) OR (Stringent < 0))) OR CpxR OR RpoE OR FadR2)) | Essential: small shift |
| F | b4160 | psd | | 5 | 5 | none | (ON) | Essential for WT growth |
| I | b0207 | yafB | | 5 | 5 | none | (ON) | Essential for WT growth |
| I | b0221 | fadF | | 1 | 1 | (NOT (FadR2) OR NOT (ArcA)) | (NOT (FadR2) OR NOT (ArcA)) | Correct |
| I | b1702 | pps | | 5 | 1 | (Cra) | ((Cra) AND (O2xt > 0)) | No knockout exhibited abolished shift |
| I | b2040 | rfbD | | 5 | 1 | none | (O2xt > 0) | No knockout exhibited abolished shift |
| I | b2308 | hisQ | | 5 | 1 | (NOT (LYSxt > 0)) | (NOT (LYSxt > 0) AND NOT (ArcA AND Fnr)) | — |
| I | b2463 | maeB | | 5 | 1 | none | (O2xt > 0) | No knockout exhibited abolished shift |
| I | b2530 | iscS | | 5 | 1 | none | (O2xt > 0) | No knockout exhibited abolished shift |
| I | b2676 | nrdF | | 5 | 1 | none | (O2xt > 0) | No knockout exhibited abolished shift |
| I | b2904 | gcvH | | 5 | 1 | ((Fis AND NOT PdhR) AND ((NOT(GcvR) AND GcvA) OR Lrp OR NOT PurR)) | (NOT (Fnr OR ArcA) AND (((NOT(GcvR) AND GcvA) OR Lrp OR NOT PurR))) | — |

TABLE 16-continued

| | | | | | | | | |
|---|---|---|---|---|---|---|---|---|
| I | b2905 | gcvT | | 5 | 1 | ((F is AND NOT PdhR) AND ((NOT(GcvR) AND GcvA) OR Lrp OR NOT PurR)) | ((O2xt > 0) AND (((NOT(GcvR) AND GcvA) OR Lrp OR NOT PurR))) | No knockout exhibited abolished shift |
| I | b2976 | glcB | | 1 | 1 | (NOT (ArcA) AND (GlcC)) | (NOT (ArcA) AND (GtaC)) | Correct |
| I | b4014 | aceB | | 5 | 1 | (NOT (IclR) AND (NOT (ArcA) OR NOT (Cra))) | ((NOT (IclR) OR NOT (Cra)) OR (NOT (ArcA))) | AND. OR change |
| I | b4015 | aceA | | 5 | 1 | (NOT (IclR) AND (NOT (ArcA) OR NOT (Cra))) | ((NOT (IclR) OR NOT (Cra)) OR (NOT (ArcA))) | AND. OR change |
| I | b4139 | aspA | −1.05 | 1 | 1 | ((Crp AND NOT (Fnr)) OR Fnr) | ((Crp AND NOT (Fnr)) OR Fnr) | Correct |
| I | b4232 | fbp | | 5 | 1 | none | (O2xt > 0) | No knockout exhibited abolished shift |
| N | b0033 | carB | | 5 | 1 | (NOT ArgR) | ((NOT ArgR) AND OxyR) | — |
| N | b0888 | trxB | | 5 | 5 | none | (ON) | Essential for WT growth |
| N | b0945 | pyrD | −0.69 | 5 | 5 | knot (CYTSxt > 0) OR (GNxt > 0) OR NOT PurR) | ((NOT (CYTSxt > 0)) OR (GNxt > 0) OR NOT PurR) | Essential for WT growth |
| N | b1062 | pyrC | | 5 | 5 | ((not (CYTSxt > 0)) OR (GNxt > 0) OR NOT PurR) | ((NOT (CYTSxt > 0)) OR (GNxt > 0) OR NOT PurR) | Essential for WT growth |
| N | b2234 | nrdA | | 1 | 1 | (NOT (ArcA)) | (NOT (ArcA)) | Correct |
| N | b2235 | nrdB | | 1 | 1 | (NOT (ArcA)) | (NOT (ArcA)) | Correct |
| N | b2476 | purC | | 5 | 5 | (NOT (PurR)) | (NOT (PurR)) | Essential for WT growth |
| N | b2518 | ndk | | 5 | 5 | none | none | Complex rule -- ANOVA: ArcA and not Fnr |
| N | b3831 | udp | −0.53 | 5 | 5 | (NOT (CytR) OR Crp) | (NOT (CytR) OR Crp) | Essential for WT growth |
| N | b4238 | nrdD | −0.77 | 1 | 1 | (Fnr) | (NOT (O2xt > 0)) | Correct |
| P | b1656 | sodB | | 5 | 1 | none | (NOT (O2xt > 0)) | No knockout exhibited abolished shift |
| P | b3908 | sodA | | 1 | 1 | (NOT (ArcA OR Fur) OR (MarA OR Rob OR SoxS)) | (NOT (ArcA OR Fur) OR (MarA OR Rob OR SoxS)) | Correct |
| R | b0034 | caiF | −1.37 | 5 | 1 | (Fnr AND Crp AND NOT NarL) | ((Fnr AND ArcA) OR Crp AND NOT NarL) | — |
| R | b0080 | fruR | −0.73 | 5 | 5 | ( NOT ( "Surplus FDP")) | (NOT ("Surplus FDP")) | Essential; again activity and transcription seem opposite |
| R | b0113 | pdhR | | 5 | 1 | ( NOT "Surplus PYR") | (NOT ("Surplus PYR") OR (NOT (ArcA) OR NOT (Fnr))) | — |
| R | b0313 | betI | | 5 | 1 | (CHOLxt > 0) | (NOT (ArcA) OR (CHOLxt > 0)) | — |
| R | b0564 | appY | −1.87 | 5 | 1 | (NOT CUB) | (NOT CitB) | No AppY-dependent genes were detected (all MA) |
| R | b0683 | fur | | 5 | 1 | ((FE2xt > 0) AND (OxyR OR SoxS)) | ((FE2xt > 0) OR (NOT(Fnr OR ArcA))) | OxyR and SoxS did not exhibit abolished shift |
| R | b0993 | torS | −0.97 | 5 | 1 | (TMAOxt > 0) | ((TMAOxt > 0) OR NOT (O2xt > 0)) | No knockout exhibited abolished shift |
| R | b1187 | fadR | | 5 | 5 | (GLCxt > 0 OR NOT (ACxt > 0)) | (GLCxt > 0 OR NOT (ACxt > 0 )) | Essential for WT growth |
| R | b1221 | narL | | 5 | 1 | ((NO3xt > 0) OR (NO2xt > 0)) | ((NOT Fnr) AND (NOT ArcA)) | Separated activity and transcription |
| R | b1323 | tyrR | −0.62 | 5 | 1 | ((TRPxt > 0) OR (TYRxt > 0) OR (PHExt > 0)) | (((TRPxt > 0) OR (TYRxt > 0) OR (PHExt > 0)) OR NOT (O2xt > 0)) | No knockout exhibited abolished shift |
| R | b1334 | fnr | | 3 | 5 | (NOT (O2xt > 0)) | (ON) | Transcription of fnr is opposite to activity |
| R | b1531 | marA | | 5 | 1 | (Salicylate > 0) | ((NOT ArcA OR NOT Fnr) OR OxyR OR (Salicylate > 0)) | — |
| R | b1827 | kdgR | | 5 | 1 | (NOT(KDGxt > 0) AND NOT(UXUA > 0) AND NOT(UXAA > 0)) | ((ArcA) AND (Fnr) AND (NOT(KDGxt > 0) AND NOT(UXUA > 0) AND NOT(UXAA > 0))) | — |
| R | b2087 | gatR_1 | | 5 | 5 | (NOT (GLTLxt > 0)) | (NOT (GLTLxt > 0)) | Essential for WT growth |
| R | b2573 | rpoE | −0.62 | 5 | 1 | ("heat shock" > 0) | (NOT (OxyR)) | Separated activity and transcription |
| R | b2707 | srlR | | 5 | 1 | (NOT (GLTxt > 0)) | (Fnr AND NOT (GLTxt > 0)) | |

TABLE 16-continued

| | | | | | | | |
|---|---|---|---|---|---|---|---|
| R | b2731 | fhlA | | 4 | 2 | ((NOT (O2xt > 0)) AND (NOT (NO3xt > 0)) AND (NOT (NO2xt > 0)) AND (NOT (TMAOxt > 0)) AND (NOT (DMSOxt > 0)) AND (FORxt > 0)) | ((NOT (NO3xt > 1 )) AND (NOT (NO2xt > 1 )) AND (NOT (TMAOxt > 1)) AND (NOT (DMSOxt > 1)) AND (FORxt > 1)) | Threshold required: trace amounts |
| R | b3357 | crp | | 5 | 5 | ("CRP noGLC") | ("CRP noGLC") | Essential for WT growth |
| R | b3423 | glpR | | 5 | 1 | (NOT (GLxt > 0)) | (NOT (GLxt > 0 ) AND (O2xt > 0 )) | No knockout exhibited abolished shift |
| R | b3806 | cyaA | −0.54 | 5 | 1 | (NOT Crp) | ((NOT Crp) AND (Fnr)) | — |
| R | b4124 | dcuR | | 4 | 2 | ( DcuS ) | (DcuS) | Threshold required; trace amounts |
| R | b4125 | dcuS | | 4 | 2 | ( (SUCCxt > 0) OR (ASPxt > 0) OR (FUMxt > 0) OR (MALxt > 0)) | ((SUCCxt > 1) OR (ASPxt > 1)OR (FUMxt > 1) OR (MALxt > 1) ) | Threshold required; trace amounts |
| R | b4401 | arcA | −0.69 | 1 | 1 | ( NOT ( O2xt > 0 ) ) | (Fnr AND NOT OxyR) | Correct - activity matches expression shift |
| T | b0314 | betT | | 5 | 3 | (NOT (BetI)) | (NOT (BetI)) | BetI transcription is opposite to activity |
| T | b0336 | codB | | 5 | 1 | (NOT (PurR)OR (NRI_hi)) | ((NOT (PurR) OR (NRI_hi)) AND OxyR) | — |
| T | b0401 | brnQ | −0.65 | 5 | 1 | none | (NOT (O2xt > 0)) | No knockout exhibited abolished shift |
| T | b0653 | gltK | | 5 | 1 | (NOT (GLCxt > 0)) | (NOT (GLCxt > 0) OR NOT (ArcA AND Fnr)) | — |
| T | b0854 | potF | | 5 | 1 | none | (NOT (ArcA AND Fnr)) | — |
| T | b0864 | artP | −0.57 | 5 | 1 | none | (NOT (O2xt > 0)) | No knockout exhibited abolished shift |
| T | b2129 | yehX | | 5 | 1 | none | (NOT (ArcA AND Fnr)) | — |
| T | b2309 | hisJ | | 5 | 1 | (NOT (LYSxt > 0)) | ((NOT ArcA OR NOT Fnr) OR OxyR AND NOT (LYSxt > 0)) | — |
| T | b2344 | fadL | | 5 | 1 | ((NOT (Crp OR FadR OR OmpR))) | (NOT (Crp OR FadR OR OmpR) OR NOT (ArcA)) | — |
| T | b2423 | cysW | | 5 | 5 | (CysB) | (CysB) | Essential for WT growth |
| T | b2425 | cysP | | 5 | 5 | (CysB) | (CysB) | Essential for WT growth |
| T | b2587 | kgtP | | 5 | 1 | none | (NOT ArcA) | — |
| T | b2677 | proV | | 5 | 1 | none | (NOT (Fnr OR ArcA)) | — |
| T | b3089 | sstT | −1.86 | 5 | 1 | none | (NOT (O2xt > 0)) | No knockout exhibited abolished shift |
| T | b3453 | ugpB | | 5 | 1 | (Crp OR PhoB) | ((Crp OR PhoB) OR (NOT (Fnr OR ArcA))) | — |
| T | b3917 | sbp | | 5 | 1 | (CysB) | (CysB AND (O2xt > 0)) | No knockout exhibited abolished shift |
| U | b0126 | yadF | | 5 | 5 | none | none | Complex rule - ANOVA: Fnr or ArcA and not (Fnr and ArcA) |
| U | b0621 | dcuC | | 4 | 2 | (Fnr OR ArcA) | (ON) | Essential for WT growth |
| U | b0963 | mgsA | | 5 | 5 | none | (ON) | Essential for WT growth |
| U | b1033 | ycdW | | 5 | 1 | none | (NOT (Fnr OR ArcA)) | — |
| U | b1297 | ycjK | | 5 | 5 | none | (ON) | Essential for WT growth |
| U | b2286 | nuoC | | 4 | 2 | (NOT (ArcA OR Fnr) OR NarL) | (ON) | Essential for growth on acetate |
| U | b2747 | ispD | | 5 | 1 | none | (O2xt > 0) | No knockout exhibited abolished shift |
| U | b3111 | tdcGa | | 4 | 2 | (Crp OR NOT(O2xt > 0)) | (Crp) | — |
| U | b3612 | yibO | −0.90 | 5 | 1 | none | (NOT (O2xt > 0)) | No knockout exhibited abolished shift |
| U | b3843 | yigC | | 5 | 5 | none | none | Very small shift. ANOVA: ArcA |
| U | b3962 | sthA | | 5 | 1 | none | (NOT ArcA) | — |

TABLE 16-continued

| | Legend | | | |
|---|---|---|---|---|
| 1 | (P:E) | 100 | L2R >+ 1.0 | |
| 2 | (0:0) | 23 | | |
| 3 | (P:−E) | 2 | | |
| 4 | (P:0) | 0 | | |
| 5 | (0:E) | 49 | −1 > L2R | |

TABLE 17

| Gene | | WT Pvalue | L2 Ratio | ArcA Pvalue | L2 Ratio | Fnr Pvalue | L2 Ratio | ArcA/Fnr Pvalue | L2 Ratio | AppY Pvalue | L2 Ratio | OxyR Pvalue | L2 Ratio | SoxS Pvalue | L2 Ratio |
|---|---|---|---|---|---|---|---|---|---|---|---|---|---|---|---|
| RT-PCR Verification Data | | | | | | | | | | | | | | | |
| acnA | RT-PCR | 0.000 | 2.497 | 0.077 | −0.756 | 0.613 | −0.173 | 0.000 | −1.839 | | | | | | |
| | Affy Chip | 0.001 | 1.301 | 0.449 | −0.204 | 0.010 | 0.501 | 0.001 | −1.289 | | | | | | |
| cyoC | RT-PCR | 0.000 | 5.181 | 0.176 | −0.710 | 0.907 | −0.053 | 0.254 | 0.480 | | | | | | |
| | Affy Chip | 0.000 | 4.155 | 0.021 | 0.421 | 0.205 | 0.555 | 0.070 | 0.174 | | | | | | |
| dadA | RT-PCR | 0.382 | −1.106 | 0.001 | −3.812 | 0.001 | −3.783 | 0.000 | −4.406 | | | | | | |
| | Affy Chip | 0.482 | −0.137 | 0.006 | −2.300 | 0.010 | −1.935 | 0.000 | −3.066 | | | | | | |
| pta | RT-PCR | 0.000 | −2.811 | 0.000 | −2.171 | 0.000 | −1.705 | 0.211 | −0.607 | | | | | | |
| | Affy Chip | 0.000 | −1.775 | 0.012 | −1.230 | 0.035 | −0.888 | 0.090 | −0.201 | | | | | | |
| sdhA | RT-PCR | 0.000 | 5.548 | 0.046 | −0.782 | | | | | 0.160 | 1.000 | | | 0.003 | 4.456 |
| | Affy Chip | 0.000 | 3.010 | 0.045 | −0.183 | | | | | 0.206 | 2.023 | | | 0.005 | 2.579 |
| sodB | RT-PCR | 0.840 | −0.182 | | | 0.005 | −5.260 | 0.002 | −4.993 | | | 0.002 | −6.225 | | |
| | Affy Chip | 0.004 | −0.204 | | | 0.171 | −2.454 | 0.000 | −3.647 | | | 0.001 | −3.419 | | |

TABLE 18

MIAME Checklist (completed information shown in open bullets)

Experiment Design:

- ○ Type of experiment: for example, is it a comparison of normal vs. diseased tissue, a time course, or is it designed to study the effects of a gene knock-out?
- ○ Seven *E. coli* strains (wild-type, five single knockouts, and one double knockout) were compared in their response to aerobic vs. anaerobic conditions.
- ○ Experimental factors: the parameters or conditions tested, such as time, dose, or genetic variation.
- ○ Strains were cultured on glucose minimal (M9) media under aerobic and anaerobic conditions.
- ○ The number of hybridizations performed in the experiment.
- ○ 43 (3 replicates of each strain × 2 conditions × 7 strains, plus one extra replicate for the wild-type anaerobic condition).
- ○ The type of reference used for the hybridizations, if any.
- ○ N/A.
- ○ Hybridization design: if applicable, a description of the comparisons made in each hybridization, whether to a standard reference sample, or between experimental samples. An accompanying diagram or table may be useful
- ○ N/A.
- ○ Quality control steps taken: for example, replicates or dye swaps.
- ○ 3–4 replicates of each strain and condition tested
- ○ RT-PCR used to confirm certain shifts
- ○ URL of any supplemental websites or database accession numbers
- ○ http://systemsbiology.ucsd.edu Samples used, extract preparation and labeling:

- • The origin of the biological sample (for instance, name of the organism, the provider of the sample) and its characteristics: for example, gender, age, developmental stage, strain, or disease state.
- ○ *Escherichia coli* K-12 MG1655, provided by the American Type Culture Collection (ATCC).
- ○ Manipulation of biological samples and protocols used: for example, growth conditions, treatments, separation techniques.
- ○ Aerobic cultures were set up using 250 ml of media in 500 ml Erlenmeyer flasks. Anaerobic cultures were set up using 200 ml of media in 250 ml Erlenmeyer flasks. All cultures were comprised

TABLE 18-continued

MIAME Checklist (completed information shown in open bullets)

- of M9 minimal medium supplemented with 2 g/l glucose. The temperature was controlled by using a circulating water bath with a stir speed of ~1000 rpm to maintain oxygen saturation. Anaerobic cultures were initially sparged with nitrogen gas and monitored for dissolved oxygen throughout the experiment. All measurements and samples were taken during exponential growth.
○ Protocol for preparing the hybridization extract: for example, the RNA or DNA extraction and purification protocol.
○ Samples were RNA-stabilized using Qiagen RNAProtect Bacterial Reagent, and total RNA was isolated from exponentially growing cells using a Qiagen RNeasy mini kit (protocols available at www1.qiagen.com). The RNA (10 micrograms) was then prepared according to the Affymetrix protocol for *E. coli* Antisense Genome Arrays (available at www.affymetrix.com). Briefly, cDNA was prepared from the total RNA via reverse transcription and RNA degradation. QIAquick PCR Purification Kits were used to clean up the cDNA synthesis product (protocol available at www1.qiagen.com). Following the purification, the cDNA was quantified and then fragmented with DNase I at 37° C. for 10 minutes. The efficiency of the fragmentation was determined by running a sample on a 2% agarose gel and staining with SYBR Gold (Molecular Probes, OR).
○ Labeling protocol(s).
○ The fragmented cDNA was labeled with Biotin-ddUTP at 37 C. for 1 hour, according to the Enzo BioArray Terminal Labeling Kit protocol (available at www.enzobio.com/lifesci_index.htm).
○ External controls (spikes).
○ None.
○ Hybridization procedures and parameters:
○ The protocol and conditions used during hybridization, blocking and washing.
○ Hybridization was performed in an Affymetrix Hybridization oven at 45° C. and 60 rpm for 16 hours, according to the protocol listed above.
○ Measurement data and specifications:
○ The quantitations based on the images.
○ Given here with the supplemental data.
○ The set of quantitations from several arrays upon which the authors base their conclusions. While access to images of raw data is not required (although its value is unquestionable), authors should make every effort to provide the following:
○ Given here with the supplemental data.
○ Type of scanning hardware and software used: this information is appropriate for a materials and methods section.
○ The Affymetrix Gene Chip Scanner and Operating Software were used to obtain the image data, according to the protocols.
○ Type of image analysis software used: specifications should be stated in the materials and methods.
○ A description of the measurements produced by the image-analysis software and a description of which measurements were used in the analysis.
○ dChip software was used for all image analysis; see www.dchip.org.
○ The complete output of the image analysis before data selection and transformation (spot quantitation matrices).
○ Given here with the supplemental data.
○ Data selection and transformation procedures.
○ See main text.
○ Final gene expression data table(s) used by the authors to make their conclusions after data selection and transformation (gene expression data matrices).
○ See main text and supplemental data.

Array Design:

- General array design, including the platform type (whether the array is a spotted glass array, an in situ synthesized array, etc.); surface and coating specifications (when known - often commercial suppliers do not provide this data); and the availability of the array (the name or make of commercially available arrays).
○ Affymetrix *E. coli* Antisense Genome Array (Part Number 900381)
- For each feature (spot) on the array, its location on the array and the ID of its respective reporter (molecule present on each spot) should be given.

TABLE 18-continued

| MIAME Checklist (completed information shown in open bullets) |
|---|
| o See the Affymetrix CDF file from manufacturer. |
| • For each reporter, its type (e.g., cDNA or oligonucleotide) should be given, along with information that characterizes the reporter molecule unambiguously, in the form of appropriate database reference(s) and sequence (if available). |
| o See the Affymetrix CDF file from manufacturer. |
| • For commercial arrays: a reference to the manufacturer should be provided, including a catalogue number and references to the manufacturer's website if available. |
| o Affymetrix *E. coli* Antisense Genome Array (Part Number 900381) |
| o http://www.affymetrix.com/products/arrays/specific/ecoli_antisense.affx |

We claim:

1. A method of refining a biosystem reaction network, wherein the steps of said method are performed on a suitably programmed computer programmed to execute the steps comprising:
    (a) providing a mathematical representation of an actual biosystem;
    (b) reconciling said mathematical representation of said actual biosystem with a legacy data set or empirical data set;
    (c) determining differences between observed behavior of said actual biosystem and in silico behavior of said reconciled mathematical representation of said actual biosystem under similar conditions;
    (d) modifying a structure by deletion of a gene of a reaction network of said reconciled mathematical representation of said actual biosystem;
    (e) determining differences between said observed behavior of said actual biosystem and in silico behavior of said modified mathematical representation of said actual biosystem under similar conditions; and
    (f) providing a visual output to a user of accuracy or coverage of said modified mathematical representation, wherein accuracy indicates the percentage of said modified mathematical representation predictions in agreement with experimental data and coverage indicates the percentage of correct experimental changes predicted by said modified mathematical representation, thereby refining a biosystem reaction network.

2. The method of claim 1, further comprising, repeating steps (d) and (e) until behavioral differences are minimized, wherein satisfaction of a predetermined accuracy criteria indicates an improvement in said biosystem reaction network.

3. The method of claim 1, further comprising repeating steps (c) through (e) under conditions different from said conditions.

4. The method of claim 3, further comprising performing iterations until behavioral differences are minimized.

5. The method of claim 4, further comprising repeating said iterations to produce an improved biosystem reaction network.

6. The method of claim 5, wherein said improved biosystem reaction network is optimized to obtain a desired accuracy or coverage.

7. The method of claim 1, wherein said actual biosystem is a prokaryotic cell, or biological process thereof.

8. The method of claim 7, wherein said prokaryotic organism is selected from the group consisting of *E. coli, B. subtilis, H. influenzae* and *H. pylori*.

9. The method of claim 8, wherein said prokaryotic cell is *E. coli*.

10. The method of claim 8, wherein said prokaryotic cell is *B. subtilis*.

11. The method of claim 8, wherein said prokaryotic cell is *H. influenzae*.

12. The method of claim 8, wherein said prokaryotic cell is *H. pylori*.

13. The method of claim 7, wherein said biological process is metabolism.

14. The method of claim 1, wherein said biosystem is a eukaryotic cell, or biological process thereof.

15. The method of claim 14, wherein said eukaryotic organism is selected from the group consisting of *S. cerevisiae* and *H. sapiens*.

16. The method of claim 15, wherein said biological process is metabolism.

17. The method of claim 15, wherein said eukaryotic cell is *S. cerevisiae*.

18. The method of claim 15, wherein said eukaryotic cell is *H. sapiens*.

* * * * *